US011371023B2

(12) United States Patent
Eguchi et al.

(10) Patent No.: US 11,371,023 B2
(45) Date of Patent: Jun. 28, 2022

(54) ARTIFICIAL TRANSCRIPTION FACTORS AND USES THEREOF

(71) Applicant: Wisconsin Alumni Research Foundation, Madison, WI (US)

(72) Inventors: Asuka Eguchi, Madison, WI (US); Aseem Z. Ansari, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 792 days.

(21) Appl. No.: 15/821,152

(22) Filed: Nov. 22, 2017

(65) Prior Publication Data

US 2018/0142215 A1    May 24, 2018

Related U.S. Application Data

(60) Provisional application No. 62/425,374, filed on Nov. 22, 2016.

(51) Int. Cl.
*C07K 14/47*  (2006.01)
*C07K 19/00*  (2006.01)
(Continued)

(52) U.S. Cl.
CPC ............ *C12N 5/0696* (2013.01); *C07K 1/047* (2013.01); *C07K 14/4702* (2013.01); *C12N 5/0647* (2013.01); *C12N 5/0657* (2013.01); *C40B 40/10* (2013.01); *C07K 2319/09* (2013.01); *C07K 2319/81* (2013.01); *C12N 2500/25* (2013.01); *C12N 2501/115* (2013.01);
(Continued)

(58) Field of Classification Search
CPC .......................... C07K 14/00; C07K 14/4702; C07K 14/4703; C07K 14/4705; C07K 2319/81; C40B 40/10; C12N 5/0647; C12N 5/0657; C12N 5/0696; C12N 2501/145; C12N 2501/40; C12N 2501/60; C12N 2506/02; C12N 2506/45
See application file for complete search history.

(56) References Cited

U.S. PATENT DOCUMENTS 7,851,216 B2 * 12/2010 Choo ................. C07K 14/4702
                                                    435/325
7,943,731 B1 *  5/2011 Wang .................... C07K 14/00
                                                    530/350
(Continued)

OTHER PUBLICATIONS

Appendix to Eguchi et al., Reprogramming cell fate with a genome-scale library of artificial transcription factors. Proceedings of the National Academy of Science USA. Dec. 5, 2016, vol. 113, No. 51, pp. E8257-E8266. (Year: 2016).*
(Continued)

*Primary Examiner* — Jeffrey E. Russel
(74) *Attorney, Agent, or Firm* — Daniel A. Blasiole; DeWitt LLP

(57) ABSTRACT

The present invention relates to artificial transcription factors (ATFs) that alter gene expression, including inducing pluripotency in cells or promoting the conversion of cells to specific cell fates. In particular, provided herein is a zinc-finger based ATF library that can be screened in cells by looking for expression of a specific gene (e.g., reporter expression), monitoring for cell surface markers or morphology, or via functional assays.

24 Claims, 50 Drawing Sheets
(45 of 50 Drawing Sheet(s) Filed in Color)
Specification includes a Sequence Listing.

(51) Int. Cl.
| | | |
|---|---|---|
| *C40B 40/10* | (2006.01) | |
| *C12N 5/0789* | (2010.01) | |
| *C12N 5/074* | (2010.01) | |
| *C12N 5/077* | (2010.01) | |
| *C07K 1/04* | (2006.01) | |

(52) U.S. Cl.
CPC .... *C12N 2501/145* (2013.01); *C12N 2501/40* (2013.01); *C12N 2501/415* (2013.01); *C12N 2501/60* (2013.01); *C12N 2501/602* (2013.01); *C12N 2501/604* (2013.01); *C12N 2501/606* (2013.01); *C12N 2501/727* (2013.01); *C12N 2506/02* (2013.01); *C12N 2506/45* (2013.01)

(56) References Cited

U.S. PATENT DOCUMENTS

| | | | |
|---|---|---|---|
| 8,940,504 B2* | 1/2015 | Steenstrup | C12Y 304/21021 435/69.1 |
| 2006/0063231 A1* | 3/2006 | Li | C07K 14/4702 435/69.1 |
| 2008/0306001 A1* | 12/2008 | Liik | A61P 17/00 514/1.1 |
| 2014/0359798 A1* | 12/2014 | Wiles | A01K 67/0275 800/18 |
| 2016/0046682 A1* | 2/2016 | Neutzn | A61P 27/02 514/1.1 |

OTHER PUBLICATIONS

Bae, K.-H., Kwon, Y.D., Shin, H.-C., Hwang, M.-S., Ryu, E.-H., Park, K.-S., Yang, H.-Y., Lee, D.-K., Lee, Y., Park, J., et al. (2003). Human zinc fingers as building blocks in the construction of artificial transcription factors. Nat Biotechnol 21, 275-280.

Bailus, B.J., Pyles, B., McAlister, M.M., O'Geen, H., Lockwood, S.H., Adams, A.N., Nguyen, J.T.T., Yu, A., Berman, R. F., and Segal, D.J. (2016). Protein delivery of an artificial transcription factor restores widespread Ube3a expression in an Angelman syndrome mouse brain. Mol Ther24, 548-555.

Blancafort, P., Magnenat, L., and Barbas, C.F. (2003). Scanning the human genome with combinatorial transcription factor libraries. Nat Biotechnol 21, 269-274.

Bloor AJC, Sánchez M-J, Green AR, Göttgens B (2002) The role of the stem cell leukemia (SCL) gene in hematopoietic and endothelial lineage specification. J Hematother Stem Cell Res 11(2):195-206.

Buganim, Y., Faddah, D.A., Cheng, A.W., Itskovich, E., Markoulaki, S., Ganz, K., Klemm, S.L., van Oudenaarden, A., and Jaenisch, R. (2012). Single-cell expression analyses during cellular reprogramming reveal an early stochastic and a late hierarchic phase. Cell 150, 1209-1222.

Burridge PW, et al. (2014) Chemically defined generation of human cardiomyocytes. Nat Methods 11(8):855-860.

Burridge PW, Keller G, Gold JD, Wu JC (2012) Production of de novo cardiomyocytes: human pluripotent stem cell differentiation and direct reprogramming. Cell Stem Cell 10(1):16-28.

Cahan, P., Li, H., Morris, S.A., Lummertz da Rocha, E., Daley, G.Q., and Collins, J.J. (2014). CellNet: network biology applied to stem cell engineering. Cell 158, 903-915.

Chavez, A., Scheiman, J., Vora, S., Pruitt, B.W., Tuttle, M., P R Iyer, E., Lin, S., Kiani, S., Guzman, C.D., Wiegand, D.J., et al. (2015). Highly efficient Cas9-mediated transcriptional programming. Nat Methods 12, 326-328.

Chen B, et al. (2009) Small molecule-mediated disruption of Wnt-dependent signaling in tissue regeneration and cancer. Nat Chem Biol 5(2):100-107.

Chen, E.Y., Tan, C.M., Kou, Y., Duan, Q., Wang, Z., Meirelles, G.V., Clark, N.R., and Ma'ayan, A. (2013). Enrichr: interactive and collaborative HTML5 gene list enrichment analysis tool. BMC Bioinformatics 14, 128.

Cheng, C., and Gerstein, M. (2012). Modeling the relative relationship of transcription factor binding and histone modifications to gene expression levels in mouse embryonic stem cells. Nucleic Acids Res 40, 553-568.

Cohen, D.E., and Melton, D. (2011). Turning straw into gold: directing cell fate for regenerative medicine. Nat Rev Genet 12, 243-252.

Doulatov S, Notta F, Laurenti E, Dick JE (2012) Hematopoiesis: a human perspective. Cell Stem Cell 10(2):120-136.

Edelson, B.S., Best, T.P., Olenyuk, B., Nickols, N.G., Doss, R.M., Foister, S., Heckel, A., and Dervan, P.B. (2004). Influence of structural variation on nuclear localization of DNA-binding polyamide-fluorophore conjugates. Nucleic Acids Res 32, 2802-2818.

Eguchi, A., Lee, G.O., Wan, F., Erwin, G.S., and Ansari, A.Z. (2014). Controlling gene networks and cell fate with precision-targeted DNA-binding proteins and small-molecule-based genome readers. Biochem J 462, 397-413.

Elcheva I, et al. (2014) Direct induction of haematoendothelial programs in human pluripotent stem cells by transcriptional regulators. Nat Commun 5:4372.

Esvelt, K.M., Mali, P., Braff, J.L., Moosburner, M., Yaung, S.J., and Church, G.M. (2013). Orthogonal Cas9 proteins for RNA-guided gene regulation and editing. Nat Methods 10, 1116-1121.

Filion, G.J.P., Zhenilo, S., Salozhin, S., Yamada, D., Prokhortchouk, E., and Defossez, P.-A. (2006). A family of human zinc finger proteins that bind methylated DNA and repress transcription. Mol Cell Biol 26, 169-181.

Gao, X., Yang, J., Tsang, J.C.H., Ooi, J., Wu, D., and Liu, P. (2013). Reprogramming to pluripotency using designer TALE transcription factors targeting enhancers. Stem Cell Reports 1, 183-197.

Gilbert, L.A., Horlbeck, M.A., Adamson, B., Villalta, J.E., Chen, Y., Whitehead, E.H., Guimaraes, C., Panning, B., Ploegh, H.L., Bassik, M.C., et al. (2014). Genome-scale CRISPR-mediated control of gene repression and activation. Cell 159, 647-661.

Gonzalez, B., Schwimmer, L.J., Fuller, R.P., Ye, Y., Asawapom-mongkol, L., and Barbas, C.F. (2010). Modular system for the construction of zinc-finger libraries and proteins. Nat Protoc 5, 791-810.

Greder, L.V., Gupta, S., Li, S., Abedin, M.J., Sajini, A., Segal, Y., Slack, J.M.W., and Dutton, J.R. (2012). Analysis of endogenous Oct4 activation during induced pluripotent stem cell reprogramming using an inducible Oct4 lineage label. Stem Cells 30, 2596-2601.

Heng, J.-C.D., Feng, B., Han, J., Jiang, J., Kraus, P., Ng, J.-H., Orlov, Y.L., Huss, M., Yang, L., Lufkin, T., et al. (2010). The nuclear receptor Nr5a2 can replace Oct4 in the reprogramming of murine somatic cells to pluripotent cells. Cell Stem Cell 6, 167-174.

Hnisz, D., Abraham, B.J., Lee, T.I., Lau, A., Saint-Andre, V., Sigova, A.A., Hoke, H.A., and Young, R.A. (2013). Super-enhancers in the control of cell identity and disease. Cell 155, 934-947.

Ieda, M., Fu, J.-D., Delgado-Olguin, P., Vedantham, V., Hayashi, Y., Bruneau, B.G., and Srivastava, D. (2010). Direct reprogramming of fibroblasts into functional cardiomyocytes by defined factors. Cell 142, 375-386.

Isalan, M., Choo, Y., and Klug, A. (1997). Synergy between adjacent zinc fingers in sequence-specific DNA recognition. Proc Natl Acad Sci USA 94, 5617-5621.

Jung et al., Wrenchnolol Derivative Optimized for Gene Activation in Cells, J. Am. Chem. Soc. 2009, 131(13):4774-4782.

Kim, J., Chu, J., Shen, X., Wang, J., and Orkin, S.H. (2008). An extended transcriptional network for pluripotency of embryonic stem cells. Cell 132, 1049-1061.

Kim, Y., Kweon, J., Kim, A., Chon, J.K., Yoo, J.Y., Kim, H.J., Kim, S., Lee, C., Jeong, E., Chung, E., et al. (2013). A ibrary of TAL effector nucleases spanning the human genome. Nat Biotechnol 31, 251-258.

Konermann, S., Brigham, M.D., Trevino, A.E., Joung, J., Abudayyeh, O.O., Barcena, C., Hsu, P.D., Habib, N., Gootenberg, J.S., Nishimasu, H., et al. (2015). Genome-scale transcriptional activation by an engineered CRISPR-Cas9 complex. Nature 517, 583-588.

(56) References Cited

OTHER PUBLICATIONS

Koudritsky, M., and Domany, E. (2008). Positional distribution of human transcription factor binding sites. Nucleic Acids Res 36, 6795-6805.

Krentz, A.D., Murphy, M.W., Zhang, T., Sarver, A.L., Jain, S., Griswold, M.D., Bardwell, V.J., and Zarkower, D. (2013). Interaction between DMRT1 function and genetic background modulates signaling and pluripotency to control tumor susceptibility in the fetal germ line. Dev Biol 377, 67-78.

Lalit PA, Hei DJ, Raval AN, Kamp TJ (2014) Induced pluripotent stem cells for post-myocardial infarction repair: remarkable opportunities and challenges. Circ Res 114(8):1328-1345.

Li, Y., Ehrhardt, K., Zhang, M.Q., and Bleris, L. (2014). Assembly and validation of versatile transcription activator-like effector libraries. Sci Rep 4, 4857.

Lian X, et al. (2012) Robust cardiomyocyte differentiation from human pluripotent stem cells via temporal modulation of canonical Wnt signaling. Proc Natl Acad Sci USA 109(27):E1848-57.

Lian X, et al. (2013) Directed cardiomyocyte differentiation from human pluripotent stem cells by modulating Wnt/β-catenin signaling under fully defined conditions. Nat Protoc 8(1):162-175.

Lujan, E., Zunder, E.R., Ng, Y.H., Goronzy, I.N., Nolan, G.P., and Wernig, M. (2015). Early reprogramming regulators identified by prospective isolation and mass cytometry. Nature 521, 352-356.

Marson, A., Levine, S.S., Cole, M.F., Frampton, G.M., Brambrink, T., Johnstone, S., Guenther, M.G., Johnston, W.K., Wernig, M., Newman, J., et al. (2008). Connecting microRNA genes to the core transcriptional regulatory circuitry of embryonic stem cells. Cell 134, 521-533.

Moretti, R., and Ansari, A.Z. (2008). Expanding the specificity of DNA targeting by harnessing cooperative assembly. Biochimie 90, 1015-1025.

Najafabadi, H.S., Mnaimneh, S., Schmitges, F.W., Garton, M., Lam, K.N., Yang, A., Albu, M., Weirauch, M.T., Radovani, E., Kim, P.M., et al. (2015). C2H2 zinc finger proteins greatly expand the human regulatory lexicon. Nat Biotechnol.

Orkin SH, Zon LI (2008) Hematopoiesis: An Evolving Paradigm for Stem Cell Biology. Cell 132(4):631-644.

Pabo, C.O., and Sauer, R.T. (1992). Transcription factors: structural families and principles of DNA recognition. Annu Rev Biochem 61, 1053-1095.

Penkert RR, Kalejta RF (2012) Tale of a tegument transactivator: the past, present and future of human CMV pp. 71. Future Virol 7(9):855-869.

Penkert RR, Kalejta RF (2013) Human embryonic stem cell lines model experimental human cytomegalovirus latency. MBio 4(3):e00298-13.

Rajala K, Pekkanen-Mattila M, Aalto-Setälä K (2011) Cardiac differentiation of pluripotent stem cells. Stem Cells Int 2011:383709.

Rebar, E.J., Huang, Y., Hickey, R., Nath, A.K., Meoli, D., Nath, S., Chen, B., Xu, L., Liang, Y., Jamieson, A.C., et al. (2002). Induction of angiogenesis in a mouse model using engineered transcription factors. Nat Med 8, 1427-1432.

Rodríguez-Martínez, J.A., Reinke, A.W., Bhimsaria, D., Keating, A.E., and Ansari, A.Z. (2016). Combinatorial dimerization of human bZIP transcription regulators confers preferences for different classes of DNA binding sites. Cell.

Saha, S., Ansari, A. Z., Jarrell, K. A., Ptashne, M. and Jarell, K. A. (2003) RNA sequences that work as transcriptional activating regions. Nucleic Acids Res. 31, 1565-1570.

Schultz DC, Ayyanathan K, Negorev D, Maul GG, Rauscher FJ (2002) SETDB1: a novel KAP-1-associated histone H3, lysine 9-specific methyltransferase that contributes to HP1-mediated silencing of euchromatic genes by KRAB zinc-finger proteins. Genes Dev 16(8):919-932.

Sekiya, S., and Suzuki, A. (2011). Direct conversion of mouse fibroblasts to hepatocyte-like cells by defined factors. Nature 475, 390-393.

Sharov, A.A., Masui, S., Sharova, L.V., Piao, Y., Aiba, K., Matoba, R., Xin, L., Niwa, H., and Ko, M.S.H. (2008). Identification of Pou5f1, Sox2, and Nanog downstream target genes with statistical confidence by applying a novel algorithm to time course microarray and genome-wide chromatin immunoprecipitation data. BMC Genomics 9, 269.

Shu, J., Wu, C., Wu, Y., Li, Z., Shao, S., Zhao, W., Tang, X., Yang, H., Shen, L., Zuo, X., et al. (2013). Induction of pluripotency in mouse somatic cells with lineage specifiers. Cell 153, 963-975.

Som, A., Harder, C., Greber, B., Siatkowski, M., Paudel, Y., Warsow, G., Cap, C., Scholer, H., and Fuellen, G. (2010). The PluriNetWork: an electronic representation of the network underlying pluripotency in mouse, and its applications. PLoS ONE 5, e15165.

Stillitano F, Karakikes I, Costa KD, Fish K (2012) Preclinical animal models for testing iPSC/ESC-based heart therapy. Drug Discov Today 9(4):e229-e236.

Takahashi, K., and Yamanaka, S. (2006). Induction of pluripotent stem cells from mouse embryonic and adult fibroblast cultures by defined factors. Cell 126, 663-676.

Takahashi, K., Okita, K., Nakagawa, M., and Yamanaka, S. (2007a). Induction of pluripotent stem cells from fibroblast cultures. Nat Protoc2, 3081-3089.

Takahashi, K., Tanabe, K., Ohnuki, M., Narita, M., Ichisaka, T., Tomoda, K., and Yamanaka, S. (2007b). Induction of pluripotent stem cells from adult human fibroblasts by defined factors. Cell 131, 861-872.

Tanenbaum, M.E., Gilbert, L.A., Qi, L.S., Weissman, J.S., and Vale, R.D. (2014). A protein-tagging system for signal amplification in gene expression and fluorescence imaging Cell 159, 635-646.

Teschendorf, C., Warrington, K.H., Jr, and Siemann, D.W. (2001). Comparison of the EF-1 alpha and the CMV promoter for engineering stable tumor cell lines using recombinant adeno-associated virus. Anticancer Research Nov. 1, 2002, 22(6A):3325-3330.

Tietjen, J.R., Donato, L.J., Bhimsaria, D., and Ansari, A.Z. (2011). Sequence-specificity and energy landscapes of DNA-binding molecules. Meth Enzymol 497, 3-30.

Triezenberg, S.J., Kingsbury, R.C., and McKnight, S.L. (1988). Functional dissection of VP16, the trans-activator of herpes simplex virus immediate early gene expression. Genes Dev 2, 718-729.

Tschulena, U., Peterson, K.R., Gonzalez, B., Fedosyuk, H., and Barbas, C.F. (2009). Positive selection of DNA-protein interactions in mammalian cells through phenotypic coupling with retrovirus production. Nat Struct Mol Biol 16, 1195-1199.

Tsuchiya S, et al. (1980) Establishment and characterization of a human acute monocytic leukemia cell line (THP-1). Int J Cancer 26(2):171-176.

Valton, J., Dupuy, A., Daboussi, F., Thomas, S., Maréchal, A., Macmaster, R., Melliand, K., Juillerat, A., and Duchateau, P. (2012). Overcoming transcription activator-like effector (TALE) DNA binding domain sensitivity to cytosine methylation. J Biol Chem 287, 38427-38432.

Vierbuchen, T., Ostermeier, A., Pang, Z.P., Kokubu, Y., Sudhof, T.C., and Wernig, M. (2010). Direct conversion of fibroblasts to functional neurons by defined factors. Nature 463, 1035-1041.

Wang, B.S., Grant, R.A., and Pabo, C.O. (2001). Selected peptide extension contacts hydrophobic patch on neighboring zinc finger and mediates dimerization on DNA. Nat Struct Biol 8, 589-593.

Wang, R., and Brattain, M.G. (2007). The maximal size of protein to diffuse through the nuclear pore is larger than 60kDa. FEBS Letters 581, 3164-3170.

Wang, T., Wei, J.J., Sabatini, D.M., and Lander, E.S. (2014). Genetic screens in human cells using the CRISPR-Cas9 system. Science 343, 80-84.

Whitfield, T.W., Wang, J., Collins, P.J., Partridge, E.C., Aldred, S.F., Trinklein, N.D., Myers, R.M., and Weng, Z. 2012). Functional analysis of transcription factor binding sites in human promoters. Genome Biol 13, R50.

Whyte, W.A., Orlando, D.A., Hnisz, D., Abraham, B.J., Lin, C.Y., Kagey, M.H., Rahl, P.B., Lee, T.I., and Young, R.A. (2013). Master transcription factors and mediator establish super-enhancers at key cell identity genes. Cell 153, 307-319.

Wolfe, S.A., Nekludova, L., and Pabo, C.O. (2000). DNA recognition by Cys2His2 zinc finger proteins. Annu Rev Biophys Biomol Struct 29, 183-212.

(56) References Cited

OTHER PUBLICATIONS

Wrighton PJ, et al. (2014) Signals from the surface modulate differentiation of human pluripotent stem cells through glycosaminoglycans and integrins. Proc Natl Acad Sci USA 111(51):18126-18131.

Wu D, Pan W (2010) GSK3: a multifaceted kinase in Wnt signaling. Trends Biochem Sci 35(3):161-168.

Yu, J., Vodyanik, M.A., Smuga-Otto, K., Antosiewicz-Bourget, J., Frane, J.L., Tian, S., Ruotti, V., Stewart, R., Slukvin, I.I., and Thomson, J.A. (2007). Induced pluripotent stem cell lines derived from human somatic cells. Science 318, 1917-1920.

Zalatan, J.G., Lee, M.E., Almeida, R., Gilbert, L.A., Whitehead, E.H., La Russa, M., Tsai, J.C., Weissman, J.S., Dueber, J.E., Qi, L.S., et al. (2015). Engineering complex synthetic transcriptional programs with CRISPR RNA scaffolds. Cell 160, 339-350.

Zhou, Y., Zhu, S., Cai, C., Yuan, P., Li, C., Huang, Y., and Wei, W. (2014). High-throughput screening of a CRISPR/Cas9 library for functional genomics in human cells. Nature 509, 487-491.

Bae, Kwang-Hee, et al. Human zinc fingers as building blocks in the construction of artificial transcription factors. Nat Biotechnol. Mar. 2003;21(3):275-80. doi: 10.1038/nbt796.

Bartsevich, Victor V., et al. Engineered zinc finger proteins for controlling stem cell fate. Stem Cells. 2003;21(6):632-7. doi: 10.1634/stemcells.21-6-632.

Beerli R. R. et al. Toward controlling gene expression at will: specific regulation of the erbB-2/HER-2 promoter by using polydactyl zinc finger proteins constructed from modular building blocks. Proc Natl Acad Sci USA. Dec. 8, 1998;95(25): 14628-33. doi: 10.1073/pnas.95.25.14628.

Blancafort, Pilar, et al. Scanning the human genome with combinatorial transcription factor libraries. Nat Biotechnol. Mar. 2003;21(3):269-74. doi: 10.1038/nbt794.

Blancafort, Pilar, et al. Genetic reprogramming of tumor cells by zinc finger transcription factors. Proc Natl Acad Sci USA. Aug. 16, 2005;102(33):11716-21. doi: 10.1073/pnas.0501162102.

Blancafort, Pilar, et al. Modulation of drug resistance by artificial transcription factors. Mol Cancer Ther. Mar. 2008;7(3):688-97. doi: 10.1158/1535-7163.MCT-07-0381.

Eguchi, Asuka. Control of Cell Fate with Artificial Transcription Factors. Ph.D. Thesis. University of Wisconsin—Madison. Published Sep. 22, 2017. Date of Final Oral Examination, Jul. 25, 2016. Part 1, 2 & 3.

Eguchi, Asuka, et al. Reprogramming cell fate with a genome-scale library of artificial transcription factors. Proc Natl Acad Sci U S A. Dec. 20, 2016;113(51):E8257-E8266. doi: 10.1073/pnas.1611142114.

Gersbach, Charles A., et al. Synthetic zinc finger proteins: the advent of targeted gene regulation and genome modification technologies. Acc Chem Res. Aug. 19, 2014;47(8):2309-18. doi: 10.1021/ar500039w.

Kwon, Ryuk-Jun, et al. Artificial transcription factors increase production of recombinant antibodies in Chinese hamster ovary cells. Biotechnol Lett. Jan. 2006;28(1):9-15. doi: 10.1007/s10529-005-4680-7.

Lee, Dong-ki, et al. Induction and characterization of taxol-resistance phenotypes with a transiently expressed artificial transcriptional activator library. Nucleic Acids Res. Aug. 10, 2004;32(14):e116. doi: 10.1093/nar/gnh114.

Lee, Jeongeun, et al. Induction of stable drug resistance in human breast cancer cells using a combinatorial zinc finger transcription factor library. PLoS One. 2011;6(7):e21112. doi: 10.1371/journal.pone.0021112.

Magnenat, Laurent, et al. In vivo selection of combinatorial libraries and designed affinity maturation of polydactyl zinc finger transcription factors for ICAM-1 provides new insights into gene regulation. J Mol Biol. Aug. 13, 2004;341(3):635-49. doi: 10.1016/j.jmb.2004.06.030.

Park, Kyung-Soon, et al. Phenotypic alteration of eukaryotic cells using randomized libraries of artificial transcription factors. Nat Biotechnol. Oct. 2003;21(10):1208-14. doi: 10.1038/nbt868.

Park, Kyung-Soon, et al. Identification and use of zinc finger transcription factors that increase production of recombinant proteins in yeast and mammalian cells. Biotechnol Prog. May-Jun. 2005;21(3):664-70. doi: 10.1021/bp049658x.

Tschulena, Ulrich, et al. Positive selection of DNA-protein interactions in mammalian cells through phenotypic coupling with retrovirus production. Nat Struct Mol Biol. Nov. 2009;16(11):1195-9. doi: 10.1038/nsmb.1677.

\* cited by examiner

FIGS. 1A-1F, CONTINUED
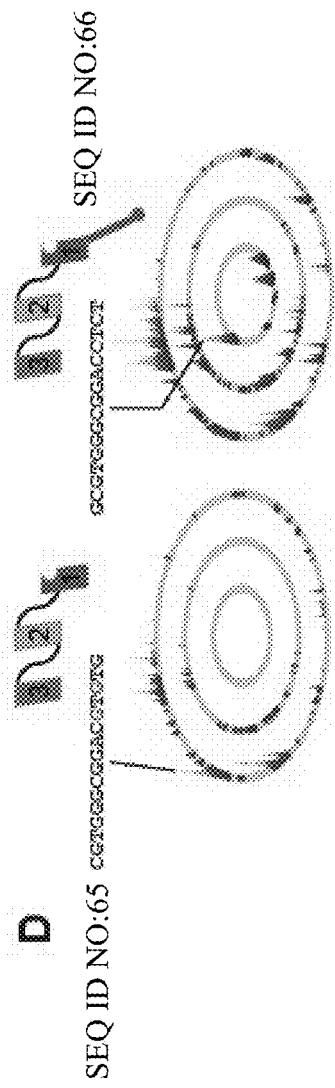
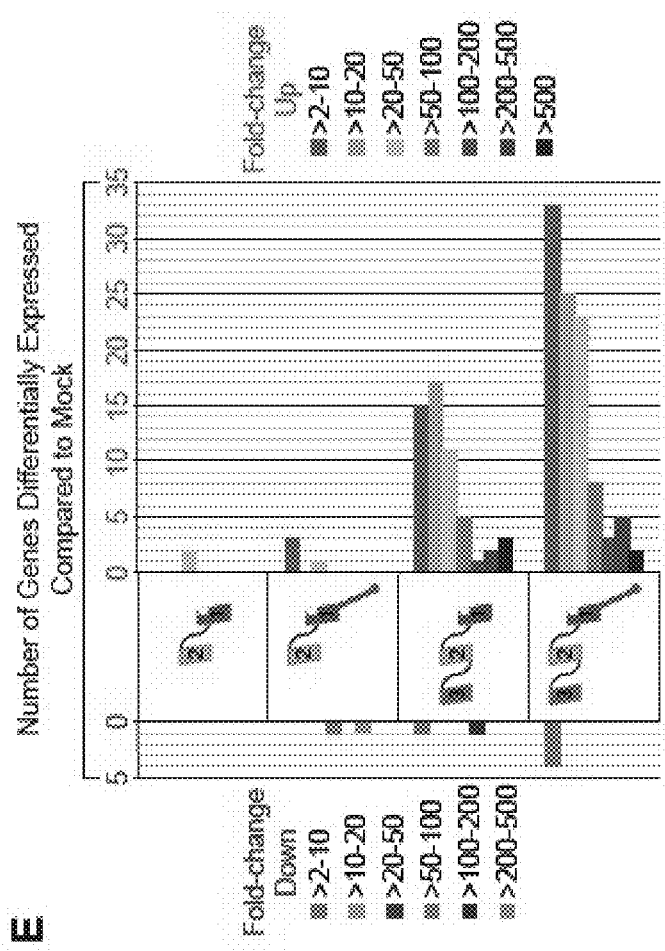

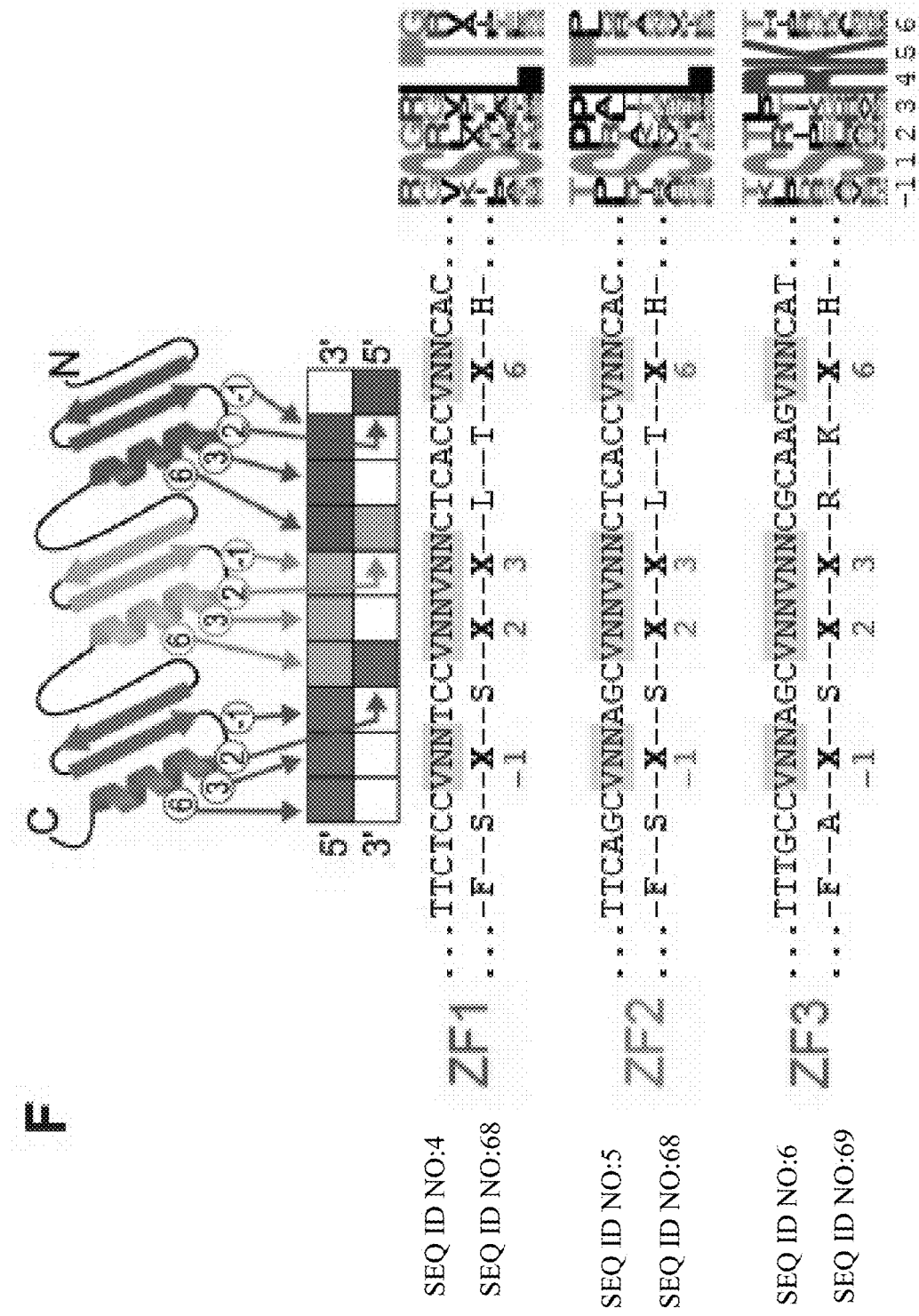
FIGS. 1A-1F, CONTINUED

FIGS. 2A-2E, CONTINUED
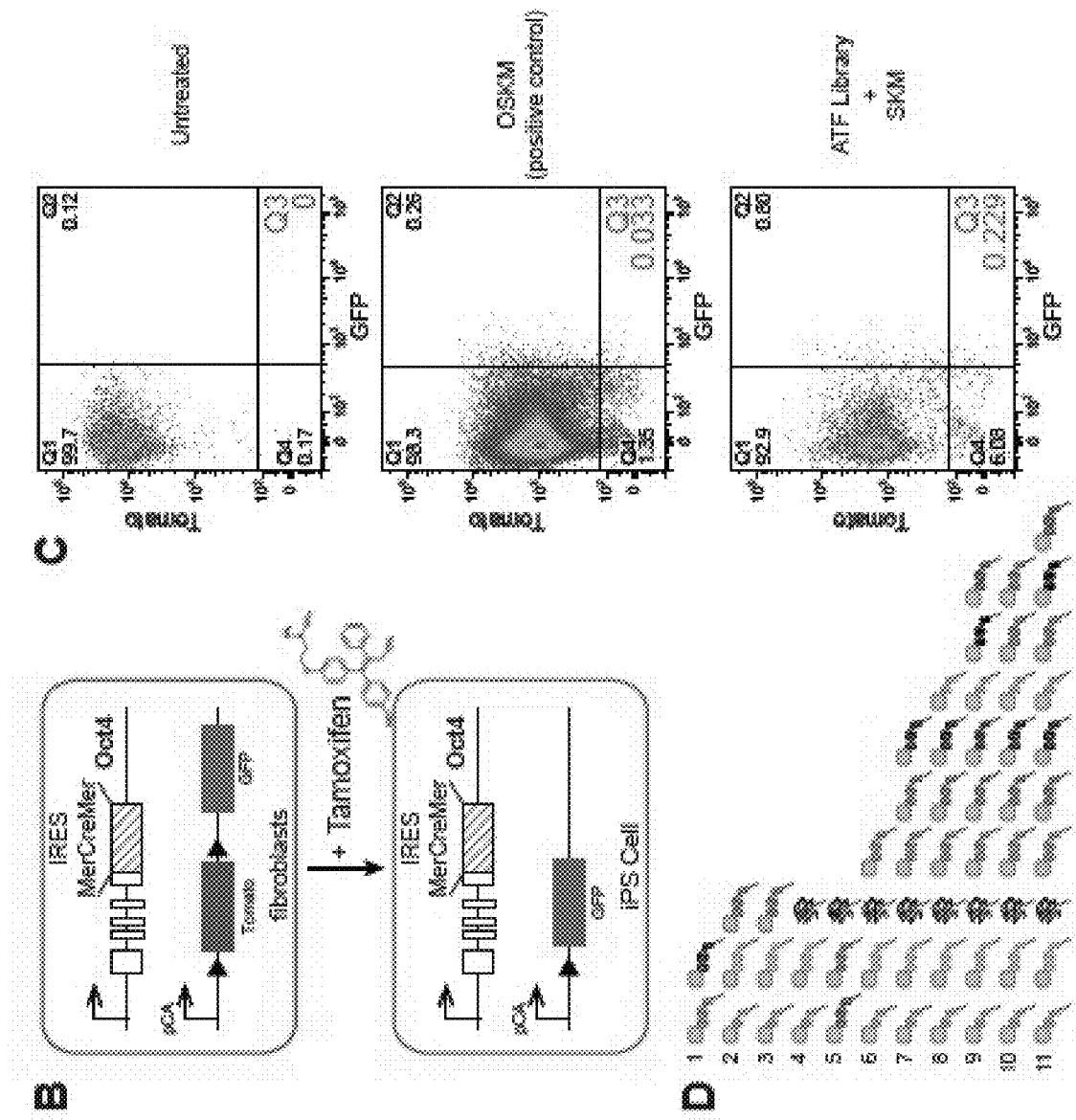

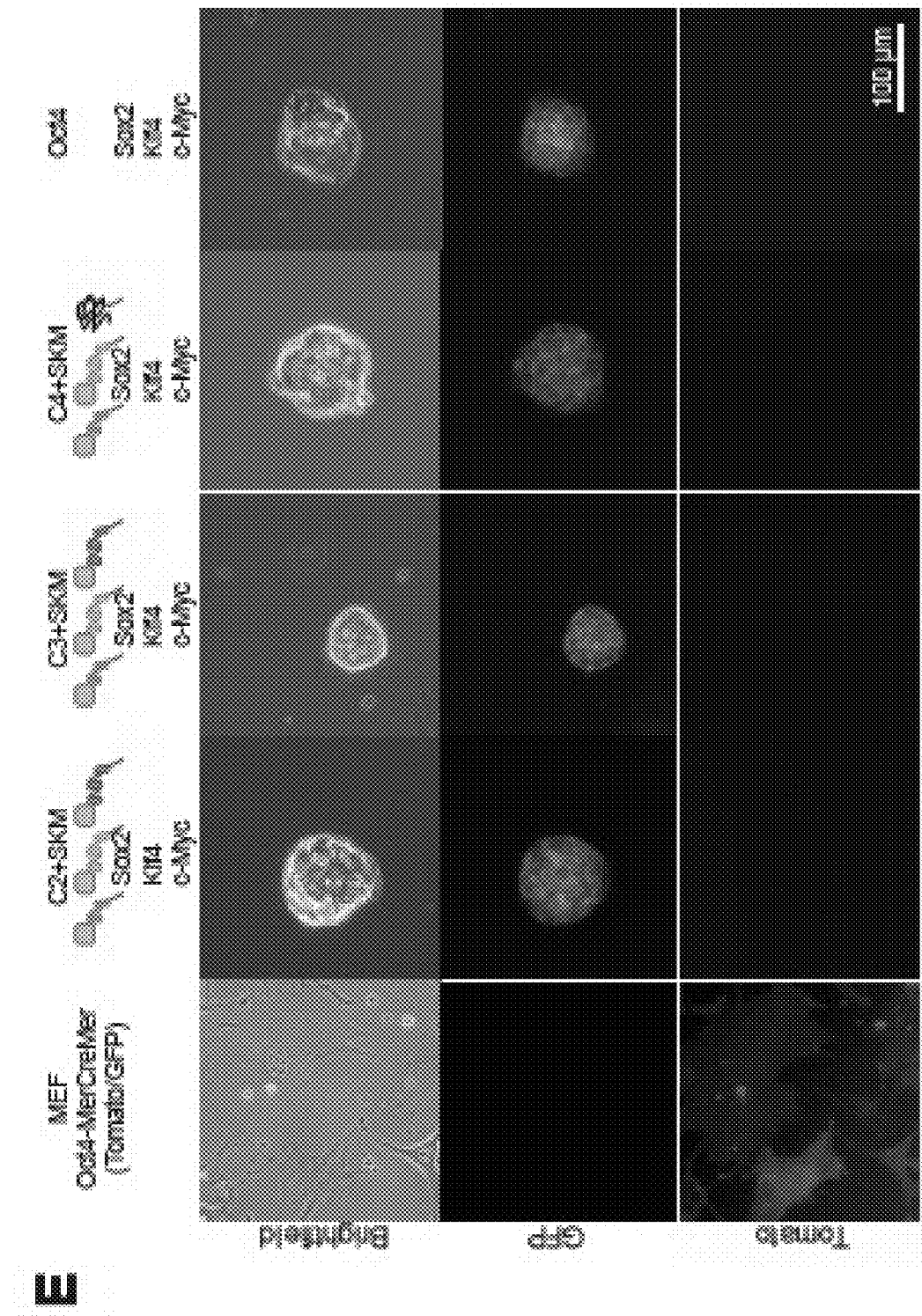
FIGS. 2A-2E, CONTINUED

|  |  | C2+SKM | | |
|---|---|---|---|---|
|  |  | iPS | EB | p-value |
| Mesoderm | T | 1.305 ± 0.334 | 3.818 ± 0.778 | 0.04121 |
| | Nkx2.5 | 1.242 ± 0.252 | 3.567 ± 0.464 | 0.01168 |
| | Kdr | 1.144 ± 0.243 | 5.450 ± 0.931 | 0.01101 |
| Endoderm | Afp | 1.303 ± 0.100 | 11.767 ± 1.698 | 0.00354 |
| | Ttr | 1.102 ± 0.292 | 13.346 ± 1.014 | 0.00032 |
| | FoxA2 | 1.403 ± 0.127 | 7.243 ± 0.347 | 0.00009 |
| Ectoderm | Nes | 1.215 ± 0.143 | 2.664 ± 0.238 | 0.00642 |
| | Nefl | 1.173 ± 0.094 | 2.571 ± 0.544 | 0.06447 |
| | Sox17 | 1.017 ± 0.033 | 6.989 ± 0.507 | 0.00030 |

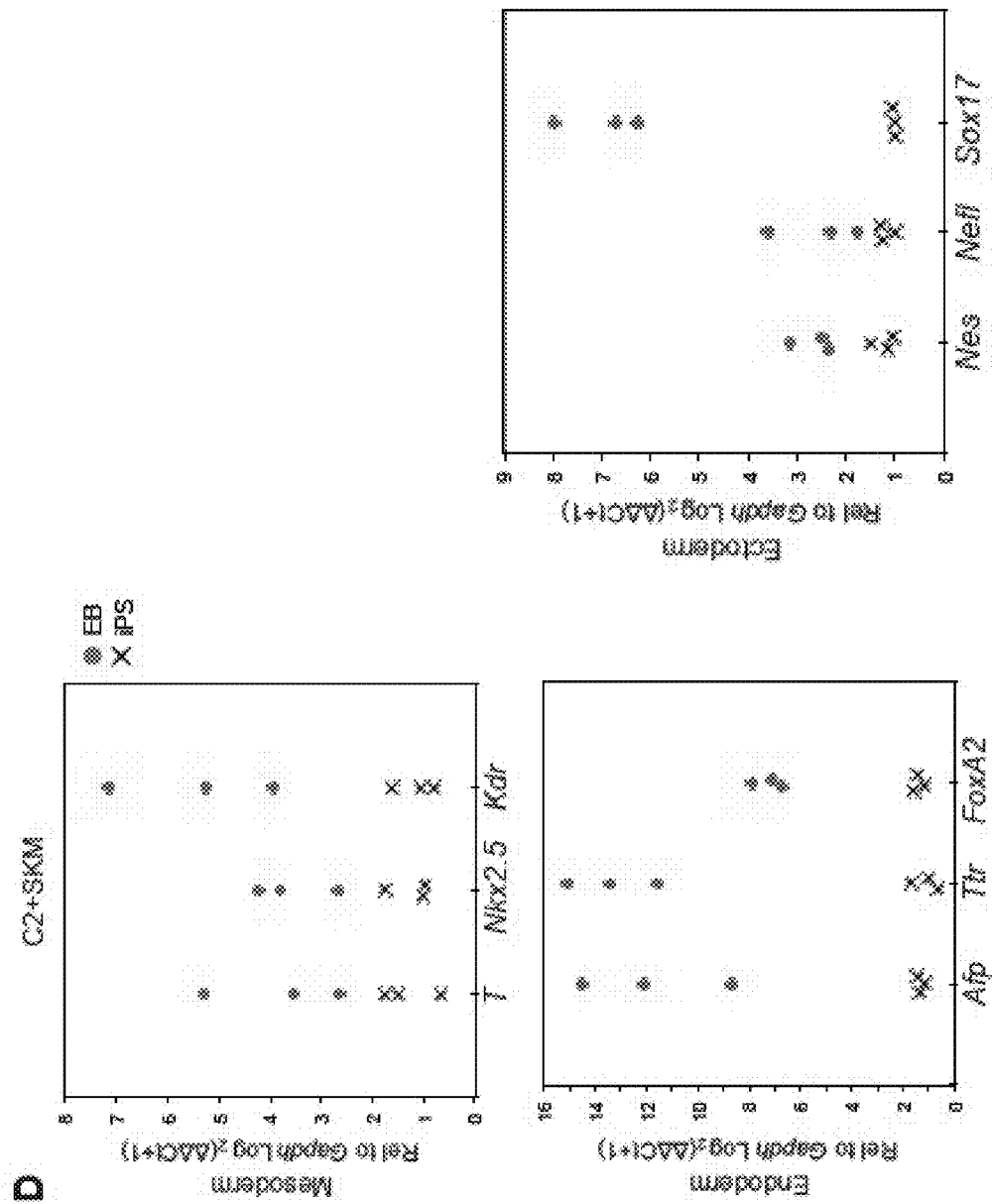
FIGS. 3A-3D, CONTINUED

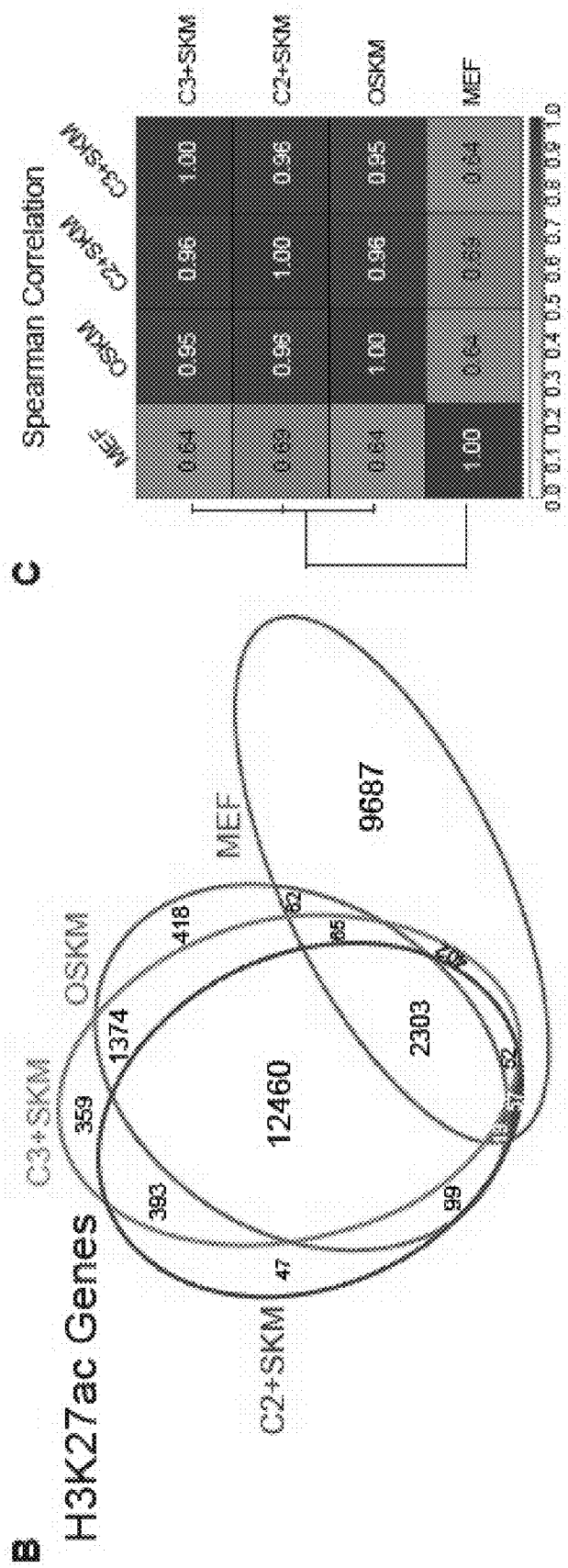
FIGS. 5A-5C, CONTINUED

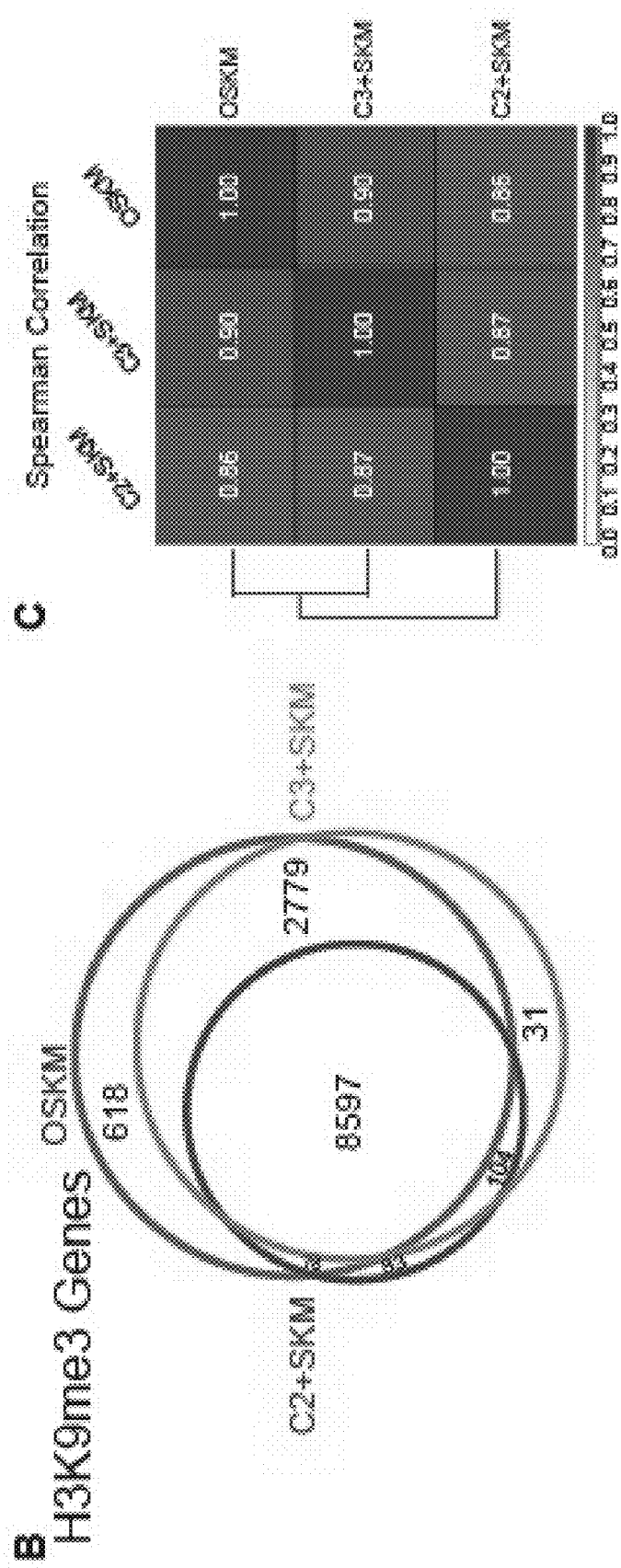
FIGS. 6A-6C, CONTINUED

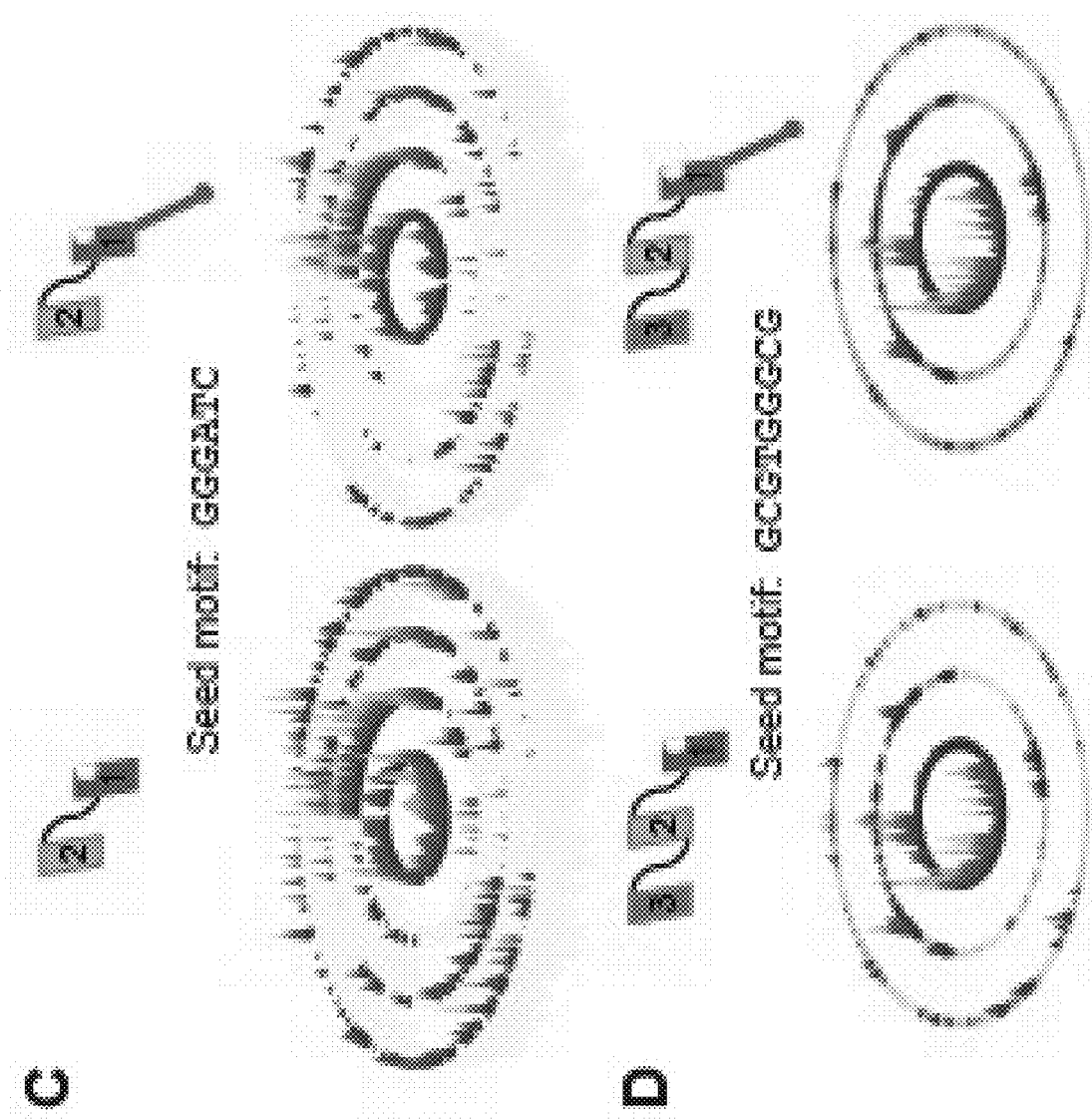
FIGS. 8A-8F, CONTINUED

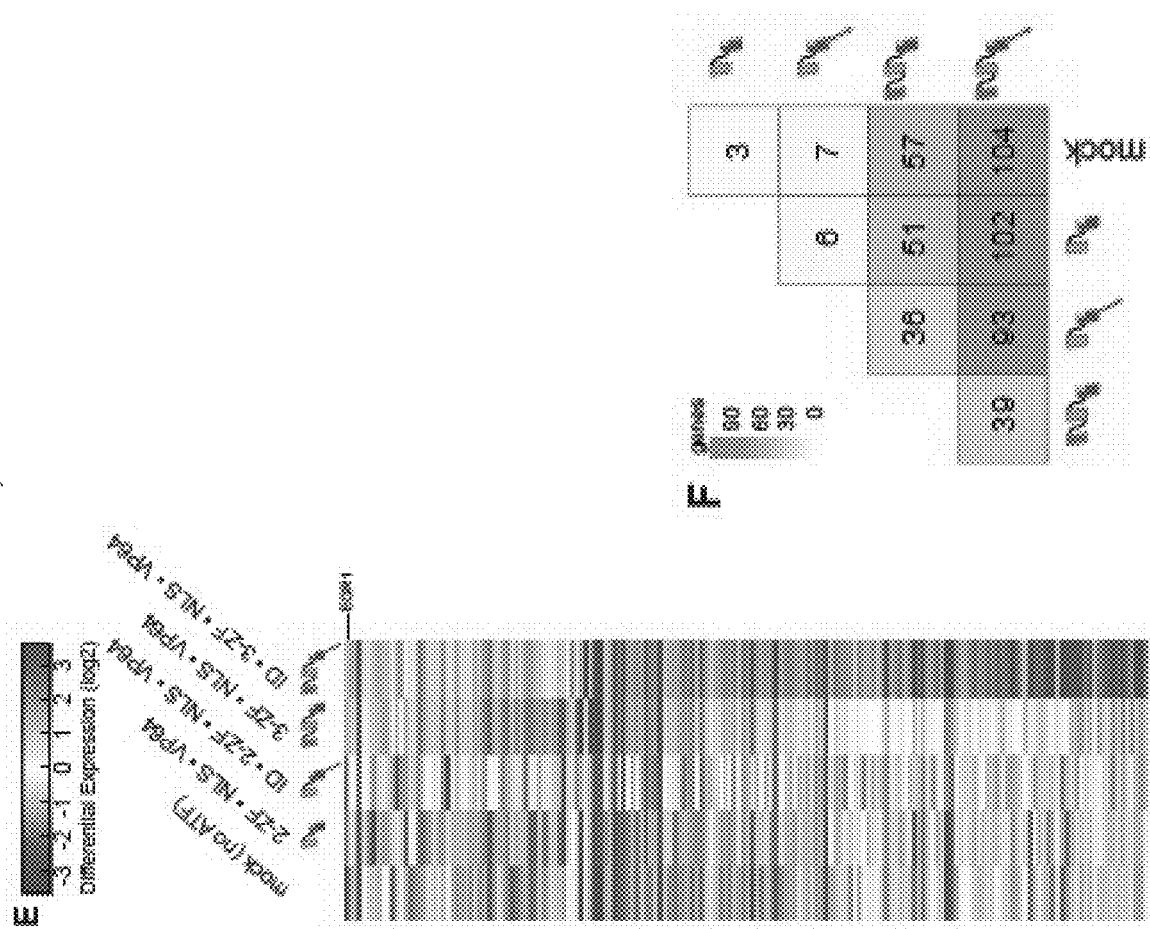
FIGS. 8A-8F, CONTINUED

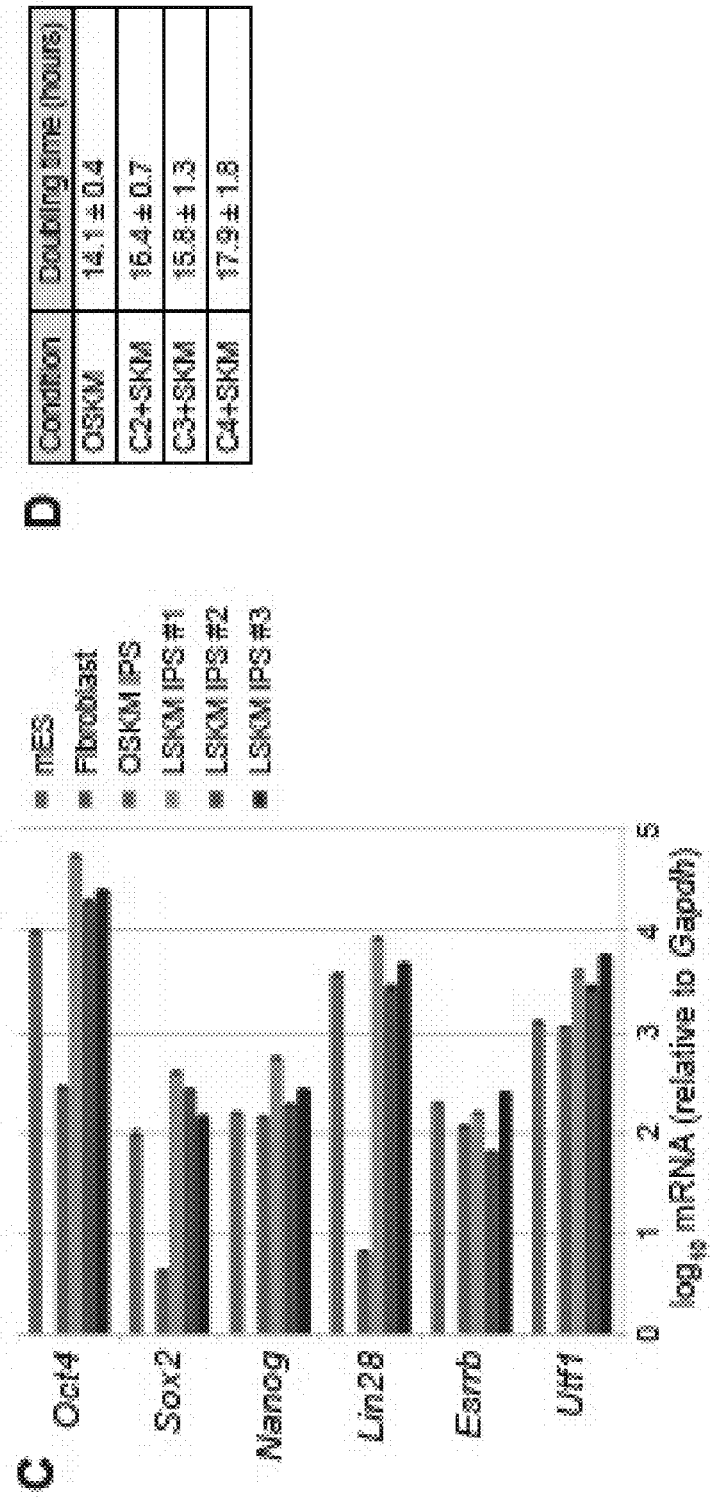
FIGS. 9A-9D, CONTINUED

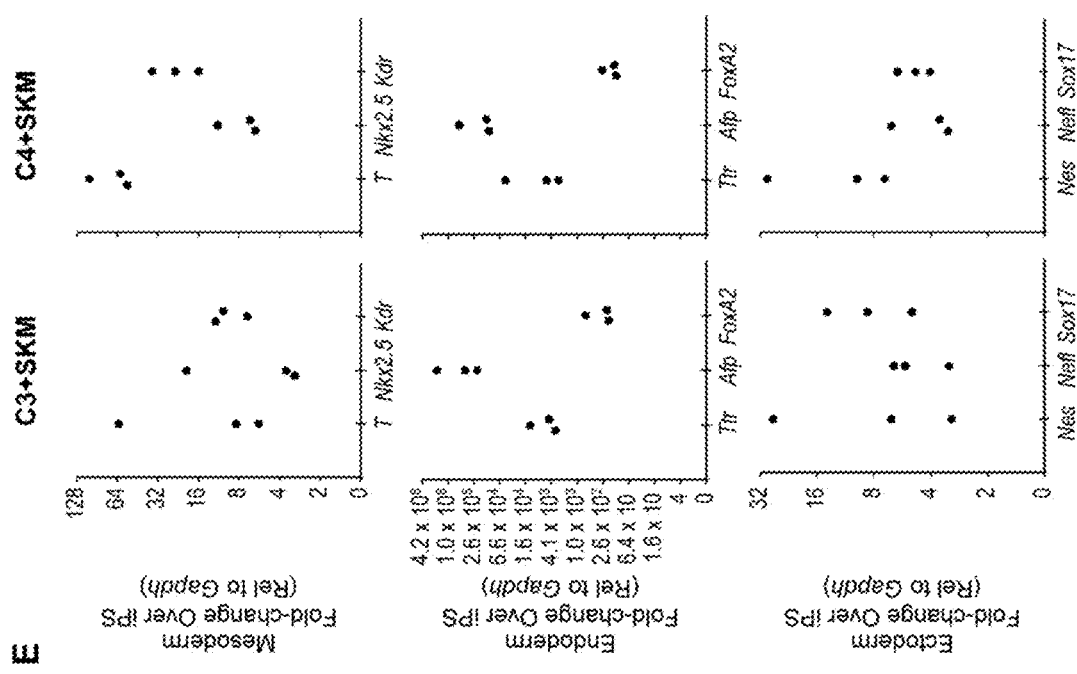
FIGS. 10A-10E, CONTINUED

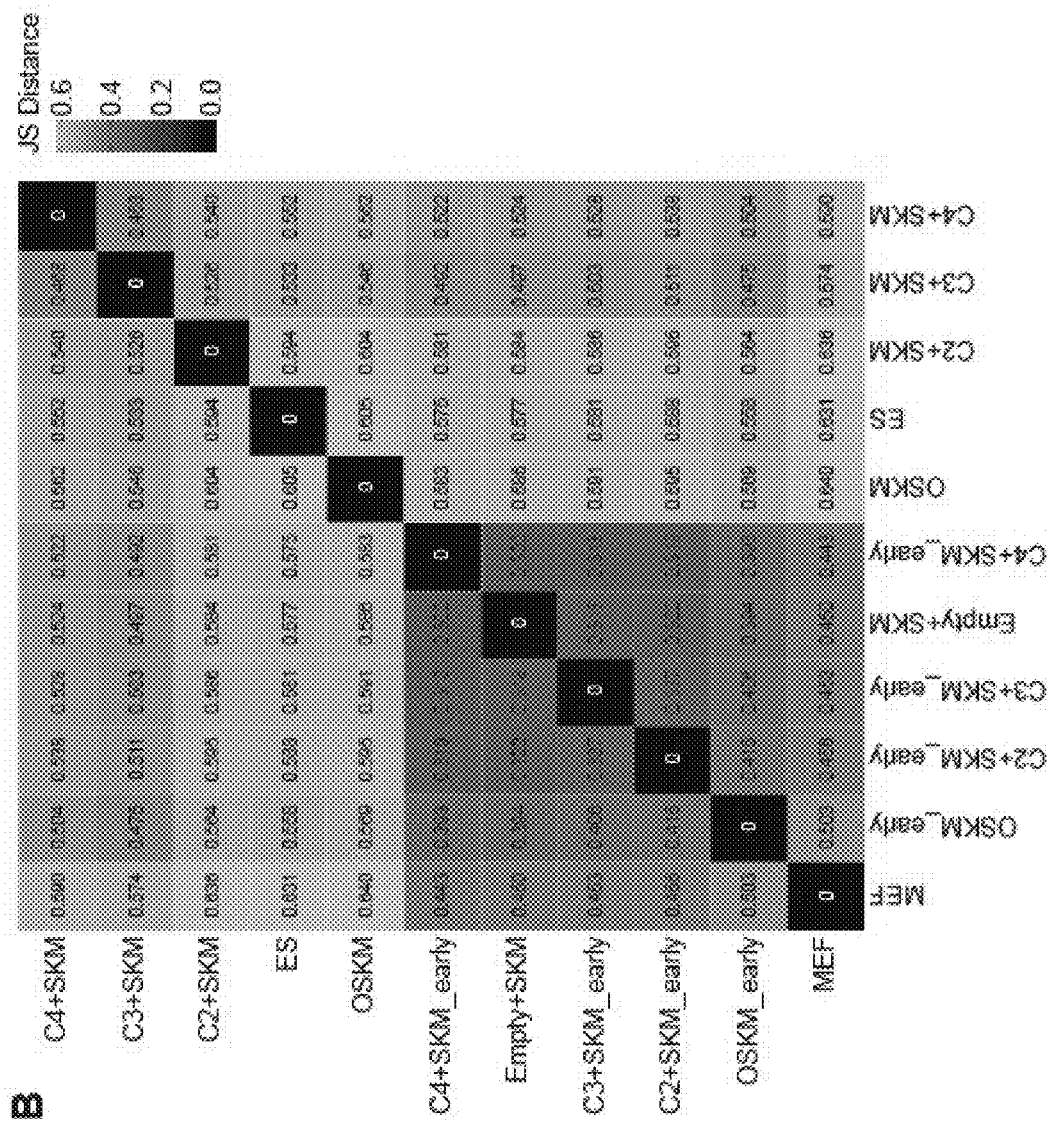
FIGS. 11A-11C, CONTINUED

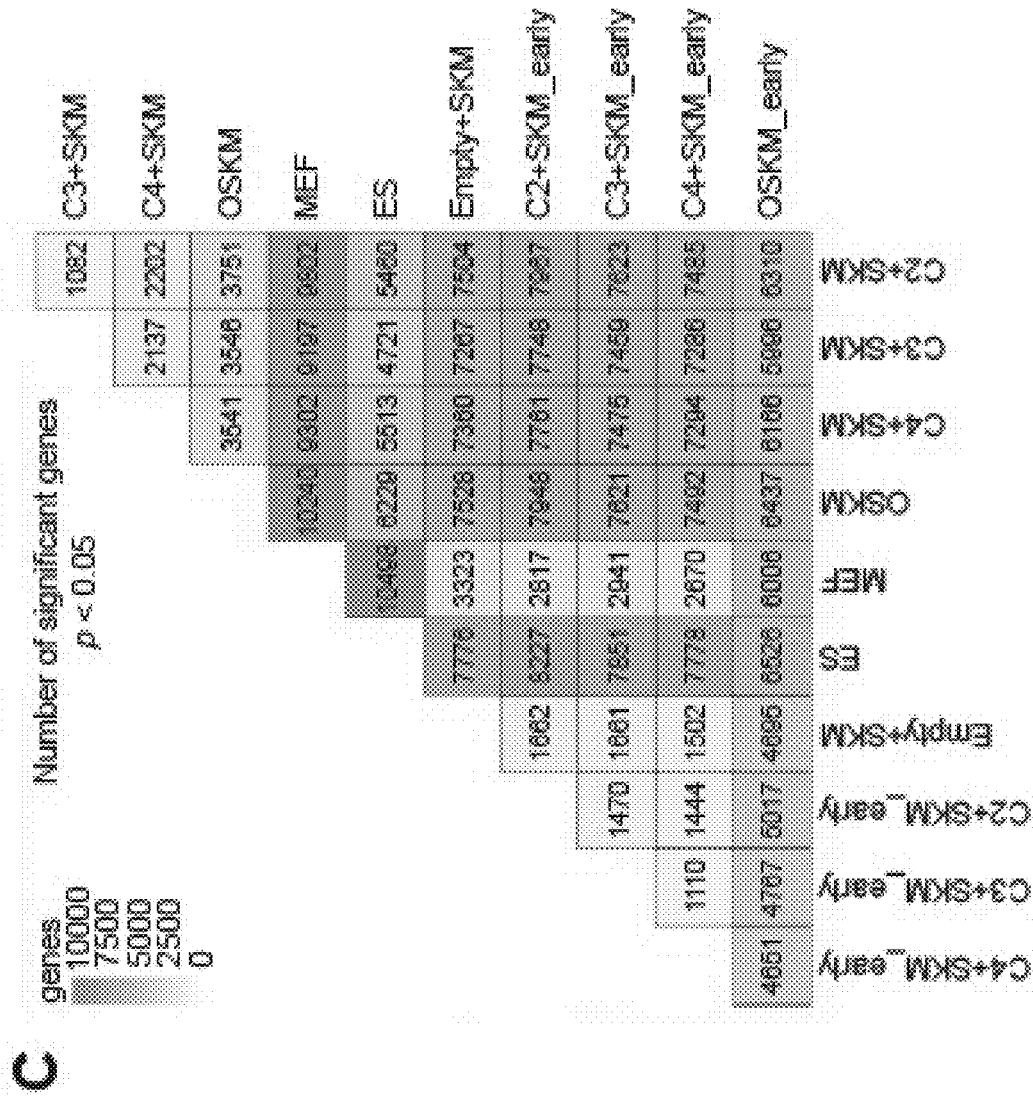
FIGS. 11A-11C, CONTINUED

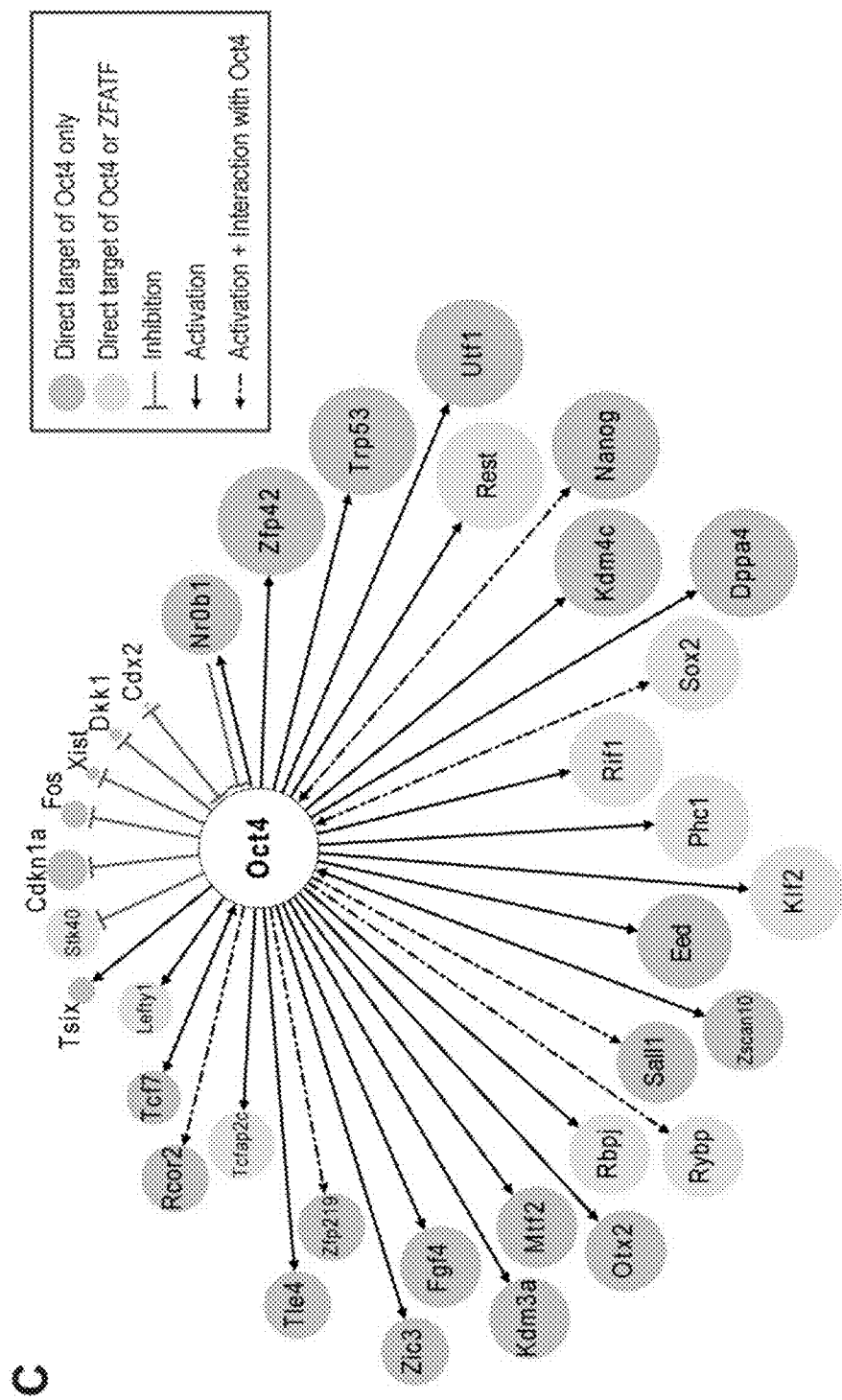
FIGS. 15A-15C, CONTINUED

FIGS. 19A-19D, Continued
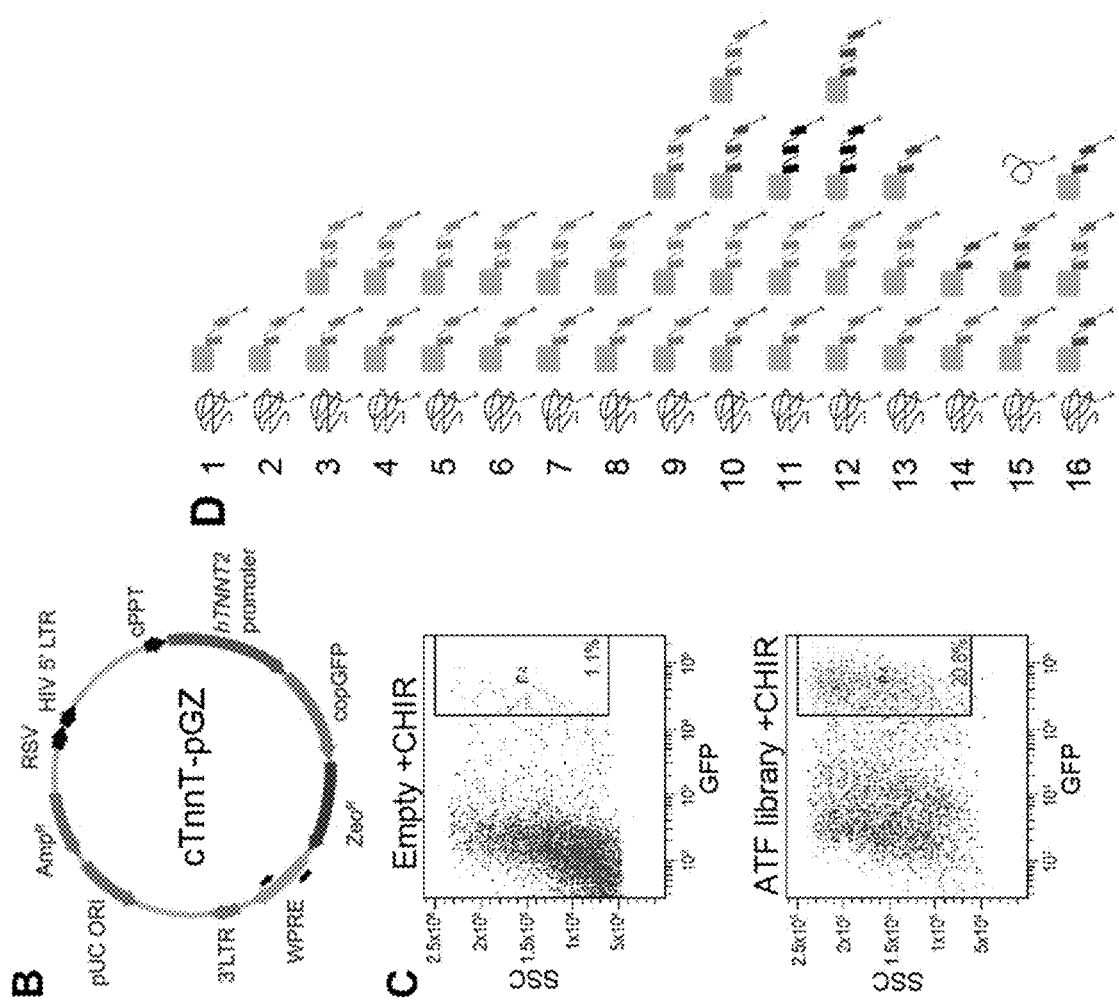

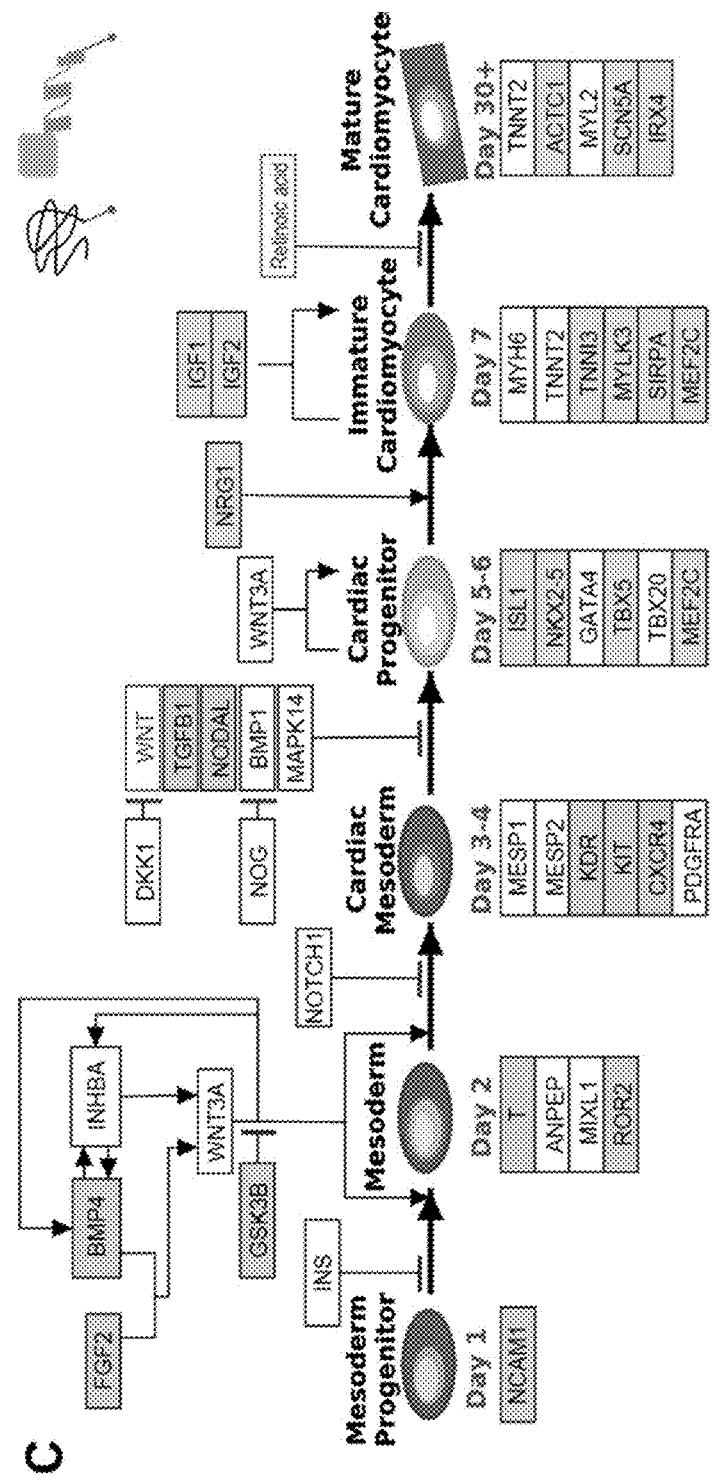
FIG. 22A-22C, Continued

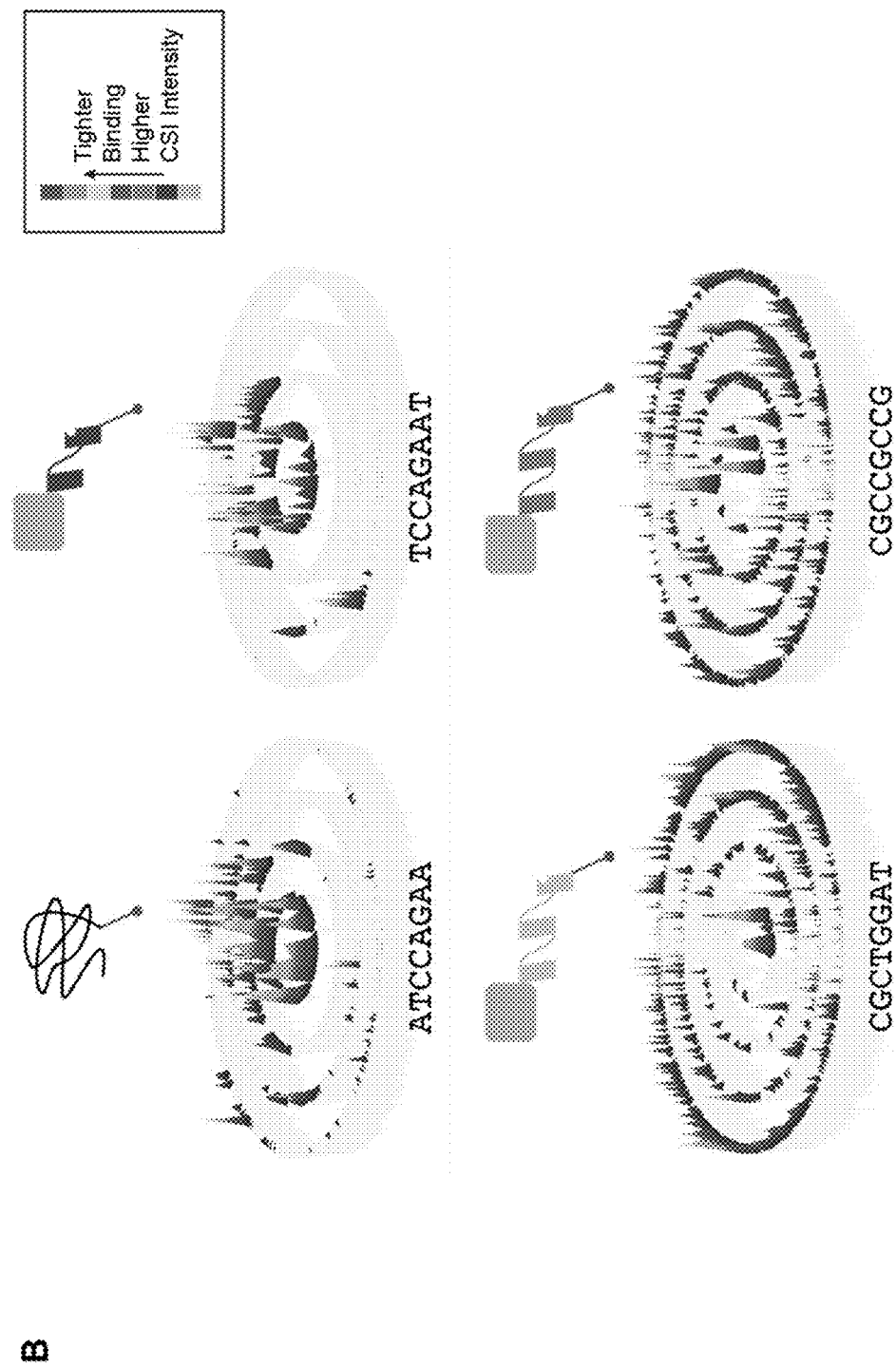
FIG. 25A-25B, Continued

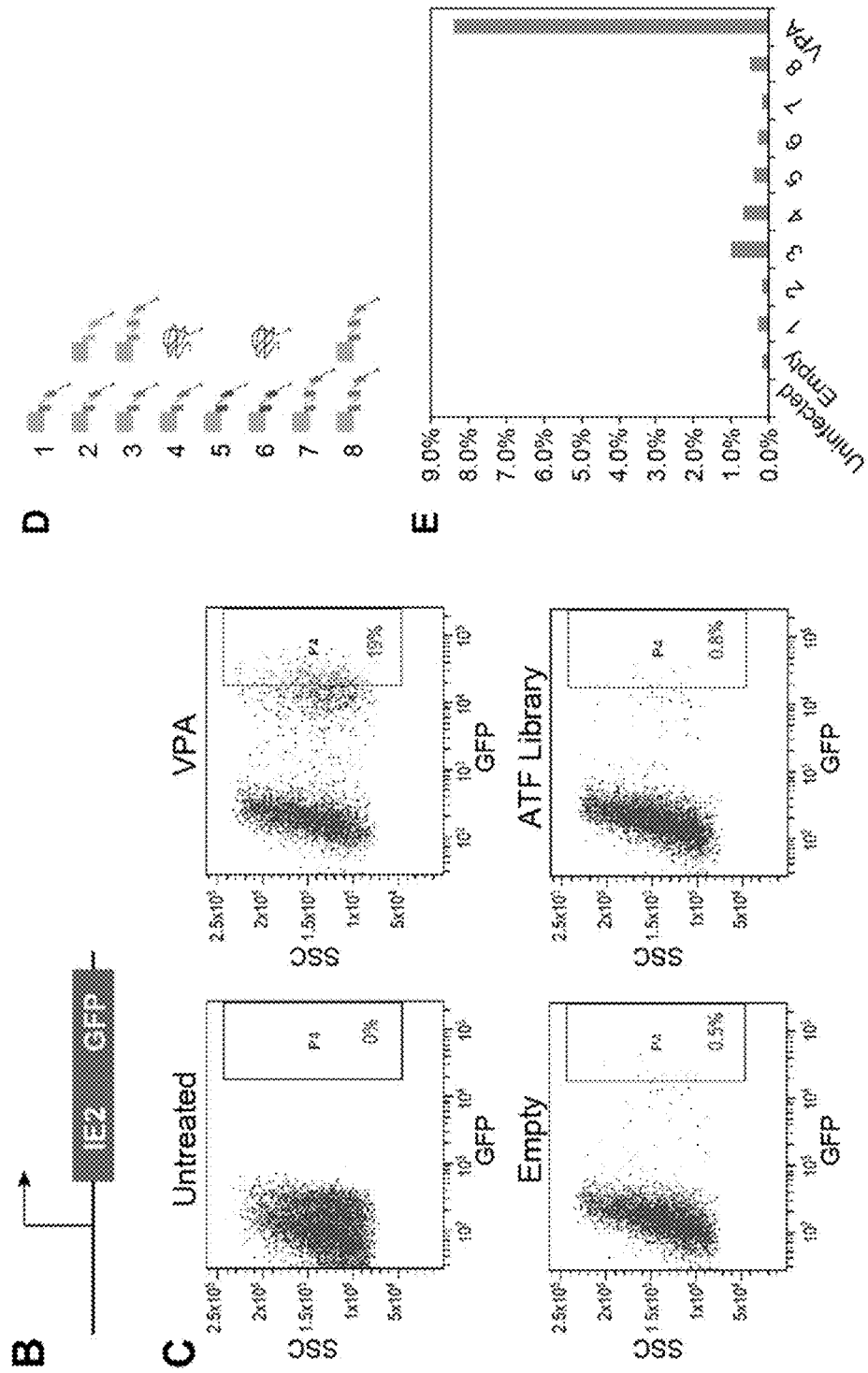
FIGS. 27A-27E, Continued

ARTIFICIAL TRANSCRIPTION FACTORS AND USES THEREOF

CROSS-REFERENCE TO RELATED APPLICATIONS

This application claims the benefit of U.S. Provisional Application No. 62/425,374, filed Nov. 22, 2016, which is incorporated herein by reference as if set forth in its entirety.

SEQUENCE LISTING

The instant application contains a Sequence Listing which has been submitted in ASCII format via EFS-Web and is hereby incorporated by reference in its entirety. The ASCII copy, created on Sep. 8, 2021, is named Sequence_Listing.txt and is 102,400 bytes in size.

STATEMENT REGARDING FEDERALLY SPONSORED RESEARCH OR DEVELOPMENT

This invention was made with government support under HL099773 awarded by the National Institutes of Health. The government has certain rights in the invention.

BACKGROUND

Artificial transcription factors (ATFs) are DNA-binding molecules designed to control gene expression in a pre-determined manner. Rather than taking the conventional approach of testing candidate factors curated from studying embryonic development or differential expression analysis, screening a gene-activating ATF library can be a highly effective and orthogonal approach to sample thousands of sites in parallel and activate a cell fate-defining transcriptional network. An ATF library can sample concurrently the level of activation for thousands of sites because each ATF has different affinity and accessibility to DNA. Because ATFs do not rely on endogenously expressed co-factors and are not restrained to feedback circuits like natural factors, they can serve as powerful agents to perturb the homeostatic state of any cell type. The target genes of the ATFs can then be used to understand the mechanism of action driving the phenotypic change or cell fate conversion.

Transcription factors are modular by nature, and each domain can be tailored to create ATFs for programmed regulation of genes and networks (Eguchi et al., *Biochemical Journal* 462(3):397-413 (2014)). The DNA-binding domain (DBD) confers sequence specificity in targeting genomic loci. The effector domain provides the ATF with function, be it transcriptional activation, repression, or modification of chromatin. Additionally, an interaction domain can be incorporated in the design such that the ATF can interact with other factors in the cell (Id.).

Among the many DBDs available to design an ATF (e.g., CRISPR/Cas9, TAL-effectors, and polyamides), zinc fingers have high affinity to DNA and can be potent regulators of transcription when fused to the appropriate effector domain. Compared to zinc fingers and TAL-effectors that can upregulate genes to biologically-relevant levels (Bailus et al., 2016; Gao et al., 2013; Rebar et al., 2002), the magnitude of transcriptional change induced by nuclease-dead CRISPR/Cas9 systems with a single guide is not as robust (Esvelt et al., 2013). Recent modifications to the CRISPR/Cas9 system have improved their impact on the level of expression of target genes; however, these modifications come at the expense of increasing their size (Chavez et al., 2015) or introducing additional effector molecules that can be recruited by Cas9 (Gilbert et al., 2014; Tanenbaum et al., 2014) or the guide RNA (Konermann et al., 2015; Zalatan et al., 2015). Unlike zinc fingers and TAL-effectors, the CRISPR/Cas9 system also requires at least two components, Cas9 and the guide, to be delivered to the same cell. Polyamides, a class of small molecule DBDs, are not genetically encoded; rather, they are added to the media and rely on cell uptake. However, the rules governing polyamide permeability are still not well understood, making delivery to cells problematic (Edelson et al., 2004).

Accordingly, there remains a need in the art for improved artificial transcription factors and efficient protocols for generating pluripotent stem cells and differentiated cell types under controlled conditions.

BRIEF SUMMARY

In a first aspect, provided herein is an artificial transcription factor comprising a polydactyl zinc finger protein comprising two or three zinc finger domains, an interaction domain, an optional nuclear localization signal, and an activation domain, where each of the two or three zinc finger domains comprises a variable domain independently encoded by nucleic acid sequence of SEQ ID NO:2 (VNN-TCC-VNN-VNN-CTC-ACC-VNN), where each VNN of SEQ ID NO:2 is a codon corresponding to an amino acid selected from the group consisting of R, H, K, D, Q, S, T, N, E, G, P, A, I, L, M, and V. The polydactyl zinc finger protein can comprise three zinc finger domains encoded by SEQ ID NO:4, SEQ ID NO:5, and SEQ ID NO:6, where each VNN of SEQ ID NOS:4, 5, and 6 is a codon corresponding to an amino acid selected from the group consisting of R, H, K, D, Q, S, T, N, E, G, P, A, I, L, M, and V. The interaction domain can comprise a 15-amino acid peptide that enables interaction with the hydrophobic face of the most 5' zinc finger domain. The activation domain can comprise four tandem repeats of DALDDFDLDML (SEQ ID NO:7). The nuclear localization signal can be encoded by an amino acid sequence selected from the group consisting of KDKKAD-KSVV (SEQ ID NO: 11) and PKKKRKV (SEQ ID NO:12).

In another aspect, provided herein is a method of reprogramming a somatic cell to pluripotency, wherein the method comprises (a) exposing a somatic cell to a plurality of artificial transcription factors, wherein the artificial transcription factors are selected from the group consisting of ZFATF1, ZFATF2, ZFATF3, ZFATF4, and ZFATF5; (b) further exposing the somatic cell to a plurality of potency determining factors comprising Sox2, Klf4, and c-Myc; and (c) culturing the exposed cells to obtain reprogrammed cells having a higher potency level than the somatic cell. The plurality of ATFs can comprise ZFATF1, ZFATF2, and ZFATF5. The plurality of ATFs can comprise ZFATF1, ZFATF2, and ZFATF4. The plurality of ATFs can comprise ZFATF1, ZFATF2, and ZFATF3. The plurality of ATFs can comprise ZFATF1 and ZFATF4.

In another aspect, provided herein is a method of directing differentiation of a pluripotent stem cell to a cardiomyocyte. The method can comprise or consist essentially of (a) exposing a pluripotent stem cell to one or more artificial transcription factors (ATFs) selected from the group consisting of ZFATF1, ZFATF2, and ATF5; and (b) culturing the exposed cells of (a) in the presence of a Wnt activator for about 7-10 days, such that a population of cells comprising cardiomyocytes is obtained. The ATFs can comprise ZFATF1, ZFATF2, and ATF5. The Wnt activator can be a GSK3 inhibitor. The GSK3 inhibitor can be CHIR99021.

In a further aspect, provided herein is a method of directing differentiation of a pluripotent stem cell to a hematopoietic lineage. The method can comprise or consist essentially of (a) exposing a pluripotent stem cell to two or more artificial transcription factors (ATFs) selected from the group consisting of ZFATF19, ZFATF20, ZFATF21, ATF5, ZFATF1, ZFATF6, ZFATF10, ZFATF13, ZFATF17, ZFATF22, ZFATF23, ZFATF24, ZFATF25, ZFATF26, ZFATF27, ZFATF28, ZFATF29, ZFATF30, and ZFATF31; and (b) culturing the exposed cells of (a) in a basal culture medium comprising FGF2, SCF, and thrombopoietin, and in the presence of TAL for about 7-10 days, such that a cell population comprising hematopoietic lineage cells is obtained. The ATFs can comprise ZFATF19, ZFATF20, ZFATF21, and ATF5, and wherein the cell population comprises erythroid-like cells. The ATFs can comprise ZFATF1, ZFATF6, ZFATF10, ZFATF13, ZFATF17, ZFATF22, ZFATF23, ZFATF24, ZFATF25, ZFATF26, ZFATF27, ZFATF28, ZFATF29, ZFATF30, and ZFATF31, and wherein the cell population comprises monocyte-like cells.

In a further aspect, provided herein is a method for preparing a zinc finger-based artificial transcription factor (ATF) library comprising a plurality of elements, whereby each element of said ATF library comprises a zinc finger backbone comprising two or three oligonucleotides, each encoding SEQ ID NO:3 ($X_{-1}$-S-$X_2$-$X_3$-L-T-$X_6$), an interaction domain, an optional nuclear localization signal, and an activation domain, wherein $X_{-1}$ is an amino acid preferably selected from the group consisting of R, H, K, D, Q, S, T, N, E, G, P, A, I, L, M, and V; $X_2$ is preferably selected from the group consisting of R, H, K, D, Q, S, T, N, E, G, P, A, I, L, M, and V; $X_3$ is preferably selected from the group consisting of R, H, K, D, Q, S, T, N, E, G, P, A, I, L, M, and V; and $X_6$ is preferably selected from the group consisting of R, H, K, D, Q, S, T, N, E, G, P, A, I, L, M, and V. The ATF library can have a complexity of about $2.62 \times 10^6$. The interaction domain can comprise a 15-amino acid peptide that enables interaction with the hydrophobic face of the most 5' zinc finger domain. The activation domain can comprise four tandem repeats of DALDDFDLDML (SEQ ID NO:7). The nuclear localization signal can be encoded by an amino acid sequence selected from the group consisting of KDKKAD-KSVV (SEQ ID NO:11) and PKKKRKV (SEQ ID NO:12).

"ZFATF5" and "ATF5" are used interchangeably herein.

In a further aspect, provided herein is a zinc finger-based artificial transcription factor (ATF) library obtained according to methods provided herein.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects, and advantages other than those set forth above will become apparent when consideration is given to the following detailed description which makes reference to the following drawings, wherein:

FIG. 14 presents twelve exemplary ATFs and their respective DNA sequences.

Samples 1 and 2 are erythroid-like cells expanded on methylcellulose. Samples 3-5 are monocyte-like cells expanded on methylcellulose. Samples 2 and 4 were sequenced as cell clusters for ATF identification. Sample 2 was comprised of 4 ATFs; sample 4 was comprised of 15 ATFs.

Figure 24:
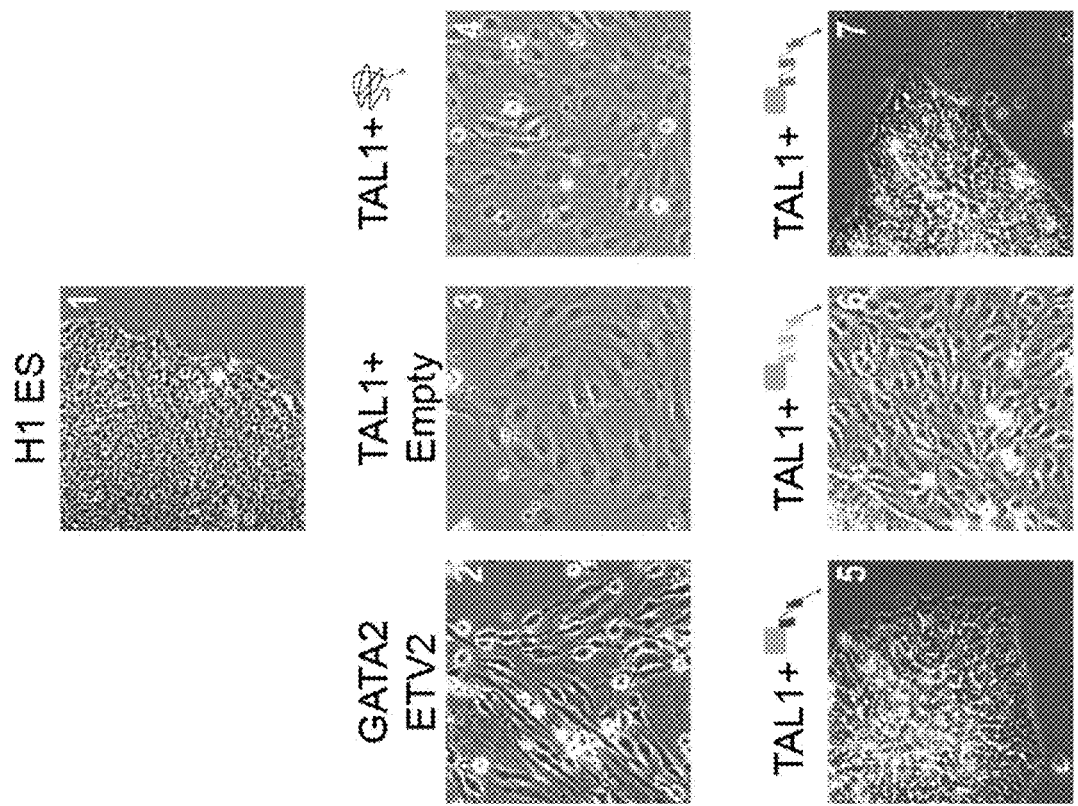

FIG. 24 presents images validating ATFs from erythroid-like cluster. The parent cell type was human H1 ES cells. GATA2+ETV2 served as positive control for the myeloid lineage. TAL1+Empty control and TAL1+ATF5 (ATF with a frameshift mutation) induced differentiation but not to the same cell type as GATA2+ETV2. Differentiated cells after treatment with TAL1+ZFATF20 (middle image, last row) have a phenotype similar to myeloid cells. Cells treated with TAL1+ZFATF19 and TAL+ZFATF21 did not differentiate.

Figures 25A, 25B:
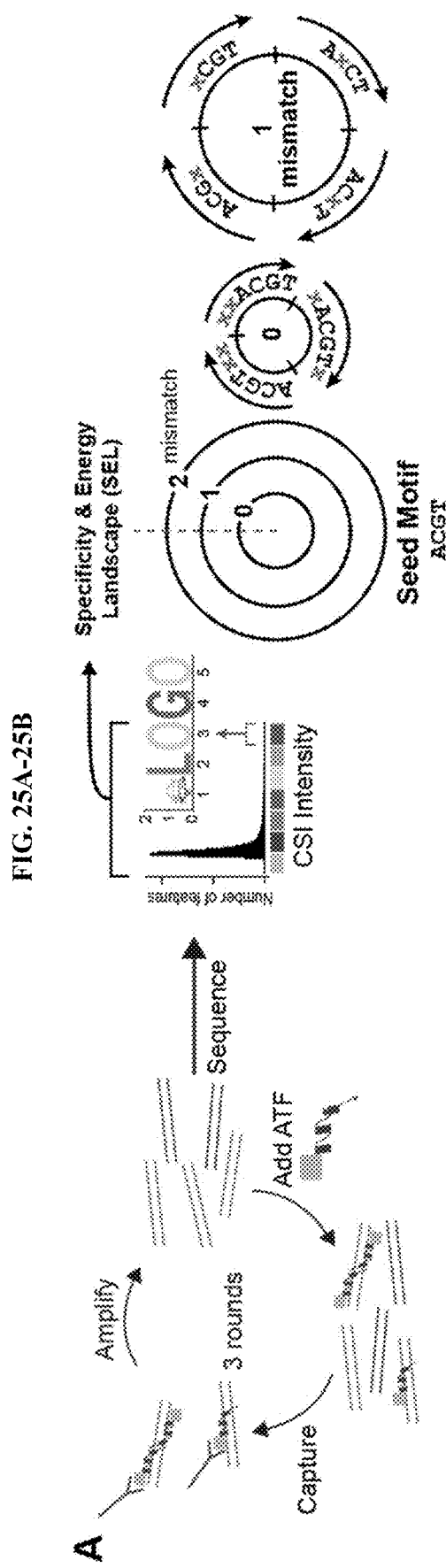

FIGS. 25A-25B demonstrate identification of ATF binding sites for hematopoiesis. (A) Cognate site identification (CSI). This method of determining the sequence specificity of DNA-binding factors involves incubating the ATF with randomized permutations of 25-bp sequences. The ATF-DNA complexes are captured with an antibody, and bound DNA is PCR-amplified for the next round of selection. Three rounds of selection are performed, and all three rounds are multiplexed and sequenced to obtain Specificity and Energy Landscapes (SELs) and position weight matrices (PWMs). SELs display the comprehensive binding preferences based on a chosen seed motif. The height of the peak is associated with affinity. Sequences that are 1-2 bp longer than the seed are arranged in concentric rings with respect to mismatches. Each ring outward from the 0-mismatch ring displays sequences to the corresponding number of mismatches. Within the mismatch rings, sequences are arranged by position of the mismatch, then alphabetically. (B) SELs of the four ATFs from the combination that induced differentiation into erythroid-like cells. Each SEL displayed shows data after three rounds of enrichment.

Figures 26A, 26B:
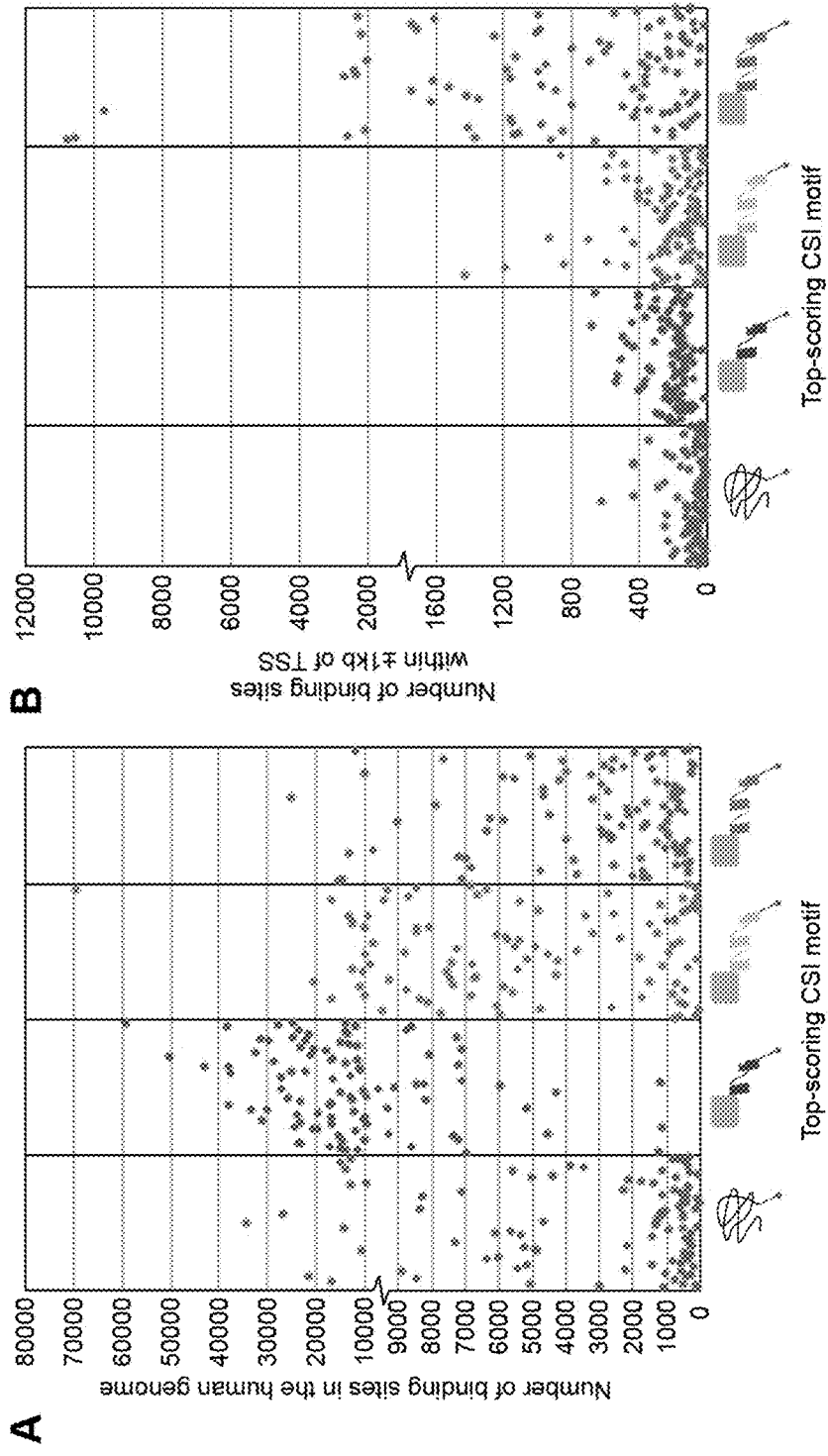

FIGS. 26A-26B represent erythroblast ATF sequences in the human genome. (A) The number of times the top 100 scoring CSI motifs appeared in the genome was quantified. Each data point represents a unique 10-bp sequence. (B) The number of times the top 100 scoring CSI motifs appeared within ±1 kb of a TSS was quantified. Each data point represents a unique 10-bp sequence. The observed frequencies near the TSS are different from the expected frequencies ($p<0.001$ for df-3 and chi-squared=14,195).

FIGS. 27A-27E illustrate use of the ATF library in HCMV gene expression. (A) Genetic screen with an ATF library. ATFs are comprised of an interaction domain, 3-zinc fingers, nuclear localization signal, VP64 activation domain, and 3×HA tag. The library has a complexity of $2.6 \times 10^6$ ATFs, each of which can target a 9-bp sequence. (1) The ATF library was cloned into a second generation lentiviral vector. The screen is performed in cells with a robust change in phenotype or a lineage-specific reporter. (2) Positive outcomes are isolated as single cells, such that combinations of ATFs, if any, can be captured. (3) Integrated ATFs are identified from single cells. (4) Identified ATFs are retested for validation. Once validated, downstream experiments can be performed to identify ATF target genes. (B) Licensing the activation of HCMV genes. THP-1 monocytes were infected with HCMV (AD169) in which immediate-early gene 2 (IE2) fused to GFP is expressed when the virus enters lytic replication. (C) Flow cytometry results 20 hours post-infection with HCMV. THP-1 monocytes transduced with the ATF library or an Empty control were infected with HCMV encoding IE2-GFP fusion protein. Approximately 0.8% of cells treated with ATFs were $GFP^+$ and 0.5% of the Empty control. THP-1 cells treated with valproic acid for 3 hours prior to HCMV infection served as the positive control (19% $GFP^+$). Untreated THP-1 cells served as negative control (0% $GFP^+$). ATF-treated cells with the greatest level of GFP expression (gate P4), were cell sorted. (D) ATFs were identified from 8 single cells by two-step nested PCR of genomic DNA. Unique ATFs are depicted with a different color. One ATF had a frameshift mutation shortly after the ID, coding for a protein that does not have a zinc finger structure. Three ATFs are made up of two fingers (light blue, pink, and red). (E) Validation of ATF hits by flow cytometry. The percentage of cells expressing IE2-GFP is displayed. Compared to the positive control (VPA), the ATFs do not activate HCMV gene expression in as many cells. The treatment numbers refer to the ATF combinations in (D). All treatments were infected with HCMV except for the first bar, uninfected.

Figures 28A, 28B:
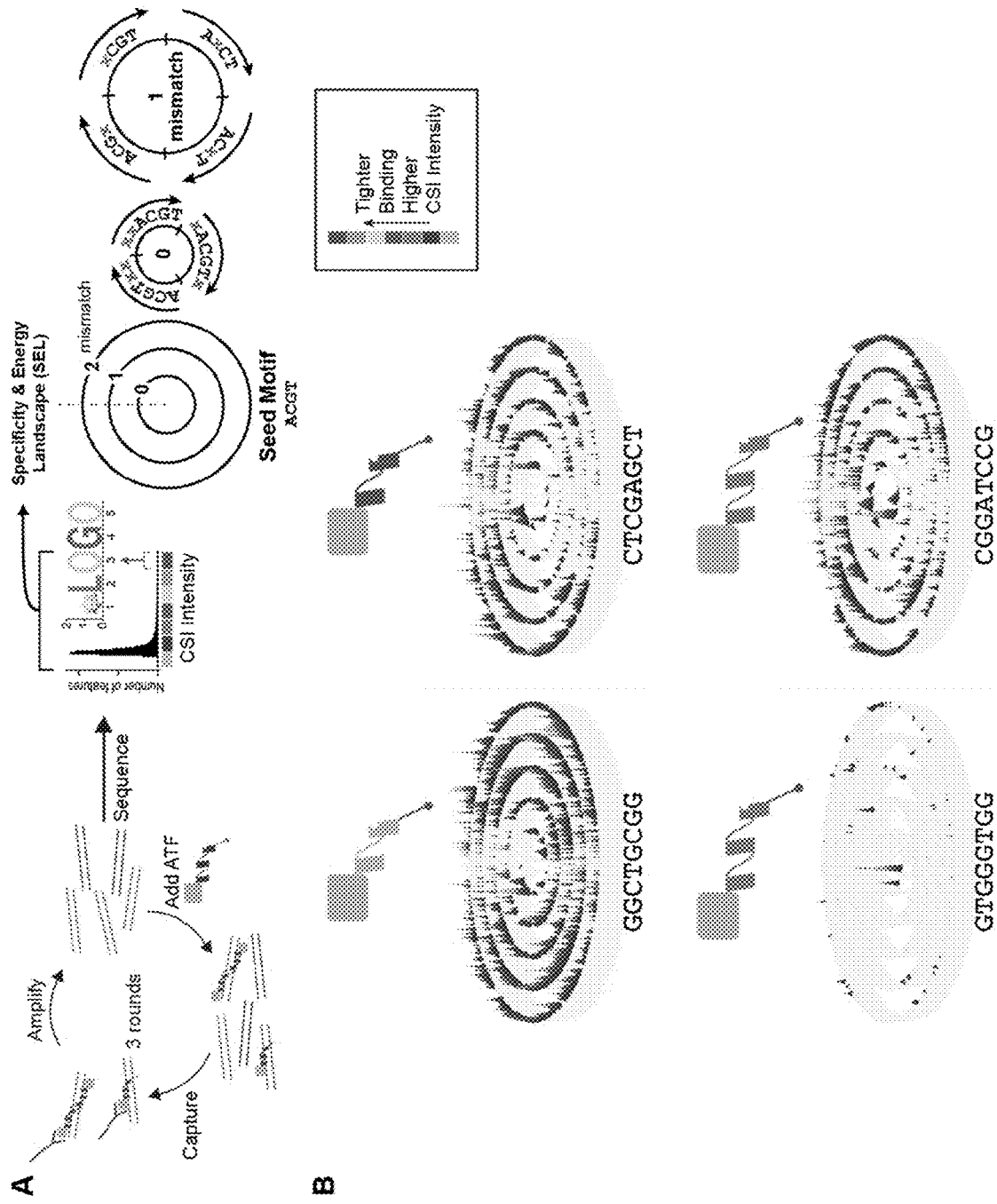

FIGS. 28A-28B demonstrate identification of ATF binding sites for HCMV activation. (A) Cognate site identification (CSI). This method of determining the sequence specificity of DNA-binding factors involves incubating the ATF with randomized permutations of 25-bp sequences. The ATF-DNA complexes are captured with an antibody, and bound DNA is PCR-amplified for the next round of selection. Three rounds of selection are performed, and all three rounds are multiplexed and sequenced to obtain Specificity and Energy Landscapes (SELs) and position weight matrices (PWMs). SELs display the comprehensive binding preferences based on a chosen seed motif. The height of the peak is associated with affinity. Sequences that are 1-2 bp longer than the seed are arranged in concentric rings with respect to mismatches. Each ring outward from the 0-mismatch ring displays sequences to the corresponding number of mismatches. Within the mismatch rings, sequences are arranged by position of the mismatch, then alphabetically. (B) SELs of four ATFs that permit the expression of HCMV genes. Each SEL displayed shows data after three rounds of enrichment.

Figures 29A, 29B:
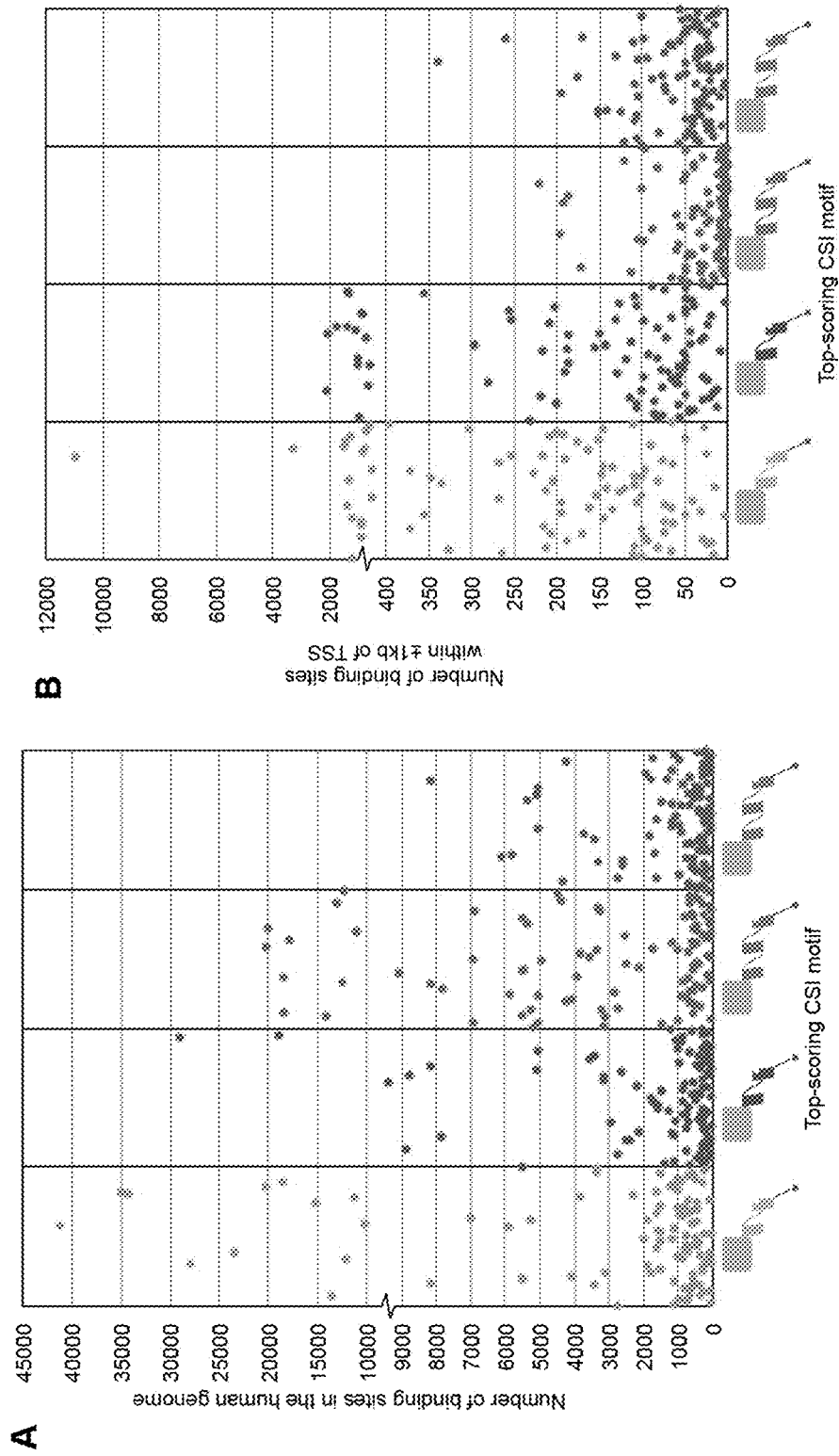

FIGS. 29A-29B represent HCMV ATF sequences in the human genome. (A) The number of times the top 100 scoring CSI motifs appeared in the genome was quantified. Each data point represents a unique 10-bp sequence. (B) The number of times the top 100 scoring CSI motifs appeared within +1 kb of a TSS was quantified. Each data point represents a unique 10-bp sequence. The observed frequencies near the TSS are different from the expected frequencies ($p<0.001$ for df-3 and chi-squared=3,797).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and compositions provided herein are based at least in part on the Inventors' discovery of zinc finger-based artificial transcription factors (ATFs) that have the ability to promote cell fate conversions. These ATFs bind DNA through cooperative assembly and function as transcriptional activators. A combination of three ATFs facilitates the conversion of fibroblasts to induced pluripotent stem cells and the differentiation of stem cells to cardiomyocytes. The capacity of these ATFs to bind regulatory elements in the genome can enable various types of mammalian cell fate conversions, aiding in the generation of relevant cell types for cell therapies, drug screening, and disease modeling. Furthermore, the compositions and methods provided herein enable the targeting of gene-regulatory elements of mammalian systems and the resetting of the transcriptional circuitry.

Advantages of the claimed compositions and materials provided herein are at least three-fold. First, the ATFs of the present invention facilitate cell type conversions without a priori knowledge of potential key regulators, and can thereby reveal new gene networks and mechanistic pathways. The capacity of these ATFs to bind regulatory elements in the genome can enable various types of mammalian cell fate conversions, aiding in the generation of relevant cell types for cell therapies, drug screening, and disease modeling. Second, the three-zinc finger ATFs provided herein are capable of activating many fold over background. Some of these three-zinc finger ATFs activate expression 329-fold over background levels. Third, the short sequence bound by zinc fingers means that such DNA-binding elements are fairly 'promiscuous' in the genome, so it was not clear that an ATF based on this, where expression profiling was intended, would be effective or satisfactory.

Accordingly, in a first aspect, provided herein are engineered zinc finger proteins ("artificial transcription factors" or ATFs) capable of precise regulation of gene expression at a given locus. As used herein, the term "artificial transcription factor" refers to an engineered or "non-naturally occurring" zinc finger protein or fusion protein that binds to a nucleic acid (e.g., DNA, RNA) and/or protein. Encompassed by the term ATF are engineered zinc fingers comprising at least one zinc finger domain, typically two zinc finger domains, three zinc finger domains, or more. A zinc finger domain is a DNA binding motif of DNA binding proteins that are most frequently discovered in eukaryotes, which is discovered in various species from yeast to higher plant life and human beings. In the present disclosure, the zinc finger domain may be a Cys2-His2 type, where two, three, or more zinc finger domains are arranged in parallel to constitute a zing finger protein.

As used herein, the term "non-naturally occurring" means, for example, one or more of the following: (a) a polypeptide comprised of a non-naturally occurring amino acid sequence; (b) a polypeptide having a non-naturally occurring secondary structure not associated with the polypeptide as it occurs in nature; (c) a polypeptide that includes one or more amino acids not normally associated with the species of organism in which that polypeptide occurs in nature; (d) a polypeptide that includes a stereoisomer of one or more of the amino acids comprising the polypeptide, which stereoisomer is not associated with the polypeptide as it occurs in nature; (e) a polypeptide that includes one or more chemical moieties other than one of the natural amino acids; or (f) an isolated portion of a naturally occurring amino acid sequence (e.g., a truncated sequence).

Figure 14:
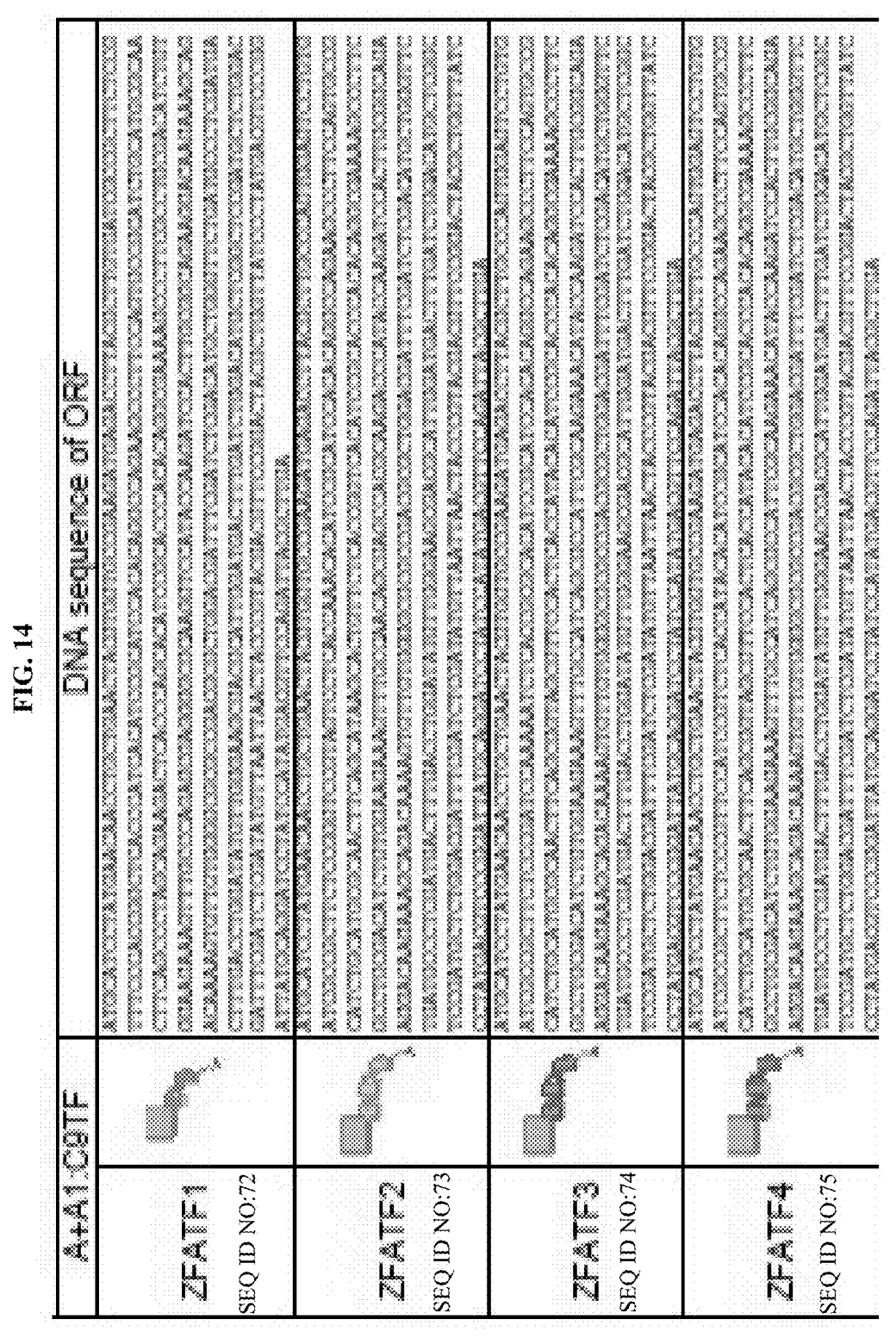
Figure 14:
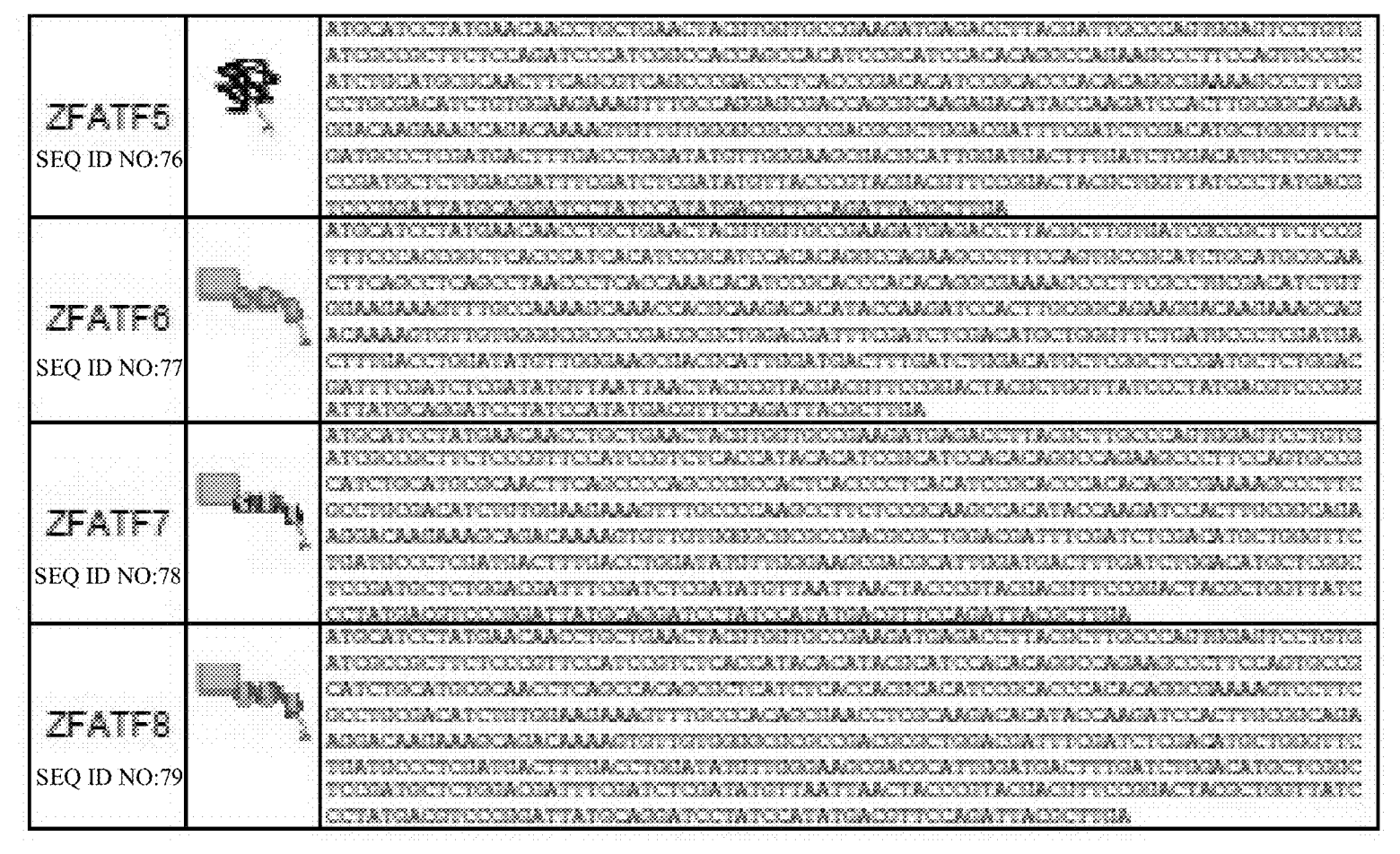
Figure 14:
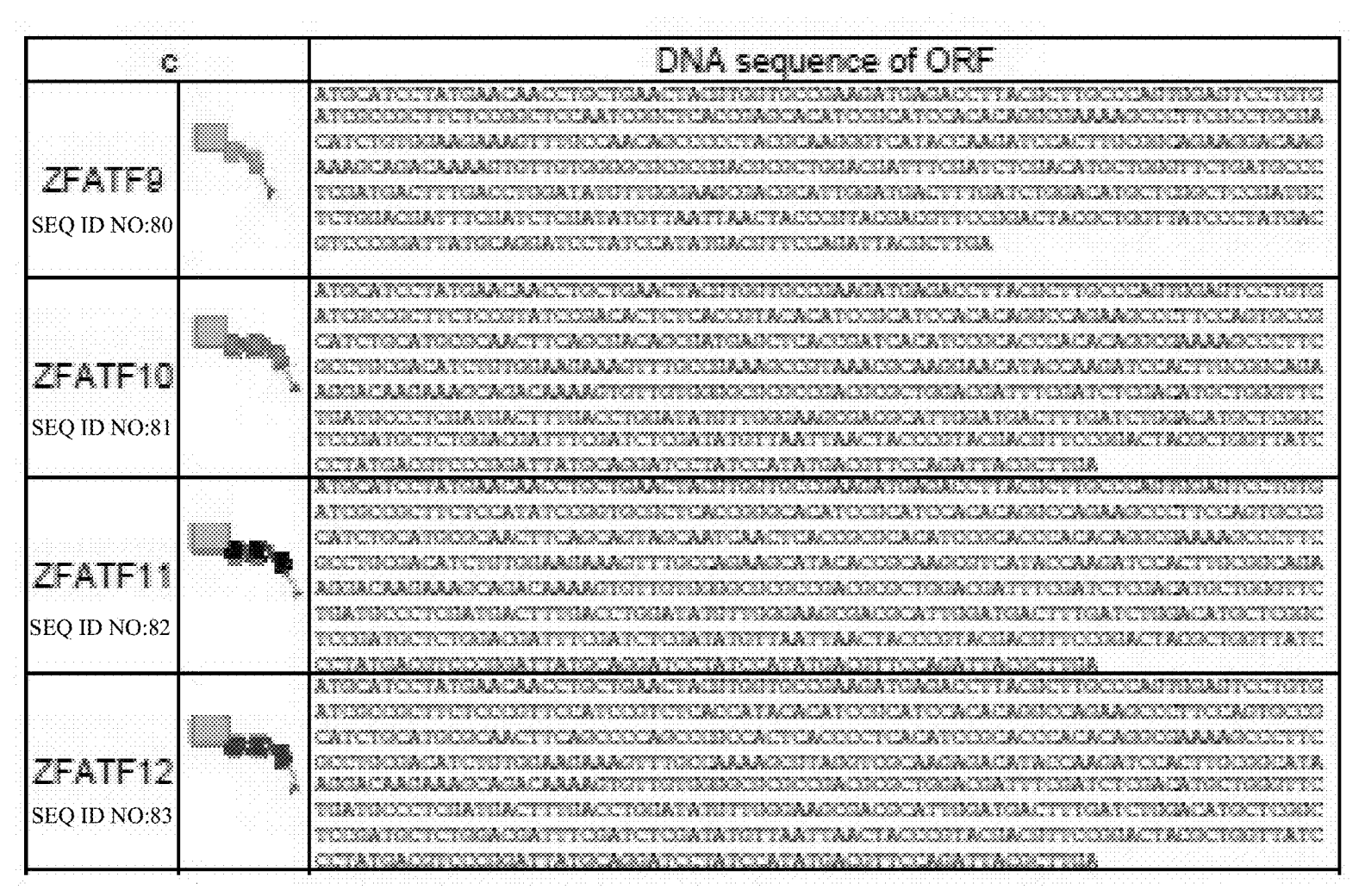

In preferred embodiments, ATFs are designed to have a particular ATF formula including two or three zinc finger domains, a nuclear localization signal (NLS), and a specific interaction domain (ID). Twelve exemplary ATFs and their respective DNA sequence open reading frames are presented in FIG. 14.

In a preferred embodiment, provided herein are ATFs comprising a polydactyl zinc finger protein comprising two or three zinc finger domains, an interaction domain, a nuclear localization signal, and an activation domain. Each of the two or three zinc finger domains comprises a variable residue region, where the variable residue positions are encoded by nucleotide sequence of SEQ ID NO:2 (VNN-TCC-VNN-VNN-CTC-ACC-VNN), where each "VNN" is a codon encoding an amino acid selected from the group consisting of R, H, K, D, Q, S, T, N, E, G, P, A, I, L, M, and V. Presented another way, the variable residue positions of the two or three zinc finger domains is encoded by amino acid sequence of SEQ ID NO:3 ($X_{-1}$-S-$X_2$-$X_3$-L-T-$X_6$), where $X_{-1}$ is an amino acid preferably selected from the group consisting of R, H, K, D, Q, S, T, N, E, G, P, A, I, L, M, and V; $X_2$ is preferably selected from the group consisting of R, H, K, D, Q, S, T, N, E, G, P, A, I, L, M, and V; $X_3$ is preferably selected from the group consisting of R, H, K, D, Q, S, T, N, E, G, P, A, I, L, M, and V; and $X_6$ is preferably selected from the group consisting of R, H, K, D, Q, S, T, N, E, G, P, A, I, L, M, and V. For a three zinc finger-containing ATF, the zinc fingers are encoded by the following sequences:

Finger1:
(SEQ ID NO: 4)
CCTTACGCTTGCCCAGTGGAGTCCTGTGATCGCCGCTTCTCC<u>VNN</u>TCC<u>VN</u>

<u>NVNN</u>CTCACC<u>VNN</u>CACATCCGCATCCACACAGGCCAGAAGCCC

Finger2:
(SEQ ID NO: 5)
TTCCAGTGCCGCATCTGCATGCGCAACTTCAGC<u>VNN</u>AGC<u>VNNVNN</u>CTCAC C<u>VNN</u>CACATCCGCACCCACACAGGCGAA Finger3:
(SEQ ID NO: 6)
AAGCCCTTCGCCTGCGACATCTGTGGAAGAAAGTTTGCC<u>VNN</u>AGC<u>VNNVN</u>

<u>N</u>CGCAAG<u>VNN</u>CATACCAAGATCCACTTGCGG where each "VNN" (underlined) reflects a variable residue within each zinc finger. Each VNN is a codon encoding an amino acid selected from the group consisting of R, H, K, D, Q, S, T, N, E, G, P, A, I, L, M, and V.

ATF Architecture:

In general, ATFs of the invention comprise a zinc finger backbone, an interaction domain (ID), and an effect domain, and can include an optional nuclear localization signal (NLS). Since the ID interacts with the first finger of EGR1, it is located at the N-terminus to be functional for dimerization with a second ATF. The other elements may be present in any order.

In some cases, the interaction domain (ID) comprises a 15-amino acid peptide that enables interaction with the hydrophobic face of the most 5' zinc finger domain. In other cases, the ID comprises fewer than or greater than 15 amino acids. For example, the ID can comprise a peptide having 10-20 amino acids (e.g., 10, 11, 12, 13, 14, 15, 16, 17, 18, 19, or 20 amino acids). In some cases, the effector domain is an activation domain. In other cases, the effector domain is a repression domain. Suitable effector domains include, without limitation, VP64 (an activation domain) and KRAB (a repression domain). Other examples are set forth in Eguchi et al., 2014.

In some cases, the activation domain is a sequence derived from VP64. VP64 is a transcriptional activator composed of four tandem copies of VP16 (Herpes Simplex Viral Protein 16, amino acids 437-447, DALDDFDLDML; SEQ ID NO:7), generally connected with glycine-serine linkers. When fused to another protein domain that can bind near the promoter of a gene, VP64 acts as a strong transcriptional activator. Other activation domains appropriate for use according to the ATF's provided herein include, without limitation, the RelA activation domain (PGLPNGLLSGDEDFSSIADMDFSALLSQISS; SEQ ID NO:8), Beta-catenin (FDTDL; SEQ ID NO:9), amphipathic helix (PEFPGIELQELQELQALLQQ; SEQ ID NO:10), RNA-based activation domains (see, for example, Saha, S., Ansari, A. Z., Jarrell, K. A., Ptashne, M. and Jarell, K. A. (2003) RNA sequences that work as transcriptional activating regions. *Nucleic Acids Res.* 31, 1565-1570), and other non-protein based activation domains. For example, synthetic molecules that mimic transcription factors include wrenchnolol or a wrenchnolol derivative, isoxazoladine, and peptoids as reviewed in Eguchi et al., 2014. See also Jung et al. (*J. Am. Chem. Soc.* 2009, 131(13):4774-4782).

The ability of a domain to activate transcription can be validated by fusing the domain to a known DNA binding domain and then determining if a reporter gene operably linked to sites recognized by the known DNA-binding domain is activated by the fusion protein.

Nuclear localization signals (NLS) are amino acid motifs conferring nuclear import through binding to proteins defined by gene ontology GO:0008139, for example clusters of basic amino acids containing a lysine residue (K) followed by a lysine (K) or arginine residue (R), followed by any amino acid (X), followed by a lysine or arginine residue (K-K/R-X-K/R consensus sequence, Chelsky D. et al., 1989 *Mol Cell Biol* 9, 2487-2492). In preferred embodiments, the NLS can be derived from human EGR1 (early growth response 1). EGR1, which is also known as Zif268 (zinc finger protein 225) or NGFI-A (nerve growth factor-induced protein A), is a mammalian transcription factor that in humans is encoded by the EGR1 gene. In some cases, the EGR1 NLS sequence is KDKKADKSVV (SEQ ID NO: 11). In other cases, a NLS sequence suitable for use according to the invention provided herein is PKKKRKV (SEQ ID NO:12), which is the simian virus 40 large T-antigen (Kalderon et al. (1984) A short amino acid sequence able to specify nuclear location. *Cell* 39, 499-509).

In some cases, ATFs of the invention further comprise a dimerization domain. An alternative method of linking DNA binding domains is the use of dimerization domains, especially heterodimerization domains (see, e.g., Pomerantz et al (1998) *Biochemistry* 37: 965-970). In this implementation, DNA binding domains are present in separate polypeptide chains. For example, a first polypeptide encodes DNA binding domain A, linker, and domain B, while a second polypeptide encodes domain C, linker, and domain D. An artisan can select a dimerization domain from the many well-characterized dimerization domains. Domains that favor heterodimerization can be used if homodimers are not desired. A particularly adaptable dimerization domain is the coiled-coil motif, e.g., a dimeric parallel or anti-parallel coiled-coil. Coiled-coil sequences that preferentially form heterodimers are also available (Lumb and Kim, (1995) *Biochemistry* 34: 8642-8648). Another species of dimerization domain is one in which dimerization is triggered by a small molecule or by a signaling event. Such dimerization domains can be utilized to provide additional levels of regulation.

ATFs for Inducing Pluripotency:

In another aspect, provided herein are methods of using ATFs and combinations of ATFs useful to induce pluripotency in mammalian somatic cells. As described in the Examples that follow, combinations of ATFs have been shown to induce somatic cell reprogramming when provided to a somatic cell in combination with potency determining factors such as Sox2, Klf4, and c-Myc. For example, provided herein is a method of reprogramming a somatic cell to pluripotency, where the method comprises (a) exposing a somatic cell to a plurality of artificial transcription factors, wherein the artificial transcription factors are selected from the group consisting of ZFATF1, ZFATF2, ZFATF3, ZFATF4, and ZFATF5; (b) further exposing the somatic cell to a plurality of potency determining factors comprising Sox2, Klf4, and c-Myc; and (c) culturing the exposed cells to obtain reprogrammed cells having a higher potency level than the somatic cell. Combinations of ATFs useful for such methods include, without limitation, (1) ZFATF1, ZFATF2, and ZFATF3; (2) ZFATF1, ZFATF2, and ZFATF4; and (3) ZFATF1, ZFATF2, and ZFATF5. Other ATFs include ZFATF6, ZFATF7, ZFATF8, ZFATF9, ZFATF10, ZFATF11, and ZATF12.

Advantageously, the present invention allows the generation of pluripotent cells, such as iPS cells, from somatic cells without requiring an addition of cell surface receptors for introducing the potency-determining factors to the somatic cells. As used herein, the term "reprogramming" refers to a genetic process whereby differentiated somatic cells are converted into de-differentiated, pluripotent cells, and thus have a greater pluripotency potential than the cells from which they were derived. That is, the reprogrammed cells express at least one of the following pluripotent cell-specific markers: SSEA-1, SSEA-3, SSEA-4, TRA-1-60, or TRA 1-81. When the ATF library was tested for reprogramming of mouse fibroblasts, the resulting mouse pluripotent cells expressed SSEA-1. Other mouse markers include Oct4, Nanog, Esrrb, Utf1, Lin28a, and Dppa2 (Buganim Y, et al. (2012) Single-cell expression analyses during cellular reprogramming reveal an early stochastic and a late hierarchic phase. *Cell* 150(6):1209-1222).

As used herein, "pluripotent cells" refer to a population of cells that can differentiate into all three germ layers (e.g., endoderm, mesoderm and ectoderm). Pluripotent cells express a variety of pluripotent cell-specific markers, have a cell morphology characteristic of undifferentiated cells (i.e., compact colony, high nucleus to cytoplasm ratio and prominent nucleolus) and form teratomas when introduced into an immunocompromised animal, such as a SCID mouse. The teratomas typically contain cells or tissues characteristic of all three germ layers. One of ordinary skill in the art can assess these characteristics by using techniques commonly used in the art. See, e.g., Thomson et al., *Science* 282:1145-1147 (1998). Pluripotent cells are capable of both proliferation in cell culture and differentiation towards a variety of lineage-restricted cell populations that exhibit multipotent properties. Multipotent somatic cells are more differentiated relative to pluripotent cells, but are not terminally differentiated. Pluripotent cells therefore have a higher potency than multipotent cells. As used herein, "reprogrammed pluripotent primate stem cells" (and similar references) refer to the pluripotent products of somatic cell reprogramming methods. Such cells are suitable for use in research and therapeutic applications currently envisioned for human ES cells.

As used herein, a "potency-determining factor" refers to a factor, such as a gene or other nucleic acid, or a functional fragment thereof, as well as an encoded factor or functional fragment thereof, used to increase the potency of a somatic cell, so that it becomes pluripotent. The potency-determining factors optionally can be present only transiently in the reprogrammed cells or can be maintained in a transcriptionally active or inactive state in the genome of the reprogrammed cells. Likewise, the potency-determining factors can be present in more than one copy in the reprogrammed cells, where the potency-determining factor can be integrated in the cell's genome, can be extra-chromosomal or both.

Generally, methods for identifying potency-determining factors include the steps of introducing genetic material encoding one or a plurality of putative potency-determining factors into somatic cells receptive to uptake of the genetic material under conditions effective to express the factors encoded on the introduced genetic material at levels sufficient to reprogram the cells to a less differentiated, higher-potency state; and observing a population of pluripotent cells after introduction of the genetic material. The pluripotent cells can be characterized by cell morphology, pluripotent cell-specific markers or both. Advantageously, the pluripotent cells can be identified by expression in the treated cells of a marker provided in the cells so as to be expressed only upon reprogramming of the cells to a pluripotent state. Through this approach, potency-determining factors capable of reprogramming somatic cells into pluripotent cells can be identified, as is described in the examples below.

Suitable somatic cells can be any somatic cell, although higher reprogramming frequencies are observed when the starting somatic cells have a doubling time about twenty-four hours. Somatic cells useful in the invention are non-embryonic cells obtained from a fetal, newborn, juvenile or adult primate, including a human. Examples of somatic cells that can be used with the methods described herein include, but are not limited to, bone marrow cells, epithelial cells, fibroblast cells, hematopoietic cells, hepatic cells, intestinal cells, mesenchymal cells, myeloid precursor cells and spleen cells. Alternatively, the somatic cells can be cells that can themselves proliferate and differentiate into other types of cells, including blood stem cells, muscle/bone stem cells, brain stem cells and liver stem cells. Multipotent hematopoietic cells, suitably myeloid precursor or mesenchymal cells, are specifically contemplated as suited for use in the methods of the invention.

In some cases, the methods comprises exposing or introducing into a somatic cell a genetic construct that enables efficient and robust delivery of ATFs and potency-determining factors to most cell types, including non-dividing and hard-to-transfect cells (primary, blood, stem cells) in vitro or in vivo. Viral-based constructs integrated into genomic DNA result in high expression levels. In addition to a DNA segment that encodes a potency-determining factor of interest, the vectors include a transcription promoter and a polyadenylation signal operatively linked, upstream and downstream, respectively, to the DNA segment. The vector can include a single DNA segment encoding a single potency-determining factor or a plurality of potency-determining factor-encoding DNA segments. A plurality of vectors can be introduced into a single somatic cell. The vector can optionally encode a selectable marker to identify cells that have taken up and express the vector. As an example, when the vector confers antibiotic resistance on the cells, antibiotic can be added to the culture medium to identify successful introduction of the vector into the cells. Integrating vectors can be employed, as in the examples, to demonstrate proof of concept. Retroviral (e.g., lentiviral) vectors are integrating vectors; however, non-integrating, episomal vectors can also be used. Such vectors can be lost from cells by dilution after reprogramming, as desired. A suitable episomal non-integrating vector is an Epstein-Barr virus (EBV) vector.

Alternative delivery methods for artificial transcription factors of the invention include transfer of nucleic acids by transfection or via viral vectors such as, but not limited to, herpes virus-, adeno virus- and adeno-associated virus-based vectors.

ATF Libraries:

In another aspect, provided herein is a library of ATFs designed to bind to and modulate the expression of a gene product. In some cases, the gene product can be a component of a cellular pathway (e.g., signaling pathway) associated with development of particular cell types. In other cases, the gene product can be a component of a cellular pathway associated with cell potency. As used herein, the term "library" is used according to its common usage in the art to denote a collection of polypeptides or, preferably, nucleic acids encoding polypeptides.

In some cases, ATFs provided herein contain regions of randomization, such that each library of ATFs will comprise or encode a repertoire of polypeptides, wherein individual polypeptides differ in sequence from each other. The same principle is present in virtually all libraries developed for selection, such as by phage display. As used herein, "randomization" refers to the variation of the sequence of the polypeptides which comprise the library, such that various amino acids may be present at any given position in different polypeptides. Randomization may be complete, such that any amino acid may be present at a given position, or partial, such that only certain amino acids are present. Preferably, the randomization is achieved by mutagenesis at the nucleic acid level, for example by synthesizing novel genes encoding mutant proteins and expressing these to obtain a variety of different proteins. Alternatively, existing genes can be themselves mutated, such by site-directed or random mutagenesis, in order to obtain the desired mutant genes.

In general, an ATF library can be obtained using any appropriate molecular biology techniques. As described in the Examples that follow, an exemplary method for obtaining a zinc finger ATF library comprises ligation-independent cloning. In particular, ligation-independent cloning into a second-generation lentiviral expression vector that contains the ccdB toxin was performed to eliminate background colonies. The first zinc finger was ordered as an oligomer with VNN codons in the variable residue positions (−1, 2, 3, and 6 of the alpha helix). The second and third zinc fingers were ordered as a separate oligo with VNN codons in the variable residue positions (−1, 2, 3, and 6 of the alpha helix). These two oligomers were amplified by PCR in a fusion reaction with a third oligomer containing the nuclear localization signal, VP64, and the HA tag. Amplified fragments were flanked by 30-bp regions with homology to the backbone vector. These homologous arms were treated with an exonuclease to create long overhangs, then cloned into the backbone vector. Plasmids comprising the oligomers cloned into the backbone vector can be transformed in highly competent bacteria.

In some cases, an ATF library can include additional variations that repress gene expression or modify chromatin.

In some cases, an ATF library as provided herein can be in cells such as engineered cells, or delivered to cells or tissues as RNA or full proteins to achieve the desired effects. This could be useful for research or therapeutic purposes.

Methods

In another aspect, provided herein are methods of using ATFs and ATF libraries as provided herein. In particular, ATFs can be used in methods for altering the potency of a cell and/or to promote differentiation of a cell into one or more particular cell types or cell lineages.

In some cases, the ATFs and ATF libraries provided herein can be used in combination with various genetic tools. For example, an ATF library can be screened for factors capable of inducing pluripotency in somatic cells (e.g., mouse embryonic fibroblasts) when expressed in the somatic cell in combination with three of the four recognized reprogramming factors (i.e., Sox2, Klf4, and c-Myc, but not Oct4). Genetic tools such as cognate site identification of the ATF binding sites, global transcriptional profiling, and characterization of the genome-wide epigenetic landscapes can be used to identify ATFs having a capacity to reprogram the somatic cell to a pluripotent state even in the absence of exogenous Oct4.

In some cases, an ATF library can be screened to identify ATFs capable of inducing differentiation of pluripotent cells such as human embryonic stem cells (ESCs) or human iPS cells into a differentiated cell type. For example, an ATF library can be screened using various combinations of Wnt pathway activators and inhibitors such as CHIR99021 ("CHIR"; a specific inhibitor of GSK3 for activation of canonical Wnt signaling) and IWP2 (which inhibits Wnt) to identify ATFs capable of standing in place of a Wnt inhibitor to induce cardiomyocyte differentiation in the presence of CHIR.

In certain embodiments, provided herein is a method of directing differentiation of a pluripotent stem cell to a cardiomyocyte. In some cases, the differentiation method comprises (a) exposing a pluripotent stem cell to one or more artificial transcription factors (ATFs) selected from the group consisting of ZFATF1, ZFATF2, and ATF5; and (b) culturing the exposed cells of (a) in the presence of an activator of Wnt/β-catenin signaling for about 7-10 days, such that a population of cells comprising cardiomyocytes is obtained. In some cases, the ATFs comprise ZFATF1, ZFATF2, and ATF5.

In some embodiments, activation of Wnt/β-catenin signaling is achieved by inhibiting Gsk3 phosphotransferase activity or Gsk3 binding interactions. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen et al. (2002), *J. Biol. Chem.*, 277(26):23330-23335, which describes a Gsk3 comprising a R96A mutation.

In some embodiments, Gsk3 is inhibited by contacting a cell with a small molecule that inhibits Gsk3 phosphotransferase activity or Gsk3 binding interactions. Suitable small molecule Gsk3 inhibitors include, but are not limited to, CHIR99021 ("CHIR"), CHIR98014, BIO-acetoxime, BIO, LiCl, SB 216763, SB 415286, AR A014418, 1-Azakenpaullone, Bis-7-indolylmaleimide, and any combinations thereof. In some embodiments, any of CHIR99021, CHIR98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 µM to about 12 µM, e.g., about 3 µM, 4 µM, 5 M, 6 µM, 7 µM, 8 µM, 9 µM, 10 µM, 11 µM, 12 µM or another concentration of CHIR99021 from about 3 µM to about 12 µM. In another embodiment, the small molecule Gsk3 inhibitor to be used is CHIR98014 at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM or another concentration of CHIR98014 from about 0.1 µM to about 1 µM. In another embodiment, the small molecule Gsk3 inhibitor to be used is BIO-acetoxime at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM or another concentration of BIO-acetoxime from about 0.1 µM to about 1 µM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Technology®, Danvers, Mass.), or a retroviral vector with an inducible expression cassette for Gsk3, e.g., a commercially available Tet-inducible retroviral RNA interference (RNAi) system from Clontech (Mountain View, Calif., Catalog No. 630926), or a cumate-inducible system from Systems Biosciences, Inc. (Mountain View, Calif.), e.g., the SparQ® system, catalog no. QM200PA-2.

In another aspect, provided herein is a method for directing differentiation of a pluripotent stem cell to a hematopoietic lineage. In some cases, the method comprises (a) exposing a pluripotent stem cell to two or more artificial transcription factors (ATFs) selected from the group consisting of ZFATF19, ZFATF20, ZFATF21, ATF5, ZFATF1, ZFATF6, ZFATF10, ZFATF13, ZFATF17, ZFATF22, ZFATF23, ZFATF24, ZFATF25, ZFATF26, ZFATF27, ZFATF28, ZFATF29, ZFATF30, and ZFATF31; and (b) culturing the exposed cells of (a) in a basal culture medium comprising FGF2, SCF, and thrombopoietin, and in the presence of TAL1 for about 7-10 days, such that a cell population comprising hematopoietic lineage cells is obtained. In some cases, the ATFs comprise ZFATF19, ZFATF20, ZFATF21, and ATF5, and the cell population comprises erythroid-like cells. In other cases, the ATFs comprise ZFATF1, ZFATF6, ZFATF10, ZFATF13, ZFATF17, ZFATF22, ZFATF23, ZFATF24, ZFATF25, ZFATF26, ZFATF27, ZFATF28, ZFATF29, ZFATF30, and ZFATF31, and the cell population comprises monocyte-like cells.

In other cases, an ATF library can be screened to identify ATFs capable of inducing differentiation of pluripotent and/or multipotent cells to various blood lineages. For example, an ATF library can be screened for ATFs capable of differentiating human pluripotent stem cells (e.g., iPS cells, embryonic stem cells) into erythroblast-like cells and monoblast-like cells. As described in the Examples that follow, screening an ATF library identified factors that promoted the differentiation of ESCs into blood lineages, and found combinations of ATFs (with TAL1(SCL)) that produced a range of phenotypes from monoblast-like to erythroblast-like cells.

In some cases, the methods provided herein include screening an ATF library for factors that promote the reactivation of latent cytomegalovirus (CMV) virus infections, the inventors identified eight ATF combinations, which can help inform the field's understanding of how CMV and its reactivation from a latent state to lytic replication is regulated.

Articles of Manufacture

In another aspect, provided herein is an article of manufacture such as a kit comprising a plurality of artificial transcription factors or an ATF library as described herein.

In certain embodiments, the kit comprises (i) a plurality of ATFs selected from the group consisting of ZFATF1, ZFATF2, ZFATF3, ZFATF4, and ZFATF5; (ii) a plurality of potency determining factors such as Sox2, Klf4, and c-Myc; and (iii) instructions describing a method for reprogramming a somatic cell to pluripotency, the method employing the ATFs and potency determining factors. In some cases, a kit provided herein further comprises or alternatively comprises instructions for designing artificial transcription factors.

It is understood that certain adaptations of the invention described in this disclosure are a matter of routine optimization for those skilled in the art, and can be implemented without departing from the spirit of the invention, or the scope of the appended claims. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come within the scope of the following claims.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In the specification and in the claims, the terms "including" and "comprising" are open-ended terms and should be interpreted to mean "including, but not limited to . . . ." These terms encompass the more restrictive terms "consisting essentially of" and "consisting of." As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising," "including," "characterized by," and "having" can be used interchangeably.

As used herein, "about" means within 5% of a stated concentration, concentration range, or amount, or within 5% of a stated time frame.

As used herein, "effective amount" means an amount of an agent sufficient to evoke a specified cellular effect according to the present invention.

The invention will be more fully understood upon consideration of the following non-limiting Examples.

EXAMPLES

Example 1: Artificial Transcription Factor Library-Guided Cell Fate

In this Example, we demonstrate that Artificial Transcription Factors (ATFs), which are tailor-made molecules designed to bind DNA and regulate transcription in a desired manner, take cells through a different path to pluripotency compared to cells expressing exogenous Oct4.

Methods

Zinc Finger ATF Constructs for Testing Architecture:

The first two or all three zinc fingers of human EGR1 were used to test the ATF architecture. The peptide sequence (HPMNNLLNYVVPKMR (SEQ ID NO: 13)) preceding the DNA-binding domain served as the interaction domain. The native nuclear localization signal for EGR1 was used to ensure entry into the nucleus. A tetrameric repeat of VP16 (VP64) served as the activation domain. Three repeats of hemagglutinin (HA) were used as a C-terminal epitope tag.

Zinc Finger ATF Library:

The scaffold of the ATF is comprised from N- to C-terminus: a 15-amino acid interaction domain, the DNA binding domain of human EGR1, NLS from EGR1, VP64, and 3×HA tag. The ATF library was created by amplifying oligos with VNN codons at the −1, 2, 3, and 6 positions relative to the recognition helix of each zinc finger. The ATF library was cloned into the second-generation pSIN vector by ligation-independent cloning. Estimation of the library complexity was measured by plating a fraction of the transformants on plates, and counting the number of colonies that grew from the fraction.

Figure 16:
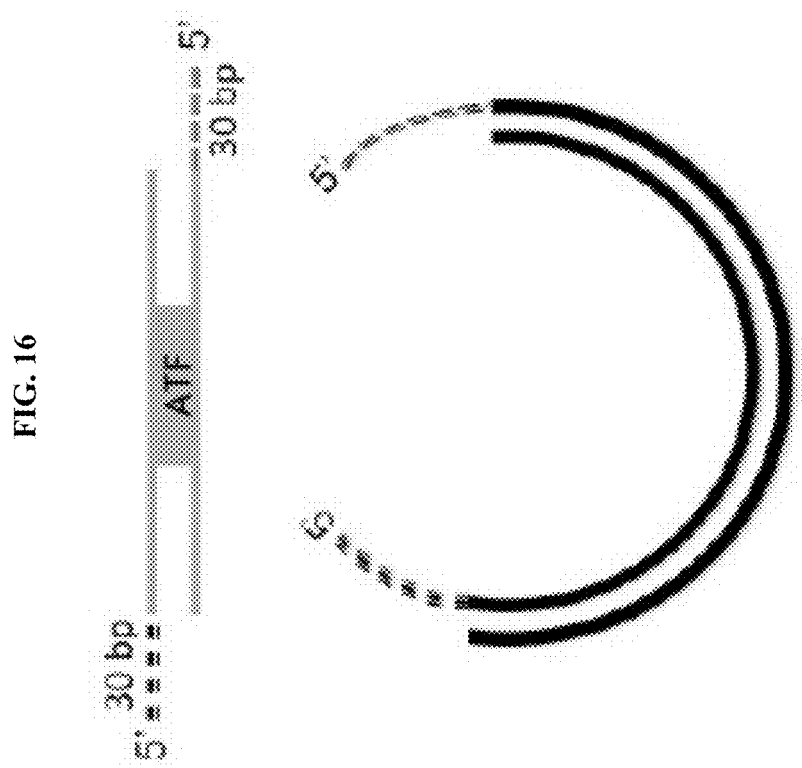
FIG. 16 illustrates a ligation-independent cloning strategy which relies on long overhangs to improve the efficiency of insertion of the cassette to the vector.
Figure 17:
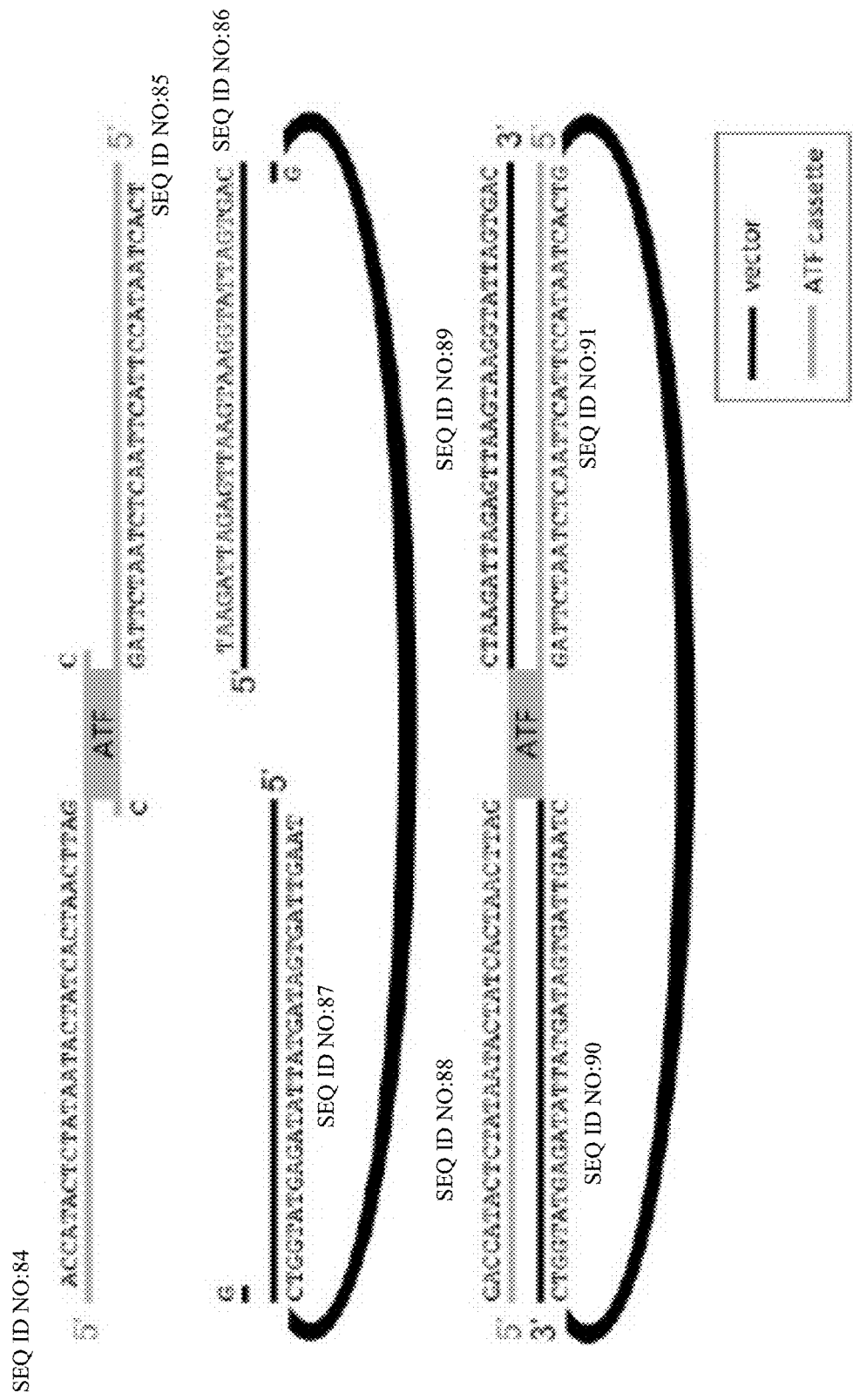
FIG. 17 illustrates a T4 DNA polymerase exonuclease reaction. A 30-bp overhang consists of three nucleotides until the position at which exonuclease activity is designed to be terminated.

The zinc finger ATF library was created by ligation-independent cloning into a second-generation lentiviral expression vector that contains the ccdB toxin to eliminate background colonies (FIG. 16). Ligation-independent cloning relies on long overhangs that improve the efficiency of insertion of the cassette to the vector. 30-bp overhangs were created by treating with T4 DNA polymerase with 3' to 5' exonuclease activity (FIG. 17). The nucleotide content in the overhangs are such that a specific nucleotide is missing. The missing nucleotide was added to the reaction to terminate exonuclease activity in a predetermined manner. The chewback of the ATF cassette was terminated with inclusion of cytosine and the pSIN vector with guanine. Homologous 30-bp overhangs were ligated together in a highly reliable manner without a DNA ligase. The long overhangs also increase the efficiency of ligation of the cassette to the vector.

A cassette containing the ccdB gene was cloned into pSIN with EcoRI and SpeI. The ccdB gene is encoded in the antisense direction (SEQ ID NO: 14)
```
5'-GAATTCGGACCATACTCTATAATACTATCACTAACTTAATTAATTAT
ATTCCCCAGAACATCAGGTTAATGGCGTTTTTGATGTCATTTTCGCGGTG
GCTGAGATCAGCCACTTCTTCCCCGATAACGGAGACCGGCACACTGGCCA
TATCGGTGGTCATCATGCGCCAGCTTTCATCCCCGATATGCACCACCGGG
TAAAGTTCACGGGAGACTTTATCTGACAGCAGACGTGCACTGGCCAGGGG
GATCACCATCCGTCGCCCGGGCGTGTCAATAATATCACTCTGTACATCCA
CAAACAGACGATAACGGCTCTCTCTTTTATAGGTGTAAACCTTAAACTGC
ATTTCACCAGCCCCTGTTCTCGTCAGCAAAAGAGCCGTTCATTTCAATAA
ACCGGGCGACCTCAGCCATCCCTTCCTGATTTTCCGCTTTCCAGCGTTCG
GCACGCAGACGACGGGCTTCATTCTGCATGGTTGTGCTTACCAGACCGGA
GATATTGACATCATATATGCCTTGAGCAACTGATAGCTGTCGCTGTCAAC
TGTCACTGTAATACGCTGCTTCATAGCATACCTCTTTTTGACATACTTCG
GGTATACATATCAGTATATATTCTTATACCGCAAAAATCAGCGCGCAAAT
ACGCATACTGTTATCTGGCTTTTAGTAAGCCGGATCCACGCGGCGTTTAC
GCCCCCCCTGCCACTCATCGCAGTACTGTTGTAATTCATTAAGCATTCTG
CCGACATGGAAGCCATCACAAACGGCATGATGAACCTGAATCGCCAGCGG
CATCAGCACCTTGTCGCCCTTGCGTATAATATTTGCCCATGGTGAAAACGG
GGGCGAAGAAGTTGTCCATATTGGCCACGTTTAAATCAAAACTGGTGAAA
```

-continued

```
CTCACCCAGGGATTGGCTGAGACGAAAAACATATTCTCAATAAACCCTTT

AGGGAAATAGGCCAGGTTTTCACCGTAACACGCCACATCTTGCGAATATA

TGTGTAGAAACTGCCGGAAATCGTCGTGGTATTCACTCCAGAGCGATGAA

AACGTTTCAGTTTGCTCATGGAAAACGGTGTAACAAGGGTGAACACTATC

CCATATCACCAGCTCACCGTCTTTCATTGCCATACGGAAGTTCGGATGAG

CATTCATCAGGCGGGCAAGAATGTGAATAAAGGCCGGATAAAACTTGTGC

TTATTTTTCTTTACGGTCTTTAAAAAGGCCGTAATATCCAGCTGAACGGT

CTGGTTATAGGTACATTGAGCAACTGACTGAAATGCCTCAAAATGTTCTT

TACGATGCCATTGGGATATATCAACGGTGGTATATCCAGTGATTTTTTC

TCCATTTTAGCTTCCTTAGCTCCTGAAAATCTCGATAACTCAAAAAATAC

GCCCGGTAGTGATCTCGAGCCGGAAGCATAAAGTGTAAATTAATTAAGAT

TAGAGTTAAGTAAGGTATTAGTGACACTAGT -3'.
```

The zinc finger ATF library was created by ordering the following oligos from IDT and fusing them to the ATF scaffold that includes the interaction domain, nuclear localization signal, activation domain, and 3×HA tag:

Oligo 1:
(SEQ ID NO: 15)
```
5'-GGTACCATGCATCCTATGAACAACCTGCTGAACTACGTGGTGCCGAA

GATGAGACCTTACGCTTGCCCAGTGGAGTCCTGTGATCGCCGCTTCTCCV

NNTCCVNNVNNCTCACCVNNCACATCCGCATCCACACAGGCCAGAAGCCC

TTCCAGTGCCGCATCTGCATGCGCAACTTCAG -3'.
```
Oligo 2:
(SEQ ID NO: 16)
```
5'-CACAACACTTTTGTCTGCTTTCTTGTCCTTCTGCCGCAAGTGGATCT

TGGTATGNNBCTTGCGNNBNNBGCTNNBGGCAAACTTTCTTCCACAGATG

TCGCAGGCGAAGGGCTTTTCGCCTGTGTGGGTGCGGATGTGNNBGGTGAG

NNBNNBGCTNNBGCTGAAGTTGCGCATGCAGATGC -3'.
``` where V stands for A, C, or G and B stands for C, G, or T

Fragment 3 (in pcDNA vector):
(SEQ ID NO: 17)
```
5'-AAGGACAAGAAAGCAGACAAAAGTGTTGTGGGCGCGCCGACGCGT

GGACGATTTCGATCTCGACATGCTGGGTTCTGATGCCCTCGATGACTTTG

ACCTGGATATGTTGGGAAGCGACGCATTGGATGACTTTGATCTGGACATG

CTCGGCTCCGATGCTCTGGACGATTTCGATCTCGATATGTTAATTAACTA

CCCGTACGACGTTCCGGACTACGCTGGTTATCCCTATGACGTCCCGGATT

ATGCAGGATCCTATCCATATGACGTTCCAGATTACGCTTGA-3'.
```

In the first PCR Oligo 2 and Fragment 3 are amplified together with forward primer 1 and reverse primer 1.

forward primer 1:
(SEQ ID NO: 18)
```
5'- CCGCATCTGCATGCGCAACTTCAGC -3'.
``` reverse primer 1:
(SEQ ID NO: 19)
```
5'- GCGGGCCCTCTAGACTCG -3'.
```

In the second PCR the product from the first PCR and Oligo1 are amplified together with forward primer 2 and reverse primer 2.

forward primer 2:
(SEQ ID NO: 20)
```
5'-ACCATACTCTATAATACTATCACTAACTTAGCCGCCACCATGCATCC

TATGAACAACCTGCTGAACTACGTGG -3'.
``` reverse primer 2:
(SEQ ID NO: 21)
```
5'-TCACTAATACCTTACTTAACTCTAATCTTAGTCAAGCGTAATCTGGA

ACGTCATATGGATAGGATCCTGC -3'.
```

Both the ATF cassette and the pSIN-ccdB vector were digested with PacI and treated with T4 DNA polymerase, which has 3' to 5' exonuclease activity. The resulting vector was gel-extracted. The ligation was performed at a ratio of 1:6 (vector:cassette) without a DNA ligase. The ligation reaction was chemically transformed in ultracompetent XL-10 Gold cells. After 1 hour recovery in SOC media without antibiotic, the transformed culture was diluted in 150 mL SOC media with ampicillin (100 µg/mL). This culture was grown on a shaker at 37° C. for 12 hours. These cultures were maxiprepped for endotoxin-free purification of pSIN-plasmid. A small fraction (1/10,000) of the culture was plated on 4 plates before overnight incubation for counting purposes.

Estimation of the library complexity was measured by plating a fraction of the transformants on plates, and counting the number of colonies that grew from the fraction. A total of 210 transformations and 25 maxipreps were performed to cover the desired complexity.

The permutation of all 10-bp sequences is $4^{10}=1,048,576$. However, on duplex DNA, the complementary sequence will also be represented on the antisense strand. Palindromic sequences do not yield new sequences on the antisense strand. Therefore, $N=(n-1)+(4^n+4^{n/2})/2$, where N is the number of permutations on duplex DNA and n is the length in bp (if even) (2). For 10-bp sequences, there are 524,809 permutations that encompass the entire binding space on duplex DNA.

Sequencing of 100 clones revealed 60% of the ATFs contain functional ATFs (53% with 3 zinc fingers, 6% with 2 zinc fingers, and 1% with 4 zinc fingers). The remainder of sequences yielded poor reads (4%) or contained a frameshift mutation (36%). Accounting for the efficiency of creating functional ATFs, we predicted $4.37 \times 10^6$ clones would be sufficient would be sufficient to achieve the desired complexity. Cloning of the library was repeated until the maxiprep cultures yielded a clone count of $5.56 \times 10^6$ CFU.

To determine the diversity of the library, the sequences of 100 functional ATFs were determined by Sanger sequencing. All 16 possible amino acids encoded by VNN codons were represented in the recognition residues. This sample size is representative of the library at a 95% confidence interval and a margin of error of 9.8%.

Cell Culture:

Oct4:Cre$^{mER\text{-}Cre\text{-}mER}$; mTmG mouse embryonic fibroblasts (MEFs) were grown in DMEM supplemented with 10% fetal bovine serum on plates coated with 0.1% gelatin. Mouse E14T ES cells and iPS cells were grown in knock-out DMEM supplemented with 15% fetal bovine serum, 1% nonessential amino acids, 2 mM L-glutamine, 1×10³ units/mL leukemia inhibitory factor, 1 mM sodium pyruvate, and 100 µM beta-mercaptoethanol. 4-hydroxytamoxifen was added at 100 nM concentration. Pluripotent cells were maintained on irradiated MEFs. Cells were maintained in a humidified 37° C. incubator with 5% $CO_2$.

Luciferase Assay:

The palindromic EGR1 binding site 5'-GCG-TGG-GCG-CGC-CCC-CGC-3' (SEQ ID NO: 1) was cloned upstream of the luciferase gene in the pGL3 basic vector (Promega). HEK293 cells were transiently co-transfected with ATF in pcDNA-CMV, the pGL3 basic luciferase reporter, and a RSV-β-galactosidase reporter. The transfection was performed with Lipofectamine® 2000 (Thermo Fisher Scientific #11668019). Cells were collected and lysed 24 hours post-transfection. Luciferase assay (Promega #E4030) was performed according to manufacture guidelines, and readings were normalized to β-galactosidase levels to account for transfection efficiency. Significance values were obtained by one-way ANOVA of the $\log_{10}$ transformed β-galactosidase-normalized luciferase values in SPSS Statistics 23.0.0.0 (IBM). A Tukey test was performed for post hoc analysis of treatments with statistically significant differences.

Retrovirus Production:

Oct4, Sox2, Klf4, and c-Myc were packaged into retrovirus with Plat-E cells as described in (Takahashi et al., 2007a).

Lentivirus Production:

ATFs and the empty control were packaged into lentivirus with HEK293FT cells using calcium phosphate transfection of pSIN expression, psPAX2 packaging, and pMD2.G envelope plasmids. Media containing virus was harvested 48-60 hours post-transfection. Lentivirus was centrifuged with a sucrose cushion at 25,000 rpm for 2 hours. Viral particles were suspended in PBS and concentrated virus was stored at −80° C. Viral titers were measured by counting cells that survived selection after 2 days in media containing puromycin (3 µg/mL). The ATF is driven by a constitutive promoter, EF1α.

Reprogramming to Pluripotent Cells:

Oct4: $Cre^{mER-Cre-mER}$; mTmG MEFs were maintained on 0.1% gelatin in DMEM supplemented with 10% FBS until the day of transduction. Lentiviruses and retroviruses were delivered to MEFs with polybrene (8 µg/mL). The ATF Library was delivered at MOI=3, and validation of ATFs were performed with MOI=3 for each ATF. The Empty lentiviral control was delivered at an MOI=9. Oct4 (500 µL), Sox2 (500 µL), Klf4 (500 µL), and c-Myc (300 µL) were delivered to the cells at the same time of ATF transduction as fresh retrovirus. Lentivirus and retrovirus was removed 18 hours after transduction. Selection of lentiviral integration events was performed 42 hours post-transduction by addition of puromycin (3 µg/mL) for 2 days in mouse ES cell media (knock-out DMEM supplemented with 15% fetal bovine serum, 1% nonessential amino acids, 2 mM L-glutamine, 1×10³ units/mL leukemia inhibitory factor, 1 mM sodium pyruvate, and 100 µM beta-mercaptoethanol). Cells undergoing reprogramming were maintained in mouse ES cell media with 4-hydroxytamoxifen (100 nM) on irradiated MEFs. Fully reprogrammed colonies were picked and expanded. To obtain doubling times, iPS cells were grown on 0.1% gelatin.

Identification of ATFs from Single Cells:

Cells with a positive phenotype for Oct4 lineage tracing activation were isolated as single cells into a 96-well plate. Amplified regions were cloned into pcDNA with a CMV promoter. ATF sequences were deciphered by Sanger sequencing with a primer for the 3' end of the CMV promoter.

TABLE 1

Primers for 2-Step Nested PCR

| Primer | Sequence (5' to 3') |
|---|---|
| ATF-forward-1 | TACTATCACTAACTTAGCCGCCACCATG (SEQ ID NO: 23) |
| ATF-reverse-1 | GAGGGCA TCAGAACCCAGCATG (SEQ ID NO: 24) |
| ATF-forward-2 | CATCAGCTAGCGCTGAACTACGTGGTGCCGAAG (SEQ ID NO: 25) |
| ATF-reverse-2 | CGCGTCGGCGCGCCCCACAACACTTTTGTCTGC (SEQ ID NO: 26) |
| CMV-forward | CGCAAATGGGCGGTAGGCGTG (SEQ ID NO: 27) |

The number of sequences obtained to reach saturation was determined by calculating the probability that the chance of finding another unique ATF is less than 1%: $(1-1/(n+1))^x < 0.01$, where n is the number of unique ATFs identified and x is the number of sequences needed.

TABLE 2

Number of Sequences Necessary for Saturation

| # of Unique ATFs Identified (n) | # of Sequences Needed (x) |
|---|---|
| 3 | 17 |
| 4 | 21 |
| 5 | 26 |
| 6 | 30 |
| 7 | 35 |
| 8 | 40 |
| 9 | 44 |
| 10 | 49 |

Embryoid Body Formation:

For embryoid body (EB) formation, pluripotent cells were seeded into ultra-low adhesion dishes at a concentration of 1×10⁵ cells/mL in knock-out DMEM supplemented with 15% fetal bovine serum, 1% nonessential amino acids, 2 mM L-glutamine, 1 mM sodium pyruvate, 100 µM beta-mercaptoethanol. Media was changed the day after seeding and every two days thereafter. EBs were collected on Day 5, 7, and 14 for RT-qPCR and immunofluorescence. Cells were maintained in a humidified 37° C. incubator with 5% $CO_2$.

Immunofluorescence:

EBs were plated on adherent plates on Day 5, 7, and 14 to culture EB outgrowths. iPS cells, EBs, or EB outgrowths were plated on glass slides coated with 0.1% gelatin for immunofluorescence. Antibody sources and dilutions are described in the Supplemental Experimental Procedures.

RT-qPCR:

RNA was extracted from cells with RNeasy Mini Kit (Qiagen #74104). RNA was converted into cDNA with SuperScript III First-Strand Synthesis System (Thermo Fisher #18080051). qPCR was performed with Bullseye EvaGreen qPCR Mix with low ROX (Midwest Scientific #BEQPCR-LR). Primer sets are listed in Table 3.

TABLE 3

Primers for qPCR

| Primer | Sequence (5' to 3') | SEQ ID NO: |
|---|---|---|
| Endogenous Oct4 forward | TCAGTGATGCTGTTGATCAGG | 28 |
| Endogenous Oct4 reverse | GCTATCTACTGTGTGTCCCAGTC | 29 |
| Endogenous Sox2 forward | CCGTTTTCGTGGTCTTGTTT | 30 |
| Endogenous Sox2 reverse | TCAACCTGCATGGACATTTT | 31 |
| Nanog forward | AAACCAGTGGTTGAAGACTAGCAA | 32 |
| Nanog reverse | GGTGCTGAGCCCTTCTGAATC | 33 |
| Lin28 forward | GAAGAACATGCAGAAGCGAAGA | 34 |
| Lin28 reverse | CCGCAGTTGTAGCACCTGTCT | 35 |
| Esrrb forward | CACCTGCTAAAAGCCATTGACT | 36 |
| Esrrb reverse | CAACCCCTAGTAGATTCGAGACGAT | 37 |
| Utf1 forward | GTCCCTCTCCGCGTTAGC | 38 |
| Utf1 reverse | GGCAGGTTCGTCATTTTCC | 39 |
| T forward | CTGTGGCTGCGCTTCAAGG | 40 |
| T reverse | ATTGGGGTCCAGGCCTGAC | 41 |
| Nkx 2.5 forward | TGACCCTGACCCAGCCAAAG | 42 |
| Nkx 2.5 reverse | GAGAAGAGCACGCGTGGCTTC | 43 |
| Kdr forward | CATCCCCCCAAGCTCAGCAC | 44 |
| Kdr reverse | ACGCTGAGCATTGGGCCAAAG | 45 |
| Afp forward | CACTGTCCAAGCAAAGCTGCG | 46 |
| Afp reverse | GAGGTCAGCTGAGGGGCTTTC | 47 |
| Ttr forward | GGATCCTGGGAGCCCTTTGC | 48 |
| Ttr reverse | TCATCTGTGGTGAGCCCGTG | 49 |
| FoxA2 forward | TGGGAGCCGTGAAGATGGAAG | 50 |
| FoxA2 reverse | CAGGCCGGCGTTCATGTTG | 51 |
| Nes forward | GCAGAGAGGCGCTGGAACAG | 52 |
| Nes reverse | CCCTGCTTCTCCTGCTCCAG | 53 |
| Nef1 forward | CTGGAGAAGCAGCTGCAGGAG | 54 |
| Nef1 reverse | CTGGCCATCTCGCTCTTCGTG | 55 |
| Sox17 forward | GCGGTTGGCACAGCAGAAC | 56 |
| Sox17 reverse | GCTCGGCCTCTTCCACGAAG | 57 |
| GAPDH forward | ACATCATCCCTGCATCCACT | 58 |
| GAPDH reverse | CCTGCTTCACCACCTTCTTG | 59 |

Chromatin Immunoprecipitation:

For chromatin immunoprecipitation, $5 \times 10^6$ cells were fixed in 1.5% formaldehyde for 15 min. Harvested cells were flash frozen, then sonicated and lysed. Lysates were precleared and immunoprecipitated overnight with H3K27ac antibody (Abcam #ab4729), H3K9me3 antibody (Abcam #ab8898), or HA antibody (Abcam #ab9110) at 4° C. Immunoprecipitated histone marks were purified with protein G magnetic beads (Life Technologies #10004D) and a series of five washes. Cross-links of protein-DNA complexes were reversed by incubating at 65° C. for 6 hours. Eluted DNA was treated with RNase A and Proteinase K.

For histone marks, $6 \times 10^6$ cells were harvested, and for ATFs, $2.5 \times 10^7$ cells were harvested. Cells were fixed in 1.5% formaldehyde, then flash frozen. Cells were lysed with a series of 3 buffers: LB1, LB2, and LB3. LB1 consisted of 10 mM HEPES, 10 mM EDTA, 0.5 mM EGTA, and 0.25% Triton X-100. LB2 consisted of 200 mM NaCl, 10 mM HEPES, 1 mM EDTA, and 0.5 mM EGTA. LB3 consisted of 50 mM Tris-HCl, 10 mM EDTA, 0.5% Empigen BB, and 1% SDS. Samples were sonicated in a Misonix sonicator (S-4000) at 60% power, 10 sec on and 10 off, for a total of 32 min total pulse time. Samples were cleared by centrifugation 17,000×g for 10 min. For pre-clearing, samples were incubated with magnetic Protein G beads (Life Technologies #10003D) for 1 hour at 4° C. After pre-clearing, 1% of each sample was saved as input. Samples were incubated with the appropriate antibody, H3K27ac antibody (Abcam #ab4729), H3K9me3 antibody (Abcam #ab8898), or HA antibody (Abcam #ab9110), overnight at 4° C. with IP Buffer (2 mM EDTA, 150 mM NaCl, 20 mM Tris-HCl, and 1% Triton X-100). Protein-DNA complexes on magnetic beads were washed in WB1 once, WB2, once, WB3 once, and TE Buffer twice. WB1 consisted of 2 mM EDTA, 20 mM Tris-HCl, 0.1% SDS, 1% Triton X-100, 150 mM NaCl). WB2 consisted of 2 mM EDTA, 20 mM Tris-HCl, 0.1% SDS, 1% Triton X-100, and 500 mM NaCl. WB3 consisted of 1 mM EDTA, 10 mM Tris-HCl, 250 mM LiCl, 1% deoxycholate, and 1% NP-40 detergent. DNA was eluted in 0.1 M $NaHCO_3$, 0.2 M NaCl, and 1% SDS (sodium dodecyl sulfate).

Protein-DNA complexes were reverse crosslinked by incubation at 65° C. for 6 hours. DNA was treated with RNase A and Proteinase K. Captured DNA was column purified (Epoch Life Sciences #1920-250). Samples were prepared for sequencing with the TruSeq ChIP Sample Preparation Kit (Illumina #IP-202-1012) as per the manufacturer instructions and quantified with a Qubit fluorometer (Life Technologies #Q32866). Three, four or six TruSeq indexed ChIP samples were pooled per lane. All samples were loaded at a final concentration of 8 pM and sequenced as single reads on the Illumina HiSeq 2500.

RNA-Seq Analysis:

Reads were aligned with Bowtie2 version 2.2.5 to either the human genome hg19 (HEK293) or mouse genome mm10 (MEFs or cells derived from MEFs). Counts were quantified with Cufflinks software, and differential expression was determined using the Cuffdiff program.

ChIP-Seq Analysis:

Reads were annotated to the mouse genome mm10 with Bowtie2 version 2.2.5. Output Sequence Alignment/Map (SAM) files of sequence data were converted to BAM files, which store the same data in a compressed, indexed, binary form, and then were sorted and indexed with Samtools 1.3. H3K27ac peaks were called with SPP and IDR using default settings. H3K27ac and H3K9me3 peaks were called with MACS2. Differential peak signals were determined by DiffBind 1.16.2. Spearman correlations were calculated with deepTools 2.2.2. ChIP peaks were visualized with Integrative Genomics Viewer (IGV). Coverage tracks were used to generate heatmaps and ChIP-seq profiles for multiple genes in deepTools.

Cognate Site Identification:

Cognate Site Identification was performed by incubating cell lysates containing zinc finger ATFs with a randomized library of 25-bp sequences. HEK293 cells were transiently transfected with ATFs using lipofectamine 2000 (Thermo Fisher #11668019). Cells that underwent a mock transfection (without an expression plasmid for ATFs) served as a negative control. Cells were harvested 48 hours post-transfection. Lysates were prepared by lysing $10^7$ cells in 300 µL of lysis buffer (50 mM Tris-HCl pH 7.5, 150 mM NaCl, 1% Triton X-100, and 0.1% Na deoxycholate). A 21.5 G syringe needle was used for mechanical lysis. Lysates were centrifuged at 10 k×g for 10 min to separate precipitated genomic DNA from protein constituents. The supernatant, containing ATF protein, was used for CSI. HA magnetic beads (MBL #M132-9) were added to the cell lysates for immunoprecipitation. The binding reaction between the ATFs and 100 nM synthetic DNA was performed in binding buffer (25 mM HEPES, 80 mM KCl, 0.2 mM EDTA, 1 mM $MgCl_2$, 0.1 mM $ZnSO_4$) at 25° C. After pull-down, three quick washes with 100 µL ice-cold binding buffer were performed to remove unbound DNA. Magnetic beads were resuspended in a PCR master mix (Lucigen #30035-1) and the DNA was amplified for 15 or 18 cycles. Amplified DNA was column purified (Qiagen #28106), and this enriched DNA pool was used for the subsequent round of enrichment, for a total of three rounds. After three rounds of selection, Illumina sequencing adapters and a unique 6 bp barcode for multiplexing were added by PCR amplification. The starting library (Round 0) was also barcoded. Up to 180 samples were combined and sequenced in a single HiSeq2000 lane.

Cognate Site Identification Data Analysis:

Illumina sequencing yielded ~180 million reads per lane. Reads were de-multiplexed by requiring an exact match to the 6 bp barcode and truncated to include only the 25 bp derived from the random portion of the library. On average, we obtained 709,300 reads per barcode. The occurrence of every k-mer (lengths 8 through 16 bp) was counted using a sliding window of size k. To correct for biases in our starting DNA library, we took the ratio of the counts of every k-mer to the expected number of counts in the mock-transfected control. The mock control was modeled using a $5^{th}$-order Markov Model derived from the sequencing reads corresponding to the starting library (Round 0). We then calculated a $$Z\text{-score} = (x - \mu)/\sigma$$

or (CSI score minus mean)/standard deviation for each k-mer, using the distribution of k-mer enrichment values (CSI score) for the ATF.

Bioinformatic Analysis of ATF Binding Sites:

The genomic locations of the top five or 100 high-scoring 10-bp motifs from CSI were identified in the mm10 genome by the findMotif utility from the UCSC Genome Browser. These genomic sites were annotated using Homer. Annotated sites were filtered to those within +1 kb of the TSS. For correlation to RNA-seq data, only the genes exhibiting a 2-fold upregulation or more and found significant at p<0.05 in three pairwise comparisons (C2+SKM iPS vs. Empty+SKM early; C2+SKM early vs. Empty+SKM early; C2+SKM iPS vs. Oct4+SKM iPS) were included. For the other ATF-derived iPS lines, the condition C2+SKM was replaced with C3+SKM or C4+SKM. The identified ATF target genes were included as nodes in the transcriptional network if they were previously implicated in pluripotency (Buganim et al., Cell 150(6):1209-1222, 2012; Heng et al., Cell Stem Cell 6(2):167-174, 2010; Kim et al., Cell 132(6): 1049-1061, 2008; Krentz et al., Dev Biol 377(1):67-78, 2013; Lujan et al., Nature 521(7552):352-356, 2015; Marson et al., Cell 134(3):521-533, 2008; Sharov et al., BMC Genomics 9(1):269, 2008; Shu et al., Cell 153(5):963-975, 2013; Som et al., PLoS ONE 5(12):e15165, 2010). The STRING database was used to identify protein-protein interactions.

Results

Figures 1A, 1B, 1C, 1D, 1E, 1F:
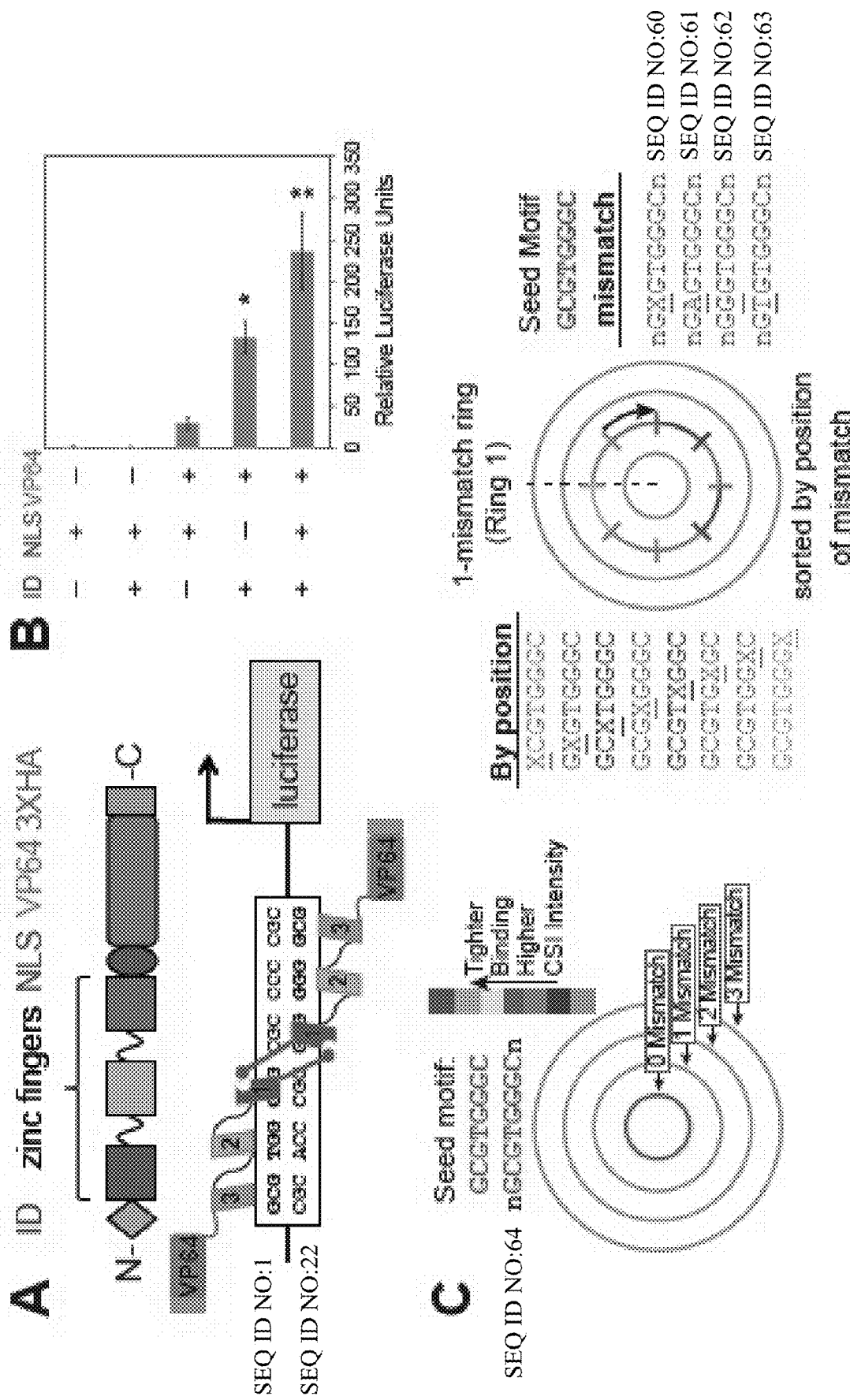
FIGS. 1A-1F illustrate exemplary ATFs designed with three zinc fingers, activation domain, and interaction domain to maximize transcriptional effects. (A) Architecture of the ATF. From N to C terminus, the ATF consists of an interaction domain (ID), three zinc fingers, a nuclear localization signal (NLS), and a VP64 activation domain. The interaction domain is a 15-amino acid peptide that enables interaction with the hydrophobic face of the first finger. The palindromic EGR1 binding site 5'-GCG-TGG-GCG-CGC-CCC-CGC-3' (SEQ ID NO: 1) was cloned upstream of a luciferase reporter for the assay in (B). (B) ATF with three zinc fingers, an interaction domain, nuclear localization signal, and a VP64 activation domain has highest level of induction. The DNA binding domain of human EGR1 was tested with and without an ID, NLS, and VP64 in the expression of a luciferase reporter in HEK293 cells (n=4, p<0.05 by one-way ANOVA with post-hoc Tukey test). (C) Specificity and Energy Landscapes (SELs). SELs display the comprehensive binding preferences of a transcription factor based on a chosen seed motif. The height of the peak indicates higher relative affinity for a given sequence. Sequences, which are one or two base pairs longer than the seed motif, are arranged in concentric rings with respect to mismatches to the seed motif. Within the mismatch rings, the sequences are arranged by position of the mismatch, then alphabetically by the actual sequence. For example, the teal section labeled with the curved arrow displays all the sequences with a mismatch at the second position. (D) The interaction domain allows the ATF to bind a greater number of sequences. The DNA binding domain of EGR1 fused to an ID binds sites recognized by a dimer, which is not recognized by a monomer. The SEL displayed shows data after three rounds of enrichment. (E) RNA-seq results show that the 3-zinc finger ATF with an ID upregulates transcription of the largest number of genes compared to the mock transfected control. Among the upregulated genes, 18 genes are expressed 50-fold or more by the 3-zinc finger ATF with an ID. All ATFs in this assay have an NLS and VP64 (n=1, p<0.0005). (F) Design of the ATF library. The residues that confer specificity (−1, 2, 3, and 6 positions) were randomized to amino acids represented by VNN codons. A library with a complexity of $2.6 \times 10^6$ members was created. The zinc finger scaffold comes from human EGR1 and is fused to the ID described in (A), NLS, and VP64. Sequencing of 100 ATFs from the library shows all 16 amino acids represented by the recognition residues. This sample size is representative of the library at a 95% confidence interval and a margin of error of 9.8%.
Figures 8A, 8B, 8C, 8D, 8E, 8F:
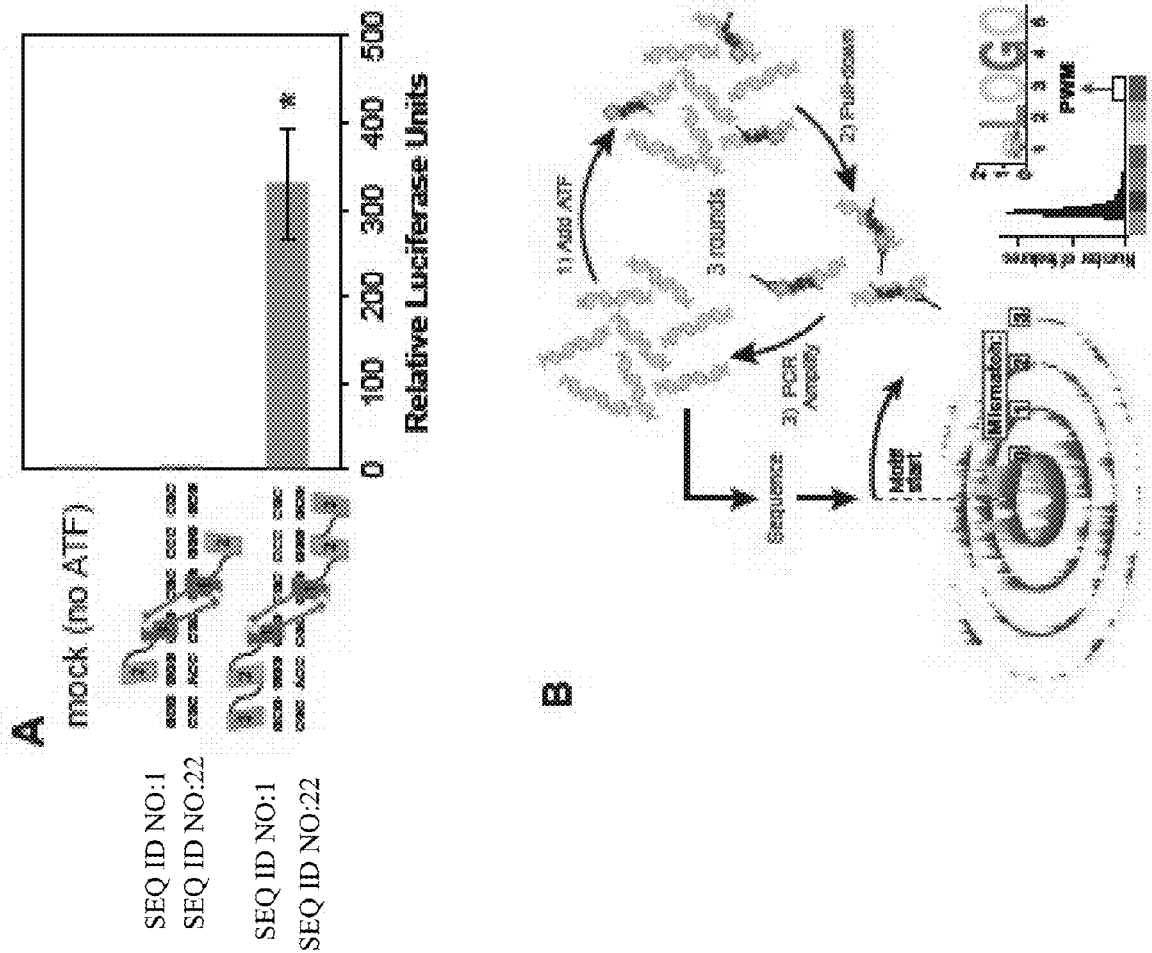
FIGS. 8A-8F demonstrate that the three zinc finger design has greatest impact on expression profile. (A) The three-zinc finger ATF induces expression 329-fold over the mock control, while the two-zinc finger ATF induces expression 2-fold in a luciferase assay performed in HEK293 cells. The DNA-binding domain comes from either the first two or all three zinc fingers of EGR1. Each ATF is also comprised of an ID, NLS, and VP64 (n=4, p<0.01 by one-way ANOVA with post-hoc Tukey test). (B) Cognate site identification (CSI). This in vitro method of determining the sequence specificity of DNA-binding factors involves incubating the transcription factor (TF) with a randomized library of 25-bp sequences. The TF-DNA complexes are captured with an antibody, and bound DNA is PCR-amplified for the next round of selection. Three rounds of selection are performed, and all three rounds are sequenced in a high-throughput manner to obtain Specificity and Energy Landscapes (SELs). Data obtained from sequencing can be used to generate position weight matrices. (C) The binding specificity of the first two zinc fingers of EGR1 changes without the third zinc finger. The first two zinc fingers of EGR1 bind 5'-TGG-GCG-3'; however, in the absence of the third zinc finger, the cognate site becomes 5'-GGG-ATC-3'. The interaction domain alters the binding preferences slightly, conferring greater specificity. The SEL displays data from three rounds of enrichment. (D) The binding specificity of the three zinc fingers of EGR1 is nearly identical when the seed motif is the 9-bp cognate site. The SEL displays data after three rounds of enrichment. (E) RNA-seq of HEK293 cells transfected with various ATFs show that the three-zinc finger ATF with an ID activates the greatest number of genes (n=1, p<0.0005). The heatmap displays 174 differentially regulated genes. The four different ATFs are: two-zinc fingers with and without an ID and three-zinc fingers with and without an ID. The DNA-binding domain is derived from EGR1, which is the first labeled row on the heatmap to highlight that the ATFs are overexpressed. All ATFs have an NLS and a VP64 activation domain. (F) Comparison of the number of differentially expressed genes when introduced with an ATF shows that the three-zinc finger ATF with the interaction domain affects the greatest number of genes (fold change >2, p<0.0005).

ATF Architecture and Library Design:

To determine the best architecture for a zinc finger ATF library, we tested the impact of each modular domain on the level of induction. The zinc finger backbone is derived from human Early Growth Response 1 (EGR1) (also known as Transcription Factor ZIF268), a well-studied scaffold for zinc finger ATFs. EGR1 comprises C2H2-type zinc fingers which bind to DNA motifs having the sequence 5'-GCG(T/G)GGGCG-3'. We fused VP64, a tetrameric repeat of the 11-amino acid activation region of VP16, a potent transactivation domain from the herpes simplex virus (FIG. 1A) (Triezenberg et al., 1988). To the N-terminus of the zinc fingers, we attached a 15-amino acid peptide that serves as an interaction domain (ID), reported to allow dimerization of the ATF to another ATF with the hydrophobic surface of the first zinc finger of EGR1 (Wang et al., 2001). This ID adds a novel layer of control to the ATF library by allowing the ATFs to capitalize on cooperative binding (Moretti and Ansari, 2008). The nuclear localization signal (NLS) comes from the native NLS of EGR1. A palindromic cognate site for EGR1 was placed upstream of a luciferase reporter to test the contribution of each domain in activating the reporter. The luciferase assay demonstrated that the activation domain is essential and the ID enhances activation about 8-fold (FIG. 1B). Nuclear localization did not dramatically enhance activation because the ATF is 23 kDa, small enough to diffuse through the nuclear pore passively (Wang and Brattain, 2007); however, we retained the NLS in the architecture to maximize the ATF's level of induction. When the ATF is too large to passively diffuse into the nucleus, an NLS is advantageously provided in the ATF. Because we wanted to create an ATF library of high complexity, which was as comprehensive as practically possible, it was necessary to determine the minimum number of zinc fingers required to have a transcriptional effect. Toward this end, we compared a two-zinc finger ATF with a three-zinc finger ATF in a luciferase assay (FIG. 8A). The two-zinc finger ATF could only activate the luciferase reporter two-fold over background, while the three-zinc finger ATF was capable of activating 329-fold over background, so we used the three-zinc finger scaffold in the final design.

Next, we identified the in vitro binding preferences for two- and three-zinc finger ATFs with and without the ID. Cognate site identification (CSI) enables the discovery of sequence specificity out of a library of 25-bp sequences (FIG. 8B) (Rodriguez-Martinez et al., 2016; Tietjen et al., 2011). This method involves multiple rounds of enrichment for sequences bound by the DNA-binding factor of interest. The enriched sequences of each round can be multiplexed and sequenced in a high-throughput manner. Rather than focusing on single consensus motifs, the comprehensive binding site specificity of the factor can be displayed in a Specificity and Energy Landscape (SEL) (FIG. 1C). Although the SELs for the ATFs with and without an ID are nearly identical for the EGR1 cognate site (FIG. 8D), there is a set of sequences only targeted by the ATF with the ID (FIG. 1D). Interestingly, the two-zinc finger ATFs target a distinct motif, rather than the expected 5'-(T/G)GG-GCG-3' site that is bound by the first two fingers of EGR1, emphasizing the dependency of neighboring zinc fingers on binding preferences (Isalan et al., 1997).

To determine how the ATFs impact global transcription, we performed RNA-seq on four ATFs with different architectures. The ATFs either had the first two or all three zinc fingers of EGR1 as the DBD, with and without the ID. Compared to the mock control, the two-zinc finger ATFs had little impact on altering the transcriptional profile (FIGS. 1E, 8E, and 8F). On the other hand, the three-zinc finger ATF with the ID altered the expression of 104 genes (100 upregulated, 4 downregulated) and the three-zinc finger ATF without the ID altered the expression of 57 genes (55 upregulated, 2 downregulated) (FIG. 1E). Most of the genes were upregulated compared to the mock control, and the repressed genes could be attributed to indirect effects of the ATFs. As the three-zinc finger ATF with the ID was capable of binding as a monomer or dimer, most of the subset of genes upregulated by the three-zinc finger ATF without the ID could also be activated by the three-zinc finger ATF with the ID (FIG. 8E). For 27 genes, the ID increased the level of induction triggered by the three-zinc finger ATF. Taking all these results into consideration, the ATF library was created on a scaffold which includes, from N to C terminus: an interaction domain, three zinc fingers with the backbone of EGR1, NLS from EGR1, VP64 activation domain, and a 3× hemagglutinin (HA) tag.

The library was created by incorporating VNN codons, where V is A, C, or G, at the recognition residues (−1, 2, 3, and 6). Use of VNN codons prevents incorporation of premature stop codons within the ORF, and permits the incorporation of 16 different amino acids (FIG. 1F). The library was cloned into a second-generation lentiviral system to ensure efficient delivery to mammalian cells. The ATF is driven by the constitutively active EF-1α promoter, which resists silencing in mammalian cells compared to other constitutive promoters (Teschendorf et al., 2001). The sequence space for all 9-bp sequences is $2.62 \times 10^5$ different sequence permutations. We created an ATF library with a complexity of $2.62 \times 10^6$, ten times the targeted sequence space. Sanger sequencing of 100 clones confirmed success of our design with incorporation of all 16 amino acids at each recognition residue, suggesting diverse representation in the library (FIG. 1F and Table 4).

TABLE 4

| | Diversity of the ATF library | | | | | | | | | | |
|---|---|---|---|---|---|---|---|---|---|---|---|
| | Finger 1 | | | | Finger 2 | | | | Finger 3 | | |
| | −1 | 2 | 3 | 6 | −1 | 2 | 3 | 6 | −1 | 2 | 3 | 6 |
| 1 | A | P | G | S | Q | L | K | V | V | H | T | R |
| 2 | R | T | R | G | L | Q | A | Q | N | D | P | L |
| 3 | K | R | G | T | T | L | P | T | E | M | H | H |
| 4 | G | G | L | R | D | M | A | P | N | H | L | L |
| 5 | L | R | L | Q | L | K | I | L | I | T | L | T |
| 6 | V | V | R | R | T | P | I | Q | T | P | V | I |
| 7 | G | T | V | V | E | E | Q | K | S | L | P | T |
| 8 | I | T | M | G | G | P | T | P | G | E | T | G |
| 9 | M | M | T | G | D | R | P | S | L | D | M | R |
| 10 | G | A | V | A | R | P | I | D | R | I | D | N |
| 11 | T | K | V | E | T | R | V | V | L | T | L | L |
| 12 | M | V | R | T | D | N | N | A | K | I | I | Q |
| 13 | N | H | R | A | G | A | G | D | L | R | Q | P |
| 14 | V | G | E | P | L | P | N | I | Q | E | G | K |
| 15 | V | E | K | K | R | H | R | R | H | T | G | K |
| 16 | G | G | R | P | T | V | Q | I | R | E | V | H |
| 17 | G | L | E | A | P | S | A | S | Q | L | I | Q |
| 18 | D | I | T | I | I | N | D | G | L | V | K | T |
| 19 | R | V | D | T | G | A | L | K | S | T | P | P |

TABLE 4-continued

| | Diversity of the ATF library | | | | | | | | | | |
|---|---|---|---|---|---|---|---|---|---|---|---|
| | Finger 1 | | | | Finger 2 | | | | Finger 3 | | |
| | −1 | 2 | 3 | 6 | −1 | 2 | 3 | 6 | −1 | 2 | 3 | 6 |
| 20 | P | K | G | R | P | K | N | L | R | N | T | R |
| 21 | R | A | G | H | T | P | I | I | K | E | H | D |
| 22 | K | G | H | V | R | H | P | H | S | T | I | R |
| 23 | E | V | N | Q | T | N | T | L | A | Q | P | T |
| 24 | E | P | R | T | L | V | P | T | V | N | T | T |
| 25 | V | A | G | A | A | T | I | Q | A | A | R | K |
| 26 | A | S | V | I | T | P | G | P | V | R | G | E |
| 27 | T | A | V | E | S | S | M | G | V | P | V | T |
| 28 | V | D | T | V | D | D | E | D | E | R | K | E |
| 29 | T | S | V | G | Q | A | T | R | P | T | L | D |
| 30 | H | I | V | V | T | T | H | R | T | V | R | Q |
| 31 | K | R | P | V | T | E | E | P | D | V | H | K |
| 32 | G | N | P | I | P | T | G | E | Q | P | G | G |
| 33 | R | G | G | G | A | H | L | T | S | A | P | H |
| 34 | R | V | L | T | R | R | S | G | R | I | L | S |
| 35 | R | I | R | I | P | P | P | P | P | L | L | P |
| 36 | A | L | I | T | L | I | L | P | V | N | R | H |
| 37 | K | L | R | V | I | G | S | H | H | H | P | T |
| 38 | I | A | D | A | T | K | A | Q | N | K | K | T |
| 39 | K | E | I | A | P | N | S | R | H | T | R | H |
| 40 | G | G | P | N | H | P | M | A | P | T | N | L |
| 41 | S | R | G | V | A | R | T | K | L | P | P | A |
| 42 | L | R | P | R | K | Q | N | N | S | R | P | H |
| 43 | N | G | G | P | H | P | P | L | R | E | Q |  |
| 44 | P | R | R | K | D | H | G | R | P | R | T | M |
| 45 | K | E | H | G | R | D | A | L | D | T | S | S |
| 46 | L | G | T | L | L | P | T | Q | I | T | I | N |
| 47 | P | K | T | G | A | G | H | E | Q | S | T | G |
| 48 | V | D | E | G | T | R | E | R | H | T | L | N |
| 49 | L | D | R | L | D | P | P | A | R | T | D | P |
| 50 | G | R | D | I | N | A | P | P | Q | I | I | V |
| 51 | V | G | V | P | L | T | Q | I | K | T | I | T |
| 52 | L | S | L | G | N | T | Q | S | S | T | I | A |
| 53 | I | L | A | G | M | K | P | T | D | R | R | G |
| 54 | R | R | A | G | D | L | K | R | E | K | E | P |
| 55 | R | R | L | R | T | T | L | V | H | H | K | P |
| 56 | A | L | P | G | H | G | P | L | S | T | A | I |
| 57 | P | R | E | I | I | K | K | P | D | N | I | M |
| 58 | G | M | S | Q | Q | P | D | L | K | Q | K | N |
| 59 | I | R | G | V | R | L | L | R | Q | T | P | I |
| 60 | R | R | G | G | I | T | P | E | P | L | R | K |
| 61 | I | G | A | G | S | N | Q | A | R | I | H | R |
| 62 | Q | R | E | V | N | K | T | T | D | T | Q | H |
| 63 | K | I | T | A | H | R | I | N | A | P | G | E |
| 64 | R | G | G | E | L | P | L | I | N | R | D | N |
| 65 | G | G | Q | R | L | H | P | M | K | R | N | T |
| 66 | R | I | Q | R | P | P | I | T | L | L | T | I |
| 67 | I | T | P | L | T | P | P | L | T | T | M | D |
| 68 | V | S | T | V | P | A | T | N | R | I | T | I |
| 69 | K | L | L | R | V | T | M | L | K | R | V | G |
| 70 | A | L | V | L | H | S | H | H | A | A | G | R |
| 71 | S | Q | E | A | D | R | I | S | L | P | A | H |
| 72 | K | D | G | G | T | I | A | G | V | G | L | V |
| 73 | R | R | K | P | P | T | K | R | E | P | T | Q |
| 74 | T | D | R | Q | P | V | A | K | K | T | K | T |
| 75 | D | L | V | E | T | P | T | Q | M | L | D | I |
| 76 | I | G | R | R | T | L | P | A | D | Q | K | I |
| 77 | K | M | T | L | A | N | L | S | K | R | P | S |
| 78 | V | E | P | P | I | V | G | Q | E | T | I | E |
| 79 | G | L | T | E | Q | V | A | E | K | R | L | P |
| 80 | V | P | E | G | A | K | N | Q | D | L | G | I |
| 81 | R | I | P | K | R | P | L | L | T | E | G | R |
| 82 | G | G | R | V | I | P | R | N | T | P | G | T |
| 83 | G | A | I | G | S | P | I | D | A | R | P | G |
| 84 | L | L | A | N | P | R | R | L | T | I | H | S |
| 85 | R | S | M | S | I | I | P | D | H | T | P | T |
| 86 | D | V | R | R | E | A | P | G | P | I | L | V |
| 87 | E | G | G | N | L | R | K | N | T | L | A | S |
| 88 | V | G | G | D | P | R | L | V | S | E | K | A |
| 89 | V | R | V | R | Q | P | R | G | A | R | S | G |
| 90 | P | K | R | R | K | G | G | V | K | D | L | A |
| 91 | V | M | M | G | I | L | H | Q | P | P | T | T |
| 92 | L | T | P | V | H | P | A | S | L | A | D | A |
| 93 | G | M | R | I | I | V | A | V | T | I | E | L |

TABLE 4-continued

Diversity of the ATF library

| | Finger 1 | | | | Finger 2 | | | | Finger 3 | | | |
|---|---|---|---|---|---|---|---|---|---|---|---|---|
| | -1 | 2 | 3 | 6 | -1 | 2 | 3 | 6 | -1 | 2 | 3 | 6 |
| 94 | P | G | L | K | D | S | L | T | P | E | A | H |
| 95 | N | V | R | V | R | R | P | K | R | G | I | R |
| 96 | I | R | L | M | P | A | P | A | D | E | D | K |
| 97 | R | G | A | A | P | A | K | P | T | P | K | Q |
| 98 | V | E | I | G | Q | I | Q | P | P | I | L | T |
| 99 | E | R | A | P | N | P | A | P | L | R | L | D |
| 100 | P | D | A | R | T | G | T | N | T | I | K | P |

Figures 2A, 2B, 2C, 2D, 2E:
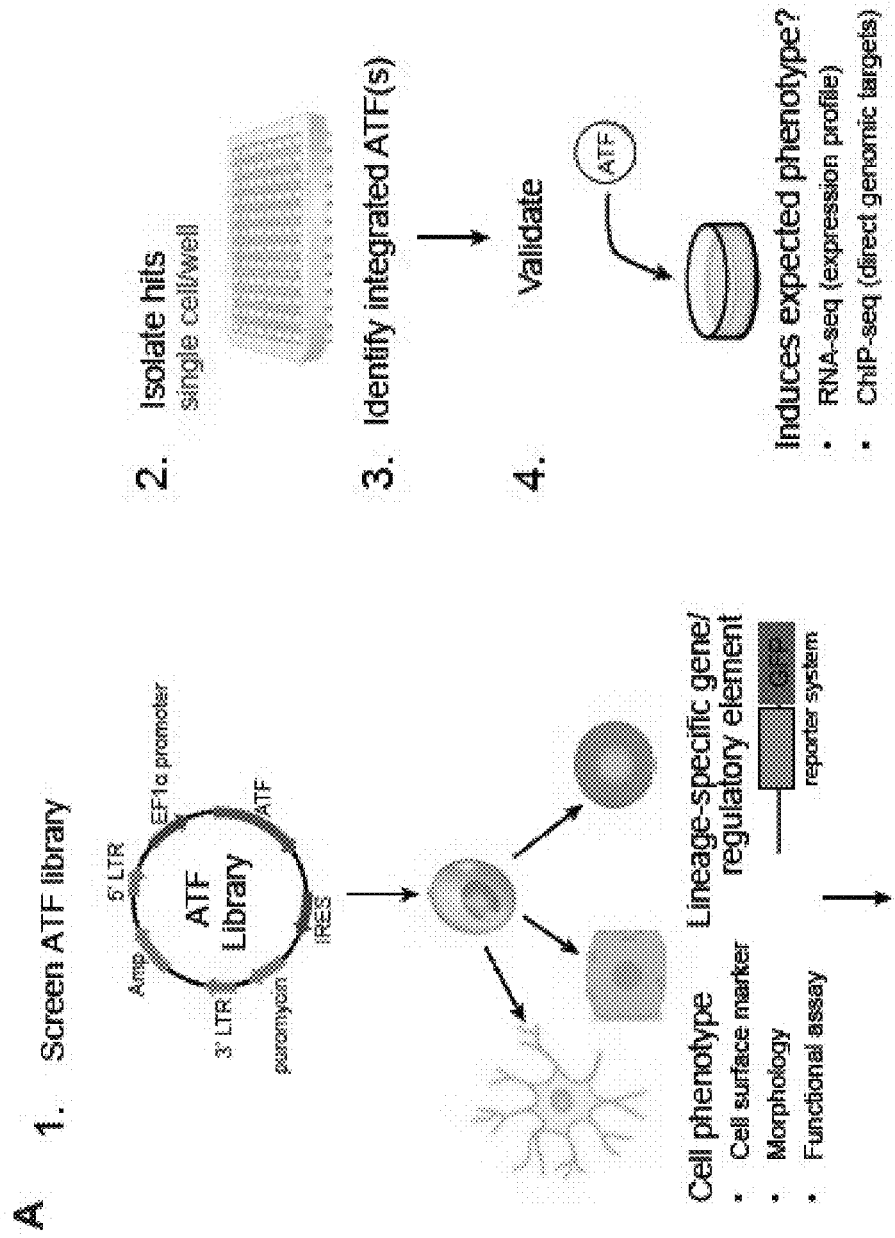
FIGS. 2A-2E demonstrate an application of the ATF library in induction of pluripotency. (A) Genetic screen with an ATF library. (1) The ATF library was cloned into pSIN, a second generation lentiviral vector. The ATF is driven by a constitutive promoter, EF1α. The puromycin resistance gene enables selection of cells with integration events. The screen can be performed on cells with a robust change in phenotype, such as the upregulation of a cell surface marker or a distinct change in morphology or function. Alternatively, a lineage-specific reporter system can be used to identify hits, or successful cell fate conversions. (2) Hits from the library are isolated as single cells, such that combinations of ATFs, if any, can be captured. (3) Integrated ATFs are identified from single cells by two-step nested PCR. (4) Identified ATFs are retested to validate whether they recapitulate the phenotype seen in the original screen. Once validated, RNA-seq can be performed to determine how the ATFs change the expression profile of the cell. Additionally, ChIP-seq can be performed to determine the direct genomic targets. (B) Testing the ATF library in mouse embryonic fibroblasts (MEFs) bearing a reporter for Oct4. These MEFs have a Tomato red reporter gene at the ROSA locus. Upon induction of Oct4, a tamoxifen-inducible Cre recombinase (MerCreMer) is co-expressed. The addition of 4-hydroxy-tamoxifen to the system results in the excision of Tomato red, which allows for the expression of GFP, thereafter. (C) Flow cytometry results at Day 15 after introduction of transcription factors. Tomato$^-$GFP$^+$ MEFs transduced with the ATF library, Sox2, Klf4, and c-Myc were isolated as single cells for further analysis. MEFs treated with Oct4, Sox2, Klf4, and c-Myc (OSKM) were used as a positive control. Untreated MEFs served as a negative control. The percentage of Tomato$^-$GFP$^+$ (Q3) was higher in the ATF library treated cells when compared to the OSKM control. Cells, which were double positive (Tomato$^+$GFP$^+$; Q2), were also collected as those in which Oct4 was expressed later than the Tomato$^-$GFP$^+$ cells (Q3). Percentages in each quadrant are displayed under the quadrant number. (D) ATFs were identified from eleven single cells from (C) by two-step nested PCR of genomic DNA. Unique ATFs are depicted with a different color. One ATF had a frameshift mutation shortly after the ID, coding for a protein, which does not have a zinc finger structure. A few ATFs, notably the blue and orange ATFs, are expressed in most of the cells analyzed. The ATF with the frameshift mutation is also expressed in many of the hits. All cells except #4 were collected as Tomato$^-$GFP$^+$ cells. Cell #4 was Tomato$^+$GFP$^+$ at Day 15. (E) Three combinations of ATFs (#2, #3, and #4) successfully replaced Oct4 in inducing pluripotency with Sox2, Klf4, and c-Myc. Micrographs of MEFs before induction of exogenous factors are Tomato$^+$GFP$^-$. iPS cells generated with ATFs are similar to those generated with OSKM and are Tomato$^-$GFP$^+$. Two ATFs in each combination are the same (blue and orange). Bars=100 µm.

ATF Library can Activate the Pluripotency Network:

We asked whether ATFs in the library could replace the key regulator of pluripotency, Oct4, in the cocktail of transcription factors that triggers the pluripotency network, Oct4, Sox2, Klf4, and c-Myc (OSKM). In order to test a library, capable of sampling thousands of sites in the genome, it was necessary to have a robust read-out of positive phenotypes (FIG. 2A). Toward this end, we used mouse embryonic fibroblasts (MEFs) isolated from a transgenic mouse line that allows lineage tracing of endogenous Oct4 transcription (FIG. 2B) (Greder et al., 2012). In these cells, tamoxifen-inducible Cre recombinase (MerCreMer) is expressed when the endogenous pluripotency associated gene, Oct4, is transcribed. In the presence of 4-hydroxytamoxifen, the recombinase removes Tomato from the ROSA locus, and transmembrane-bound GFP is expressed. Consequently, Tomato$^+$GFP$^-$ MEFs become Tomato$^-$GFP$^+$ cells after endogenous Oct4 is activated, and GFP expression is maintained in all their cell progeny.

Figures 9A, 9B, 9C, 9D:
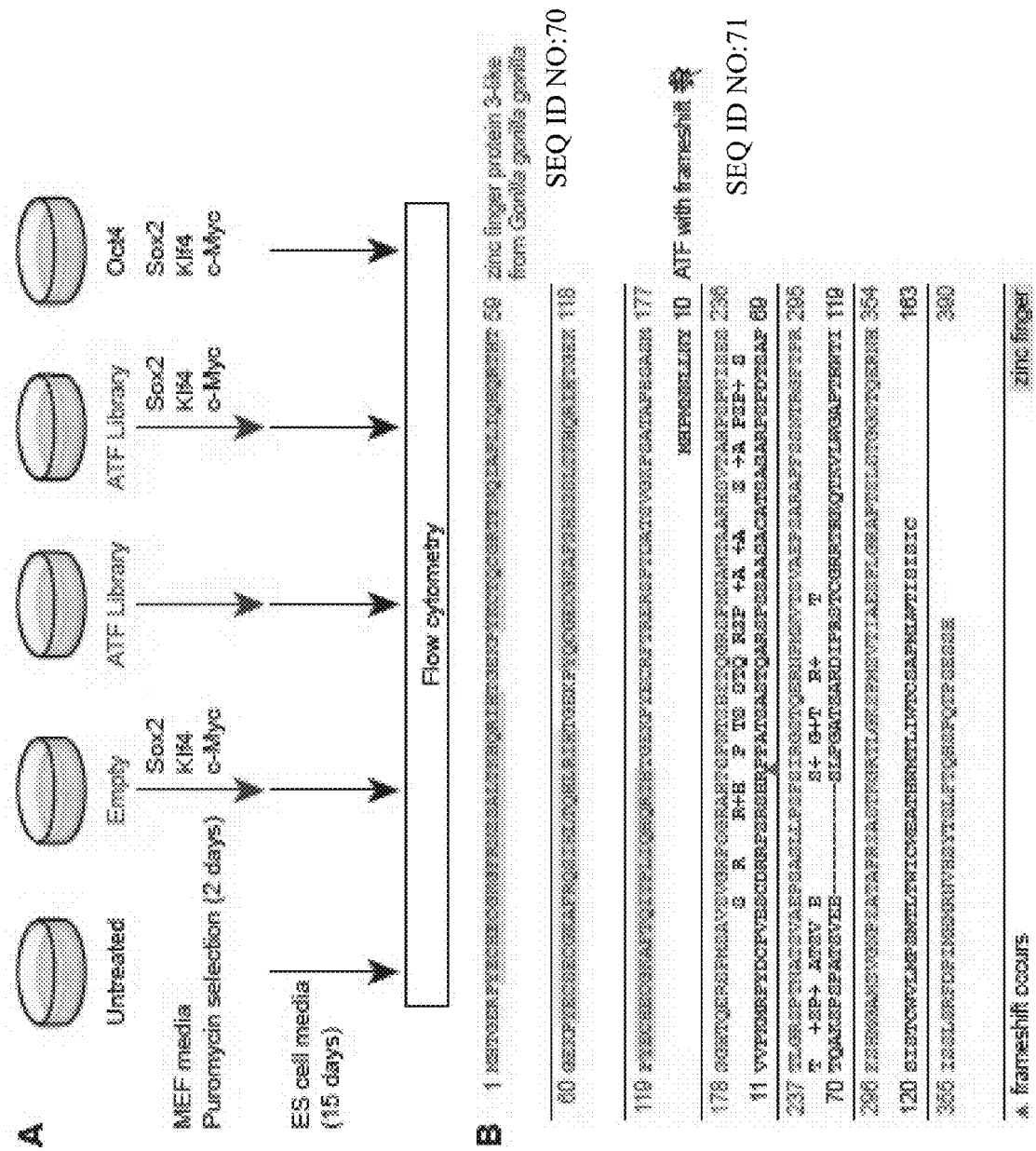
FIGS. 9A-9D demonstrate that iPS lines expanded from the ATF screen express pluripotency markers. (A) Conditions for the ATF library screen. Oct4, Sox2, Klf4, and c-Myc were delivered by retrovirus, where indicated. Second generation lentiviruses (highlighted in blue) were used to deliver the ATF library and an empty ORF control to account for false positive events that may arise from integration of a strong constitutive promoter at relevant genomic sites. Puromycin selection was performed for two days in MEFs treated with lentiviruses to select for integration events. After 15 days of culture in ES cell media, the Tomato$^-$GFP$^+$ cells were isolated by flow cytometry. (B) Homologous region between the ATF with the frameshift mutation and zinc finger protein 3-like from *Gorilla gorilla* is C-terminal to the DNA-binding domain. The *G. gorilla* protein (blue) contains 34 amino acids that match the ATF with the frameshift mutation (red). Within the homologous region, there are 10 amino acids, which contain similar side chains (+). Highlighted in yellow are the five zinc fingers of the *G. gorilla* protein. The position at which the single nucleotide frameshift mutation occurs in the ATF is indicated with a red arrow (after 34th amino acid). (C) RT-qPCR results of pluripotency markers, Oct4, Sox2, Nanog, Lin28a, Esrrb, and Utf1, in colonies of iPS cells generated with the ATF library+SKM (LSKM) show comparable levels of endogenous gene expression when compared to levels in mouse ES cells and iPS cells generated with OSKM. These colonies are derived from iPS cells expressing mixed combinations of ATFs. For each gene, transcript levels for MEFs are set to 1. Transcript levels are normalized to Gapdh. (D) Doubling time in hours of iPS cells generated with OSKM and ATFs+SKM. Values are mean±SEM (n=3).

The ATF library was transduced in MEFs (MOI=3) with Sox2, Klf4, and c-Myc (SKM). As a positive control, we delivered OSKM to MEFs (FIG. 9A). To account for reprogramming events induced by SKM, alone, we delivered lentivirus with an empty ORF in place of the ATF. The lentivirus with the empty ORF accounted for false positive events that could arise from lentiviral delivery or integration of a strong constitutive promoter at relevant genomic sites. We also included a condition with the ATF library alone, as well as untreated MEFs. The lentiviruses encode a puromycin resistance gene, used for selection of cells with integration events. After 15 days in culture with ES cell media, Tomato$^-$GFP$^+$ cells were sorted by flow cytometry. Compared to OSKM, MEFs treated with the ATF library underwent significant cell death. Among those that survived, 0.229% of the ATF library+SKM cells were Tomato$^-$GFP$^+$, compared to 0.033% for OSKM, and 0% for untreated MEFs (FIG. 2C). No Tomato$^-$GFP$^+$ cells were observed in the cells treated with ATF library alone, or Empty+SKM control. Tomato$^-$GFP$^+$ cells from the condition of ATF library+SKM were isolated as single cells for further analysis. Of the ATF library+SKM cells, a small fraction (0.8%) of cells were Tomato$^+$GFP$^+$. Because the half-life of Tomato fluorescent protein is ~24 hours, there is a period of time after Oct4 is activated when the cells are double positive. We sorted these cells separately to determine whether the ATFs expressed in the double positive cells were different from those expressed in the Tomato$^-$GFP$^+$ cells.

Since multiple ATFs can potentially act in concert to activate the pluripotency network, we identified the ATFs from single cells to capture ATF combinations that had been sufficient, in concert with exogenous SKM, to activate endogenous Oct4 transcription and induce GFP expression. Preliminary evaluation of iPS colonies derived from the screen with mixed combinations of ATFs showed high levels of pluripotency markers (FIG. 9C). Eleven isolated GFP$^+$ cells were subjected to two-step nested PCR of genomic DNA, and sequencing results revealed 11 unique combinations of ATFs (FIG. 2D and Table 5). The range of ATFs varied between two and ten ATFs within a single cell. ZFATF1 (blue) and ZFATF2 (orange) appeared in most of the combinations; however, an additional ATF was necessary for conversion to a bona fide iPS cell state. One ATF from cells #4-11 obtained a frameshift mutation near the N-terminus, resulting in a 163-aa protein product that does not code for a zinc finger protein (ZFATF5). Only the interaction domain, as well as the first 19 amino acids of the first zinc finger, remain intact. Protein homology at the primary structure revealed that the ATF with the frameshift mutation has low homology to zinc finger protein 3-like from *Gorilla gorilla* (*G. gorilla*); however, the homology occurs not in the DBD of the *G. gorilla* protein, but in the region C-terminal to the DBD (FIG. 9B). Homology to this uncharacterized transcription factor suggests that the ATF with the frameshift mutation retains a functional role, although the mechanism of regulating gene expression is not obvious from the primary structure.

TABLE 5

Experimental conditions with trial numbers.

| Condition | Alias | iPS cells Trials generated | | Lentivirus | Retrovirus |
|---|---|---|---|---|---|
| 1 | OSKM | 5 | yes (n = 5) | N/A | Oct4, Sox2, Klf4, c-Myc |
| 2 | Empty + SKM | 5 | no | Empty | Sox2, Klf4, c-Myc |
| 3 | C2 + SKM | 5 | yes (n = 5) | ZFATF1, ZFATF2, ZFATF3 | Sox2, Klf4, c-Myc |
| 4 | C3 + SKM | 5 | yes (n = 5) | ZFATF1, ZFATF2, ZFATF4 | Sox2, Klf4, c-Myc |
| 5 | C4 + SKM | 5 | yes (n = 5) | ZFATF1, ZFATF2, ZFATF5 | Sox2, Klf4, c-Myc |
| 6 | ZFATF1 + ZFATF2 + SKM | 3 | no | ZFATF1, ZFATF2 | Sox2, Klf4, c-Myc |
| 7 | ZFATF1 + ZFATF3 + SKM | 3 | no | ZFATF1, ZFATF3 | Sox2, Klf4, c-Myc |
| 8 | ZFATF1 + ZFATF4 + SKM | 3 | yes (n = 1) | ZFATF1, ZFATF4 | Sox2, Klf4, c-Myc |
| 9 | ZFATF1 + ZFATF5 + SKM | 1 | no | ZFATF1, ZFATF5 | Sox2, Klf4, c-Myc |

TABLE 5-continued

Experimental conditions with trial numbers.

| Condition | Alias | Trials | iPS cells generated | Lentivirus | Retrovirus |
|---|---|---|---|---|---|
| 10 | ZFATF2 + ZFATF3 + SKM | 3 | no | ZFATF2, ZFATF3 | Sox2, Klf4, c-Myc |
| 11 | ZFATF2 + ZFATF4 + SKM | 3 | no | ZFATF2, ZFATF4 | Sox2, Klf4, c-Myc |
| 12 | ZFATF2 + ZFATF5 + SKM | 2 | no | ZFATF2, ZFATF5 | Sox2, Klf4, c-Myc |
| 13 | ZFATF1 + SKM | 3 | no | ZFATF1 | Sox2, Klf4, c-Myc |
| 14 | ZFATF2 + SKM | 3 | no | ZFATF2 | Sox2, Klf4, c-Myc |
| 15 | ZFATF3 + SKM | 3 | no | ZFATF3 | Sox2, Klf4, c-Myc |
| 16 | ZFATF4 + SKM | 3 | no | ZFATF4 | Sox2, Klf4, c-Myc |
| 17 | ZFATF5 + SKM | 1 | no | ZFATF5 | Sox2, Klf4, c-Myc |
| 18 | C2 + SK | 1 | no | ZFATF1, ZFATF2, ZFATF3 | Sox2, Klf4 |
| 19 | C2 | 1 | no | ZFATF1, ZFATF2, ZFATF3 | N/A |
| 20 | C3 + SK | 3 | no | ZFATF1, ZFATF2, ZFATF4 | Sox2, Klf4 |
| 21 | C3 | 1 | no | ZFATF1, ZFATF2, ZFATF4 | N/A |
| 22 | C4 + SK | 3 | no | ZFATF1, ZFATF2, ZFATF5 | Sox2, Klf4 |
| 23 | C4 | 3 | no | ZFATF1, ZFATF2, ZFATF5 | N/A |
| 24 | C1 + SKM | 5 | no | ZFATF6, ZFATF7 | Sox2, Klf4, c-Myc |
| 25 | C5 + SKM | 5 | no | ZFATF4, ZFATF5, ZFATF8 | Sox2, Klf4, c-Myc |
| 26 | C6 + SKM | 3 | no | ZFATF1, ZFATF2, ZFATF5, ZFATF6 | Sox2, Klf4, c-Myc |
| 27 | C7 + SKM | 3 | no | ZFATF1, ZFATF2, ZFATF3, ZFATF5, ZFATF6, ZFATF7 | Sox2, Klf4, c-Myc |
| 28 | C8 + SKM | 2 | no | ZFATF1, ZFATF2, ZFATF3, ZFATF5, ZFATF6, ZFATF7, ZFATF9 | Sox2, Klf4, c-Myc |
| 29 | C9 + SKM | 2 | no | ZFATF1, ZFATF2, ZFATF3, ZFATF5, ZFATF6, ZFATF8, ZFATF9, ZFATF11, ZFATF12 | Sox2, Klf4, c-Myc |
| 30 | C10 + SKM | 2 | no | ZFATF1, ZFATF2, ZFATF3, ZFATF4, ZFATF5, ZFATF6, ZFATF7, ZFATF9, ZFATF10 | Sox2, Klf4, c-Myc |
| 31 | C11 + SKM | 2 | no | ZFATF1, ZFATF2, ZFATF3, ZFATF5, ZFATF6, ZFATF7, ZFATF8, ZFATF9, ZFATF10, ZFATF11 | Sox2, Klf4, c-Myc |
| 32 | C1 + SK | 3 | no | ZFATF6, ZFATF7 | Sox2, Klf4 |
| 33 | C1 | 1 | no | ZFATF6, ZFATF7 | N/A |
| 34 | C5 + SKM | 1 | no | ZFATF4, ZFATF5, ZFATF8 | Sox2, Klf4 |
| 35 | C5 | 1 | no | ZFATF4, ZFATF5, ZFATF8 | N/A |
| 36 | ZFATF1 | 1 | no | ZFATF1 | N/A |
| 37 | ZFATF2 | 1 | no | ZFATF2 | N/A |
| 38 | ZFATF5 | 1 | no | ZFATF5 | N/A |
| 39 | ZFATF1-5 + SKM | 2 | no | ZFATF1, ZFATF2, ZFATF3, ZFATF4, ZFATF5 | Oct4, Sox2, c-Myc |
| 40 | C2 + OSKM | 1 | yes (n = 1) | ZFATF1, ZFATF2, ZFATF3 | Oct4, Sox2, Klf4, c-Myc |
| 41 | C3 + OSKM | 1 | no | ZFATF1, ZFATF2, ZFATF4 | Oct4, Sox2, Klf4, c-Myc |
| 42 | GFP | 5 | no | N/A | GFP |

Figures 3A, 3B, 3C, 3D:
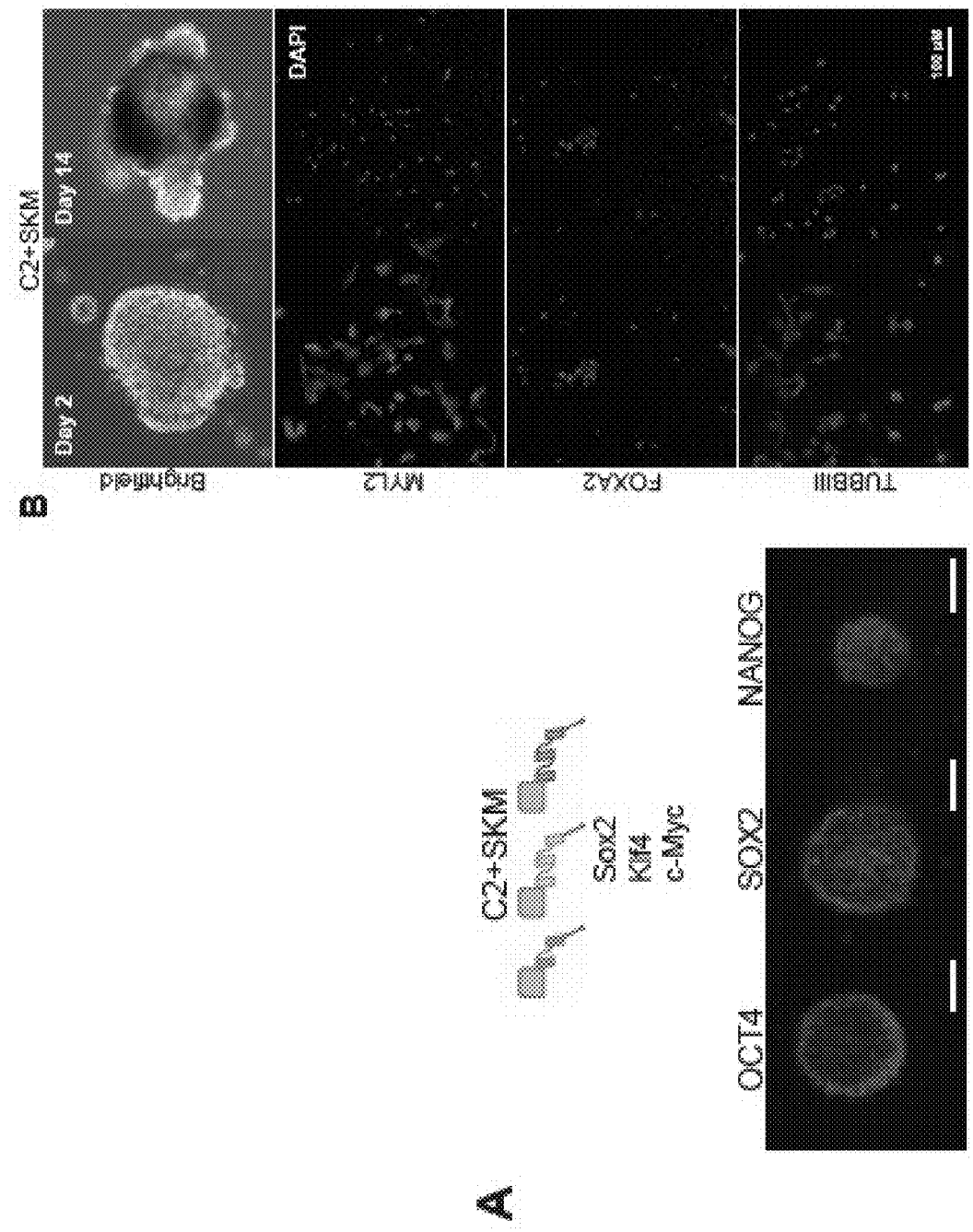
FIGS. 3A-3D demonstrate that iPS (induced pluripotent stem) cells generated with ATFs are pluripotent. (A) Immunofluorescence staining of iPS colonies with OCT4, SOX2, and NANOG. These iPS cells were generated with Combination #2+SKM. Bars=100 µm. (B) Embryoid bodies were cultured with iPS cells generated with Combination #2+SKM. Micrographs were taken at Day 2 and Day 14 of differentiation. Immunofluorescence staining for MYL2 (mesoderm), FOXA2 (endoderm), and TUBB3 (ectoderm) of embryoid body outgrowths show potential to differentiate into all three germ layers. Each micrograph was also stained with DAPI to label nuclei. Bars=100 µm. (C) Embryoid bodies derived from Combination #2+SKM iPS cells differentiate into all three germ layers. RT-qPCR results from RNA harvested from ATF-generated iPS cells and embryoid bodies derived from them. Markers for mesoderm are brachyury (T), NK2 homeobox 5 (Nkr2-5), and kinase insert domain protein receptor (Kdr). Markers for endoderm are alpha fetoprotein (Afp), transthyretin (Ttr), and forkhead box A2 (Foxa2). Markers for ectoderm are nestin (Nes), neurofilament, light polypeptide (Nefl), and SRY-box 17 (Sox17). Values are $\log_2(\Delta\Delta Ct+1)\pm$SEM relative to Gapdh (n=3). A Student's two-tailed t-test was used to determine p values. A p value of <0.1 was considered significant. (D) Data points for RT-qPCR results described in (C). Values are $\log_2(\Delta\Delta Ct+1)$ relative to Gapdh (n=3).
Figures 10A, 10B, 10C, 10D, 10E:
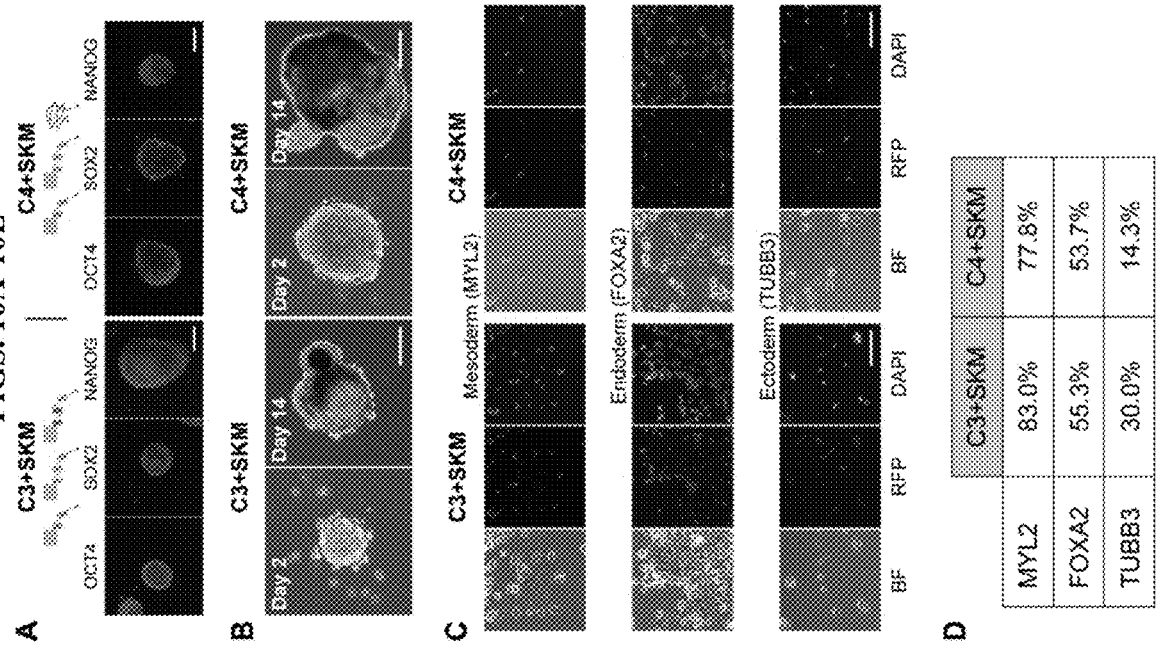
FIGS. 10A-10E demonstrate functional pluripotency of C3+SKM and C4+SKM iPS cells. (A) Immunofluorescence staining of iPS colonies with OCT4, SOX2, and NANOG. Bars=100 µm. (B) Embryoid bodies were cultured with iPS cells generated with C3+SKM or C4+SKM. Micrographs were taken at Day 2 and Day 14 of differentiation. Bars=100 µm. (C) Immunofluorescence staining for MYL2 (mesoderm), FOXA2 (endoderm), and TUBB3 (ectoderm) of embryoid body outgrowths on Day 14 of differentiation. DAPI labels nuclei. Bar=100 µm. (D) Percentage of positive cells in (C). (E) Embryoid bodies derived from C3+SKM or C4+SKM iPS cells differentiate into all three germ layers. RT-qPCR results from RNA harvested from ATF-generated iPS cells and embryoid bodies derived from them. Markers for mesoderm (T, Nkx2-5, and Kdr) were measured at Day 7. Markers for endoderm (Ttr, Afp, and FoxA2) were measured on Day 11. Markers for ectoderm (Nes, Nefl, and Sox17) were measured on Day 14. Data points represent fold-change over iPS cells of ΔΔCt relative to Gapdh (n=3).

All ATF combinations identified in the screen for endogenous Oct4 expression were re-validated to determine whether they were true positives. Among the eleven ATF combinations, #2, #3, and #4 could generate colonies of iPS cells when expressed with Sox2, Klf4, and c-Myc (FIG. 2E and Exhibit A, Dataset 1). Interestingly, Combination #4 came from the Tomato+GFP+ cells, in which Oct4 was activated before the Tomato signal dissipated. During the validation step, MEFs expressing ATF Combination #4+SKM became iPS cells ~28 days later than the iPS cells generated by the other ATF combinations or OSKM. The doubling times for the iPS cells generated with Combinations #2 and #3 were comparable to that of iPS cells generated with OSKM; however, the doubling time for iPS cells expressing Combination #4 was slightly longer (FIG. 9D). iPS cells generated with ATFs demonstrated capacity for self-renewal and have been cultured beyond 65 passages.

iPS Cells Generated with ATFs are Pluripotent:

iPS cells generated with ATFs were further characterized for markers of pluripotency. Immunofluorescence was performed to confirm expression of pluripotency markers, OCT4, SOX2, and NANOG (FIGS. 3A and 10A). To determine whether the iPS cells generated with ATFs were functionally pluripotent, we generated embryoid bodies and measured markers of the germ layers by immunofluorescence and RT-qPCR. Immunocytochemistry was used to detect myosin light polypeptide 2 (mesoderm), forkhead box A2 (endoderm), and beta III tubulin (ectoderm) in outgrowths from the embryoid bodies (FIGS. 3B and 10B). Furthermore, RT-qPCR results for brachyury, NK2 homeobox 5, and kinase insert domain receptor (mesoderm); alpha fetoprotein, transthyretin, and forkhead box A2 (endoderm); nestin, neurofilament light polypeptide, and SRY-box 17 (ectoderm) confirmed differentiation into all three germ layers (FIGS. 3C, 3D, 10C, and 10D). Compellingly, beating cardiomyocytes were observed in embryoid outgrowths from EBs derived from iPS cells generated by ATFs. Taken together, the embryoid body data suggests that the iPS cells generated with ATFs are functionally pluripotent.

Figures 4A, 4B, 4C, 4D, 4E, 4F, 4G, 4H:
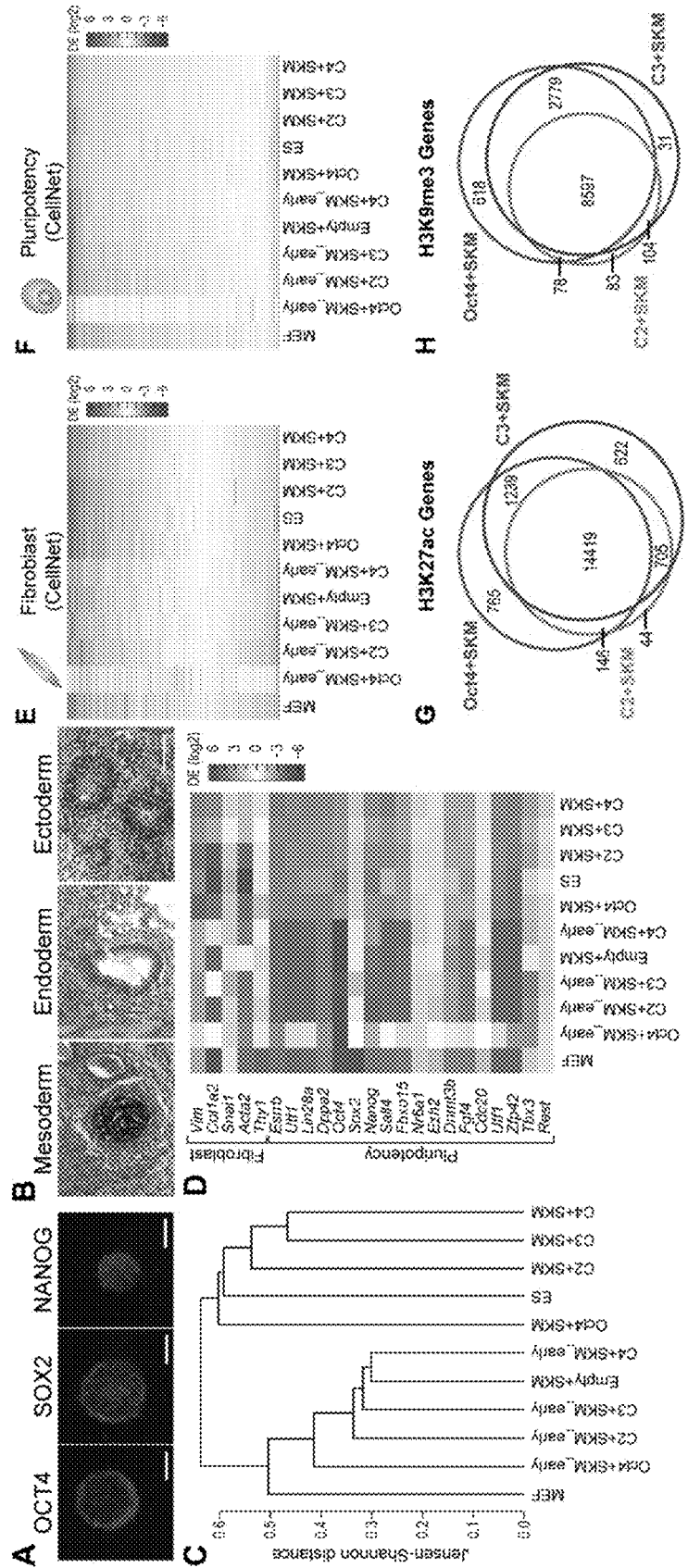
FIGS. 4A-4H demonstrate that iPS cells generated with ATFs are pluripotent. (A) Immunofluorescence staining of C2+SKM iPS colonies with OCT4, SOX2, and NANOG. Bars=100 µm. (B) Teratoma assay results show differentiation into mesoderm, endoderm, and ectoderm. Bar=100 µm. (C) iPS cells generated with ATFs cluster with mouse ES cells and iPS cells generated with Oct4+SKM. Samples marked early are MEFs transduced with the indicated factors before conversion into iPS cells between Day 18-27 (n=3 or 4). (D) A heatmap of fibroblast and pluripotency markers of iPS cells generated with ATFs shows downregulation of fibroblast genes and upregulation of pluripotency genes. Scale displays differential expression $\log_2$(ratio relative to mean). (E) A heatmap of 853 genes from the CellNet fibroblast gene regulatory network (GRN) show iPS cells generated with ATFs obtain transcriptional profiles similar to that of other pluripotent cells (Oct4+SKM iPS cells and ES cells). Scale displays differential expression $\log_2$(ratio relative to mean). (F) A heatmap of 705 genes from the CellNet pluripotency GRN show iPS cells generated with ATFs have expression profiles similar to that of other pluripotent cells. Scale displays differential expression $\log_2$(ratio relative to mean). (G) H3K27ac marks, specifying active regions of chromatin, appear in a common set of genes for Oct4+SKM iPS cells, C2+SKM iPS cells, and C3+SKM iPS cells. H3K27ac peaks were annotated to genes with Homer to create Venn diagrams for genes. ChIP enrichment among treatments was determined to be significant at an FDR <0.1 by DiffBind (n=2). (H) H3K9me3 marks, specifying repressed regions of chromatin, appear in a common set of genes for Oct4+SKM iPS cells, C2+SKM iPS cells, and C3+SKM iPS cells. H3K9me3 peaks were annotated to genes with Homer to create Venn diagrams for genes. ChIP enrichment among treatments was determined to be significant at an FDR <0.1 by DiffBind (n=2).
Figures 11A, 11B, 11C:
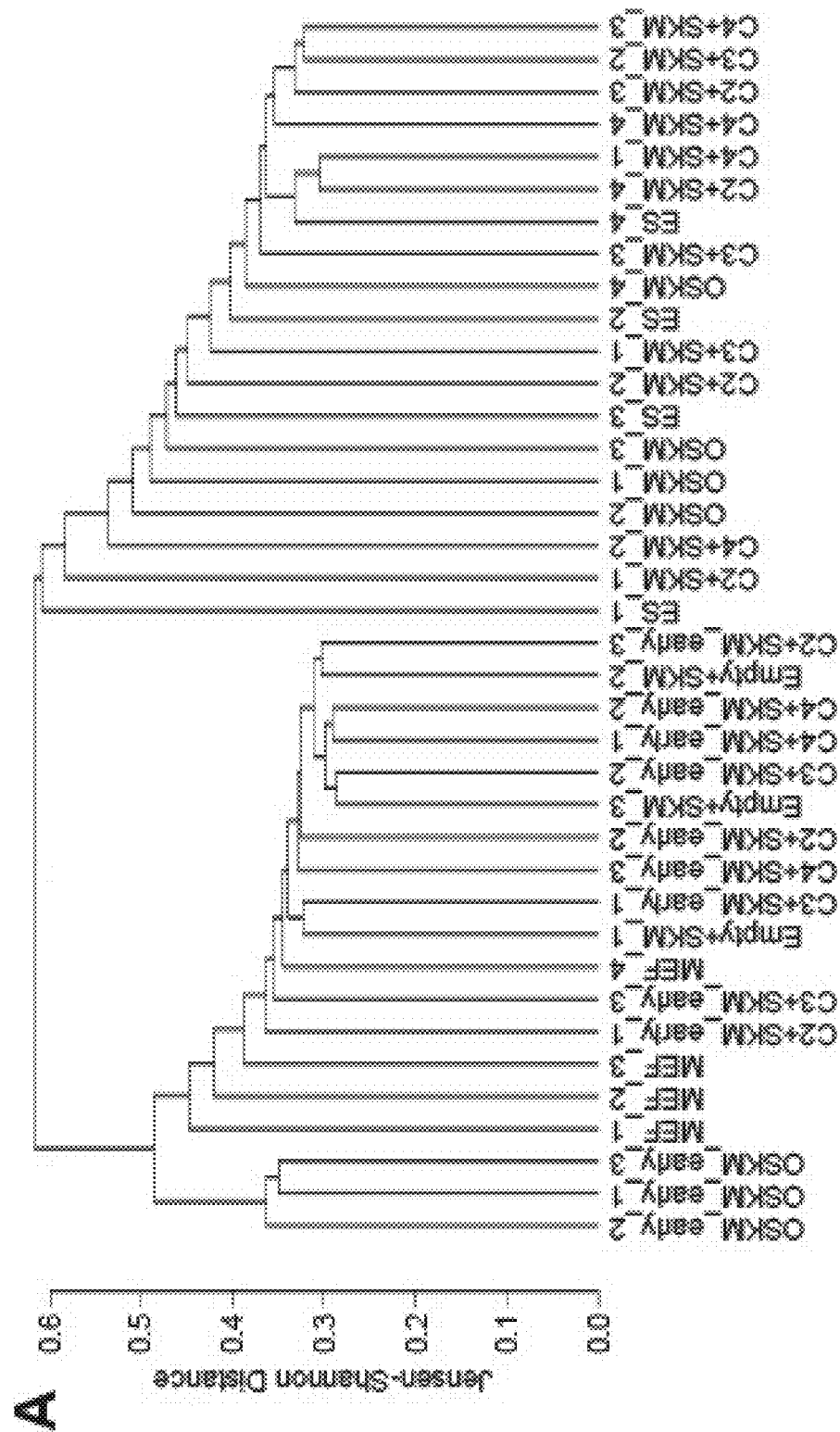
FIGS. 11A-11C present results of RNA-Seq analysis. (A) Clustergram of replicates generated from genome-wide RNA-seq data of the following conditions: mouse embryonic fibroblasts (MEF), mouse ES cells (ES), iPS cells generated by Oct4, Sox2, Klf4, c-Myc (OSKM), iPS cells generated with Combination #2+SKM (C2+SKM), iPS cells generated with Combination #3+SKM (C3+SKM), and iPS cells generated with Combination #4+SKM (C4+SKM), and MEFs transduced with lentivirus with an empty ORF+SKM (Empty+SKM). The samples marked early are MEFs transduced with the indicated factors before conversion into iPS cells (n=3 or 4). (B) Jensen-Shannon distance for conditions described in (A). (C) Number of differentially expressed genes for every pairwise comparison (p<0.05).

From morphological and select gene marker analysis, we focused on global transcriptome analysis of the ATF-treated cells. Comparison of genome-wide transcriptional profiles showed that the iPS cells generated with ATFs cluster with mouse ES cells and iPS cells generated with OSKM (FIGS. 4A and 11A). Cells at early stages of reprogramming clustered with MEFs and Empty+SKM. iPS cells generated with ATFs show an upregulation of pluripotency markers and a downregulation of fibroblast markers (FIG. 4B). Using the 853 genes that make up the fibroblast gene regulatory network (GRN) and the 705 genes that make up the pluripotency GRN from CellNet (Cahan et al., 2014), we compared the expression profiles of iPS cells generated with ATFs to those of other pluripotent cells and MEFs. Our genome-wide analysis indicates our ATF-induced iPS cells display a high degree of similarity with pluripotent cells generated using exogenous retrovirally-delivered Oct4. It is important to note that, at early stages of reprogramming, ATF-treated cells have a different profile compared to OSKM-treated cells (FIGS. 4C and 4D). These differences suggest other underlying regulators beyond what is characterized in the GRNs of CellNet guide cells to pluripotency (FIG. 4D). Once fully reprogrammed to the pluripotent state, global transcriptional profiling shows iPS cells generated with ATFs share more similarity amongst themselves than to OSKM or ES cells (FIGS. 4A and 11C). ATF levels at early stages of reprogramming were detectable; however, once converted to iPS cells, the lentiviral elements controlling the expression of ATFs are silenced, a further confirmation that the cells were fully reprogrammed with the endogenous pluripotency circuitry activated.

Figures 5A, 5B, 5C:
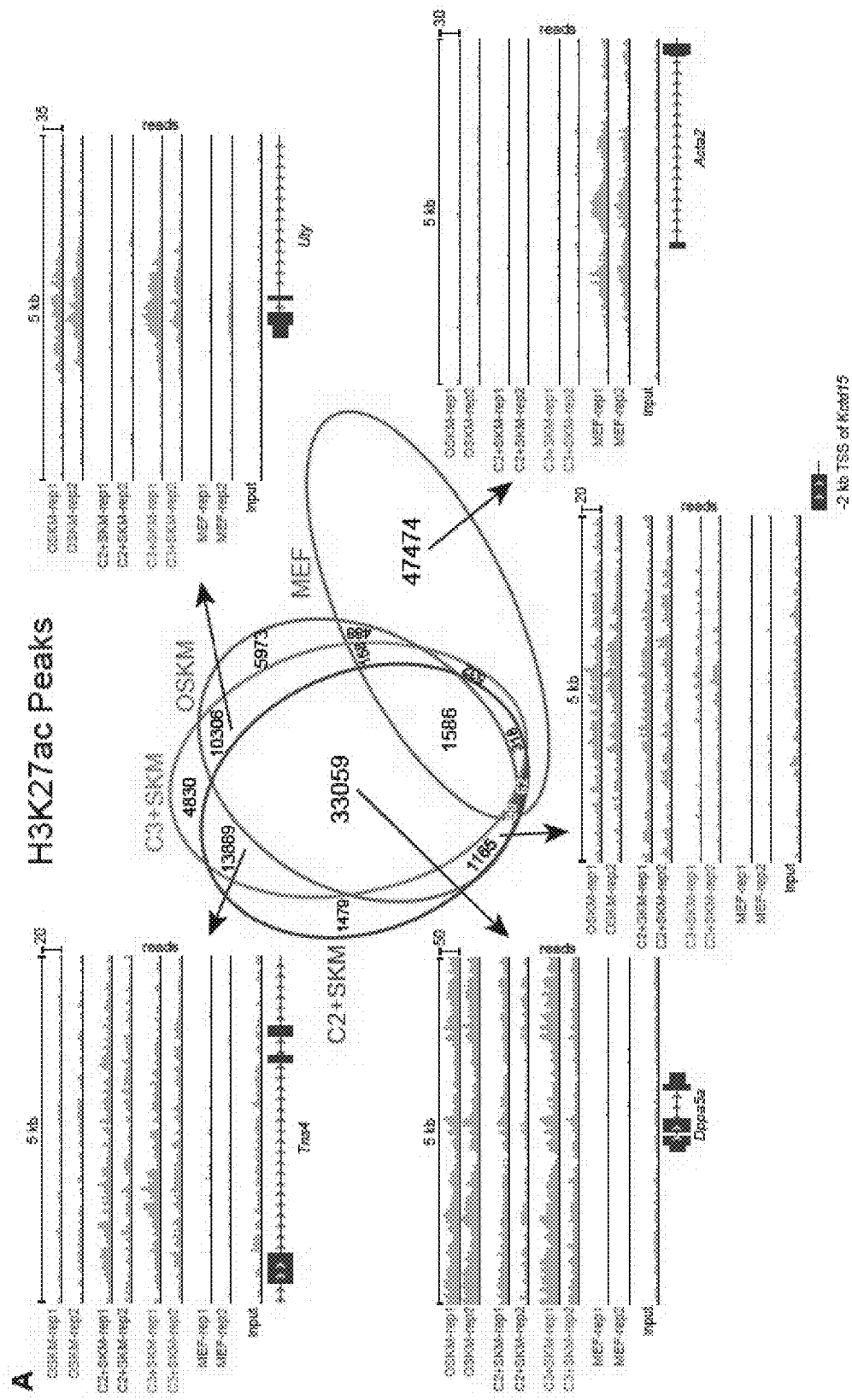
FIGS. 5A-5C demonstrate that iPS cells generated with ATFs have similar sets of active histone marks as iPS cells generated with Oct4, Sox2, Klf4, c-Myc ("OSKM"). The genome-wide chromatin modification landscapes in ATF-induced iPS cells were compared to iPS cells generated with Oct4+SKM. Specifically, ChIP-seq was performed on histone 3 lysine 27 acetylation (H3K27ac), the marker delineating active promoters and super-enhancers that define cell identity (Whyte et al., 2013; Hnisz et al., 2013), and histone 3 lysine 9 trimethylation (H3K9me3), the marker that is strongly correlated to repressed regions of the genome that are bound by heterochromatin protein 1 (Schultz et al., 2002). (A) A large fraction of H3K27ac marks, an active mark for super-enhancers, is shared among OSKM iPS cells, Combination #2+SKM iPS cells, and Combination #3+SKM iPS cells. MEFs exhibit a unique set of H3K27ac peaks compared to iPS cells in this study (MEF data from Mouse ENCODE). ChIP enrichment among treatments was determined to be significant at an FDR <0.1 by DiffBind (n=2). ChIP traces over a 5 kb window for representative examples are shown for the Venn diagram categories. (B) Peaks were annotated to genes with Homer to create Venn diagrams for genes. (C) Spearman correlation shows that iPS cells correlate better with each other than to MEFs.
Figures 6A, 6B, 6C:
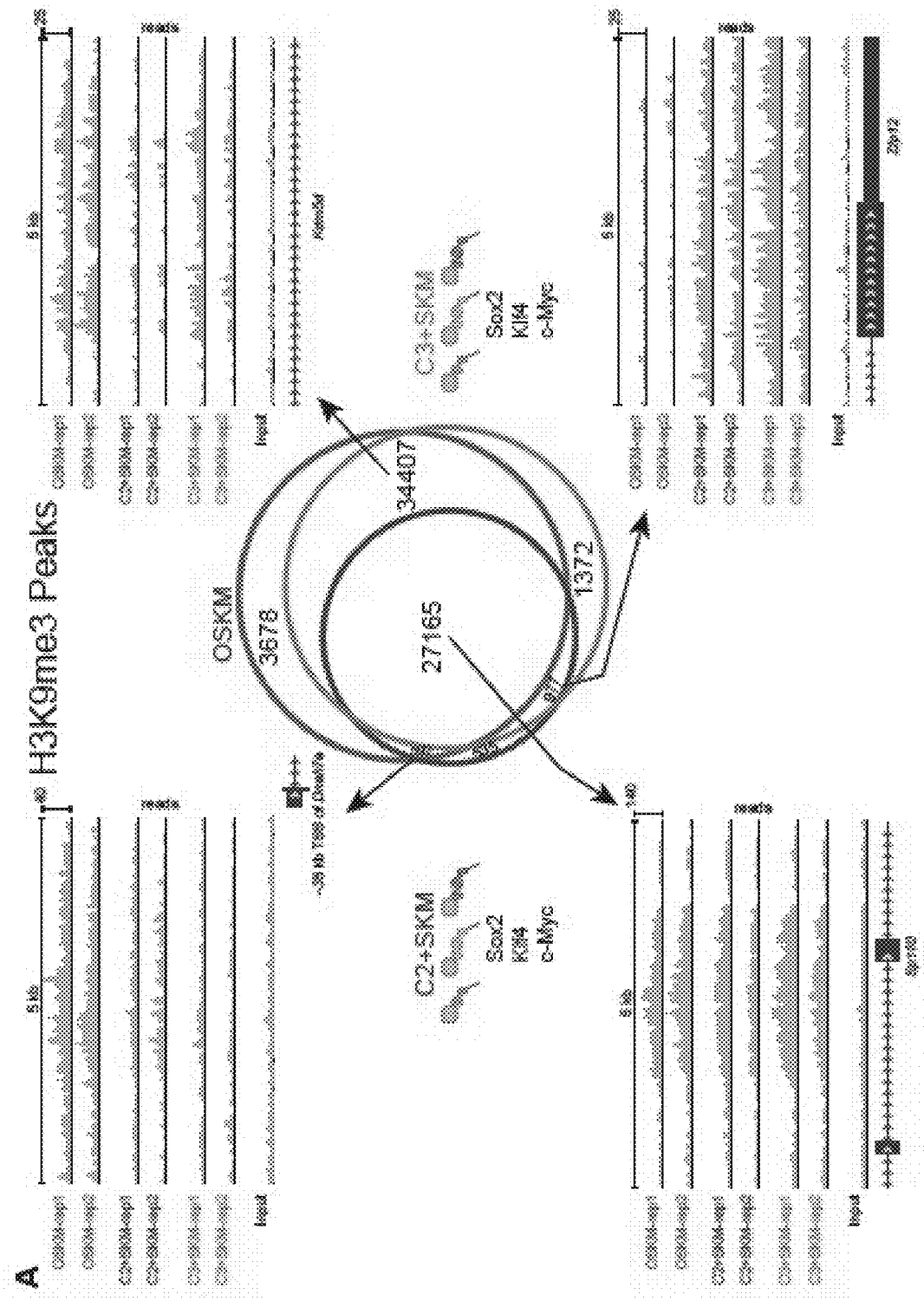
FIGS. 6A-6C demonstrate that iPS cells generated with ATFs have similar sets of repressive histone marks as iPS cells generated with Oct4, Sox2, Klf4, c-Myc ("OSKM"). (A) A subset of H3K9me3 marks, a marker of repressed loci, is shared among OSKM iPS cells, Combination #2+SKM iPS cells, and Combination #3+SKM iPS cells. More peaks are shared between OSKM iPS cells and Combination #3+SKM iPS cells. ChIP enrichment among treatments was determined to be significant at an FDR <0.1 by DiffBind (n=2). ChIP traces over a 5 kb window for representative examples are shown for the overlapping Venn diagram categories. (B) Peaks were annotated to genes with Homer to create Venn diagrams for genes. (C) Spearman correlation shows that Combination #3+SKM iPS cells correlate slightly better to OSKM iPS cells than do Combination #2+SKM iPS.

Signature Epigenetic Landscapes at ATF-Activated Pluripotency Genes:

The chromatin structure of iPS cells generated with ATFs was compared to those generated with OSKM. Specifically, ChIP-seq was performed on histone 3 lysine 27 acetylation (H3K27ac), a marker for super-enhancers (Hnisz et al., 2013; Whyte et al., 2013), and histone 3 lysine 9 trimethylation (H3K9me3), a marker of heterochromatic repressed regions of chromatin. The pluripotent cells shared similar sets of peaks for H3K27ac regardless of whether they were generated with ATFs or with natural factors (FIGS. 5A and 5B). Likewise, H3K9me3 peaks were similar for ATF-generated iPS cells and OSKM-generated iPS cells, although there was greater overlap for OSKM and Combination #3+SKM (FIGS. 6A and 6B). There was more similarity between OSKM-generated iPS cells and iPS cells generated with Combination #3+SKM. Comparison of the super-enhancer peaks of the iPS cells in this study to those of MEFs in the mouse ENCODE data revealed the greatest number of differences between MEFs to iPS cells and the greatest number of overlaps occurred among the iPS cells generated with ATFs+SKM and OSKM (FIGS. 5A and 5B). Although mouse ENCODE data for H3K9me3 was not available, both repressive and active histone marks show very strong correlations among the iPS cells induced by ATFs+SKM and by OSKM (FIGS. 5C and 6C).

Figures 7A, 7B, 7C:
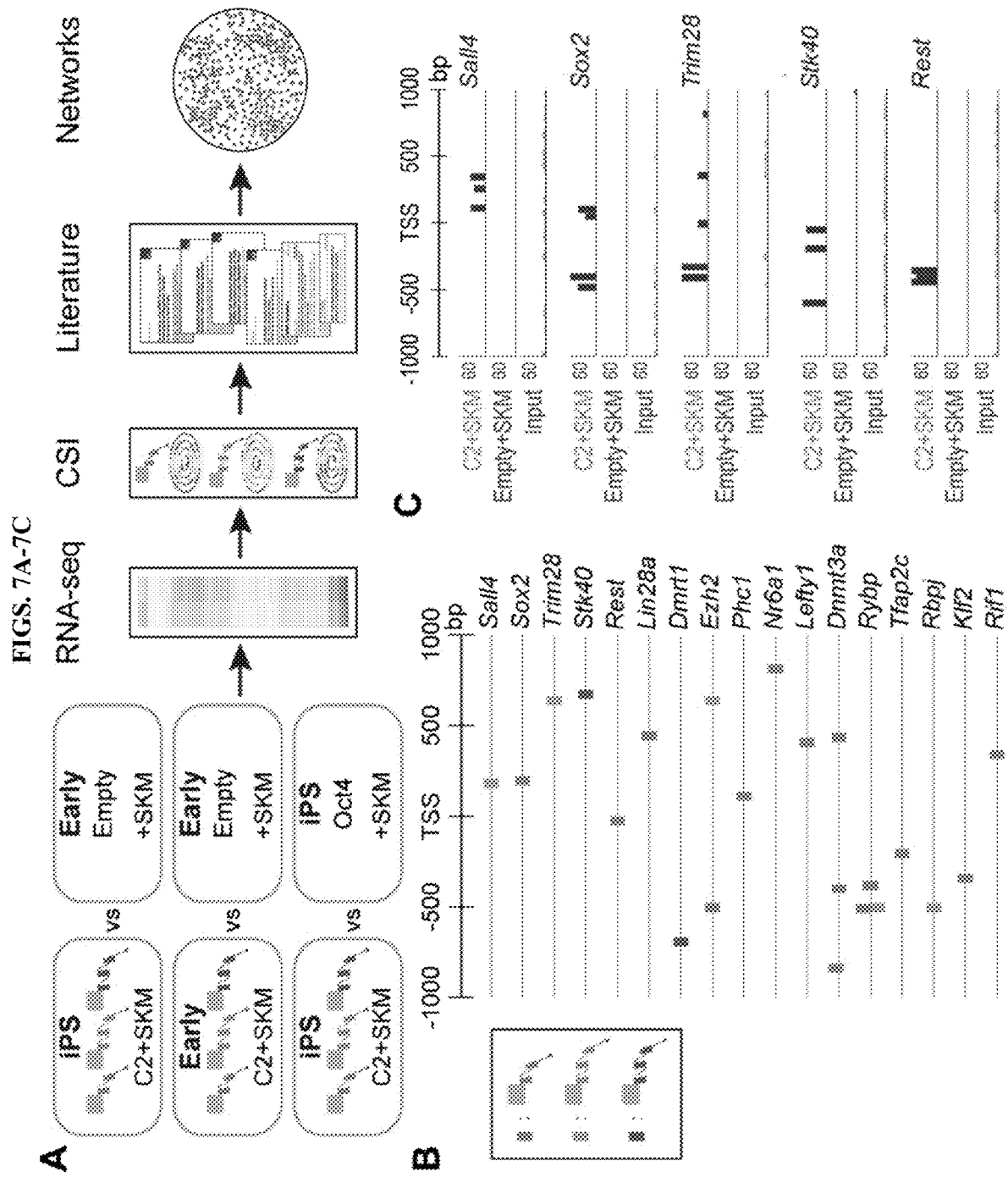
FIGS. 7A-7C demonstrate that ATFs activate key regulators of the pluripotency network. (A) Workflow for determining ATF target genes for C2+SKM. Three pairwise comparisons were made: 1) C2+SKM iPS cells vs Empty+ SKM cells, 2) C2+SKM early cells vs Empty+SKM cells, 3) C2+SKM iPS cells vs Oct4+SKM iPS cells. Genes upregulated >2-fold (p<0.05) in the cells transduced with ATFs with ATF binding sites within a ±1 kb window of the TSS were determined to be potential targets. Binding sites were identified by using the top 5 scoring 10-bp motifs from CSI. These target genes were used to build the network in FIG. 6A with information from the literature and the STRING database. (B) Differentially expressed pluripotency genes with ATF binding sites within ±1 kb of the transcriptional start site (TSS). ATF binding sites were derived from the top 5 scoring 10-bp motifs from CSI for C2+SKM. (C) ChIP-seq signal for HA tag on ATFs for five predicted targets in FIG. 5B. Traces display total reads for C2+SKM and Empty+ SKM cells at an intermediate stage before reprogramming to a pluripotent state.
Figures 13A, 13B:
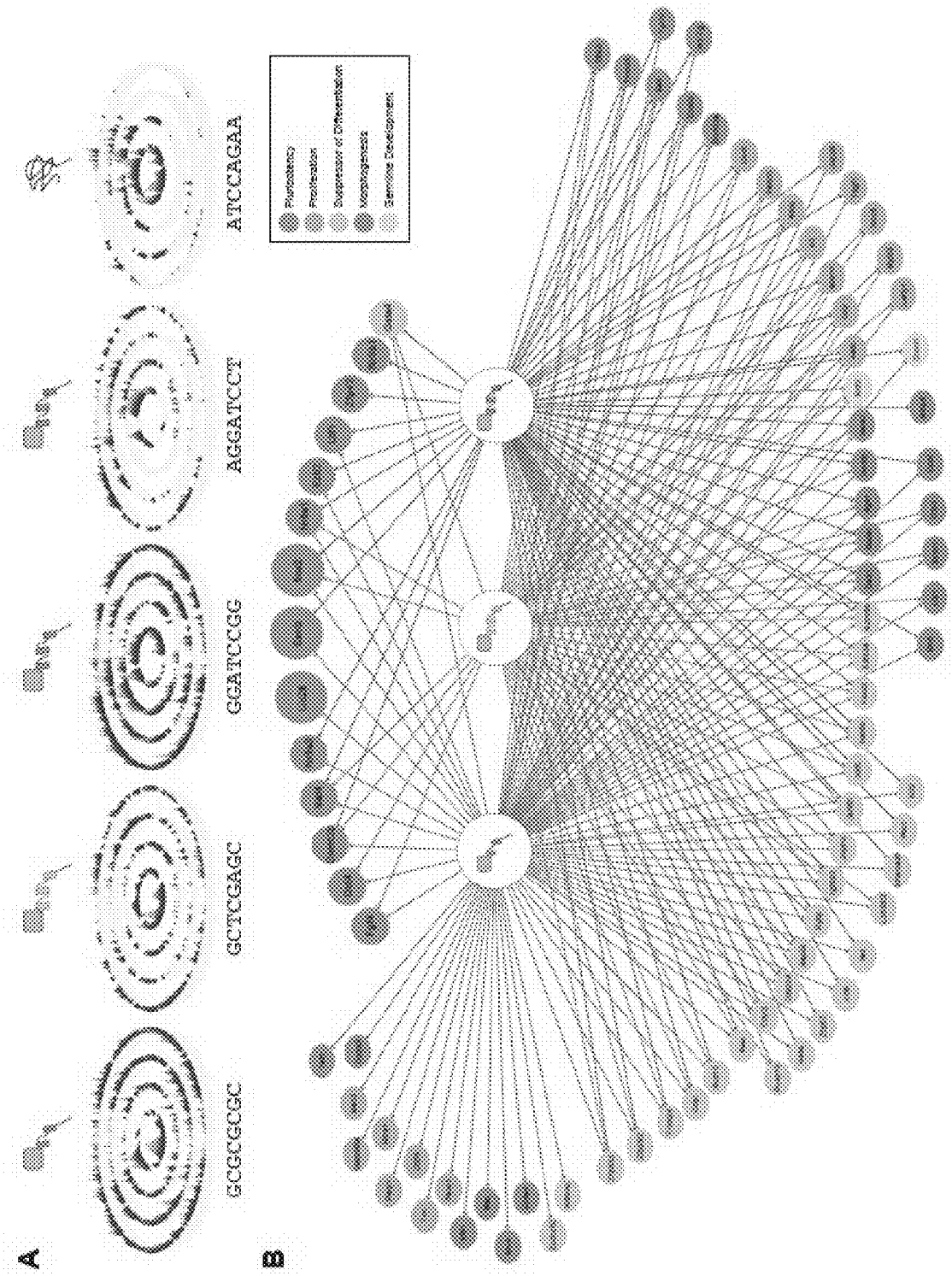
FIGS. 13A-13B demonstrate that ATFs target key regulators of pluripotency. (A) Specificity and Energy Landscapes (SELs) of the five ATFs found in this study to replace Oct4. The first two ATFs (blue and orange) appear in all three combinations. The SEL displayed shows data after three rounds of enrichment. (B) Target genes of the ATFs in Combination #2 when the top 100 scoring 10-bp motifs are used from CSI. These genes have an ATF target site ±1 kb of the TSS and are upregulated >2-fold in cells with ATFs expressed. Colors indicate gene ontology: pluripotency (purple), proliferation (red), suppressor of differentiation (gray), morphogenesis (teal), and germline development (pink). The size of the node highlights their importance as upstream regulators.

ATF-Triggered Networks:

The ATF targets were examined by integrating Cognate Site Identification (CSI) sequence energy landscapes of ATFs with global transcription obtained by RNA-seq (FIG. 7A). The preferred binding sites of the ATFs were determined by CSI (FIG. 13A). To pinpoint the genes in the pluripotency network activated by the ATFs, the top five binding motifs for each ATF were determined bioinformatically. Binding sites within ±1 kb of the transcriptional start site (TSS) were considered in the analysis. We chose this narrow window based on ATF design principles (Rebar et al., 2002), the tendency of sequence-specific TFs to exhibit a peak −300 bp relative to the TSS (Koudritsky and Domany, 2008), and evidence that the predictive power of TF binding on gene regulation drops significantly when the binding sites examined are beyond 2 kb from the TSS (Cheng and Gerstein, 2012; Whitfield et al., 2012). Genes, expressed >2-fold more in iPS cells generated from ATFs than Empty+SKM cells and were statistically significant, were filtered with the gene list with ATF binding sites within ±1 kb of the TSS. Two other pairwise comparisons (ATF Combination #2/3/4+SKM at the early stage versus iPS stage and ATF Combination #2/3/4+SKM iPS cells versus OSKM iPS cells) were included in the analysis. Finally, those genes, upregulated >2-fold and exhibited ATF binding sites, were further examined for being implicated in inducing pluripotency from previous studies (FIG. 7B and Exhibit A, Dataset 2) (Buganim et al., Cell 150(6): 1209-1222, 2012; Heng et al., *Cell Stem Cell* 6(2):167-174, 2010; Kim et al., *Cell* 132(6):1049-1061, 2008; Krentz et al., *Dev Biol* 377(1):67-78, 2013; Lujan et al., *Nature* 521(7552):352-356, 2015; Marson et al., *Cell* 134(3):521-533, 2008; Sharov et al., *BMC Genomics* 9(1):269, 2008; Shu et al., *Cell* 153(5):963-975, 2013; Som et al., *PLoS ONE* 5(12):e15165, 2010). The super-enhancer profiles for the ATF target genes show H3K27ac peaks that confirm that they are actively expressed (FIG. 7C). A gene regulatory network based on the CSI results and differential expression data was built using information from the literature and the STRING database (FIG. 7D).

Next, we expanded our analysis to include high and medium affinity binding sites from CSI data of Combination #2. We used the top 100-scoring 10-bp motifs to identify genes, potentially targeted by the ATFs (FIG. 13B). The target genes were not filtered with expression data in this comprehensive analysis of the CSI data. Gene set enrichment analysis with Enrichr (Chen et al., 2013) for 2897 genes with a sum CSI score of 20 or greater, in other words, six or more ATF target sites within ±1 kb of the TSS showed an overrepresentation of genes found in PluriNetWork for *M. musculus* (FIG. 7E) (Som et al., *PLoS ONE* 5(12): e15165, 2010). This analysis was then performed for Combinations #3 and #4, and similar results were obtained, suggesting that the different ATF combinations activate similar nodes of the pluripotency network.

Figure 12:
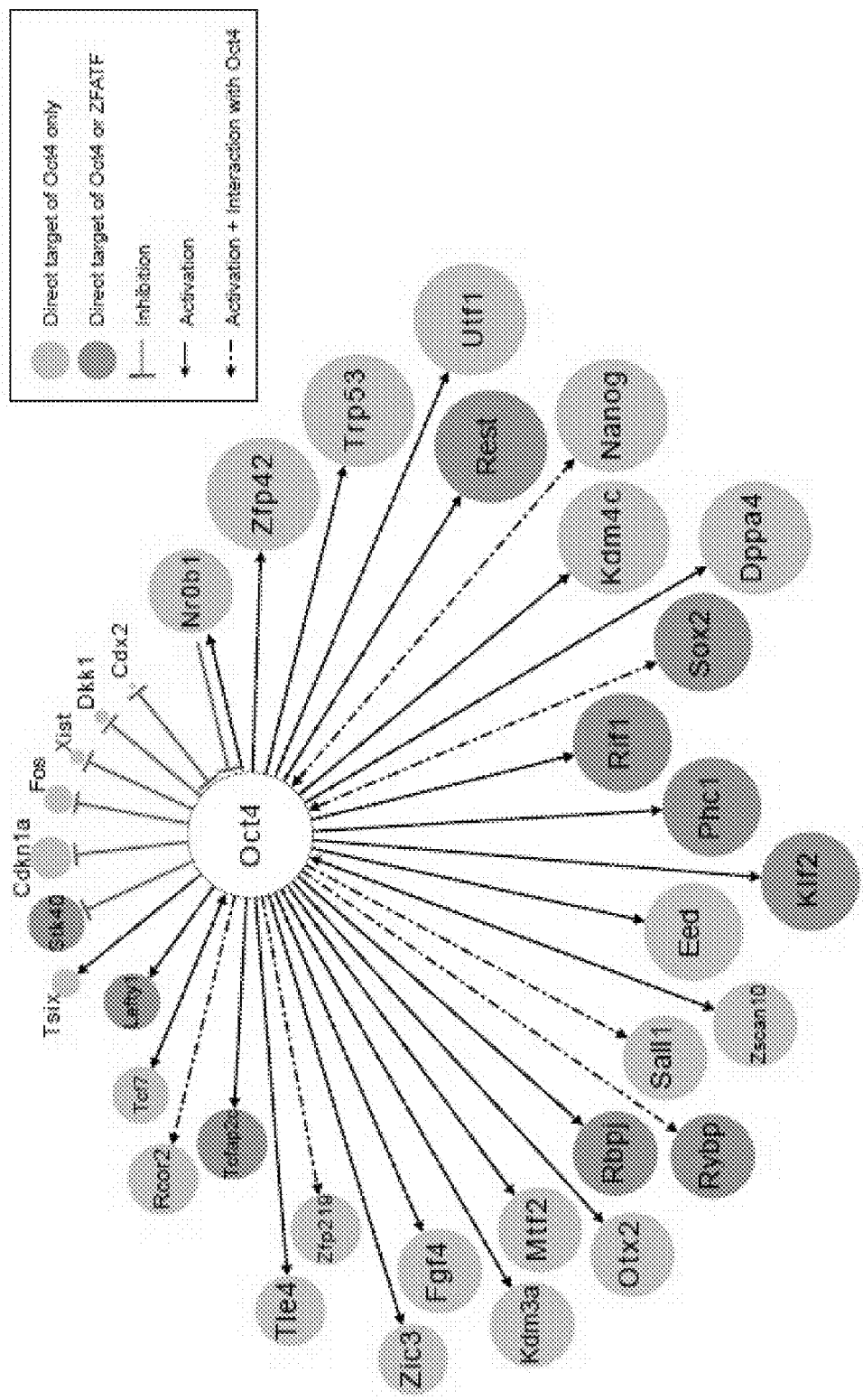
FIG. 12 demonstrates direct Oct4 targets. The direct targets of Oct4 from PluriNetWork (Som et al., 2010) were compared with ZFATF targets. Direct targets of Oct4 are colored light green. The direct targets of Oct4 or a ZFATF are colored purple. Protein-protein interactions are indicated by dashed lines. Activation of a gene is indicated by an arrow, while repression is indicated by a red segment ending with a perpendicular bar. The size of the node reflects level of expression in OSKM iPS cells.

Surprisingly, our data demonstrates that Oct4 does not appear to be the primary target as it ranks 4788 for the sum CSI score for Combination #2, 3929 for Combination #3, and 5225 for Combination #4. Other genes with higher sum CSI scores would be targeted by ATFs directly, and those that are key regulators in the pluripotency circuitry, subsequently, trigger the activation of Oct4. A comparison of Oct4 targets with the ATF targets reveals striking differences (FIGS. 7D and 12). Thus, Oct4 is indirectly activated by the ATFs, and the path the MEFs take to reprogram to the iPS state is different than the path taken when treated with OSKM.

Figures 15A, 15B, 15C:
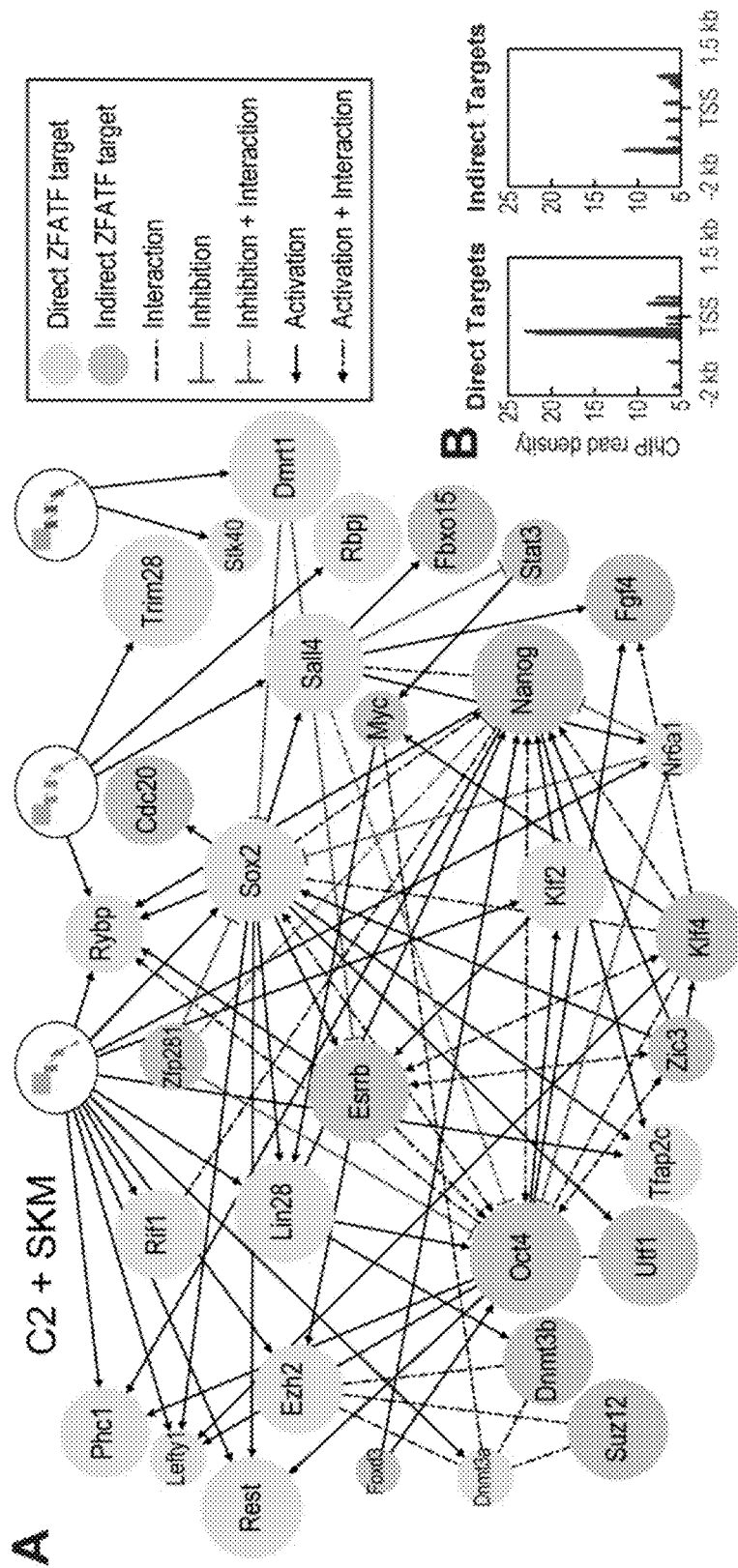
FIGS. 15A-15C demonstrate transcriptional networks activated by ATFs and Oct4. (A) Nodes of the pluripotency network activated by the ATFs of C2. The size of the node reflects level of expression in C2+SKM iPS cells. (B) ChIP read density in C2+SKM early cells for HA-tagged ATFs for 17 direct target genes (left) and 15 indirect target genes (right) for nodes in FIG. 6A. Traces represent coverage across a window of −2 kb to +1.5 kb relative to the TSS. (C) Direct targets of Oct4. The size of the node reflects level of expression in Oct4+SKM iPS cells.

A gene regulatory network based on the CSI results and differential expression data was built using information from the literature and the STRING database (FIG. 15A) (Szklarczyk D, et al. (2015) *Nucleic Acids Res* 43 (Database issue):D447-52). Greater ATF occupancy near the TSS for the 17 predicted targets in the gene regulatory network suggests they are direct targets (FIG. 15B). A comparison of direct OCT4 targets with the ATF target genes reveals striking differences (FIG. 15C) (Som A, et al. (2010) *PLoS ONE* 5(12):e15165).

These differences suggest that ATFs activate the pluripotency network through different nodes than the exogenously expressed Oct4. While the primary targets may differ at the outset, the eventual iPS cells show remarkable convergence in the transcriptome profiles and epigenetic landscapes.

Discussion

Zinc finger, TAL effector, and CRISPR/Cas9 libraries have been tested for loss-of-function phenotypes, acquisition of resistance to a drug, or upregulation of specific genes (Bae et al., 2003; Blancafort et al., 2003; Kim et al., 2013; Konermann et al., 2015; Li et al., 2014; Tschulena et al., 2009; Wang et al., 2014; Zhou et al., 2014); however, this is the first report of a gain-of-function screen to reprogram fibroblasts to iPS cells, a feat that requires drastic transcriptional and epigenetic changes. We screened a zinc finger library of high complexity, not previously tested in mammalian cells. Furthermore, the capacity for the ATFs to cooperatively bind target genes provides the ATF library with a unique feature to sample a larger set of binding sites and activate to greater extent due to synergy. Previous, conventional zinc finger libraries consisted of ATFs created by shuffling ~55 zinc finger units, previously characterized to bind specific triplets of nucleotides (Gonzalez et al., 2010). The library used in this study uses a much larger repertoire of residues, incorporating 16 of the 20 possible amino acids in the recognition residues, greatly expanding the target space of the ATFs. A survey of natural zinc fingers found in eukaryotes reports that all amino acids are represented in the recognition residues (Najafabadi et al., 2015).

Because we are using a large library of ATFs, capable of sampling thousands of genes in parallel, there is a potential for our ATFs to activate endogenous Oct4 directly; however, in our analysis, we find that the ATFs seem to activate Oct4 indirectly. ChIP-seq of the ATFs was not possible due to silencing of the lentiviral elements in iPS cells. Although ChIP-seq at an earlier stage before full conversion can provide insight on the genomic targets of the ATFs, the signal for functionally relevant ATF binding sites would be challenging to detect due to low frequency of conversion of parental fibroblasts to iPS cells.

Application of the ATF library in this gain-of-function screen demonstrates that zinc finger ATFs can perturb the transcriptional profile of a cell to levels that are sufficiently robust to induce a dramatic phenotypic change. Like natural TFs, the ATFs in this study target 9-10 bp sites and can bind cooperatively as homodimers and heterodimers to a much larger and perhaps less frequent 18 bp site. As each ATF in the library will have unique sequence preferences and varying degrees of affinity for DNA, a wide range of outcomes can be elicited upon introduction of these ATFs. Unlike natural TFs, ATFs do not necessarily rely on partner proteins, and thus, transcriptional networks can be stimulated from any homeostatic state.

In summary, this study provides a compelling support for our design principles and demonstrates unequivocally that an ATF library can be used in a gain-of-function screen for different cell fate conversions. Interestingly, during the early stages of conversion, cells expressing ATFs+SKM exhibited a different transcriptional profile from those expressing OSKM; however, in the final iPS cell state, the expression profiles of all the pluripotent cell types were similar both at the molecular and functional levels. The differences in molecular signatures at the early stage suggest that the MEFs take different dedifferentiation routes to the same pluripotent state.

In addition to providing a means to perform a forward genetic screen, this Example describes a strategy for identifying cell-fate defining transcriptional networks. By integrating expression data with in vitro binding site data, we were able to identify the nodes of the transcriptional network implicated in the induction of pluripotency. Furthermore, ATF libraries can be used to identify unanticipated regulatory networks in an unbiased manner. This technology enables the pursuit of elusive cell phenotypes or direct conversions, considered challenging to achieve by conventional methods.

Example 2—Cardiomyocyte Differentiation Using ATFs

Differentiation into cardiomyocytes is valuable for disease modeling, drug testing, and heart regeneration. Current methods to differentiate human pluripotent stem cells into cardiomyocytes involve temporal modulation the Wnt pathway with small molecule inhibitors. While current methods are efficient for the derivation of ventricular cardiomyocytes, these cardiomyocytes resemble a more fetal phenotype, and robust differentiation into other subtypes, such as atrial cells and nodal cardiomyocytes, remains difficult.

An unbiased, artificial transcription factor (ATF) library-based approach circumvents this challenge and allows for the selection of a particular cell fate. To demonstrate that an ATF library can be used as an unbiased screen for cardiomyocyte differentiation, we tested our gene-activating zinc finger ATF library in which each ATF targets a 9-bp sequence. This library is composed of $2.6 \times 10^6$ ATFs, a complexity that encompasses 10-times the sequence space of all 9-bp permutations. An important and distinguishing feature of our ATF design is the incorporation of an interaction domain that allows two ATFs to dimerize and activate target genes in a synergistic manner. We tested the ATF library in replacing the function of the Wnt pathway inhibitors used to derive cardiomyocytes. Our results suggest that the ATF library can be used to differentiate cells into more challenging subtypes, such as atrial cardiomyocytes.

ATF Library Screening in Cardiomyocyte Differentiation

Figures 18A, 18B, 18C:
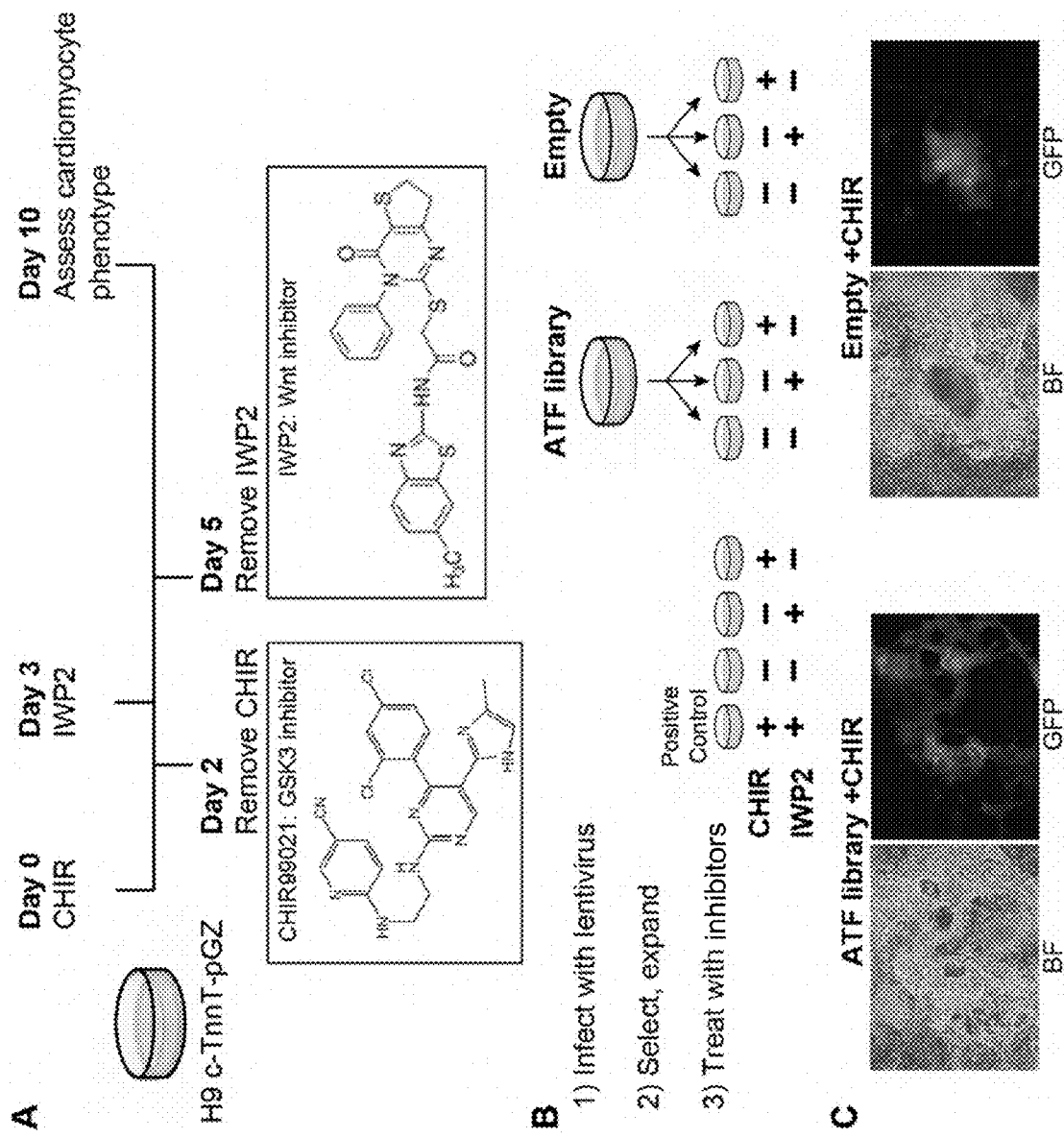
FIGS. 18A-18C illustrates a particular embodiment of ATF-mediated cardiomyocyte differentiation by modulation of the Wnt pathway on H9 c-TnnT-pGZ cells. (A) ES cells were maintained in E8 until nearly confluent. On Day 0, the GSK3 inhibitor, CHIR99021 was added to the differentiation medium (RPMI 1640+B27 without insulin) to promote differentiation into mesoderm. On Day 3, the Wnt maturation inhibitor, IWP2 was added to promoted differentiation into cardiomyocytes. On Day 10, the expression of TNNT2 was evaluated by the expression of GFP. From Day 9 onwards, cardiomyocytes are maintained in RPMI 1640+B27 with insulin. (B) The ATF library was tested to replace the function of the Wnt pathway inhibitors. Human pluripotent stem cells bearing a reporter for TNNT2 were transduced with lentiviruses encoding either ATFs or no open reading frame (Empty). Cells were treated with puromycin to select for transduced cells. The differentiation protocol was performed in the presence or absence of one or more inhibitors. (C) ATFs were capable of replacing the Wnt maturation inhibitor, IWP2. Approximately 21% of the ATF library +CHIR-treated cells were GFP$^+$. Only 1.1% of the Empty+CHIR-treated cells were GFP$^+$, so the expected false positive rate is approximately 5.3%. Cells of the ATF library +CHIR formed larger sheaths of cardiomyocytes with regular beating compared to the Empty +CHIR treatment.

Directed differentiation to cardiomyocytes involves modulation of the Wnt pathway to induce a step-wise transition to mesodermal progenitor cells, followed by specification into cardiomyocytes (FIG. 18A). First, cells are treated with CHIR99021, a GSK3 inhibitor, resulting in the activation of the Wnt pathway. GSK3 is a kinase that phosphorylates β-catenin and mediates its ubiquitination and subsequent proteasomal degradation. By inhibiting GSK3, β-catenin target genes are activated, inducing specification into mesoderm. The progenitor cells at this point express T (Brachyury). Three days after treatment with the GSK3 inhibitor, the Wnt pathway is suppressed with IWP2 to promote specification into cardiomyocytes. IWP2 is a molecule that inhibits Porcupine, an enzyme that palmitoylates Wnt proteins for secretion. By Day 10 of differentiation, cells express cardiomyocyte-specific genes, TNNT2 (cardiac troponin T2), GATA4, and NKX2.5 at high levels.

We asked if the temporal modulations of the Wnt pathway could be regulated with ATFs. Toward this end, we tested the ATF library in H9 human embryonic stem (ES) cells bearing a GFP reporter for TNNT2. In these H9-cTnnT-pGZ cells, the promoter of TNNT2 drives the expression of GFP and zeocin, permitting the isolation of cells that express the cardiomyocyte-specific marker (FIG. 19B).

The ATF library was cloned into a second generation lentiviral vector. The screen is performed in cells with a robust change in phenotype or a lineage-specific reporter. H9-cTnnT-pGZ cells were transduced with ATFs or lentiviruses without an ORF (Empty control) (FIG. 18B). After selection of integration events with puromycin (FIG. 19A), cells were treated with the Wnt pathway inhibitors at the appropriate time points (FIG. 18A). Positive outcomes were isolated as single cells, such that combinations of ATFs, if any, can be captured. Integrated ATFs were identified from such single cells and retested for validation. Once validated, downstream experiments were be performed to identify ATF target genes. For example, by omitting the GSK3 inhibitor (CHIR), the Wnt inhibitor (IWP2), or both, we asked whether ATFs could replace the function of these inhibitors. ATFs were able to replace the function of the Wnt inhibitor, IWP2 (FIG. 18C).

Figures 19A, 19B, 19C, 19D:
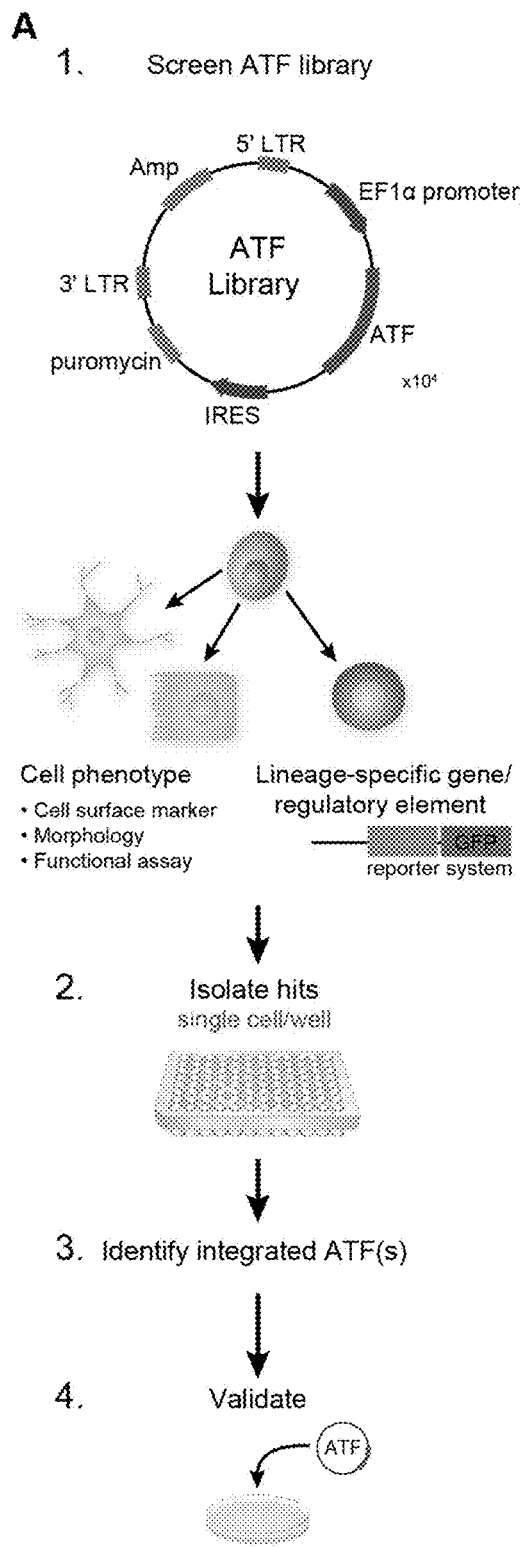
FIGS. 19A-19D demonstrate use of an ATF library to promote cardiomyocyte differentiation. (A) Genetic screen with an ATF library. ATFs are comprised of an interaction domain, 3-zinc fingers, nuclear localization signal, VP64 activation domain, and 3×HA tag. The library has a complexity of $2.6 \times 10^6$ ATFs, each of which can target a 9-bp sequence. (B) A cardiomyocyte lineage-specific reporter cell line was created by lentiviral delivery of the human troponin T (TNNT2) promoter driving expression of copGFP and zeocin resistance (cTnnT-pGZ). (C) Flow cytometry results at Day 10 after treatment with CHIR99021. GFP$^+$ H9 cTnnT-pGZ cells transduced with the ATF library were isolated as single cells for further analysis. Cells treated with lentivirus with an Empty ORF (negative control) were used to determine the frequency of false positive events. Percentages in the gated box are displayed in green. (D) ATFs were identified from 16 single cells by two-step nested PCR of genomic DNA. Unique ATFs are depicted with a different color. Two ATFs had a frameshift mutation shortly after the ID, coding for a protein that does not have a zinc finger structure. The frameshifted ATF and light blue ATF are expressed in 15/16 cells analyzed. Three ATFs are made up of two fingers (light blue, red, and purple). The combination, C3+CHIR, comprised of the frameshifted ATF (ATF5), blue ATF (ZFATF1), and orange ATF (ZFATF2), were retested in the validation step.

After treatment with the GSK3 inhibitor, these cells could differentiate into cardiomyocytes and express the GFP reporter for TNNT2 (FIG. 19C). Flow cytometry of ATF-treated cells resulted in 20.8% of cells expressing GFP compared to 1.1% for the Empty control. Differentiation into cardiomyocytes in the Empty control could be attributed to spontaneous differentiation, introduction of a strong promoter (EF1α) to a locus proximal to a positive regulator of cardiomyocyte differentiation, disruption of a negative regulator of cardiomyocyte differentiation from lentiviral integration, or activation of genes in response to delivery of lentivirus. The Empty control demonstrated the rate of expected false positive events to be 5.3%. By cell sorting, we isolated the GFP+ cells as single cells (FIG. 19A). From 16 single cells, we found 10 unique combinations of ATFs capable of replacing the function of the Wnt inhibitor, IWP2 (FIG. 19D and Table 6). One combination occurred in two cells and another combination in six cells. ATF5 and ATF1 appeared in every cell except one. Due to the recurring nature of Combination #3-8 (C3+CHIR), we focused on retesting this combination of ATFs as well as subsets of this combination.

TABLE 6

Sequences of ATF Hits in Cardiomyocyte Differentiation

| ATF | DNA sequence |
| --- | --- |
| ZFATF1 | ATGCATCCTATGAACAACCTGCTGAACTACGTGGTGCCGA<br>AGATGAGACCTTACGCTTGTGATCGCCGCTTCTCCGTTTCC<br>CACCGGCTCACCCATCACATCCGCATCCACACAGGCCAGA<br>AGCCCTTCCAGTGCCGCATCTGCATGCGCAACTTCAGCCCT<br>AGCAGAAGACTCACCCAGCACATCCGCACCCACACAGGCG<br>AAAAGCCCTTCGCCTGCGACATCTGTGGAAGAAAGTTTGC<br>CCAGAGCGAGGGGCGCAAGGTCCATACCAAGATCCACTTG<br>CGGCAGAAGGACAAGAAAGCAGACAAAAGTGTTGTGGGG<br>CGCGCCGACGCGCTGGACGATTTCGATCTCGACATGCTGG<br>GTTCTGATGCCCTCGATGACTTTGACCTGGATATGTTGGGA<br>AGCGACGCATTGGATGACTTTGATCTGGACATGCTCGGCT<br>CCGATGCTCTGGACGATTTCGATCTCGATATGTTAATTAAC |

TABLE 6-continued

Sequences of ATF Hits in Cardiomyocyte Differentiation

| ATF | DNA sequence |
| --- | --- |
| | TACCCGTACGACGTTCCGGACTACGCTGGTTATCCCTATGA<br>CGTCCCGGATTATGCAGGATCCTATCCATATGACGTTCCAG<br>ATTACGCTTGA (SEQ ID NO: 72) |
| ZFATF2 | ATGCATCCTATGAACAACCTGCTGAACTACGTGGTGCCGA<br>AGATGAGACCTTACGCTTGCCCAGTGGAGTCCTGTGATCG<br>CCGCTTCTCCGGGTCCGTAGTCCTCACCAAACACATCCGCA<br>TCCACACAGGCCAGAAGCCCTTCCAGTGCCGCATCTGCAT<br>GCGCAACTTCAGCATAAGCACTGTTCTCACCGGTCACATC<br>CGCACCCACACAGGCGAAAAGCCCTTCGCCTGCGACATCT<br>GTGGAAGAAAGTTTGCCAACAGCGAGCCACGCAAGACCC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 73) |
| ATF5 | ATGCATCCTATGAACAACCTGCTGAACTACGTGGTGCCGA<br>AGATGAGACCTTACGATTGCCCAGTGGAGTCCTGTGATCG<br>CCGCTTCTCCAGATCCCATCGGCCACCAGCCACATCCGCAT<br>CCACACAGGCCAGAAGCCCTTCCAGTGCCGCATCTGCATG<br>CGCAACTTCAGCGTCAGCCCGACCCTCACCCGACACATCC<br>GCACCCACACAGGCGAAAAGCCCTTCGCCTGCGACATCTG<br>TGGAAGAAAGTTTGCCAGGAGCGACCAGCGCAAGAGACA<br>TACCAAGATCCACTTGCGGCAGAAGGACAAGAAAGCAGA<br>CAAAAGTGTTGTGGGGCGCGCCGACGCGCTGGACGATTTC<br>GATCTCGACATGCTGGGTTCTGATGCCCTCGATGACTTTGA<br>CCTGGATATGTTGGGAAGCGACGCATTGGATGACTTTGAT<br>CTGGACATGCTCGGCTCCGATGCTCTGGACGATTTCGATCT<br>CGATATGTTACCCGTACGACGTTCCGGACTACGCTGGTTAT<br>CCCTATGACGTCCCGGATTATGCAGGATCCTATCCATATGA<br>CGTTCCAGATTACGCTTGA (SEQ ID NO: 76) |
| ZFATF6 | ATGCATCCTATGAACAACCTGCTGAACTACGTGGTGCCGA<br>AGATGAGACCTTACGCTTGTGATCGCCGCTTCTCCGTTTCC<br>CACCGGCTCACCCATCACATCCGCATCCACACAGGCCAGA<br>AGCCCTTCCAGTGCCGCATCTGCATGCGCAACTTCAGCCTC<br>AGCCTAACCCTCACCAAACACATCCGCACCCACACAGGCG<br>AAAAGCCCTTCGCCTGCGACATCTGTGGAAGAAAGTTTGC<br>CAAAAGCAAACCACGCAAGACACATACCAAGATCCACTTG<br>CGGCAGAAGGACAAGAAAGCAGACAAAAGTGTTGTGGGG<br>CGCGCCGACGCGCTGGACGATTTCGATCTCGACATGCTGG<br>GTTCTGATGCCCTCGATGACTTTGACCTGGATATGTTGGGA<br>AGCGACGCATTGGATGACTTTGATCTGGACATGCTCGGCT<br>CCGATGCTCTGGACGATTTCGATCTCGATATGTTAATTAAC<br>TACCCGTACGACGTTCCGGACTACGCTGGTTATCCCTATGA<br>CGTCCCGGATTATGCAGGATCCTATCCATATGACGTTCCAG<br>ATTACGCTTGA (SEQ ID NO: 77) |
| ZFATF11 | ATGCATCCTATGAACAACCTGCTGAACTACGTGGTGCCGA<br>AGATGAGACCTTACGCTTGCCCAGTGGAGTCCTGTGATCG<br>CCGCTTCTCCATATCCGGTGCGCTCACCGGGCACATCCGCA<br>TCCACACAGGCCAGAAGCCCTTCCAGTGCCGCATCTGCAT<br>GCGCAACTTCAGCAGTAGCAATCAACTCACCGCGCACATC<br>CGCACCCACACAGGCGAAAAGCCCTTCGCCTGCGACATCT<br>GTGGAAGAAAGTTTGCCAGAAGCATACACCGCAAGCGTCA<br>TACCAAGATCCACTTGCGGCAGAAGGACAAGAAAGCAGA<br>CAAAAGTGTTGTGGGGCGCGCCGACGCGCTGGACGATTTC<br>GATCTCGACATGCTGGGTTCTGATGCCCTCGATGACTTTGA<br>CCTGGATATGTTGGGAAGCGACGCATTGGATGACTTTGAT<br>CTGGACATGCTCGGCTCCGATGCTCTGGACGATTTCGATCT<br>CGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 82) |
| ZFATF13 | ATGCATCCTATGAACAACCTGCTGAACTACGTGGTGCCGA<br>AGATGAGACCTTACGCTTGTGATCGCCGCTTCTCCGTTTCC<br>CACCGGCTCACCCATCACATCCGCATCCACACAGGCCAGA<br>AGCCCTTCCAGTGCCGCATCTGCATGCGCAACTTCAGCCCT<br>AGCAGAAGACTCACCCAGCACATCCGCACCCACACAGGCG |

TABLE 6-continued

Sequences of ATF Hits in Cardiomyocyte Differentiation

| ATF | DNA sequence |
|---|---|
| | AAAAGCCCTTCGCCTGCGACATCTGTGGAAGAAAGTTTGC<br>CAGGAGCGACCAGCGCAAGAGACATACCAAGATCCACTT<br>GCGGCAGAAGGACAAGAAAGCAGACAAAAGTGTTGTGGG<br>GCGCGCCGACGCGCTGGACGATTTCGATCTCGACATGCTG<br>GGTTCTGATGCCCTCGATGACTTTGACCTGGATATGTTGGG<br>AAGCGACGCATTGGATGACTTTGATCTGGACATGCTCGGC<br>TCCGATGCTCTGGACGATTTCGATCTCGATATGTTAATTAA<br>CTACCCGTACGACGTTCCGGACTACGCTGGTTATCCCTATG<br>ACGTCCCGGATTATGCAGGATCCTATCCATATGACGTTCCA<br>GATTACGCTTGA (SEQ ID NO: 92) |
| ZFATF14 | ATGCATCCTATGAACAACCTGCTGAACTACGTGGTGCCGA<br>AGATGAGACCTTACGCTTGCCCAGTGGAGTCCTGTGATCG<br>CCGCTTCTCCCGTTCCATCCGTCTCACCATACACATCCGCA<br>TCCACACAGGCCAGAAGCCCTTCCAGTGCCGCATCTGCAT<br>GCGCAACTTCAGCGGTAGCGTTCAACTCACCATACACATC<br>CGCACCCACACAGGCGAAAAGCCCTTCGCCTGCGACATCT<br>GTGGAAGAAAGTTTGCCCACAGCGAACCTCGCAAGACACA<br>TACCAAGATCCACTTGCGGCAGAAGGACAAGAAAGCAGA<br>CAAAAGTGTTGTGGGGCGCGCCGACGCGCTGGACGATTTC<br>GATCTCGACATGCTGGGTTCTGATGCCCTCGATGACTTTGA<br>CCTGGATATGTTGGGAAGCGACGCATTGGATGACTTTGAT<br>CTGGACATGCTCGGCTCCGATGCTCTGGACGATTTCGATCT<br>CGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 93) |
| ZFATF15 | ATGCATCCTATGAACAACCTGCTGAACTACGTGGTGCCGA<br>AGATGAGACCTTACGCTTGCCCAGTGGAGTCCTGTGATCG<br>CCGCTTCTCCGGGTCCAGCGGGCTCACCATGCACATCCGC<br>ATCCACACAGGCCAGAAGCCCTTCCAGTGCCGCATCTGCA<br>TGCGCAACTTCAGCCTAAGCACAACACTCACCAACCACAT<br>CCGCACCCACACAGGCGAAAAGCCCTTCGCCTGCGACATC<br>TGTGGAAGAAAGTTTGCCACAAGCCGTACACGCAAGCGGC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 94) |
| ZFATF16 | ATGCATCCTATGAACAACCTGCTGAACTACGTGGTGCCGA<br>AGATGAGACCTTACGCTTGCCCAGTGGAGTCCTGTGATCG<br>CCGCTTCTCCCGTTCCATCCGTCTCACCATACACATCCGCA<br>TCCACACAGGCCAGAAGCCCTTCCAGTGCCGCATCTGCAT<br>GCGCAACTTCAGCCACAGCCCGCAACTCACCCCTCACATC<br>CGCACCCACACAGGCGAAAAGCCCTTCGCCTGCGACATCT<br>GTGGAAGAAAGTTTGCCGAAAGCCGTAAACGCAAGGAAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 95) |
| ZFATF17 | ATGCATCCTATGAACAACCTGCTGAACTACGTGGTGCCGA<br>AGATGAGACCTTACGCTTGCCCAGTGGAGTCCTGTGATCG<br>CCGCTTCTCCCGTTCCATCCGTCTCACCATACACATCCGCA<br>TCCACACAGGCCAGAAGCCCTTCCAGTGCCGCATCTGCAT<br>GCGCAACTTCAGCGGTAGCGTTCCACTCACCATACACATC<br>CGCACCCACACAGGCGAAAAGCCCTTCGCCTGCGACATCT<br>GTGGAAGAAAGTTTGCCAGGAGCGACCAGCGCAAGAGAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG |

TABLE 6-continued

Sequences of ATF Hits in Cardiomyocyte Differentiation

| ATF | DNA sequence |
|---|---|
| | ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 96) |
| ATF18 | ATGCATCCTATGAACAACCTGCTGAACTACGTGGTGCCGA<br>AGATGAGACCTTACGCTTGCCCAGTGGAGCCCTGTGATCG<br>CCGCTTCTCCCGTTCCATCCGTCTCACCATACACATCCGCA<br>TCCACACAGGCCAGAAGCCCTTCCAGTGCAGCATCTGCAT<br>GCGCAACTTCAGCGGTAGCGATCAACTCACCATAAACAAC<br>CGCACCAACACAGGCGAAAAGCCATACGCATGA (SEQ ID NO: 97) |
| ZFATF19 | ATGCATCCTATGAACAACCTGCTGAACTACGTGGTGCCGA<br>AGATGAGACCTTACGCTTGCCCAGTGGAGTCCTGTGATCG<br>CCGCTTCTCCATATCCGGTGCGCTCACCGGGCACATCCGCA<br>TCCACACAGGCCAGAAGCCCTTCGCCTGCGACATCTGTGG<br>AAGAAAGTTTGCCAGGAGCGACCAGCGCAAGAGACATAC<br>CAAGATCCACTTGCGGCAGAAGGACAAGAAAGCAGACAA<br>AAGTGTTGTGGGGCGCGCCGACGCGCTGGACGATTTCGAT<br>CTCGACATGCTGGGTTCTGATGCCCTCGATGACTTTGACCT<br>GGATATGTTGGGAAGCGACGCATTGGATGACTTTGATCTG<br>GACATGCTCGGCTCCGATGCTCTGGACGATTTCGATCTCGA<br>TATGTTAATTAACTACCCGTACGACGTTCCGGACTACGCTG<br>GTTATCCCTATGACGTCCCGGATTATGCAGGATCCTATCCA<br>TATGACGTTCCAGATTACGCTTGA (SEQ ID NO: 98) |

Figure 20:
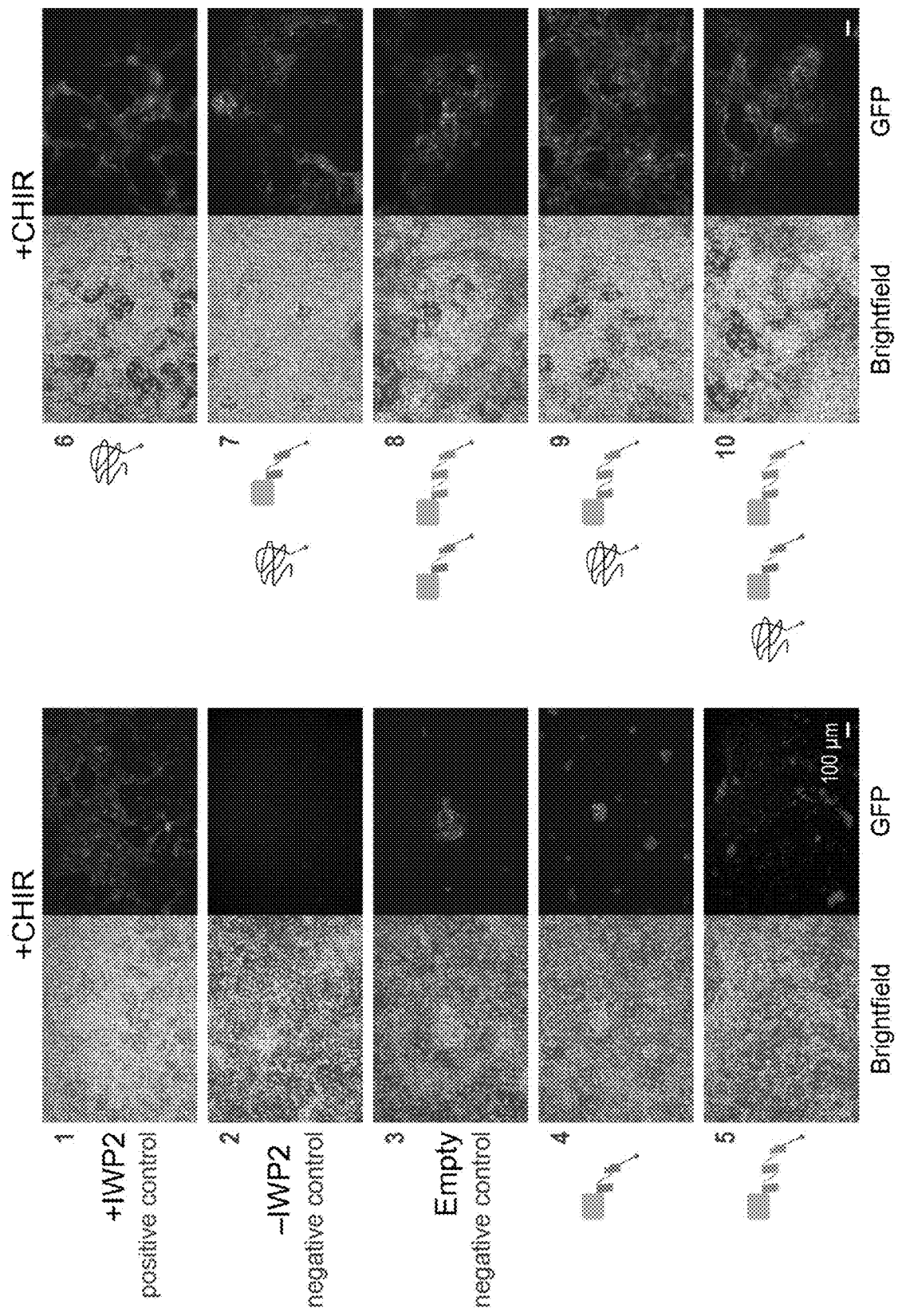
FIG. 20 demonstrates validation of ATFs from the cardiomyocyte screen. H9 cTnnT-pGZ cells were transduced with lentiviruses encoding ATFs. After selection for transduced cells, cells were treated with the GSK3 inhibitor, CHIR99021. On Day 3 of differentiation, the positive control was also treated with the Wnt maturation inhibitor, IWP2. No other condition was treated with IWP2. On Day 10, cells were evaluated for expression of GFP, structure of cardiomyocyte sheaths, and capacity to beat.

Compared to the positive control in which H9-cTnnT-pGZ cells are treated with both inhibitors (CHIR and IWP2), C3+CHIR could generate cardiomyocytes just as efficiently. We also qualitatively assessed the quality of the cardiomyocytes by evaluating their capacity to beat and form large cardiomyocyte sheaths. The cardiomyocytes derived from C3+CHIR formed large beating sheaths with a strong, regular beat, demonstrating functional changes in phenotype. Subsets of C3+CHIR that also generated healthy cardiomyocytes, include Treatment 7, Treatment 8, and Treatment 9 (FIG. 20). Compared to the positive control, cells expressing two or more ATFs generated cardiomyocytes of equal quality. Treatment 9 produced cardiomyocytes at a high efficiency, equal to or greater than the positive control. Treatment 6 demonstrated that one ATF was sufficient to replace the function of IWP2; however, the cardiomyocyte sheets were narrower for this treatment. The Empty control accounts for spontaneous differentiation due to lentiviral delivery or random integration of a strong promoter at a relevant site in the genome. The differentiated cells in Treatments 3, 4, and 5 were morphologically different from the cardiomyocytes in the positive control despite being GFP and exhibited irregular beating. Of the subsets, Treatment 9 (ATF5+ZFATF2+CHIR) most efficiently generated cardiomyocytes. When ATF5 was expressed alone with CHIR treatment (Treatment 9), we were able to generate cardiomyocytes; however, narrower sheaths formed, suggesting lower efficiencies in conversion. Other subsets, including ATFs expressed one at a time, did not generate healthy cardiomyocytes with a regular beat.

ATF Targets and Mechanism of Action

Figures 21A, 21B:
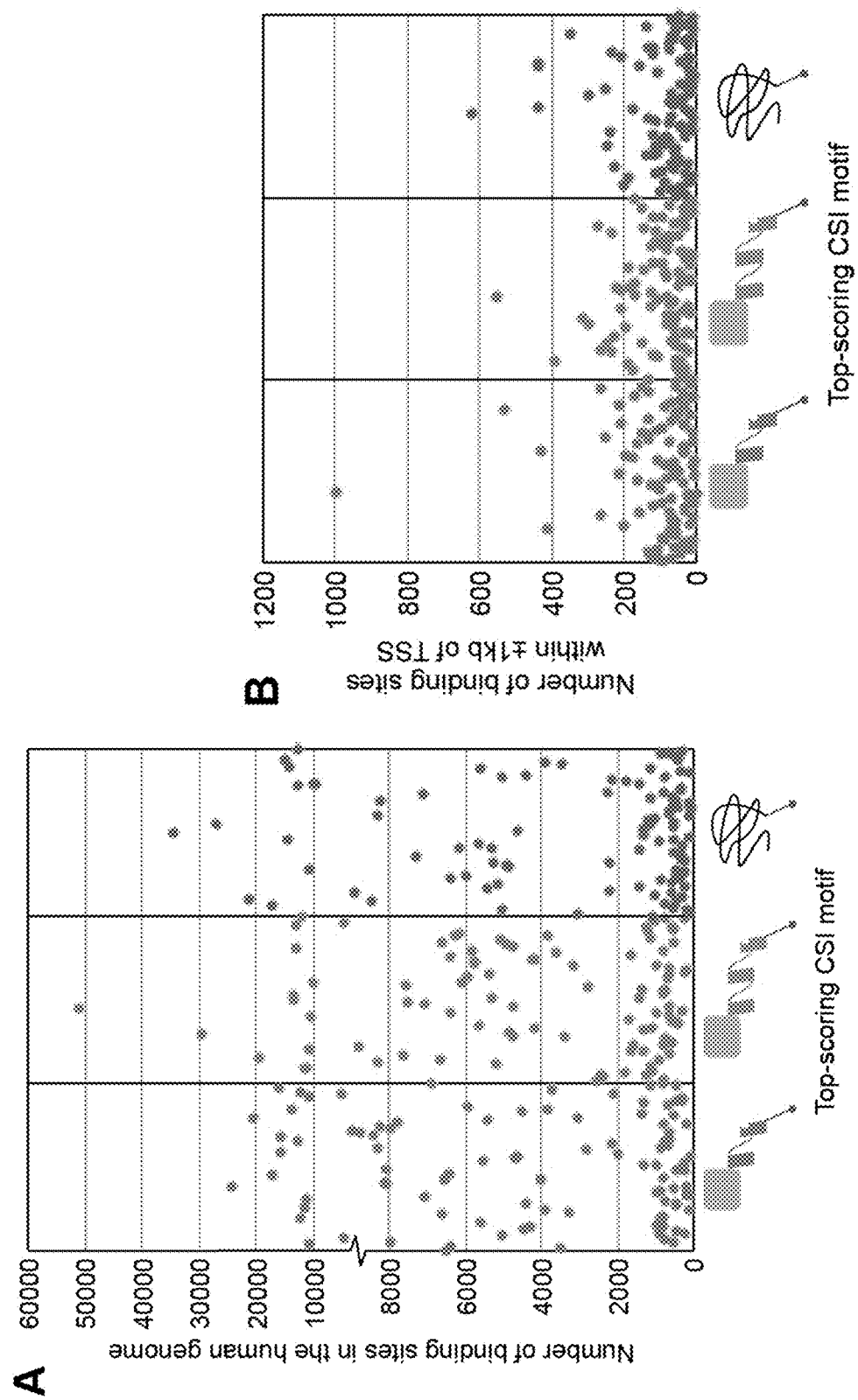
FIGS. 21A-21B present a representation of cardiomyocyte ATF sequences in the human genome. (A) The number of times the top 100 scoring CSI motifs appeared in the genome was quantified. Each data point represents a unique 10-bp sequence. (B) The number of times the top 100 scoring CSI motifs appeared within ±1 kb of a TSS was quantified. Each data point represents a unique 10-bp sequence. The observed frequencies near the TSS are different from the expected frequencies (p<0.001 for df-2 and chi-squared=172).

In order to identify the ATF target genes, cognate site identification (CSI) described in Chapter 3, was used to find the top 100 scoring motifs for each ATF. The locations of these top-scoring motifs were identified in the human genome, then annotated to the nearest genes. The frequency of occurrence in the genome was plotted as well as the frequency within ±1 kb of a transcription start site (TSS) (FIGS. 21A-21B). Table 6 presents the frequency of occurrence of ATF binding sites for the top 100 scoring CSI motifs. ATFs: The ATFs of C3+CHIR. Total: The number of ATF binding sites in the human genome for the top 100 scoring CSI motifs. Near TSS: The number of ATF binding sites within ±1 kb of a TSS. Genes: The number of genes with ATF binding sites within ±1 kb of a TSS. Cardiomyocyte: The number of cardiomyocyte genes with ATF binding sites within ±1 kb of a TSS. Early: The number of cardiomyocyte genes with ATF binding sites within ±1 kb of a TSS expressed at an early stage. Middle: The number of cardiomyocyte genes with ATF binding sites within ±1 kb of a TSS expressed at a middle stage. Late: The number of cardiomyocyte genes with ATF binding sites within ±1 kb of a TSS expressed at a late stage of differentiation. Cardiomyocyte markers: see Burridge et al., 2012 *Cell Stem Cell* 10(1): 16-28; Stillitano et al., 2012 *Drug Discov Today* 9(4):e229-e236.

Figures 22A, 22B, 22C:
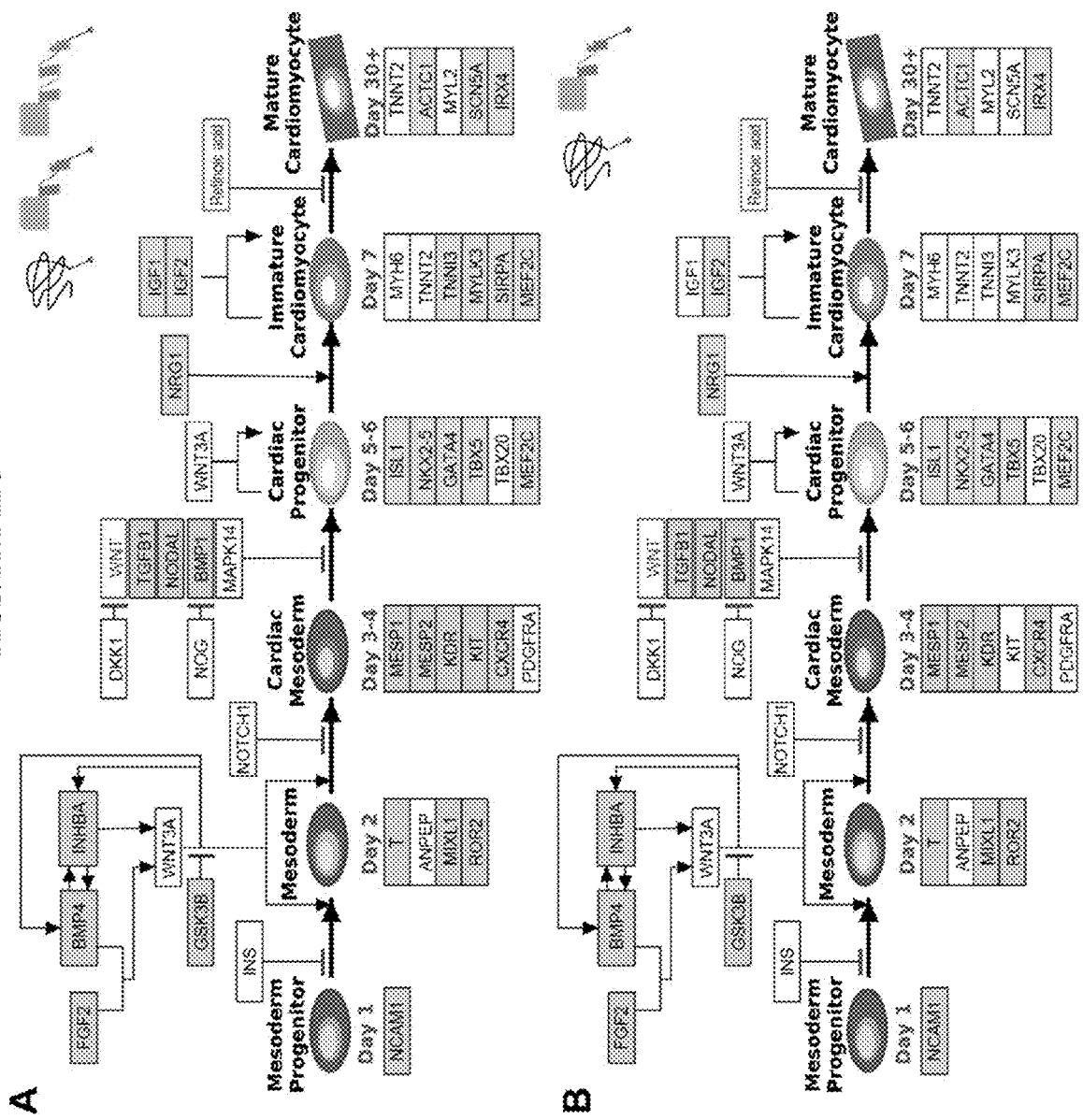
FIGS. 22A-22C illustrate target genes of ATFs. The locations of the top 10 scoring 10-bp sequences from CSI were determined in the human genome. Genes highlighted in blue (early genes), green (middle genes), and yellow (late genes) have an ATF binding site within ±1 kb of the TSS. (A) Target genes of ATF5, ZFATF1, and ZFATF2 (Treatment 10). (B) Target genes of ATF5 and ZFATF1 (Treatment 7). (C) Target genes of ATF5 and ZFATF2 (Treatment 9).

Although there are more than 370,000 medium to high affinity binding sites in the genome, fewer than 10,000 are near a TSS (Table 7). Among those that are near a TSS, 30 genes are markers of cardiomyocytes for C3+CHIR. ATF5 targets the greatest number of cardiomyocyte genes, consistent with the result that ATF5+CHIR can generate cardiomyocytes, albeit at a lower efficiency than C3+CHIR. Also consistent with the bioinformatic analysis is that a larger fraction of ATF binding sites for Treatment 9 (ATF5+ZFATF2+CHIR) occur for late genes, rather than early ones, compared to C3+CHIR, increasing the efficiency of conversion to cardiomyocytes from mesodermal progenitor cells (FIGS. 22A-22C).

Materials and Methods

Cell Culture:

H9 cTnnT-pGZ cells were maintained in E8 (DMEM/F12 with HEPES, 64 mg/L L-ascorbic acid, 14 μg/L sodium selenium, 100 μg/L FGF2, 19.4 mg/L insulin, 10.7 mg/L transferrin, and 2 μg/L TGFβ1) on Matrigel® substrate (BD Biosciences, NJ). Cells were passaged with 0.5 mM EDTA. For cardiomyocyte differentiation, cells were maintained in RPMI 1640+B27 without insulin for the first 9 days and in RPMI 1640+B27 with insulin after Day 9. Differentiation was performed by addition of CHIR99021 (6 μM) on Day 0 and IWP2 (5 μM) on Day 3. Cells were maintained in a humidified 37° C. incubator with 5% $CO_2$.

Lentivirus Production:

ATFs and the empty control were packaged into lentivirus using a second-generation lentiviral system. Lentivirus was produced in HEK293T cells by calcium phosphate transfection of pSIN expression, psPAX2 packaging, and pMD2.G envelope plasmids. Media containing virus was harvested 48-60 hours post-transfection. Lentivirus was centrifuged with a sucrose cushion at 25,000 rpm for 2 hours. Viral particles were suspended in PBS and concentrated virus was stored at −80° C. Viral titers were measured by counting HEK293T cells that survived selection after 2 days in media containing puromycin (3 μg/mL).

Lentivirus Transduction:

Lentiviruses were delivered to H9 cTnnT-pGZ cells with 8 μg/mL polybrene. Selection was performed in media containing puromycin (1 μg/mL first day, 1.5 μg/mL second day). The ATF was driven by a constitutive promoter, EF1α.

TABLE 7

ATF binding site summary

| ATFs | Total | Near TSS | Genes | Cardiomyocyte | Early | Middle | Late |
|---|---|---|---|---|---|---|---|
| ATF5 | 374,143 | 9,197 | 7,514 | 16 | 5 | 4 | 7 |
| ZFATF1 | 468,693 | 9,889 | 7,925 | 15 | 5 | 6 | 4 |
| ZFATF2 | 477,041 | 9,872 | 7,811 | 12 | 1 | 2 | 9 |
| ATF5 + ZFATF1 + ZFATF2 | 1,319,877 | 28,958 | 16,654 | 30 | 8 | 8 | 14 |
| ATF5 + ZFATF1 | 842,836 | 19,086 | 12,949 | 25 | 8 | 7 | 10 |
| ATF5 + ZFATF2 | 851,184 | 19,069 | 12,861 | 24 | 6 | 5 | 13 |

Discussion

This study demonstrates that an ATF library can be used as an effective forward genetic screen to identify transcriptional regulators of cardiomyocyte differentiation. By testing the ATF library in the context of replacing the function of the Wnt pathway inhibitors, we were able to show that ATFs can promote differentiation into cardiomyocytes after conversion to mesodermal progenitor cells. By developing a high throughput strategy of sequencing ATFs, the ability to identify the ATFs responsible for cardiomyocyte differentiation from single cells is much more straightforward. Bioinformatic analysis of CSI motifs suggests that the ATFs target cardiomyocyte-specific genes. Additional analysis on upstream targets by chromatin immunoprecipitation as well as further characterization of the ATF-generated cardiomyocytes would aid in the understanding of how the ATFs induce differentiation. Comparisons of cardiomyocyte-specific transcripts would allow us to determine the contribution of the ATFs in inducing differences in quality of cardiomyocytes and efficiency of conversion.

Flow Cytometry:

Flow Cytometry was conducted for GFP using a FACS Calibur flow cytometer (BD). Cells were sorted into a 96-well plate for single-cell isolation.

Identification of ATFs from Single Cells:

ATF sequences were identified by 3-step PCR followed by high-throughput sequencing. In the first round of PCR, ATFs were amplified with primer set 1 (Table 8). During the third PCR step, amplicons were barcoded with Illumina indexes (Epicentre RSBC10948, SSIP1202, SSIP1203, and SSIP1204). 48 cells were multiplexed on a MiSeq chip with paired-end 250 bp reads.

TABLE 8

Primer Sequences for ATF Identification

| Primer | 5'-3' |
|---|---|
| Forward 1 | TCAAGCCTCAGACAGTGGTTC (SEQ ID NO: 111) |

TABLE 8-continued

Primer Sequences for ATF Identification

| Primer | 5'-3' |
|---|---|
| Reverse 1 | TCACTAATACCTTACTTAACTCTAATCTTAGTCAAGC GTAATCTGGAACGTCATATGGATAGGATCCTGC (SEQ ID NO: 112) |
| Forward 2 | TACTATCACTAACTTAGCCGCCACCATG (SEQ ID NO: 113) |
| Reverse 2 | GTGACTGGAGTTCAGACGTGTGCTCTTCCGATCTGTC CTTCTGCCGCAAGTGGAT (SEQ ID NO: 114) |
| Forward 3 | AATGATACGGCGACCACCGAGATCTACACTCTTTCCC TACACGACGCTCTTCCGATCTGCTGAACTACGTGGTG CCGAAG (SEQ ID NO: 115) |
| Reverse 3 | CAAGCAGAAGACGGCATACGAGATXXXXXXGTGACTG GAGTTCAGACGTGTGCTCTTCCGATCT (SEQ ID NO: 116) |

X indicates nucleotides from barcodes.

Sequencing data was analyzed by searching for sequences identifying fingers 1, 2, and 3 (Table 9).

TABLE 9

Identifying Sequences

| Region | 5'-3' |
|---|---|
| 5' zinc finger 1 | TGTGATCGCCGCTTCTCC (SEQ ID NO: 117) |
| 3' zinc finger 1 | CTGTGTGGATGCGGATGTG (SEQ ID NO: 118) |
| 5' zinc finger 2 | TGCATGCGCAACTTCAGC (SEQ ID NO: 119) |
| 3' zinc finger 2 | TTCGCCTGTGTGGGTGCGGATGTG (SEQ ID NO: 120) |
| 5' zinc finger 3 | TGTGGAAGAAAGTTTGCC (SEQ ID NO: 121) |
| 3' zinc finger 3 | CGCAAGTGGATCTTGGTATG (SEQ ID NO: 122) |

Microscopy:

Micrographs were taken with a 10× objective on a Zeiss Observer A1 with an AxioCam ICm1.

Cognate Site Identification:

HEK293 cells were transiently transfected with ATFs using Lipofectamine 2000 (Thermo Fisher #11668019). Cells that underwent a mock transfection (without an expression plasmid for ATFs) served as a negative control. Cells were harvested 48 hours post-transfection. Lysates were prepared by lysing $10^7$ cells in 300 μL of lysis buffer (50 mM Tris-HCl pH 7.5, 150 mM NaCl, 1% Triton X-100, and 0.1% Na deoxycholate). A 21.5 G syringe needle was used for mechanical lysis. Lysates were centrifuged at 10 k×g for 10 min to separate precipitated genomic DNA from protein constituents. The supernatant, containing ATF protein, was used for CSI. HA magnetic beads (MBL #M132-9) were added to the cell lysates for immunoprecipitation. The binding reaction between the ATFs and 100 nM synthetic DNA was performed in binding buffer (25 mM HEPES, 80 mM KCl, 0.2 mM EDTA, 1 mM MgCl$_2$, 0.1 mM ZnSO$_4$) at 25° C. After pull-down, three quick washes with 100 μL ice-cold binding buffer were performed to remove unbound DNA. Magnetic beads were resuspended in a PCR master mix (Lucigen #30035-1) and the DNA was amplified for 15 or 18 cycles. Amplified DNA was column purified (Qiagen #28106), and this enriched DNA pool was used for the subsequent round of enrichment, for a total of three rounds. After three rounds of selection, Illumina sequencing adapters and a unique 6 bp barcode for multiplexing were added by PCR amplification. The starting library (Round 0) was also barcoded. Up to 180 samples were combined and sequenced in a single HiSeq2000 lane.

Illumina sequencing yielded ~180 million reads per lane. Reads were de-multiplexed by requiring an exact match to the 6 bp barcode and truncated to include only the 25 bp derived from the random portion of the library. On average, we obtained 709,300 reads per barcode. The occurrence of every k-mer (lengths 8 through 16 bp) was counted using a sliding window of size k. To correct for biases in our starting DNA library, we took the ratio of the counts of every k-mer to the expected number of counts in the mock-transfected control. The mock control was modeled using a 5th-order Markov Model derived from the sequencing reads corresponding to the starting library (Round 0). We then calculated a Z-score=$(x-\mu)/\sigma$ or (CSI score minus mean)/standard deviation for each k-mer, using the distribution of k-mer enrichment values (CSI score) for the ATF.

Bioinformatic Analysis of ATF Binding Sites:

The genomic locations of the top five or 100 high-scoring 10-bp motifs from CSI were identified in the mm10 genome by the findMotif utility from the UCSC Genome Browser. These genomic sites were annotated using Homer. Annotated sites were filtered to those within +1 kb of the TSS.

REFERENCES

All publications, including but not limited to patents and patent applications, cited below are herein incorporated by reference as though set forth in their entirety in the present application.

Bae, K.-H., Kwon, Y. D., Shin, H.-C., Hwang, M.-S., Ryu, E.-H., Park, K.-S., Yang, H.-Y., Lee, D.-K., Lee, Y., Park, J., et al. (2003). Human zinc fingers as building blocks in the construction of artificial transcription factors. Nat Biotechnol 21, 275-280.

Bailus, B. J., Pyles, B., McAlister, M. M., O'Geen, H., Lockwood, S. H., Adams, A. N., Nguyen, J. T. T., Yu, A., Berman, R. F., and Segal, D. J. (2016). Protein delivery of an artificial transcription factor restores widespread Ube3a expression in an Angelman syndrome mouse brain. Mol Ther 24, 548-555.

Blancafort, P., Magnenat, L., and Barbas, C. F. (2003). Scanning the human genome with combinatorial transcription factor libraries. Nat Biotechnol 21, 269-274.

Buganim, Y., Faddah, D. A., Cheng, A. W., Itskovich, E., Markoulaki, S., Ganz, K., Klemm, S. L., van Oudenaarden, A., and Jaenisch, R. (2012). Single-cell expression analyses during cellular reprogramming reveal an early stochastic and a late hierarchic phase. Cell 150, 1209-1222.

Burridge P W, et al. (2014) Chemically defined generation of human cardiomyocytes. *Nat Methods* 11(8):855-860.

Burridge P W, Keller G, Gold J D, Wu J C (2012) Production of de novo cardiomyocytes: human pluripotent stem cell differentiation and direct reprogramming. *Cell Stem Cell* 10(1): 16-28.

Cahan, P., Li, H., Morris, S. A., Lummertz da Rocha, E., Daley, G. Q., and Collins, J. J. (2014). CellNet: network biology applied to stem cell engineering. Cell 158, 903-915.

Chavez, A., Scheiman, J., Vora, S., Pruitt, B. W., Tuttle, M., P R Iyer, E., Lin, S., Kiani, S., Guzman, C. D., Wiegand, D. J., et al. (2015). Highly efficient Cas9-mediated transcriptional programming. Nat Methods 12, 326-328.

Chen B, et al. (2009) Small molecule-mediated disruption of Wnt-dependent signaling in tissue regeneration and cancer. *Nat Chem Biol* 5(2): 100-107.

Chen, E. Y., Tan, C. M., Kou, Y., Duan, Q., Wang, Z., Meirelles, G. V., Clark, N. R., and Ma'ayan, A. (2013). Enrichr: interactive and collaborative HTML5 gene list enrichment analysis tool. BMC Bioinformatics 14, 128.

Cheng, C., and Gerstein, M. (2012). Modeling the relative relationship of transcription factor binding and histone modifications to gene expression levels in mouse embryonic stem cells. Nucleic Acids Res 40, 553-568.

Cohen, D. E., and Melton, D. (2011). Turning straw into gold: directing cell fate for regenerative medicine. Nat Rev Genet 12, 243-252.

Edelson, B. S., Best, T. P., Olenyuk, B., Nickols, N. G., Doss, R. M., Foister, S., Heckel, A., and Dervan, P. B. (2004). Influence of structural variation on nuclear localization of DNA-binding polyamide-fluorophore conjugates. Nucleic Acids Res 32, 2802-2818.

Eguchi, A., Lee, G. O., Wan, F., Erwin, G. S., and Ansari, A. Z. (2014). Controlling gene networks and cell fate with precision-targeted DNA-binding proteins and small-molecule-based genome readers. Biochem J 462, 397-413.

Esvelt, K. M., Mali, P., Braff, J. L., Moosburner, M., Yaung, S. J., and Church, G. M. (2013). Orthogonal Cas9 proteins for RNA-guided gene regulation and editing. Nat Methods 10, 1116-1121.

Filion, G. J. P., Zhenilo, S., Salozhin, S., Yamada, D., Prokhortchouk, E., and Defossez, P.-A. (2006). A family of human zinc finger proteins that bind methylated DNA and repress transcription. Mol Cell Biol 26, 169-181.

Gao, X., Yang, J., Tsang, J. C. H., Ooi, J., Wu, D., and Liu, P. (2013). Reprogramming to pluripotency using designer TALE transcription factors targeting enhancers. Stem Cell Reports 1, 183-197.

Gilbert, L. A., Horlbeck, M. A., Adamson, B., Villalta, J. E., Chen, Y., Whitehead, E. H., Guimaraes, C., Panning, B., Ploegh, H. L., Bassik, M. C., et al. (2014). Genome-scale CRISPR-mediated control of gene repression and activation. Cell 159, 647-661.

Gonzalez, B., Schwimmer, L. J., Fuller, R. P., Ye, Y., Asawapornmongkol, L., and Barbas, C. F. (2010). Modular system for the construction of zinc-finger libraries and proteins. Nat Protoc 5, 791-810.

Greder, L. V., Gupta, S., Li, S., Abedin, M. J., Sajini, A., Segal, Y., Slack, J. M. W., and Dutton, J. R. (2012). Analysis of endogenous Oct4 activation during induced pluripotent stem cell reprogramming using an inducible Oct4 lineage label. Stem Cells 30, 2596-2601.

Heng, J.-C. D., Feng, B., Han, J., Jiang, J., Kraus, P., Ng, J.-H., Orlov, Y. L., Huss, M., Yang, L., Lufkin, T., et al. (2010). The nuclear receptor Nr5a2 can replace Oct4 in the reprogramming of murine somatic cells to pluripotent cells. Cell Stem Cell 6, 167-174.

Hnisz, D., Abraham, B. J., Lee, T. I., Lau, A., Saint-André, V., Sigova, A. A., Hoke, H. A., and Young, R. A. (2013). Super-enhancers in the control of cell identity and disease. Cell 155, 934-947.

Ieda, M., Fu, J.-D., Delgado-Olguin, P., Vedantham, V., Hayashi, Y., Bruneau, B. G., and Srivastava, D. (2010). Direct reprogramming of fibroblasts into functional cardiomyocytes by defined factors. Cell 142, 375-386.

Isalan, M., Choo, Y., and Klug, A. (1997). Synergy between adjacent zinc fingers in sequence-specific DNA recognition. Proc Natl Acad Sci USA 94, 5617-5621.

Kim, J., Chu, J., Shen, X., Wang, J., and Orkin, S. H. (2008). An extended transcriptional network for pluripotency of embryonic stem cells. Cell 132, 1049-1061.

Kim, Y., Kweon, J., Kim, A., Chon, J. K., Yoo, J. Y., Kim, H. J., Kim, S., Lee, C., Jeong, E., Chung, E., et al. (2013). A library of TAL effector nucleases spanning the human genome. Nat Biotechnol 31, 251-258.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2015). Genome-scale transcriptional activation by an engineered CRISPR-Cas9 complex. Nature 517, 583-588.

Koudritsky, M., and Domany, E. (2008). Positional distribution of human transcription factor binding sites. Nucleic Acids Res 36, 6795-6805.

Krentz, A. D., Murphy, M. W., Zhang, T., Sarver, A. L., Jain, S., Griswold, M. D., Bardwell, V. J., and Zarkower, D. (2013). Interaction between DMRT1 function and genetic background modulates signaling and pluripotency to control tumor susceptibility in the fetal germ line. Dev Biol 377, 67-78.

Lalit P A, Hei D J, Raval A N, Kamp T J (2014) Induced pluripotent stem cells for post-myocardial infarction repair: remarkable opportunities and challenges. *Circ Res* 114(8): 1328-1345.

Li, Y., Ehrhardt, K., Zhang, M. Q., and Bleris, L. (2014). Assembly and validation of versatile transcription activator-like effector libraries. Sci Rep 4, 4857.

Lian X, et al. (2012) Robust cardiomyocyte differentiation from human pluripotent stem cells via temporal modulation of canonical Wnt signaling. *Proc Natl Acad Sci USA* 109(27):E1848-57.

Lian X, et al. (2013) Directed cardiomyocyte differentiation from human pluripotent stem cells by modulating Wnt/β-catenin signaling under fully defined conditions. *Nat Protoc* 8(1): 162-175.

Lujan, E., Zunder, E. R., Ng, Y. H., Goronzy, I. N., Nolan, G. P., and Wernig, M. (2015). Early reprogramming regulators identified by prospective isolation and mass cytometry. Nature 521, 352-356.

Marson, A., Levine, S. S., Cole, M. F., Frampton, G. M., Brambrink, T., Johnstone, S., Guenther, M. G., Johnston, W. K., Wernig, M., Newman, J., et al. (2008). Connecting microRNA genes to the core transcriptional regulatory circuitry of embryonic stem cells. Cell 134, 521-533.

Moretti, R., and Ansari, A. Z. (2008). Expanding the specificity of DNA targeting by harnessing cooperative assembly. Biochimie 90, 1015-1025.

Najafabadi, H. S., Mnaimneh, S., Schmitges, F. W., Garton, M., Lam, K. N., Yang, A., Albu, M., Weirauch, M. T., Radovani, E., Kim, P. M., et al. (2015). C2H2 zinc finger proteins greatly expand the human regulatory lexicon. Nat Biotechnol.

Pabo, C. O., and Sauer, R. T. (1992). Transcription factors: structural families and principles of DNA recognition. Annu Rev Biochem 61, 1053-1095.

Rajala K, Pekkanen-Mattila M, Aalto-Setälä K (2011) Cardiac differentiation of pluripotent stem cells. *Stem Cells Int* 2011:383709.

Rebar, E. J., Huang, Y., Hickey, R., Nath, A. K., Meoli, D., Nath, S., Chen, B., Xu, L., Liang, Y., Jamieson, A. C., et al. (2002). Induction of angiogenesis in a mouse model using engineered transcription factors. Nat Med 8, 1427-1432.

Rodriguez-Martinez, J. A., Reinke, A. W., Bhimsaria, D., Keating, A. E., and Ansari, A. Z. (2016). Combinatorial dimerization of human bZIP transcription regulators confers preferences for different classes of DNA binding sites. Cell.

Sekiya, S., and Suzuki, A. (2011). Direct conversion of mouse fibroblasts to hepatocyte-like cells by defined factors. Nature 475, 390-393.

Schultz D C, Ayyanathan K, Negorev D, Maul G G, Rauscher F J (2002) SETDB1: a novel KAP-1-associated histone H3, lysine 9-specific methyltransferase that contributes to HP1-mediated silencing of euchromatic genes by KRAB zinc-finger proteins. Genes Dev 16(8):919-932.

Sharov, A. A., Masui, S., Sharova, L. V., Piao, Y., Aiba, K., Matoba, R., Xin, L., Niwa, H., and Ko, M. S. H. (2008). Identification of Pou5f1, Sox2, and Nanog downstream target genes with statistical confidence by applying a novel algorithm to time course microarray and genomewide chromatin immunoprecipitation data. BMC Genomics 9, 269.

Shu, J., Wu, C., Wu, Y., Li, Z., Shao, S., Zhao, W., Tang, X., Yang, H., Shen, L., Zuo, X., et al. (2013). Induction of pluripotency in mouse somatic cells with lineage specifiers. Cell 153, 963-975.

Som, A., Harder, C., Greber, B., Siatkowski, M., Paudel, Y., Warsow, G., Cap, C., Schöler, H., and Fuellen, G. (2010). The PluriNetWork: an electronic representation of the network underlying pluripotency in mouse, and its applications. PLoS ONE 5, e15165.

Stillitano F, Karakikes I, Costa K D, Fish K (2012) Preclinical animal models for testing iPSC/ESC-based heart therapy. Drug Discov Today 9(4):e229-e236.

Takahashi, K., and Yamanaka, S. (2006). Induction of pluripotent stem cells from mouse embryonic and adult fibroblast cultures by defined factors. Cell 126, 663-676.

Takahashi, K., Okita, K., Nakagawa, M., and Yamanaka, S. (2007a). Induction of pluripotent stem cells from fibroblast cultures. Nat Protoc 2, 3081-3089.

Takahashi, K., Tanabe, K., Ohnuki, M., Narita, M., Ichisaka, T., Tomoda, K., and Yamanaka, S. (2007b). Induction of pluripotent stem cells from adult human fibroblasts by defined factors. Cell 131, 861-872.

Tanenbaum, M. E., Gilbert, L. A., Qi, L. S., Weissman, J. S., and Vale, R. D. (2014). A protein-tagging system for signal amplification in gene expression and fluorescence imaging. Cell 159, 635-646.

Teschendorf, C., Warrington, K. H., Jr, and Siemann, D. W. (2001). Comparison of the EF-1 alpha and the CMV promoter for engineering stable tumor cell lines using recombinant adeno-associated virus. Anticancer . . . .

Tietjen, J. R., Donato, L. J., Bhimsaria, D., and Ansari, A. Z. (2011). Sequence-specificity and energy landscapes of DNA-binding molecules. Meth Enzymol 497, 3-30.

Triezenberg, S. J., Kingsbury, R. C., and McKnight, S. L. (1988). Functional dissection of VP16, the trans-activator of herpes simplex virus immediate early gene expression. Genes Dev 2, 718-729.

Tschulena, U., Peterson, K. R., Gonzalez, B., Fedosyuk, H., and Barbas, C. F. (2009). Positive selection of DNA-protein interactions in mammalian cells through phenotypic coupling with retrovirus production. Nat Struct Mol Biol 16, 1195-1199.

Valton, J., Dupuy, A., Daboussi, F., Thomas, S., Marechal, A., Macmaster, R., Melliand, K., Juillerat, A., and Duchateau, P. (2012). Overcoming transcription activator-like effector (TALE) DNA binding domain sensitivity to cytosine methylation. J Biol Chem 287, 38427-38432.

Vierbuchen, T., Ostermeier, A., Pang, Z. P., Kokubu, Y., Südhof, T. C., and Wernig, M. (2010). Direct conversion of fibroblasts to functional neurons by defined factors. Nature 463, 1035-1041.

Wang, B. S., Grant, R. A., and Pabo, C. O. (2001). Selected peptide extension contacts hydrophobic patch on neighboring zinc finger and mediates dimerization on DNA. Nat Struct Biol 8, 589-593.

Wang, R., and Brattain, M. G. (2007). The maximal size of protein to diffuse through the nuclear pore is larger than 60 kDa. FEBS Letters 581, 3164-3170.

Wang, T., Wei, J. J., Sabatini, D. M., and Lander, E. S. (2014). Genetic screens in human cells using the CRISPR-Cas9 system. Science 343, 80-84.

Whitfield, T. W., Wang, J., Collins, P. J., Partridge, E. C., Aldred, S. F., Trinklein, N. D., Myers, R. M., and Weng, Z. (2012). Functional analysis of transcription factor binding sites in human promoters. Genome Biol 13, R50.

Whyte, W. A., Orlando, D. A., Hnisz, D., Abraham, B. J., Lin, C. Y., Kagey, M. H., Rahl, P. B., Lee, T. I., and Young, R. A. (2013). Master transcription factors and mediator establish super-enhancers at key cell identity genes. Cell 153, 307-319.

Wrighton P J, et al. (2014) Signals from the surface modulate differentiation of human pluripotent stem cells through glycosaminoglycans and integrins. Proc Natl Acad Sci USA 111(51):18126-18131.

Wolfe, S. A., Nekludova, L., and Pabo, C. O. (2000). DNA recognition by Cys2His2 zinc finger proteins. Annu Rev Biophys Biomol Struct 29, 183-212.

Wu D, Pan W (2010) GSK3: a multifaceted kinase in Wnt signaling. Trends Biochem Sci 35(3):161-168.

Yu, J., Vodyanik, M. A., Smuga-Otto, K., Antosiewicz-Bourget, J., Frane, J. L., Tian, S., Ruotti, V., Stewart, R., Slukvin, I. I., and Thomson, J. A. (2007). Induced pluripotent stem cell lines derived from human somatic cells. Science 318, 1917-1920.

Zalatan, J. G., Lee, M. E., Almeida, R., Gilbert, L. A., Whitehead, E. H., La Russa, M., Tsai, J. C., Weissman, J. S., Dueber, J. E., Qi, L. S., et al. (2015). Engineering complex synthetic transcriptional programs with CRISPR RNA scaffolds. Cell 160, 339-350.

Zhou, Y., Zhu, S., Cai, C., Yuan, P., Li, C., Huang, Y., and Wei, W. (2014). High-throughput screening of a CRISPR/Cas9 library for functional genomics in human cells. Nature 509, 487-491.

Example 3—Differentiation of Pluripotent Stem Cells into Blood Lineages Using ATFs Hematopoietic stem and progenitor cells (HSPCs) continually replenish cells of the blood lineage throughout the lifetime of an individual (1). Although fundamental regulators that guide cells toward hematopoietic fates are known, the precise mechanisms by which the largely quiescent pool of HSPCs proliferate then differentiate are not known (2). HSPCs can give rise to all mature blood cells, and the first step of specification occurs as they differentiate to common myeloid progenitors (CMPs) and common lymphoid progenitors (CLPs). Hematopoietic stem and progenitor cell (HSPC) give rise to common myeloid progenitors (CMPs) and common lymphoid progenitors (CLPs). CMPs differentiate into megakaryocyte/erythroid progenitors and granulocyte/macrophage progenitors, which can differentiate further into specialized cell types of the blood (1).

To overcome these challenges, we created an artificial transcription factor (ATF) library composed of $2.6 \times 10^6$ ATFs, a complexity that encompasses 10-times the sequence space of all 9-bp permutations. An important and distinguishing feature of our ATF design is the incorporation of an interaction domain that allows two ATFs to dimerize and activate target genes in a synergistic manner. We tested the ATF library in inducing differentiation into blood lineages. As demonstrated in this Example, the ATF library can serve as a powerful forward genetic screen to identify regulators of hematopoiesis.

Library Screening in Blood Differentiation

Figures 23A, 23B, 23C:
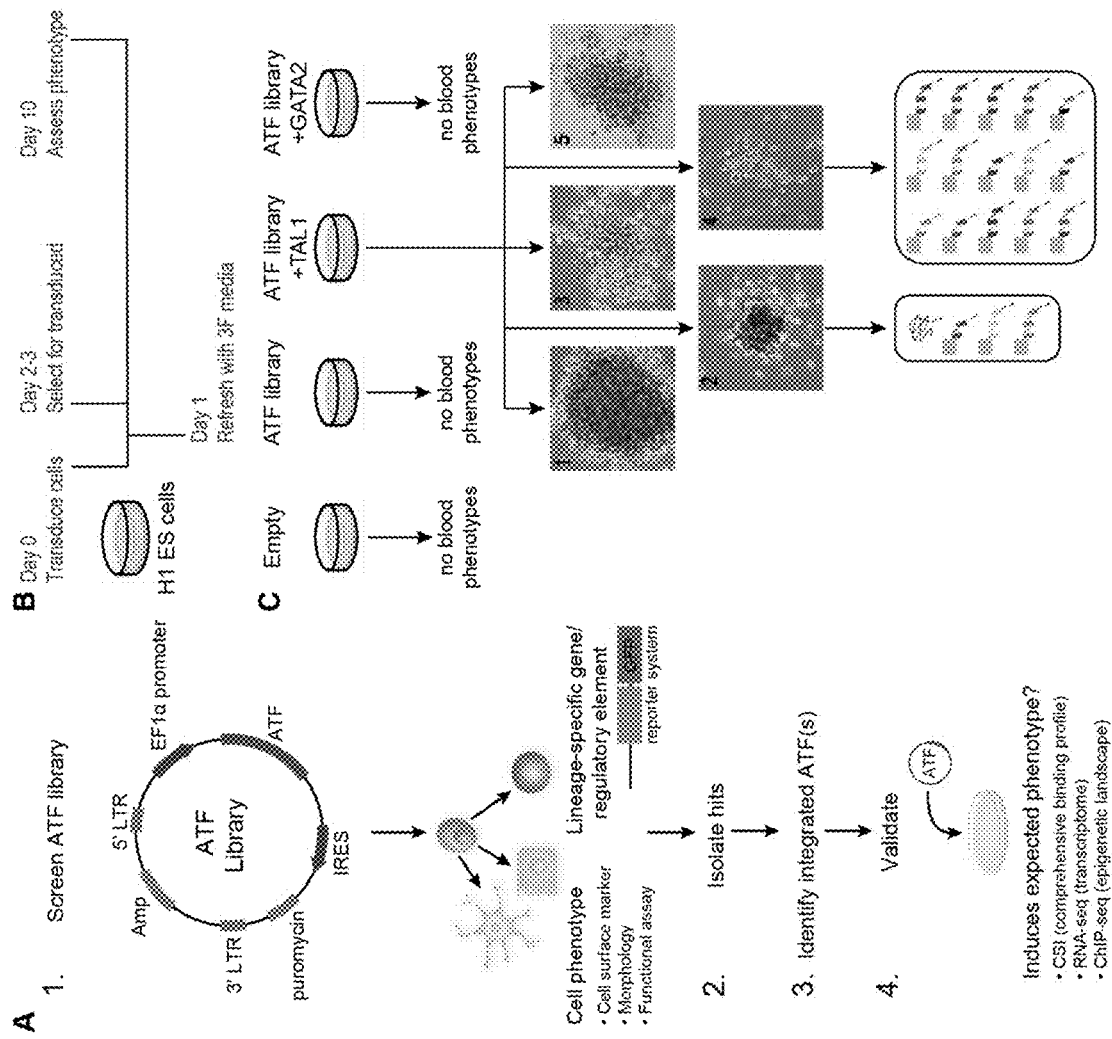
FIGS. 23A-23C illustrate use of the ATF library for hematopoietic differentiation. (A) Genetic screen with an ATF library. ATFs are comprised of an interaction domain, 3-zinc fingers, nuclear localization signal, VP64 activation domain, and 3×HA tag. The library has a complexity of $2.6 \times 10^6$ ATFs, each of which can target a 9-bp sequence. (B) Inducing hematopoiesis. Human H1 ES cells are maintained in mTESR1™ medium (StemCell Technologies, Inc., Vancouver, Calif.) until the day of transduction. ATFs and natural factors are delivered by lentivirus on Day 0. From Day 1 onward, cells are maintained in 3F media, composed of mTeSR basal medium with FGF2, SCF, and thrombopoietin (3). Cells undergo 2 days of selection for transduction events with puromycin. On Day 10, cells are assessed for morphological changes to blood phenotypes. (C) ATF library+TAL1 generates cells of the hematopoietic lineage.

The ATF library was tested for morphological changes under conditions that provide extrinsic signals to differentiate to blood lineages (FIG. 23B) (3). A critical consideration to take when performing a forward genetic screen of this nature is to have a robust read-out of positive phenotypes (FIG. 23A). I relied on the expertise of the Slukvin lab to select for distinct morphological changes to blood cell types. Human H1 ES cells were treated with the ATF library, ATF library+TAL1, and ATF library+GATA2. Pluripotent cells were also transduced with lentivirus without an ORF (Empty) to account for false positive events induced by integration of a strong constitutive promoter upstream of a gene that induces hematopoiesis, disruption of a gene that represses hematopoiesis, or the cell's stress response to lentiviral infection. Among the treatments, cells treated with the ATF library+TAL1 differentiated into erythroblast-like cells and monocyte-like cells (FIG. 23C). Clusters of differentiated cells were expanded on methylcellulose, and expanded cells were pooled for collection.

Two pools of cells were sequenced for ATF identification: one of the erythroid-like phenotype and one of the monocyte-like phenotype. A combination of 4 ATFs were identified from the erythroid-like cells, and 15 ATFs were identified from the monocyte-like cells (FIG. 23C and Table 10). Because sequencing was not performed at a single cell level, when multiple ATFs were identified in the screen, it was not possible to determine the exact combinations that occurred simultaneously in a cell. Since fewer ATFs were identified for the erythroblast-like cells, the 4 ATFs identified from this phenotype were retested in the validation step (FIG. 23A). As a positive control, GATA2 and ETV2 (Condition 2) were overexpressed to induce differentiation to myeloid cells (FIG. 24) (3). TAL1 was expressed with each ATF individually and with an Empty control as a negative control. TAL1+ZFATF20 (Condition 6) generated cells of similar phenotype as the positive control. While TAL1+Empty (Condition 3) did not induce differentiation in the initial screen, in the validation step, the negative control did induce differentiation to endothelial-like cells, although their change in morphology was not as pronounced as with GATA2+ETV2 or Condition 6. TAL1+ATF5 (Condition 4) exhibited cells of a similar phenotype to those of TAL1+ Empty. Conditions 5 and 7 did not yield any differentiated cells.

TABLE 10

Sequences of ATF Hits in Hematopoietic Differentiation

| ATF | DNA sequence |
|---|---|
| ZFATF1 | ATGCATCCTATGAACAACCTGCTGAACTACGTGGTGCCGA AGATGAGACCTTACGCTTGTGATCGCCGCTTCTCCGTTTCC CACCGGCTCACCCATCACATCCGCATCCACACAGGCCAGA AGCCCTTCCAGTGCCGCATCTGCATGCGCAACTTCAGCCCT AGCAGAAGACTCACCCAGCACATCCGCACCCACACAGGCG AAAAGCCCTTCGCCTGCGACATCTGTGGAAGAAAGTTTGC |
| | CCAGAGCGAGGGGCGCAAGGTCCATACCAAGATCCACTTG CGGCAGAAGGACAAGAAAGCAGACAAAAGTGTTGTGGGG CGCGCCGACGCGCTGGACGATTTCGATCTCGACATGCTGG GTTCTGATGCCCTCGATGACTTTGACCTGGATATGTTGGGA AGCGACGCATTGGATGACTTTGATCTGGACATGCTCGGCT CCGATGCTCTGGACGATTTCGATCTCGATATGTTAATTAAC TACCCGTACGACGTTCCGGACTACGCTGGTTATCCCTATGA CGTCCCGGATTATGCAGGATCCTATCCATATGACGTTCCAG ATTACGCTTGA (SEQ ID NO: 72) |
| ATF5 | ATGCATCCTATGAACAACCTGCTGAACTACGTGGTGCCGA AGATGAGACCTTACGATTGCCCAGTGGAGTCCTGTGATCG CCGCTTCTCCAGATCCCATCGGCCACCAGCCACATCCGCAT CCACACAGGCCAGAAGCCCTTCCAGTGCCGCATCTGCATG CGCAACTTCAGCGTCAGCCCGACCCTCACCCGACACATCC GCACCCACACAGGCGAAAAGCCCTTCGCCTGCGACATCTG TGGAAGAAAGTTTGCCAGGAGCGACCAGCGCAAGAGACA TACCAAGATCCACTTGCGGCAGAAGGACAAGAAAGCAGA CAAAAGTGTTGTGGGGCGCGCCGACGCGCTGGACGATTTC GATCTCGACATGCTGGGTTCTGATGCCCTCGATGACTTTGA CCTGGATATGTTGGGAAGCGACGCATTGGATGACTTTGAT CTGGACATGCTCGGCTCCGATGCTCTGGACGATTTCGATCT CGATATGTTACCCGTACGACGTTCCGGACTACGCTGGTTAT CCCTATGACGTCCCGGATTATGCAGGATCCTATCCATATGA CGTTCCAGATTACGCTTGA (SEQ ID NO: 76) |
| ZFATF6 | ATGCATCCTATGAACAACCTGCTGAACTACGTGGTGCCGA AGATGAGACCTTACGCTTGTGATCGCCGCTTCTCCGTTTCC CACCGGCTCACCCATCACATCCGCATCCACACAGGCCAGA AGCCCTTCCAGTGCCGCATCTGCATGCGCAACTTCAGCCTC AGCCTAACCCTCACCAAACACATCCGCACCCACACAGGCG AAAAGCCCTTCGCCTGCGACATCTGTGGAAGAAAGTTTGC CAAAAGCAAACCACGCAAGACACATACCAAGATCCACTTG CGGCAGAAGGACAAGAAAGCAGACAAAAGTGTTGTGGGG CGCGCCGACGCGCTGGACGATTTCGATCTCGACATGCTGG GTTCTGATGCCCTCGATGACTTTGACCTGGATATGTTGGGA AGCGACGCATTGGATGACTTTGATCTGGACATGCTCGGCT CCGATGCTCTGGACGATTTCGATCTCGATATGTTAATTAAC TACCCGTACGACGTTCCGGACTACGCTGGTTATCCCTATGA CGTCCCGGATTATGCAGGATCCTATCCATATGACGTTCCAG ATTACGCTTGA (SEQ ID NO: 77) |
| ZFATF10 | ATGCATCCTATGAACAACCTGCTGAACTACGTGGTGCCGA AGATGAGACCTTACGCTTGCCCAGTGGAGTCCTGTGATCG CCGCTTCTCCGTATCCGACACTCTCACCGTACACATCCGCA TCCACACAGGCCAGAAGCCCTTCCAGTGCCGCATCTGCAT GCGCAACTTCAGCGACAGCGATGAGCTCACCGATCACATC CGCACCCACACAGGCGAAAAGCCCTTCGCCTGCGACATCT GTGGAAGAAAGTTTGCCGAAAGCCGTAAACGCAAGGAAC ATACCAAGATCCACTTGCGGCAGAAGGACAAGAAAGCAG ACAAAAGTGTTGTGGGGCGCGCCGACGCGCTGGACGATTT CGATCTCGACATGCTGGGTTCTGATGCCCTCGATGACTTTG ACCTGGATATGTTGGGAAGCGACGCATTGGATGACTTTGA TCTGGACATGCTCGGCTCCGATGCTCTGGACGATTTCGATC TCGATATGTTAATTAACTACCCGTACGACGTTCCGGACTAC GCTGGTTATCCCTATGACGTCCCGGATTATGCAGGATCCTA TCCATATGACGTTCCAGATTACGCTTGA (SEQ ID NO: 81) |
| ZFATF13 | ATGCATCCTATGAACAACCTGCTGAACTACGTGGTGCCGA AGATGAGACCTTACGCTTGTGATCGCCGCTTCTCCGTTTCC CACCGGCTCACCCATCACATCCGCATCCACACAGGCCAGA AGCCCTTCCAGTGCCGCATCTGCATGCGCAACTTCAGCCCT AGCAGAAGACTCACCCAGCACATCCGCACCCACACAGGCG AAAAGCCCTTCGCCTGCGACATCTGTGGAAGAAAGTTTGC CAGGAGCGACCAGCGCAAGAGACATACCAAGATCCACTT GCGGCAGAAGGACAAGAAAGCAGACAAAAGTGTTGTGGG GCGCGCCGACGCGCTGGACGATTTCGATCTCGACATGCTG GGTTCTGATGCCCTCGATGACTTTGACCTGGATATGTTGGG AAGCGACGCATTGGATGACTTTGATCTGGACATGCTCGGC TCCGATGCTCTGGACGATTTCGATCTCGATATGTTAATTAA CTACCCGTACGACGTTCCGGACTACGCTGGTTATCCCTATG ACGTCCCGGATTATGCAGGATCCTATCCATATGACGTTCCA GATTACGCTTGA (SEQ ID NO: 92) |

TABLE 10-continued

Sequences of ATF Hits in Hematopoietic Differentiation

| ATF | DNA sequence |
|---|---|
| ZFATF17 | ATGCATCCTATGAACAACCTGCTGAACTACGTGGTGCCGA<br>AGATGAGACCTTACGCTTGCCCAGTGGAGTCCTGTGATCG<br>CCGCTTCTCCCGTTCCATCCGTCTCACCATACACATCCGCA<br>TCCACACAGGCCAGAAGCCCTTCCAGTGCCGCATCTGCAT<br>GCGCAACTTCAGCGGTAGCGTTCCACTCACCATACACATC<br>CGCACCCACACAGGCGAAAAGCCCTTCGCCTGCGACATCT<br>GTGGAAGAAAGTTTGCCAGGAGCGACCAGCGCAAGAGAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO:<br>96) |
| ZFATF19 | ATGCATCCTATGAACAACCTGCTGAACTACGTGGTGCCGA<br>AGATGAGACCTTACGCTTGCCCAGTGGAGTCCTGTGATCG<br>CCGCTTCTCCCATATCCGGTGCGTCCGCGGCACATCCGCA<br>TCCACACAGGCCAGAAGCCCTTCGCCTGCGACATCTGTGG<br>AAGAAAGTTTGCCAGGAGCGACCAGCGCAAGAGACATAC<br>CAAGATCCACTTGCGGCAGAAGGACAAGAAAGCAGACAA<br>AAGTGTTGTGGGGCGCGCCGACGCGCTGGACGATTTCGAT<br>CTCGACATGCTGGGTTCTGATGCCCTCGATGACTTTGACCT<br>GGATATGTTGGGAAGCGACGCATTGGATGACTTTGATCTG<br>GACATGCTCGGCTCCGATGCTCTGGACGATTTCGATCTCGA<br>TATGTTAATTAACTACCCGTACGACGTTCCGGACTACGCTG<br>GTTATCCCTATGACGTCCCGGATTATGCAGGATCCTATCCA<br>TATGACGTTCCAGATTACGCTTGA (SEQ ID NO: 98) |
| ZFATF20 | ATGCATCCTATGAACAACCTGCTGAACTACGTGGTGCCGA<br>AGATGAGACCTTACGATTGCCCAGTGGAGTCCTGTGATCG<br>CCGCTTCTCCCAGTCCGTGAATCTCACCGTGCACATCCGCA<br>TCCACACAGGCCAGAAGCCCTTCCAGTGCCGCATCTGCAT<br>GCGCAACTTCAGCGCCAGCCCCCGCTCACCATACACATC<br>CGCACCCACACAGGCGAAAAGCCCTTCGCCTGCGACATCT<br>GTGGAAGAAAGTTTGCCAGGAGCGACCAGCGCAAGAGAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO:<br>99) |
| ZFATF21 | ATGCATCCTATGAACAACCTGCTGAACTACGTGGTGCCGA<br>AGATGAGACCTTACGATTGCCCAGTGGAGTCCTGTGATCG<br>CCGCTTCTCCGTTTCCCACCGGCTCACCCATCACATCCGCA<br>TCCACACAGGCCAGAAGCCCTTCCAGTGCCGCATCTGCAT<br>GCGCAACTTCAGCGTCAGCCCGACCCTCACCCGACACATC<br>CGCACCCACACAGGCGAAAAGCCCTTCGCCTGCGACATCT<br>GTGGAAGAAAGTTTGCCAGGAGCGACCAGCGCAAGAGAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO:<br>100) |
| ZFATF22 | ATGCATCCTATGAACAACCTGCTGAACTACGTGGTGCCGA<br>AGATGAGACCTTACGCTTGCCCAGTGGAGTCCTGTGATCG<br>CCGCTTCTCCCGTTCCATCCGTCTCACCATACACATACGCA<br>TCCACACAGGCCAGAAGCCCTTCCAGTGCCGCATCTGCAT<br>GCGCAACTTCAGCCACGACGCTCATCTCACCCGACACATC<br>CGCACCCACACAGGCGAAAAGCCCTTCGCCTGCGACATCT<br>GTGGAAGAAAGTTTGCCAGGAGCGACCAGCGCAAGAGAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO:<br>101) |
| ZFATF23 | ATGCATCCTATGAACAACCTGCTGAACTACGTGGTGCCGA<br>AGATGAGACCTTACGCTTGCCCAGTGGAGTCCTGTGATCG<br>CCGCTTCTCCGTTTCCCACCGGCTCACCCATCACATCCGCA<br>TCCACACAGGCCAGAAGCCCTTCCAGTGCCGCATCTGCAT<br>GCGCAACTTCAGCCCTAGCAGAAGACTCACCCAGCACATC<br>CGCACCCACACAGGCGAAAAGCCCTTCGCCTGCGACATCT<br>GTGGAAGAAAGTTTGCCCAGAGCGAGGGGCGCAAGGTCC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO:<br>102) |
| ZFATF24 | ATGCATCCTATGAACAACCTGCTGAACTACGTGGTGCCGA<br>AGATGAGACCTTACGCTTGTGATCGCCGCTTCTCCGTTTCC<br>CACCGGCTCACCCATCACATCCGCATCCACACAGGCCAGA<br>AGCCCTTCCAGTGCCGCATCTGCATGCGCAACTTCAGCGA<br>CAGCGATGAGCTCACCGATCACATCCGCACCCACACAGGC<br>GAAAAGCCCTTCGCCTGCGACATCTGTGGAAGAAAGTTTG<br>CCAGGAGCGACCAGCGCAAGAGACATACCAAGATCCACTT<br>GCGGCAGAAGGACAAGAAAGCAGACAAAAGTGTTGTGGG<br>GCGCGCCGACGCGCTGGACGATTTCGATCTCGACATGCTG<br>GGTTCTGATGCCCTCGATGACTTTGACCTGGATATGTTGGG<br>AAGCGACGCATTGGATGACTTTGATCTGGACATGCTCGGC<br>TCCGATGCTCTGGACGATTTCGATCTCGATATGTTAATTAA<br>CTACCCGTACGACGTTCCGGACTACGCTGGTTATCCCTATG<br>ACGTCCCGGATTATGCAGGATCCTATCCATATGACGTTCCA<br>GATTACGCTTGA (SEQ ID NO: 103) |
| ZFATF25 | ATGCATCCTATGAACAACCTGCTGAACTACGTGGTGCCGA<br>AGATGAGACCTTACGCTTGCCCAGTGGAGTCCTGTGATCG<br>CCGCTTCTCCGTTTCCCACCGGCTCACCCATCACATCCGCA<br>TCCACACAGGCCAGAAGCCCTTCCAGTGCCGCATCTGCAT<br>GCGCAACTTCAGCGACGACGATGAGCTCACCGATCACATC<br>CGCACCCACACAGGCGAAAAGCCCTTCGCCTGCGACATCT<br>GTGGAAGAAAGTTTGCCCAGAGCGAGGGGCGCAAGGTCC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO:<br>104) |
| ZFATF26 | ATGCATCCTATGAACAACCTGCTGAACTACGTGGTGCCGA<br>AGATGAGACCTTACGCTTGTGATCGCCGCTTCTCCGTTTCC<br>CACCGGCTCACCCATCACATCCGCATCCACACAGGCCAGA<br>AGCCCTTCCAGTGCCGCATCTGCATGCGCAACTTCAGCGTC<br>AGCCCGACCCTCACCCGACACATCCGCACCCACACAGGCG<br>AAAAGCCCTTCGCCTGCGACATCTGTGGAAGAAAGTTTGC<br>CAGGAGCGACCAGCGCAAGAGACATACCAAGATCCACTT<br>GCGGCAGAAGGACAAGAAAGCAGACAAAAGTGTTGTGGG<br>GCGCGCCGACGCGCTGGACGATTTCGATCTCGACATGCTG<br>GGTTCTGATGCCCTCGATGACTTTGACCTGGATATGTTGGG<br>AAGCGACGCATTGGATGACTTTGATCTGGACATGCTCGGC<br>TCCGATGCTCTGGACGATTTCGATCTCGATATGTTAATTAA<br>CTACCCGTACGACGTTCCGGACTACGCTGGTTATCCCTATG<br>ACGTCCCGGATTATGCAGGATCCTATCCATATGACGTTCCA<br>GATTACGCTTGA (SEQ ID NO: 105) |
| ZFATF27 | ATGCATCCTATGAACAACCTGCTGAACTACGTGGTGCCGA<br>AGATGAGACCTTACGCTTGCCCAGTGGAGTCCTGTGATCG |

TABLE 10-continued

Sequences of ATF Hits in Hematopoietic Differentiation

| ATF | DNA sequence |
|---|---|
| | CCGCTTCTCCGTATCCGACGCTCTCACCGTACACATCCGCA<br>TCCACACAGGCCAGAAGCCCTTCCAGTGCCGCATCTGCAT<br>GCGCAACTTCAGCGTCAGCCCGACCCTCACCCGACACATC<br>CGCACCCACACAGGCGAAAAGCCCTTCGCCTGCGACATCT<br>GTGGAAGAAAGTTTGCCAGGAGCGACCAGCGCAAGAGAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 106) |
| ZFATF28 | ATGCATCCTATGAACAACCTGCTGAACTACGTGGTGCCGA<br>AGATGAGACCTTACGATTGCCCAGTGGAGTCCTGTGATCG<br>CCGCTTCTCCGTTTCCCACCGGCTCACCCATCACATCCGCA<br>TCCACACAGGCCAGAAGCCCTTCCAGTGCCGCATCTGCAT<br>GCGCAACTTCAGCCTCAGCCTAACCCTCACCAAACACATC<br>CGCACCCACACAGGCGAAAAGCCCTTCGCCTGCGACATCT<br>GTGGAAGAAAGTTTGCCAAAAGCAAACCACGCAAGACAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 107) |
| ZFATF29 | ATGCATCCTATGAACAACCTGCTGAACTACGTGGTGCCGA<br>AGATGAGACCTTACGCTTGCCCAGTGGAGTCCTGTGATCG<br>CCGCTTCTCCGTATCCGACGCTCTCACCGTACACATCCGCA<br>TCCACACAGGCCAGAAGCCCTTCCAGTGCCGCATCTGCAT<br>GCGCAACTTCAGCGTCAGCCCGACCCTCACCCGACACATC<br>CGCACCCACACAGGCGAAAAGCCCTTCGCCTGCGACATCT<br>GTGGAAGAAAGTTTGCCGAAAGCCGTAAACGCAAGGAAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 108) |
| ZFATF30 | ATGCATCCTATGAACAACCTGCTGAACTACGTGGTGCCGA<br>AGATGAGACCTTACGATTGCCCAGTGGAGTCCTGTGATCG<br>CCGCTTCTCCGTATCCGACGCTCTCACCGTACACATCCGCA<br>TCCACACAGGCCAGAAGCCCTTCCAGTGCCGCATCTGCAT<br>GCGCAACTTCAGCGACAGCGATGAGCTCACCGATCACATC<br>CGCACCCACACAGGCGAAAAGCCCTTCGCCTGCGACATCT<br>GTGGAAGAAAGTTTGCCGAAAGCCGTAAACGCAAGGAAC<br>ATACCAAGATCCACTTGCGGCAGAAGGACAAGAAAGCAG<br>ACAAAAGTGTTGTGGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 109) |
| ZFATF31 | ATGCATCCTATGAACAACCTGCTGAACTACGTGGTGCCGA<br>AGATGAGACCTTACGATTGTGATCGCCGCTTCTCCGTTTCC<br>CACCGGCTCACCCATCACATCCGCACCCACACAGGCGAAA<br>AGCCCTTCGCCTGCGACATCTGTGGAAGAAAGTTTGCCAG<br>AAGCATACACCGCAAGCGTCATACCAAGATCCACTTGCGG<br>CAGAAGGACAAGAAAGCAGACAAAAGTGTTGTGGGGCGC<br>GCCGACGCGCTGGACGATTTCGATCTCGACATGCTGGGTT<br>CTGATGCCCTCGATGACTTTGACCTGGATATGTTGGGAAG<br>CGACGCATTGGATGACTTTGATCTGGACATGCTCGGCTCC |
| | GATGCTCTGGACGATTTCGATCTCGATATGTTAATTAACTA<br>CCCGTACGACGTTCCGGACTACGCTGGTTATCCCTATGACG<br>TCCCGGATTATGCAGGATCCTATCCATATGACGTTCCAGAT<br>TACGCTTGA (SEQ ID NO: 110) |

ATF Targets

To identify the ATF target genes, cognate site identification (CSI) described in Chapter 3, was used to find the top 100 scoring motifs for each ATF (FIG. 25A). The sequence and energy landscapes (SELs) for the ATFs depict the comprehensive sequence specificity for each ATF (FIG. 25B). The locations of these top-scoring motifs were identified in the human genome, then annotated to the nearest genes. The frequency of occurrence in the genome was plotted as well as the frequency within ±1 kb of a transcription start site (TSS) (FIGS. 26A-26B). Although ZFATF19 (purple) had the most binding sites in the genome, ZFATF21 (brown) had the most binding sites near the TSS.

Discussion

This screen for morphological changes to blood lineages demonstrates that an ATF library can be used as a forward genetic screen to identify regulators of hematopoiesis. By testing the ATF library with TAL1, we were able to show that ATFs can promote differentiation into erythroid-like cells. Because ATF identification was not performed at the single cell level, we could not capture the combination of ATFs that induced the conversions to erythroid-like and monocyte-like cells. However, only four ATFs were expressed in the erythroid-like cells, so we were able to test them individually with TAL1 in the validation step. While TAL1 alone did not seem to induce differentiation in the initial screen, in the validation experiment, TAL1+Empty induced differentiation to endothelial-like cells. TAL1 has, indeed, been implicated in blood and endothelial development (4), although its capacity to differentiate pluripotent stem cells to blood lineages remains to be examined. Though morphologically distinct from TAL+ZFATF20, the propensity for TAL1+Empty to induce differentiation must also be further explored at the transcriptional level. In addition, chromatin-immunoprecipitation could be performed to elucidate the binding sites in cells. To better identify the combination of factors that induce differentiation into blood lineages, positive outcomes from future screens should be isolated as single cells for ATF identification. The results from this study suggests that the ATF library can be applied to other unanswered questions in the hematopoietic stem cell field.

Materials and Methods

Cell Culture:

Human H1 ES cells were grown in mTESR1™ medium (StemCell Technologies, Inc., Vancouver, Calif.) on Matrigel® substrate (BD Biosciences, NJ). For differentiation into blood lineages, cells were cultured in 3F media, composed of mTeSR basal media with FGF2 (20 ng/mL), SCF (100 ng/mL), and thrombopoietin (50 ng/mL). Expansion of cells with hematopoietic phenotypes was performed on methylcellulose. Cells were maintained in a humidified 37° C. incubator with 5% $CO_2$.

Lentivirus Production:

ATFs and the empty control were packaged into lentivirus using a second-generation lentiviral system. Lentivirus was produced in HEK293T cells by calcium phosphate transfection of pSIN expression, psPAX2 packaging, and pMD2.G envelope plasmids. Media containing virus was harvested 48-60 hours post-transfection. Lentivirus was centrifuged with a sucrose cushion at 25,000 rpm for 2 hours. Viral particles were suspended in PBS and concentrated virus was stored at −80° C. Viral titers were measured by counting HEK293T cells that survived selection after 2 days in media containing puromycin (3 µg/mL).

Lentiviral Transduction:

Lentiviruses were delivered to H1 cells with 8 µg/mL polybrene. Selection was performed in media containing puromycin (1 µg/mL first day, 1.5 µg/mL second day). The ATF was driven by a constitutive promoter, EF1α.

Identification of ATFs:

Cells exhibiting a phenotype of the hematopoietic lineage were picked an expanded on methylcellulose. Two-step nested PCR was performed from cell clusters after expansion. The first round of amplification was performed with ATF-forward-1 and ATF-reverse-1 primers (400 nM final concentration) in a 50 µL volume or 40 cycles. The second round of amplification was performed with 10 µL of the first PCR reaction, ATF-forward-2 and ATF-reverse-2 primers (400 nM final concentration) for 35 cycles. The second PCR reaction was purified and digested with AscI and NheI. The digested product was cloned into pcDNA 3.1 at the AscI and NheI restriction sites. Sanger sequencing was performed on the clones with the CMV-forward primer.

The number of sequences obtained to reach saturation was determined by calculating the probability that the chance of finding another unique ATF is less than 1%. $(1-1/(n+1))^x < 0.01$, where n is the number of unique ATFs identified and x is the number of sequences needed.

Microscopy:

Micrographs were taken with a 10× objective on a Zeiss Observer. A1 with an AxioCam ICm1.

Cognate Site Identification:

HEK293 cells were transiently transfected with ATFs using Lipofectamine 2000 (Thermo Fisher #11668019). Cells that underwent a mock transfection (without an expression plasmid for ATFs) served as a negative control. Cells were harvested 48 hours post-transfection. Lysates were prepared by lysing $10^7$ cells in 300 µL of lysis buffer (50 mM Tris-HCl pH 7.5, 150 mM NaCl, 1% Triton X-100, and 0.1% Na deoxycholate). A 21.5 G syringe needle was used for mechanical lysis. Lysates were centrifuged at 10 k×g for 10 min to separate precipitated genomic DNA from protein constituents. The supernatant, containing ATF protein, was used for CSI. HA magnetic beads (MBL #M132-9) were added to the cell lysates for immunoprecipitation. The binding reaction between the ATFs and 100 nM synthetic DNA was performed in binding buffer (25 mM HEPES, 80 mM KCl, 0.2 mM EDTA, 1 mM $MgCl_2$, 0.1 mM $ZnSO_4$) at 25° C. After pull-down, three quick washes with 100 µL ice-cold binding buffer were performed to remove unbound DNA. Magnetic beads were resuspended in a PCR master mix (Lucigen #30035-1) and the DNA was amplified for 15 or 18 cycles. Amplified DNA was column purified (Qiagen #28106), and this enriched DNA pool was used for the subsequent round of enrichment, for a total of three rounds. After three rounds of selection, Illumina sequencing adapters and a unique 6 bp barcode for multiplexing were added by PCR amplification. The starting library (Round 0) was also barcoded. Up to 180 samples were combined and sequenced in a single HiSeq2000 lane.

Cognate Site Identification Data Analysis:

Illumina sequencing yielded ~180 million reads per lane. Reads were de-multiplexed by requiring an exact match to the 6 bp barcode and truncated to include only the 25 bp derived from the random portion of the library. On average, we obtained 709,300 reads per barcode. The occurrence of every k-mer (lengths 8 through 16 bp) was counted using a sliding window of size k. To correct for biases in our starting DNA library, we took the ratio of the counts of every k-mer to the expected number of counts in the mock-transfected control. The mock control was modeled using a 5th-order Markov Model derived from the sequencing reads corresponding to the starting library (Round 0). We then calculated a Z-score=$(x-\mu)/\sigma$ or (CSI score minus mean)/standard deviation for each k-mer, using the distribution of k-mer enrichment values (CSI score) for the ATF.

Bioinformatic Analysis of ATF Binding Sites:

The genomic locations of the top five or 100 high-scoring 10-bp motifs from CSI were identified in the mm10 genome by the findMotif utility from the UCSC Genome Browser. These genomic sites were annotated using Homer. Annotated sites were filtered to those within +1 kb of the TSS.

REFERENCES

1. Orkin S H, Zon L I (2008) Hematopoiesis: An Evolving Paradigm for Stem Cell Biology. *Cell* 132(4):631-644.
2. Doulatov S, Notta F, Laurenti E, Dick J E (2012) Hematopoiesis: a human perspective. *Cell Stem Cell* 10(2):120-136.
3. Elcheva I, et al. (2014) Direct induction of haematoendothelial programs in human pluripotent stem cells by transcriptional regulators. *Nat Commun* 5:4372.
4. Bloor A J C, Sanchez M-J, Green A R, Göttgens B (2002) The role of the stem cell leukemia (SCL) gene in hematopoietic and endothelial lineage specification. *J Hematother Stem Cell Res* 11(2):195-206.

Example 4—Inducing Lytic Replication of Cytomegalovirus with ATFs

A majority of the population is infected with human cytomegalovirus (HCMV), a member of the β-herpesvirus family; however, the virus only exhibits pathogenic effects in immunocompromised individuals (1). Once cells are infected with HCMV, virions can either enter a latent state, in which a few viral genes are expressed, or enter a lytic state, in which the viral genes are robustly expressed, the viral genome is replicated, and new virions are produced to spread to other cells. The production of virions results in death of the host cell. It is remains unclear how long cells with HCMV in the latent state can survive. After latency is established, HCMV can reactivate, eliciting responses of the lytic state (1).

The exact mechanism controlling whether HCMV genes are expressed remains to be elucidated. Curiously, HCMV in pluripotent and hematopoietic stem cells establishes latency (2). The repressor protein Death Domain Associated Protein (DAXX) recruits histone deacetylases (HDACs) to the viral genome, and viral genes are silenced. In differentiated cells, the viral tegument protein, pp71, targets DAXX for degradation, and its degradation leads to expression of immediate early genes that facilitate viral replication in the lytic state. In undifferentiated cells, pp71 remains cytoplasmic. The cellular signals that regulate translation of pp71 to the nucleus are poorly understood.

We investigated the transcriptional mechanism that permits viral gene expression using an artificial transcription factor (ATF) library comprising 2.6×10⁶ ATFs, a complexity that encompasses 10-times the sequence space of all 9-bp permutations. An important and distinguishing feature of our ATF design is the incorporation of an interaction domain that allows two ATFs to dimerize and activate target genes in a synergistic manner. We tested the ATF library in permitting the expression of HCMV genes in monocytes where HCMV remains latent. Our results suggest that the ATF library can serve as a powerful forward genetic screen to identify regulators of lytic replication. Pinpointing the key nodes of a transcriptional network sufficient to license lytic replication would be therapeutic targets to prevent HCMV pathogenesis.

ATF Library Screening for Lytic Replication

We tested the ATF library in THP-1 cells, a human monocytic leukemia cell line, that has the potential to differentiate into macrophages (3). When HCMV infects THP-1 cells, viral genes are not expressed. Pretreatment with valproic acid (VPA), an HDAC inhibitor, followed by HCMV infection, results in the expression of viral proteins in about a quarter of the cell population. To test the ability of the ATF library to permit expression of viral genes, an HCMV strain AD169 expressing a fusion protein IE2-GFP (immediate early gene 2 fused to green fluorescent protein) was used to screen for lytic replication (FIG. 27B) (2).

Figures 27A, 27B, 27C, 27D, 27E:
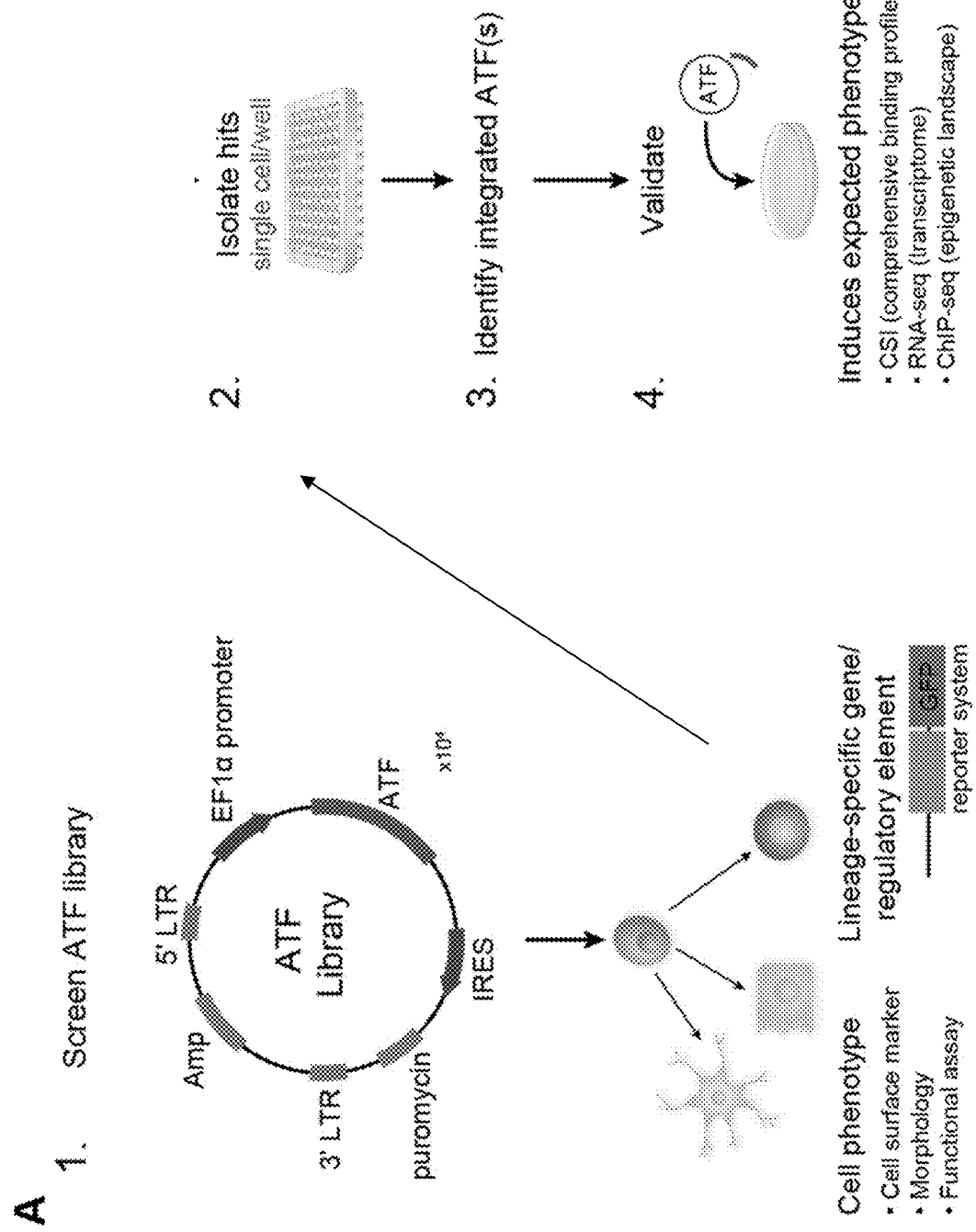

For the ATF library screen, THP-1 cells were transduced with either the ATF library (multiplicity of infection=1) or lentiviruses lacking an open reading frame (Empty) but retaining the EF1α promoter and the puromycin selection gene. After selection of integration events with puromycin, cells were infected with HCMV and expression of the IE2-GFP reporter gene was assessed 20 hours later. Approximately, 0.8% of cells from the ATF-treated were GFP⁺, while only 0.5% of cells from the Empty control were GFP⁺ (FIG. 27C). The frequency of positive outcomes from the Empty control allows us to determine the rate of false positive events to expect out of the screen. For the HCMV screen, we expect a false positive rate of about 63% (⅝), which is quite high compared to other ATF library screens described in this thesis. Approximately 19% of cells pretreated with VPA followed by HCMV infection expressed IE2-GFP, and THP-1 cells uninfected with HCMV expressed no IE2-GFP. ATF-treated cells with the greatest GFP expression were isolated as single cells by cell sorting (FIGS. 27A and 27C). ATFs expressed in the sorted cells were identified by two-step nested PCR (FIG. 27D and Table 11). Each cell expressed one or two ATFs, one of which was common in four cells.

TABLE 11

Sequences of ATF Hits in HCMV Lytic Replication

| ATF | DNA sequence |
|---|---|
| ZFATF1 | ATGCATCCTATGAACAACCTGCTGAACTACGTGGTGCCGA AGATGAGACCTTACGCTTGTGATCGCCGCTTCTCCGTTTCC CACCGGCTCACCCATCACATCCGCATCCACACAGGCCAGA AGCCCTTCCAGTGCCGCATCTGCATGCGCAACTTCAGCCCT AGCAGAAGACTCACCCAGCACATCCGCACCCACACAGGCG AAAAGCCCTTCGCCTGCGACATCTGTGGAAGAAAGTTTGC CCAGAGCGAGGGGCGCAAGGTCCATACCAAGATCCACTTG CGGCAGAAGGACAAGAAAGCAGACAAAAGTGTTGTGGGG CGCGCCGACGCGCTGGACGATTTCGATCTCGACATGCTGG GTTCTGATGCCCTCGATGACTTTGACCTGGATATGTTGGGA AGCGACGCATTGGATGACTTTGATCTGGACATGCTCGGCT CCGATGCTCTGGACGATTTCGATCTCGATATGTTAATTAAC TACCCGTACGACGTTCCGGACTACGCTGGTTATCCCTATGA CGTCCCGGATTATGCAGGATCCTATCCATATGACGTTCCAG ATTACGCTTGA (SEQ ID NO: 72) |
| ZFATF2 | ATGCATCCTATGAACAACCTGCTGAACTACGTGGTGCCGA AGATGAGACCTTACGCTTGCCCAGTGGAGTCCTGTGATCG CCGCTTCTCCGGGTCCGTAGTCCTCACCAAACACATCCGCA TCCACACAGGCCAGAAGCCCTTCCAGTGCCGCATCTGCAT GCGCAACTTCAGCATAAGCACTGTTCTCACCGGTCACATC CGCACCCACACAGGCGAAAAGCCCTTCGCCTGCGACATCT GTGGAAGAAAGTTTGCCAACAGCGAGCCACGCAAGACCC ATACCAAGATCCACTTGCGGCAGAAGGACAAGAAAGCAG ACAAAAGTGTTGTGGGGCGCGCCGACGCGCTGGACGATTT CGATCTCGACATGCTGGGTTCTGATGCCCTCGATGACTTTG ACCTGGATATGTTGGGAAGCGACGCATTGGATGACTTTGA TCTGGACATGCTCGGCTCCGATGCTCTGGACGATTTCGATC TCGATATGTTAATTAACTACCCGTACGACGTTCCGGACTAC GCTGGTTATCCCTATGACGTCCCGGATTATGCAGGATCCTA TCCATATGACGTTCCAGATTACGCTTGA (SEQ ID NO: 73) |
| ATF5 | ATGCATCCTATGAACAACCTGCTGAACTACGTGGTGCCGA AGATGAGACCTTACGATTGCCCAGTGGAGTCCTGTGATCG CCGCTTCTCCAGATCCCATCGGCCACCAGCCACATCCGCAT CCACACAGGCCAGAAGCCCTTCCAGTGCCGCATCTGCATG CGCAACTTCAGCGTCAGCCCGACCCTCACCCGACACATCC GCACCCACACAGGCGAAAAGCCCTTCGCCTGCGACATCTG TGGAAGAAAGTTTGCCAGGAGCGACCAGCGCAAGAGACA TACCAAGATCCACTTGCGGCAGAAGGACAAGAAAGCAGA CAAAAGTGTTGTGGGGCGCGCCGACGCGCTGGACGATTTC GATCTCGACATGCTGGGTTCTGATGCCCTCGATGACTTTGA CCTGGATATGTTGGGAAGCGACGCATTGGATGACTTTGAT CTGGACATGCTCGGCTCCGATGCTCTGGACGATTTCGATCT CGATATGTTACCCGTACGACGTTCCGGACTACGCTGGTTAT CCCTATGACGTCCCGGATTATGCAGGATCCTATCCATATGA CGTTCCAGATTACGCTTGA (SEQ ID NO: 76) |
| ZFATF6 | ATGCATCCTATGAACAACCTGCTGAACTACGTGGTGCCGA AGATGAGACCTTACGCTTGTGATCGCCGCTTCTCCGTTTCC CACCGGCTCACCCATCACATCCGCATCCACACAGGCCAGA AGCCCTTCCAGTGCCGCATCTGCATGCGCAACTTCAGCCTC AGCTAACCCTCACCAAACACATCCGCACCCACACAGGCG AAAAGCCCTTCGCCTGCGACATCTGTGGAAGAAAGTTTGC CAAAAGCAAACCACGCAAGACACATACCAAGATCCACTTG CGGCAGAAGGACAAGAAAGCAGACAAAAGTGTTGTGGGG CGCGCCGACGCGCTGGACGATTTCGATCTCGACATGCTGG GTTCTGATGCCCTCGATGACTTTGACCTGGATATGTTGGGA AGCGACGCATTGGATGACTTTGATCTGGACATGCTCGGCT CCGATGCTCTGGACGATTTCGATCTCGATATGTTAATTAAC TACCCGTACGACGTTCCGGACTACGCTGGTTATCCCTATGA CGTCCCGGATTATGCAGGATCCTATCCATATGACGTTCCAG ATTACGCTTGA (SEQ ID NO: 77) |
| ZFATF7 | ATGCATCCTATGAACAACCTGCTGAACTACGTGGTGCCGA AGATGAGACCTTACGCTTGCCCAGTGGAGTCCTGTGATCG CCGCTTCTCCCGTTCCATCCGTCTCACCATACACATCCGCA TCCACACAGGCCAGAAGCCCTTCCAGTGCCGCATCTGCAT GCGCAACTTCAGCCCCAGCCCGCCACTCACCCCTCACATC CGCACCCACACAGGCGAAAAGCCCTTCGCCTGCGACATCT GTGGAAGAAAGTTTGCCCCAAGCCTTCTCCGCAAGCCACA TACCAAGATCCACTTGCGGCAGAAGGACAAGAAAGCAGA CAAAAGTGTTGTGGGGCGCGCCGACGCGCTGGACGATTTC GATCTCGACATGCTGGGTTCTGATGCCCTCGATGACTTTGA CCTGGATATGTTGGGAAGCGACGCATTGGATGACTTTGAT CTGGACATGCTCGGCTCCGATGCTCTGGACGATTTCGATCT CGATATGTTAATTAACTACCCGTACGACGTTCCGGACTAC GCTGGTTATCCCTATGACGTCCCGGATTATGCAGGATCCTA TCCATATGACGTTCCAGATTACGCTTGA (SEQ ID NO: 78) |
| ZFATF9 | ATGCATCCTATGAACAACCTGCTGAACTACGTGGTGCCGA AGATGAGACCTTACGCTTGCCCAGTGGAGTCCTGTGATCG CCGCTTCTCCGGCTCCAATCGGCTCACCGAGCACATCCGC ATCCACACAGGCGAAAAGCCTTCGCCTGCGACATCTGTG GAAGAAAGTTTGCCAACAGCCCCCTACGCAAGGGTCATAC CAAGATCCACTTGCGGCAGAAGGACAAGAAAGCAGACAA AAGTGTTGTGGGGCGCGCCGACGCGCTGGACGATTTCGAT CTCGACATGCTGGGTTCTGATGCCCTCGATGACTTTGACCT GGATATGTTGGGAAGCGACGCATTGGATGACTTTGATCTG |

TABLE 11-continued

Sequences of ATF Hits in HCMV Lytic Replication

| ATF | DNA sequence |
|---|---|
| | GACATGCTCGGCTCCGATGCTCTGGACGATTTCGATCTCGA<br>TATGTTAATTAACTACCCGTACGACGTTCCGGACTACGCTG<br>GTTATCCCTATGACGTCCCGGATTATGCAGGATCCTATCCA<br>TATGACGTTCCAGATTACGCTTGA (SEQ ID NO: 80) |
| ZFATF23 | ATGCATCCTATGAACAACCTGCTGAACTACGTGGTGCCGA<br>AGATGAGACCTTACGCTTGCCCAGTGGAGTCCTGTGATCG<br>CCGCTTCTCCGTTTCCCACCGGCTCACCCATCACATCCGCA<br>TCCACACAGGCCAGAAGCCCTTCCAGTGCCGCATCTGCAT<br>GCGCAACTTCAGCCCTAGCAGAAGACTCACCCAGCACATC<br>CGCACCCACACAGGCGAAAAGCCCTTCGCCTGCGACATCT<br>GTGGAAGAAAGTTTGCCCAGAGCGAGGGGCGCAAGGTCC<br>ATACCAAGATCCACTTGCGGCAGAAGGACAAGAAAGCAG<br>ACAAAAGTGTTGTGGGCGCGCCGACGCGCTGGACGATTT<br>CGATCTCGACATGCTGGGTTCTGATGCCCTCGATGACTTTG<br>ACCTGGATATGTTGGGAAGCGACGCATTGGATGACTTTGA<br>TCTGGACATGCTCGGCTCCGATGCTCTGGACGATTTCGATC<br>TCGATATGTTAATTAACTACCCGTACGACGTTCCGGACTAC<br>GCTGGTTATCCCTATGACGTCCCGGATTATGCAGGATCCTA<br>TCCATATGACGTTCCAGATTACGCTTGA (SEQ ID NO: 102) |

Validation of the ATFs from the screen showed minimal effects of the ATFs on IE2-GFP expression compared to the Empty control (FIG. 27E). It is important to note that the positive control (VPA) had fewer cells expressing IE2-GFP (8.4%) than in the original screen (19%/). Even the Empty control exhibited fewer cells expressing IE2-GFP (0.2% from 0.5%). This lower yield of IE2-GFP-expressing cells could be attributed to decreased levels of HCMV infection. HCMV must be sonicated to disaggregate the virions that tend to clump after freezing. A different sonicator was used for disaggregation in the validation step than in the original screen, resulting in different HCMV preparations. Experimental conditions could be optimized to increase HCMV infection for the purposes of revalidating the ATFs; however the high false positive rate suggests that the IE2-GFP system may not be a good system for ATF library testing.

ATF Targets and Mechanism of Action

To identify the ATF target genes, cognate site identification (CSI) described in Chapter 3, was used to find the top 100 scoring motifs for each ATF (FIG. 28A). The sequence and energy landscapes (SELs) for the ATFs depict the comprehensive sequence specificity for each ATF (FIG. 28B). The locations of these top-scoring motifs were identified in the human genome, then annotated to the nearest genes. The frequency of occurrence in the genome was plotted as well as the frequency within ±1 kb of a transcription start site (TSS) (FIGS. 29A-29B). ZFATF7 (brown ATF) appears to be highly specific, but white its preferred sites are highly represented in the human genome, they are less represented near the TSS.

Discussion

The HCMV screen for regulators permitting the expression of the viral genome to initiate productive lytic replication demonstrates that a system with a low false positive rate is critical for successfully identifying ATF hits. By comparing the number of cells that express IE2-GFP in the Empty control to the ATF library, it was apparent that the cell's response to lentiviral infection or the leaky nature of IE2-GFP expression makes it difficult to achieve a low false positive rate that is conducive to validating the ATF hits. While the validation step needs to be further optimized and replicated, this forward genetic screen demonstrated the challenge in testing an ATF library in a system where there may be false positives. The ATF library can either be tested in a different system to address the questions of licensing HCMV gene expression, or more cells must be sequenced for ATF validation, such that ATFs can be validated despite the high false positive rate.

Materials and Methods

Cell Culture:

THP-1 monocytes were grown in RPMI 1640 media supplemented with 10% FBS and 0.05 mM β-mercaptoethanol. Cells were maintained at a density of $2 \times 10^4$-$1 \times 10^6$ cells/mL. Cells were maintained in a humidified 37° C. incubator with 5% $CO_2$.

Lentivirus Production:

ATFs and the empty control were packaged into lentivirus using a second-generation lentiviral system. Lentivirus was produced in HEK293T cells by calcium phosphate transfection of pSIN expression, psPAX2 packaging, and pMD2.G envelope plasmids. Media containing virus was harvested 48-60 hours post-transfection. Lentivirus was centrifuged with a sucrose cushion at 25,000 rpm for 2 hours. Viral particles were suspended in PBS and concentrated virus was stored at −80° C. Viral titers were measured by counting HEK293T cells that survived selection after 2 days in media containing puromycin (3 μg/mL).

Lentiviral Transduction:

Lentiviruses were delivered to THP-1 monocytes with 16 μg/mL polybrene by spinoculation. Cells were transduced with lentivirus at a density of $3 \times 10^5$ cells/mL while spinning at 1000×g for 1 hour at 25° C. (MOI=1). Selection was performed in media containing puromycin (1 μg/mL). The ATF was driven by a constitutive promoter, EF1α.

HCMV Infection:

HCMV (AD169 strain) with the IE2-GFP reporter gene was thawed on ice and sonicated at 50% power 0.5 seconds on and 0.5 seconds off for 2×10 pulses. HCMV was placed on ice between sets of pulses. At a density of $8 \times 10^5$ cells/mL, THP-1 cells were infected with HCMV for 1 hour at 37° C. with agitation every 15 min. For VPA pretreatment, cells were treated at a final concentration of 1 mM for 3 hours, then infected with HCMV.

Identification of ATFs:

Cells exhibiting a phenotype of the hematopoietic lineage were picked an expanded on methylcellulose. Two-step nested PCR was performed from cell clusters after expansion. The first round of amplification was performed with ATF-forward-1 and ATF-reverse-1 primers (400 nM final concentration) in a 50 μL volume or 40 cycles. The second round of amplification was performed with 10 μL of the first PCR reaction, ATF-forward-2 and ATF-reverse-2 primers (400 nM final concentration) for 35 cycles. The second PCR reaction was purified and digested with AscI and NheI. The digested product was cloned into pcDNA 3.1 at the AscI and NheI restriction sites. Sanger sequencing was performed on the clones with the CMV-forward primer.

The number of sequences obtained to reach saturation was determined by calculating the probability that the chance of finding another unique ATF is less than 1%. $(1-1/(n+1))^x < 0.01$, where n is the number of unique ATFs identified and x is the number of sequences needed.

Cognate Site Identification:

HEK293 cells were transiently transfected with ATFs using Lipofectamine 2000 (Thermo Fisher #11668019). Cells that underwent a mock transfection (without an expression plasmid for ATFs) served as a negative control. Cells were harvested 48 hours post-transfection. Lysates were prepared by lysing $10^7$ cells in 300 μL of lysis buffer (50 mM Tris-HCl pH 7.5, 150 mM NaCl, 1% Triton X-100, and 0.1% Na deoxycholate). A 21.5 G syringe needle was used for mechanical lysis. Lysates were centrifuged at 10 k×g for 10 min to separate precipitated genomic DNA from protein constituents. The supernatant, containing ATF protein, was used for CSI. HA magnetic beads (MBL #M132-9) were added to the cell lysates for immunoprecipitation. The binding reaction between the ATFs and 100 nM synthetic DNA was performed in binding buffer (25 mM HEPES, 80 mM KCl, 0.2 mM EDTA, 1 mM $MgCl_2$, 0.1 mM $ZnSO_4$) at 25° C. After pull-down, three quick washes with 100 μL ice-cold binding buffer were performed to remove unbound DNA. Magnetic beads were resuspended in a PCR master mix (Lucigen #30035-1) and the DNA was amplified for 15 or 18 cycles. Amplified DNA was column purified (Qiagen #28106), and this enriched DNA pool was used for the subsequent round of enrichment, for a total of three rounds. After three rounds of selection, Illumina sequencing adapters and a unique 6 bp barcode for multiplexing were added by PCR amplification. The starting library (Round 0) was also barcoded. Up to 180 samples were combined and sequenced in a single HiSeq2000 lane.

Cognate Site Identification Data Analysis:

Illumina sequencing yielded ~180 million reads per lane. Reads were de-multiplexed by requiring an exact match to the 6 bp barcode and truncated to include only the 25 bp derived from the random portion of the library. On average, we obtained 709,300 reads per barcode. The occurrence of every k-mer (lengths 8 through 16 bp) was counted using a sliding window of size k. To correct for biases in our starting DNA library, we took the ratio of the counts of every k-mer to the expected number of counts in the mock-transfected control. The mock control was modeled using a 5th-order Markov Model derived from the sequencing reads corresponding to the starting library (Round 0). We then calculated a Z-score=$(x-\mu)/\sigma$ or (CSI score minus mean)/standard deviation for each k-mer, using the distribution of k-mer enrichment values (CSI score) for the ATF.

Bioinformatic Analysis of ATF Binding Sites:

The genomic locations of the top five or 100 high-scoring 10-bp motifs from CSI were identified in the mm10 genome by the findMotif utility from the UCSC Genome Browser. These genomic sites were annotated using Homer. Annotated sites were filtered to those within +1 kb of the TSS.

REFERENCES

1. Penkert R R, Kalejta R F (2012) Tale of a tegument transactivator: the past, present and future of human CMV pp 71. *Future Virol* 7(9):855-869.
2. Penkert R R, Kalejta R F (2013) Human embryonic stem cell lines model experimental human cytomegalovirus latency. *MBio* 4(3):e00298-13.
3. Tsuchiya S, et al. (1980) Establishment and characterization of a human acute monocytic leukemia cell line (THP-1). *Int J Cancer* 26(2):171-176.

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. An artificial transcription factor comprising a polydactyl zinc finger protein comprising an interaction domain, an activation domain, and two zinc finger domains, each of the two zinc finger domains comprising a variable domain independently encoded by nucleic acid sequence of SEQ ID NO:2 (VNN-TCC-VNN-VNN-CTC-ACC-VNN), wherein each VNN of SEQ ID NO:2 is a codon corresponding to an amino acid selected from the group consisting of R, H, K, D, Q, S, T, N, E, G, P, A, I, L, M, and V, with the proviso that the variable domain in at least one of the two zinc finger domains has a sequence of one of SEQ ID NOS:123-341.

2. The artificial transcription factor of claim 1, wherein the polydactyl zinc finger protein comprises three zinc finger domains encoded by SEQ ID NO:4, SEQ ID NO:5, and SEQ ID NO:6, wherein each VNN of SEQ ID NOS:4, 5, and 6 is a codon corresponding to an amino acid selected from the group consisting of R, H, K, D, Q, S, T, N, E, G, P, A, I, L, M, and V.

3. The artificial transcription factor of claim 1, wherein the interaction domain comprises a 15-amino acid peptide that enables interaction with the hydrophobic face of the most N-terminal zinc finger domain.

4. The artificial transcription factor of claim 1, wherein the activation domain comprises four tandem repeats of DALDDFDLDML (SEQ ID NO:7).

5. The artificial transcription factor of claim 1, further comprising a nuclear localization signal.

6. The artificial transcription factor of claim 5, wherein the nuclear localization signal is encoded by an amino acid sequence selected from the group consisting of KDKKAD-KSVV (SEQ ID NO:11) and PKKKRKV (SEQ ID NO:12).

7. A method of reprogramming a somatic cell to pluripotency, wherein the method comprises:
(a) exposing a somatic cell to a plurality of artificial transcription factors (ATFs), wherein the plurality of ATFs comprises at least one of ZFATF1 and ZFATF2;
(b) further exposing the somatic cell to a plurality of potency determining factors comprising Sox2, Klf4, and c-Myc; and
(c) culturing the exposed cells to obtain reprogrammed cells having a higher potency level than the somatic cell.

8. The method of claim 7, wherein the plurality of ATFs comprises ZFATF1, ZFATF2, and ZFATF5.

9. The method of claim 7, wherein the plurality of ATFs comprises ZFATF1 and ZFATF2.

10. A method of directing differentiation of a pluripotent stem cell to a somatic cell, wherein the method comprises;
(a) exposing a pluripotent stem cell to one or more artificial transcription factors (ATFs), wherein, to produce a cardiomyocyte somatic cell, the one or more ATFs comprise at least one of ZFATF1 and ZFATF2, and wherein, to produce a hematopoietic somatic cell, the one or more ATFs comprise at least one of ZFATF20, ZFATF21, ZFATF1, ZFATF6, ZFATF10, ZFATF13, ZFATF17, ZFATF22, ZFATF23, ZFATF24, ZFATF25, ZFATF26, ZFATF27, ZFATF28, ZFATF29, and ZFATF30; and
(b) culturing the exposed cells of (a) for about 7-10 days, wherein to produce a cardiomyocyte somatic cell, the exposed cells are cultured in the presence of a Wnt activator, and wherein, to produce a hematopoietic somatic cell, the exposed cells are cultured in a basal culture medium comprising FGF2, SCF, and thrombopoietin, and in the presence of TAL1.

11. The method of claim 10, wherein the ATFs comprise ZFATF1, ZFATF2, and ATF5.

12. The method of claim 10, wherein the ATFs comprise ZFATF19, ZFATF20, ZFATF21, and ATF5, and wherein a cell population comprising erythroid-like cells is produced.

13. The method of claim 10, wherein the ATFs comprise ZFATF1, ZFATF6, ZFATF10, ZFATF13, ZFATF17, ZFATF22, ZFATF23, ZFATF24, ZFATF25, ZFATF26, ZFATF27, ZFATF28, ZFATF29, ZFATF30, and ZFATF31, and wherein a cell population comprising monocyte-like cells is produced.

14. A method for preparing a zinc finger-based artificial transcription factor (ATF) library comprising generating a plurality of elements, whereby each element of said ATF library comprises:
a zinc finger backbone comprising two oligonucleotides, each of the two oligonucleotides encoding SEQ ID NO:3 (X1-S-X2-X3-L-T-X6);
an interaction domain-encoding sequence; and
an activation domain-encoding sequence,
wherein X1 is an amino acid selected from the group consisting of R, H, K, D, Q, S, T, N, E, G, P, A, I, L, M, and V; X2 is selected from the group consisting of R, H, K, D, Q, S, T, N, E, G, P, A, I, L, M, and V; X3 is selected from the group consisting of R, H, K, D, Q, S, T, N, E, G, P, A, I, L, M, and V; and X6 is selected from the group consisting of R, H, K, D, Q, S, T, N, E, G, P, A, I, L, M, and V, wherein at least one element encodes the artificial transcription factor of claim 1.

15. The method of claim 14, wherein the ATF library has a complexity of about $2.62 \times 10^6$.

16. The method of claim 14, wherein the interaction domain comprises a 15-amino acid peptide that enables interaction with the hydrophobic face of the most N-terminal zinc finger domain.

17. The method of claim 14, wherein the activation domain comprises four tandem repeats of DALDDFDLDML (SEQ ID NO:7).

18. A zinc finger-based artificial transcription factor (ATF) library obtained according to the method of claim 14.

19. The artificial transcription factor of claim 1, wherein the variable domain in each of the two zinc finger domains has a sequence of one of SEQ ID NOS:123-341.

20. The artificial transcription factor of claim 1, wherein the variable domain in at least one of the two zinc finger domains has a sequence of one of SEQ ID NOS:123-147.

21. The artificial transcription factor of claim 1, wherein the variable domain in each of the two zinc finger domains has a sequence of one of SEQ ID NOS:123-147.

22. The artificial transcription factor of claim 1, wherein the variable domain in at least one of the two zinc finger domains has a sequence of one of SEQ ID NOS:123-128, 131, 136, and 138-145.

23. The artificial transcription factor of claim 1, wherein the variable domain in each of the two zinc finger domains has a sequence of one of SEQ ID NOS:123-128, 131, 136, and 138-145.

24. The artificial transcription factor of claim 1, wherein the variable domain in at least one of the two zinc finger domains has a sequence of one of SEQ ID NOS: 123, 124, 131, 136, 139, 142, and 144.

* * * * *

SEQUENCE LISTING

```
<160> NUMBER OF SEQ ID NOS: 341

<210> SEQ ID NO 1
<211> LENGTH: 18
<212> TYPE: DNA
<213> ORGANISM: Homo sapiens

<400> SEQUENCE: 1
gcgtgggcgc gcccccgc                                                 18

<210> SEQ ID NO 2
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t

<400> SEQUENCE: 2
vnntccvnnv nnctcaccvn n                                             21
```

<210> SEQ ID NO 3
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is an amino acid selected from the group
      consisting of R, H, K, D, Q, S, T, N, E, G, P, A, I, L, M, and V
<220> FEATURE:
<221> NAME/KEY: MISC_FEATURE
<222> LOCATION: (3)..(3)
<223> OTHER INFORMATION: X is an amino acid selected from the group
      consisting of R, H, K, D, Q, S, T, N, E, G, P, A, I, L, M
<220> FEATURE:
<221> NAME/KEY: MISC_FEATURE
<222> LOCATION: (4)..(4)
<223> OTHER INFORMATION: X is an amino acid selected from the group
      consisting of R, H, K, D, Q, S, T, N, E, G, P, A, I, L, M
<220> FEATURE:
<221> NAME/KEY: MISC_FEATURE
<222> LOCATION: (7)..(7)
<223> OTHER INFORMATION: X is an amino acid selected from the group
      consisting of R, H, K, D, Q, S, T, N, E, G, P, A, I, L, M, and V

<400> SEQUENCE: 3

Xaa Ser Xaa Xaa Leu Thr Xaa
1               5

<210> SEQ ID NO 4
<211> LENGTH: 93
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t

<400> SEQUENCE: 4
ccttacgctt gcccagtgga gtcctgtgat cgccgcttct ccvnntccvn nvnnctcacc    60
vnncacatcc gcatccacac aggccagaag ccc                                93

<210> SEQ ID NO 5
<211> LENGTH: 78
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 5
ttccagtgcc gcatctgcat gcgcaacttc agcvnnagcv nnvnnctcac cvnncacatc    60
cgcacccaca caggcgaa                                                  78

<210> SEQ ID NO 6
<211> LENGTH: 81
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 6
aagcccttcg cctgcgacat ctgtggaaga aagtttgccv nnagcvnnvn ncgcaagvnn    60
cataccaaga tccacttgcg g                                              81

<210> SEQ ID NO 7
<211> LENGTH: 11
<212> TYPE: PRT
<213> ORGANISM: herpes simplex virus

<400> SEQUENCE: 7

Asp Ala Leu Asp Asp Phe Asp Leu Asp Met Leu
1               5                   10

<210> SEQ ID NO 8
<211> LENGTH: 31
<212> TYPE: PRT
<213> ORGANISM: Artificial Sequence
<220> FEATURE:
<223> OTHER INFORMATION: synthetic

<400> SEQUENCE: 8

Pro Gly Leu Pro Asn Gly Leu Leu Ser Gly Asp Glu Asp Phe Ser Ser
1               5                   10                  15

Ile Ala Asp Met Asp Phe Ser Ala Leu Leu Ser Gln Ile Ser Ser
            20                  25                  30

<210> SEQ ID NO 9
<211> LENGTH: 5
<212> TYPE: PRT
<213> ORGANISM: Artificial Sequence
<220> FEATURE:
<223> OTHER INFORMATION: synthetic

<400> SEQUENCE: 9

Phe Asp Thr Asp Leu
1               5

<210> SEQ ID NO 10
<211> LENGTH: 20
<212> TYPE: PRT
<213> ORGANISM: Artificial Sequence
<220> FEATURE:
<223> OTHER INFORMATION: synthetic

<400> SEQUENCE: 10

Pro Glu Phe Pro Gly Ile Glu Leu Gln Glu Leu Gln Glu Leu Gln Ala
1               5                   10                  15

Leu Leu Gln Gln
            20

<210> SEQ ID NO 11
<211> LENGTH: 10
<212> TYPE: PRT
<213> ORGANISM: Homo sapiens

<400> SEQUENCE: 11

Lys Asp Lys Lys Ala Asp Lys Ser Val Val
1               5                   10

<210> SEQ ID NO 12
<211> LENGTH: 7
<212> TYPE: PRT
<213> ORGANISM: Simian virus 40

<400> SEQUENCE: 12

Pro Lys Lys Lys Arg Lys Val
1               5

<210> SEQ ID NO 13
<211> LENGTH: 15
<212> TYPE: PRT
<213> ORGANISM: Artificial Sequence
<220> FEATURE:
<223> OTHER INFORMATION: synthetic

<400> SEQUENCE: 13

His Pro Met Asn Asn Leu Leu Asn Tyr Val Val Pro Lys Met Arg
1               5                   10                  15

<210> SEQ ID NO 14
<211> LENGTH: 1478
<212> TYPE: DNA
<213> ORGANISM: Artificial Sequence
<220> FEATURE:
<223> OTHER INFORMATION: synthetic

<400> SEQUENCE: 14
gaattcggac catactctat aatactatca ctaacttaat taattatatt ccccagaaca      60
tcaggttaat ggcgtttttg atgtcatttt cgcggtggct gagatcagcc acttcttccc    120
cgataacgga gaccggcaca ctggccatat cggtggtcat catgcgccag ctttcatccc    180
cgatatgcac caccgggtaa agttcacggg agactttatc tgacagcaga cgtgcactgg    240
ccagggggat caccatccgt cgcccgggcg tgtcaataat atcactctgt acatccacaa    300
acagacgata acggctctct ctttttatagg tgtaaaacctt aaactgcatt tcaccagccc    360

```
ctgttctcgt cagcaaaaga gccgttcatt tcaataaacc gggcgacctc agccatccct        420
tcctgatttt ccgcttttcca gcgttcggca cgcagacgac gggcttcatt ctgcatggtt       480
gtgcttacca gaccggagat attgacatca tatatgcctt gagcaactga tagctgtcgc        540
tgtcaactgt cactgtaata cgctgcttca tagcatacct cttttttgaca tacttcgggt      600 atacatatca gtatatattc ttataccgca aaaatcagcg cgcaaatacg catactgtta        660
tctggctttt agtaagccgg atccacgcgg cgtttacgcc ccccctgcca ctcatcgcag        720
tactgttgta attcattaag cattctgccg acatggaagc catcacaaac ggcatgatga        780
acctgaatcg ccagcggcat cagcaccttg tcgccttgcg tataatattt gcccatggtg        840
aaaacggggg cgaagaagtt gtccatattg gccacgttta aatcaaaact ggtgaaactc        900
acccagggat tggctgagac gaaaaacata ttctcaataa accctttagg gaaataggcc       960
aggttttcac cgtaacacgc cacatcttgc gaatatatgt gtagaaactg ccggaaatcg       1020
tcgtggtatt cactccagag cgatgaaaac gtttcagttt gctcatggaa acggtgtaa        1080 caagggtgaa cactatccca tatcaccagc tcaccgtctt tcattgccat acggaagttc       1140
ggatgagcat tcatcaggcg ggcaagaatg tgaataaagg ccggataaaa cttgtgctta      1200
tttttcttta cggtctttaa aaaggccgta atatccagct gaacggtctg gttataggta       1260
cattgagcaa ctgactgaaa tgcctcaaaa tgttctttac gatgccattg ggatatatca      1320
acggtggtat atccagtgat ttttttctcc attttagctt ccttagctcc tgaaaatctc       1380
gataactcaa aaaatacgcc cggtagtgat ctcgagccgg aagcataaag tgtaaattaa      1440
ttaagattag agttaagtaa ggtattagtg acactagt                                1478

<210> SEQ ID NO 15
<211> LENGTH: 179
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t

<400> SEQUENCE: 15
ggtaccatgc atcctatgaa caacctgctg aactacgtgg tgccgaagat gagaccttac        60
gcttgcccag tggagtcctg tgatcgccgc ttctccvnnt ccvnnvnnct caccvnncac       120
atccgcatcc acacaggcca gaagcccttc cagtgccgca tctgcatgcg caacttcag        179

<210> SEQ ID NO 16
<211> LENGTH: 182
<212> TYPE: DNA
<213> ORGANISM: Artificial Sequence
<220> FEATURE:
<223> OTHER INFORMATION: synthetic
<220> FEATURE:
<221> NAME/KEY: misc_feature
```

```
<222> LOCATION: (55)..(56)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (139)..(140)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t
<220> FEATURE:
<221> NAME/KEY: misc_feature
<222> LOCATION: (151)..(152)
<223> OTHER INFORMATION: n is a, c, g, or t
<220> FEATURE:
<221> NAME/KEY: misc_feature
<222> LOCATION: (157)..(158)
<223> OTHER INFORMATION: n is a, c, g, or t

<400> SEQUENCE: 16
cacaacactt tgtctgctt tcttgtcctt ctgccgcaag tggatcttgg tatgnnbctt      60
gcgnnbnnbg ctnnbggcaa actttcttcc acagatgtcg caggcgaagg gcttttcgcc    120
tgtgtgggtg cggatgtgnn bggtgagnnb nnbgctnnbg ctgaagttgc gcatgcagat    180
gc                                                                  182

<210> SEQ ID NO 17
<211> LENGTH: 288
<212> TYPE: DNA
<213> ORGANISM: Artificial Sequence
<220> FEATURE:
<223> OTHER INFORMATION: synthetic

<400> SEQUENCE: 17
aaggacaaga aagcagacaa aagtgttgtg gggcgcgccg acgcgctgga cgatttcgat     60
ctcgacatgc tgggttctga tgccctcgat gactttgacc tggatatgtt gggaagcgac   120
gcattggatg actttgatct ggacatgctc ggctccgatg ctctggacga tttcgatctc   180
gatatgttaa ttaactaccc gtacgacgtt ccggactacg ctggttatcc ctatgacgtc   240
ccggattatg caggatccta tccatatgac gttccagatt acgcttga               288

<210> SEQ ID NO 18
<211> LENGTH: 25
<212> TYPE: DNA
<213> ORGANISM: Artificial Sequence
<220> FEATURE:
<223> OTHER INFORMATION: synthetic

<400> SEQUENCE: 18
ccgcatctgc atgcgcaact tcagc                                          25

<210> SEQ ID NO 19
<211> LENGTH: 18
<212> TYPE: DNA
<213> ORGANISM: Artificial Sequence
<220> FEATURE:
```

<223> OTHER INFORMATION: synthetic

<400> SEQUENCE: 19
gcgggccctc tagactcg                                          18

<210> SEQ ID NO 20
<211> LENGTH: 73
<212> TYPE: DNA
<213> ORGANISM: Artificial Sequence
<220> FEATURE:
<223> OTHER INFORMATION: synthetic

<400> SEQUENCE: 20
accatactct ataatactat cactaactta gccgccacca tgcatcctat gaacaacctg    60
ctgaactacg tgg                                               73

<210> SEQ ID NO 21
<211> LENGTH: 70
<212> TYPE: DNA
<213> ORGANISM: Artificial Sequence
<220> FEATURE:
<223> OTHER INFORMATION: synthetic

<400> SEQUENCE: 21
tcactaatac cttacttaac tctaatctta gtcaagcgta atctggaacg tcatatggat    60
aggatcctgc                                                   70

<210> SEQ ID NO 22
<211> LENGTH: 18
<212> TYPE: DNA
<213> ORGANISM: Homo sapiens

<400> SEQUENCE: 22
cgcacccgcg cggggggcg                                         18

<210> SEQ ID NO 23
<211> LENGTH: 28
<212> TYPE: DNA
<213> ORGANISM: Artificial Sequence
<220> FEATURE:
<223> OTHER INFORMATION: synthetic

<400> SEQUENCE: 23
tactatcact aacttagccg ccaccatg                               28

<210> SEQ ID NO 24
<211> LENGTH: 22
<212> TYPE: DNA
<213> ORGANISM: Artificial Sequence
<220> FEATURE:
<223> OTHER INFORMATION: synthetic

<400> SEQUENCE: 24
gagggcatca gaacccagca tg                                     22

<210> SEQ ID NO 25
<211> LENGTH: 33
<212> TYPE: DNA
<213> ORGANISM: Artificial Sequence
<220> FEATURE:
<223> OTHER INFORMATION: synthetic

<400> SEQUENCE: 25
catcagctag cgctgaacta cgtggtgccg aag                         33

```
<210> SEQ ID NO 26
<211> LENGTH: 33
<212> TYPE: DNA
<213> ORGANISM: Artificial Sequence
<220> FEATURE:
<223> OTHER INFORMATION: synthetic

<400> SEQUENCE: 26
cgcgtcggcg cgccccacaa cactttgtc tgc                                    33

<210> SEQ ID NO 27
<211> LENGTH: 21
<212> TYPE: DNA
<213> ORGANISM: Artificial Sequence
<220> FEATURE:
<223> OTHER INFORMATION: synthetic

<400> SEQUENCE: 27
cgcaaatggg cggtaggcgt g                                                21

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
tcagtgatgc tgttgatcag g                                                21

<210> SEQ ID NO 29
<211> LENGTH: 23
<212> TYPE: DNA
<213> ORGANISM: Artificial Sequence
<220> FEATURE:
<223> OTHER INFORMATION: synthetic

<400> SEQUENCE: 29
gctatctact gtgtgtccca gtc                                              23

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
ccgttttcgt ggtcttgttt                                                  20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
tcaacctgca tggacatttt                                                  20

<210> SEQ ID NO 32
<211> LENGTH: 24
<212> TYPE: DNA
<213> ORGANISM: Artificial Sequence
<220> FEATURE:
```

<223> OTHER INFORMATION: synthetic

<400> SEQUENCE: 32
aaaccagtgg ttgaagacta gcaa                                          24

<210> SEQ ID NO 33
<211> LENGTH: 21
<212> TYPE: DNA
<213> ORGANISM: Artificial Sequence
<220> FEATURE:
<223> OTHER INFORMATION: synthetic

<400> SEQUENCE: 33
ggtgctgagc ccttctgaat c                                             21

<210> SEQ ID NO 34
<211> LENGTH: 22
<212> TYPE: DNA
<213> ORGANISM: Artificial Sequence
<220> FEATURE:
<223> OTHER INFORMATION: synthetic

<400> SEQUENCE: 34
gaagaacatg cagaagcgaa ga                                            22

<210> SEQ ID NO 35
<211> LENGTH: 21
<212> TYPE: DNA
<213> ORGANISM: Artificial Sequence
<220> FEATURE:
<223> OTHER INFORMATION: synthetic

<400> SEQUENCE: 35
ccgcagttgt agcacctgtc t                                             21

<210> SEQ ID NO 36
<211> LENGTH: 23
<212> TYPE: DNA
<213> ORGANISM: Artificial Sequence
<220> FEATURE:
<223> OTHER INFORMATION: synthetic

<400> SEQUENCE: 36
cacctgctaa aaagccattg act                                           23

<210> SEQ ID NO 37
<211> LENGTH: 25
<212> TYPE: DNA
<213> ORGANISM: Artificial Sequence
<220> FEATURE:
<223> OTHER INFORMATION: synthetic

<400> SEQUENCE: 37
caacccctag tagattcgag acgat                                         25

<210> SEQ ID NO 38
<211> LENGTH: 18
<212> TYPE: DNA
<213> ORGANISM: Artificial Sequence
<220> FEATURE:
<223> OTHER INFORMATION: synthetic

<400> SEQUENCE: 38
gtccctctcc gcgttagc                                                 18

<210> SEQ ID NO 39
<211> LENGTH: 19
<212> TYPE: DNA
<213> ORGANISM: Artificial Sequence
<220> FEATURE:
<223> OTHER INFORMATION: synthetic

<400> SEQUENCE: 39
ggcaggttcg tcattttcc                                                19

<210> SEQ ID NO 40
<211> LENGTH: 19
<212> TYPE: DNA
<213> ORGANISM: Artificial Sequence
<220> FEATURE:
<223> OTHER INFORMATION: synthetic

<400> SEQUENCE: 40
ctgtggctgc gcttcaagg                                                19

<210> SEQ ID NO 41
<211> LENGTH: 19
<212> TYPE: DNA
<213> ORGANISM: Artificial Sequence
<220> FEATURE:
<223> OTHER INFORMATION: synthetic

<400> SEQUENCE: 41
attggggtcc aggcctgac                                                19

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
tgaccctgac ccagccaaag                                               20

<210> SEQ ID NO 43
<211> LENGTH: 21
<212> TYPE: DNA
<213> ORGANISM: Artificial Sequence
<220> FEATURE:
<223> OTHER INFORMATION: synthetic

<400> SEQUENCE: 43
gagaagagca cgcgtggctt c                                             21

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44 catccccca agctcagcac                                                20

<210> SEQ ID NO 45
<211> LENGTH: 21
<212> TYPE: DNA
<213> ORGANISM: Artificial Sequence
<220> FEATURE:
<223> OTHER INFORMATION: synthetic

```
<400> SEQUENCE: 45
acgctgagca ttgggccaaa g                                              21

<210> SEQ ID NO 46
<211> LENGTH: 21
<212> TYPE: DNA
<213> ORGANISM: Artificial Sequence
<220> FEATURE:
<223> OTHER INFORMATION: synthetic

<400> SEQUENCE: 46
cactgtccaa gcaaagctgc g                                              21

<210> SEQ ID NO 47
<211> LENGTH: 21
<212> TYPE: DNA
<213> ORGANISM: Artificial Sequence
<220> FEATURE:
<223> OTHER INFORMATION: synthetic

<400> SEQUENCE: 47
gaggtcagct gagggctttc                                                21

<210> SEQ ID NO 48
<211> LENGTH: 20
<212> TYPE: DNA
<213> ORGANISM: Artificial Sequence
<220> FEATURE:
<223> OTHER INFORMATION: synthtetic

<400> SEQUENCE: 48
ggatcctggg agccctttgc                                                20

<210> SEQ ID NO 49
<211> LENGTH: 20
<212> TYPE: DNA
<213> ORGANISM: Artificial Sequence
<220> FEATURE:
<223> OTHER INFORMATION: synthetic

<400> SEQUENCE: 49
tcatctgtgg tgagcccgtg                                                20

<210> SEQ ID NO 50
<211> LENGTH: 21
<212> TYPE: DNA
<213> ORGANISM: Artificial Sequence
<220> FEATURE:
<223> OTHER INFORMATION: synthetic

<400> SEQUENCE: 50
tgggagccgt gaagatggaa g                                              21

<210> SEQ ID NO 51
<211> LENGTH: 19
<212> TYPE: DNA
<213> ORGANISM: Artificial Sequence
<220> FEATURE:
<223> OTHER INFORMATION: synthetic

<400> SEQUENCE: 51
caggccggcg ttcatgttg                                                 19

<210> SEQ ID NO 52
<211> LENGTH: 20
```

```
<212> TYPE: DNA
<213> ORGANISM: Artificial Sequence
<220> FEATURE:
<223> OTHER INFORMATION: synthetic

<400> SEQUENCE: 52
gcagagaggc gctggaacag                                                    20

<210> SEQ ID NO 53
<211> LENGTH: 20
<212> TYPE: DNA
<213> ORGANISM: Artificial Sequence
<220> FEATURE:
<223> OTHER INFORMATION: synthetic

<400> SEQUENCE: 53
ccctgcttct cctgctccag                                                    20

<210> SEQ ID NO 54
<211> LENGTH: 21
<212> TYPE: DNA
<213> ORGANISM: Artificial Sequence
<220> FEATURE:
<223> OTHER INFORMATION: synthetic

<400> SEQUENCE: 54
ctggagaagc agctgcagga g                                                  21

<210> SEQ ID NO 55
<211> LENGTH: 21
<212> TYPE: DNA
<213> ORGANISM: Artificial Sequence
<220> FEATURE:
<223> OTHER INFORMATION: synthetic

<400> SEQUENCE: 55
ctggccatct cgctcttcgt g                                                  21

<210> SEQ ID NO 56
<211> LENGTH: 19
<212> TYPE: DNA
<213> ORGANISM: Artificial Sequence
<220> FEATURE:
<223> OTHER INFORMATION: synthetic

<400> SEQUENCE: 56
gcggttggca cagcagaac                                                     19

<210> SEQ ID NO 57
<211> LENGTH: 20
<212> TYPE: DNA
<213> ORGANISM: Artificial Sequence
<220> FEATURE:
<223> OTHER INFORMATION: synthetic

<400> SEQUENCE: 57
gctcggcctc ttccacgaag                                                    20

<210> SEQ ID NO 58
<211> LENGTH: 20
<212> TYPE: DNA
<213> ORGANISM: Artificial Sequence
<220> FEATURE:
<223> OTHER INFORMATION: synthetic

<400> SEQUENCE: 58
```

```
acatcatccc tgcatccact                                                    20
```

```
<210> SEQ ID NO 59
<211> LENGTH: 20
<212> TYPE: DNA
<213> ORGANISM: Artificial Sequence
<220> FEATURE:
<223> OTHER INFORMATION: synthetic

<400> SEQUENCE: 59
cctgcttcac caccttcttg                                                    20
```

```
<210> SEQ ID NO 60
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 60 ngngtgggcn                                                               10
```

```
<210> SEQ ID NO 61
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 61 ngagtgggcn                                                               10
```

```
<210> SEQ ID NO 62
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 62 ngggtgggcn                                                               10
```

```
<210> SEQ ID NO 63
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 63 ngtgtgggcn                                                            10

<210> SEQ ID NO 64
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 64 ngcgtgggcn                                                            10

<210> SEQ ID NO 65
<211> LENGTH: 16
<212> TYPE: DNA
<213> ORGANISM: Artificial Sequence
<220> FEATURE:
<223> OTHER INFORMATION: synthetic

<400> SEQUENCE: 65
cgtgggcgga cgtgtg                                                     16

<210> SEQ ID NO 66
<211> LENGTH: 16
<212> TYPE: DNA
<213> ORGANISM: Artificial Sequence
<220> FEATURE:
<223> OTHER INFORMATION: synthetic

<400> SEQUENCE: 66
gcgtgggcgg acctct                                                     16

<210> SEQ ID NO 67
<211> LENGTH: 14
<212> TYPE: DNA
<213> ORGANISM: Artificial Sequence
<220> FEATURE:
<223> OTHER INFORMATION: synthetic

<400> SEQUENCE: 67
gtgggcggac ctct                                                       14

<210> SEQ ID NO 68
<211> LENGTH: 10
<212> TYPE: PRT
```

```
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 68

Phe Ser Xaa Ser Xaa Xaa Leu Thr Xaa His
1               5                   10

<210> SEQ ID NO 69
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 69

Phe Ala Xaa Ser Xaa Xaa Arg Lys Xaa His
1               5                   10

<210> SEQ ID NO 70
<211> LENGTH: 390
<212> TYPE: PRT
<213> ORGANISM: Gorilla gorilla

<400> SEQUENCE: 70

Met His Thr Gly Glu Arg Pro Tyr Glu Cys His Glu Cys Gly Lys Gly
1               5                   10                  15

Phe Arg Asn Ser Ser Ala Leu Thr Lys His Gln Arg Ile His Thr Gly
                20                  25                  30

Glu Lys Pro Tyr Lys Cys Thr Gln Cys Gly Arg Thr Phe Asn Gln Ile
            35                  40                  45

Ala Pro Leu Ile Gln His Gln Arg Thr His Thr Gly Glu Lys Pro Tyr
        50                  55                  60

Glu Cys Ser Glu Cys Gly Lys Ala Phe Arg Gln Ser Ile His Leu Thr
65                  70                  75                  80

Gln His Leu Arg Ile His Thr Gly Glu Lys Pro Tyr Gln Cys Gly Glu
                85                  90                  95

Cys Gly Lys Ala Phe Ser His Ser Ser Leu Thr Lys His Gln Arg
                100                 105                 110

Ile His Thr Gly Glu Lys Pro Tyr Glu Cys His Glu Cys Gly Lys Ala
            115                 120                 125

Phe Thr Gln Ile Thr Pro Leu Ile Gln His Gln Arg Thr His Thr Gly
```

```
            130                 135                 140
Glu Lys Pro Tyr Glu Cys Arg Phe Thr Arg Glu Arg Ser Pro Thr Asp
145                 150                 155                 160

Ala Thr Ser Val Gly Lys Pro Ser Ala Thr Ala Pro His Ser Ala Ser
                165                 170                 175

Met Ser Gly His Thr Gln Glu Arg Ser Pro Met Ser Ala Val Ser Val
            180                 185                 190

Gly Arg Pro Ser Gly Arg Ala His Thr Ser Pro Asn Thr Ser Glu Ser
        195                 200                 205

Thr Gln Gly Arg Ser Pro Met Asn Ala Met Thr Ala Ala Arg His Ser
    210                 215                 220

Val Thr Ala His Pro Ser Pro Asn Ile Ser Glu Ser Thr Leu Gly Arg
225                 230                 235                 240

Ser Pro Thr Asn Ala Thr Ser Val Ala Glu Pro Ser Ala Ser Leu Leu
                245                 250                 255

Pro Ser Phe Ser Ile Arg Gly Ser Thr Gln Glu Arg Asn Pro Met Asn
            260                 265                 270

Val Thr Ser Val Ala Glu Pro Ser Ala Arg Ala Pro Phe Ser Ser Asn
        275                 280                 285

Thr Arg Gly Phe Thr Pro Arg Lys Ser His Met Gly Ala Met Ser Val
    290                 295                 300

Gly Asn Pro Ser Ala Thr Ala Pro Arg Ser Ala Ser Thr Lys Gly Arg
305                 310                 315                 320

Thr Leu Gly Lys Ser Pro Met Ser Val Thr Ile Ala Glu Ser Pro Leu
                325                 330                 335

Gly Arg Ala Pro Thr Ser Leu Ser Thr Gly Gly Ser Thr Gln Glu Arg
            340                 345                 350

Asn His Ile Ser Ser Leu Ser Arg Phe Asp Pro Ile Met His Met Arg
        355                 360                 365

Asn Val His Ser Tyr Thr Ser Leu Phe Thr Gln His Ser Pro Gln Thr
    370                 375                 380

Pro Ser Glu Ser Ser His
385                 390

<210> SEQ ID NO 71
<211> LENGTH: 163
<212> TYPE: PRT
<213> ORGANISM: Homo sapiens

<400> SEQUENCE: 71

Met His Pro Met Asn Asn Leu Leu Asn Tyr Val Val Pro Lys Met Arg
1               5                   10                  15

Pro Tyr Asp Cys Pro Val Glu Ser Cys Asp Arg Arg Phe Ser Arg Ser
                20                  25                  30

His Arg Pro Pro Ala Thr Ser Ala Ser Thr Gln Ala Arg Ser Pro Ser
            35                  40                  45

Ser Ala Ser Ala Cys Ala Thr Ser Ala Ser Ala Arg Pro Ser Pro
        50                  55                  60

Asp Thr Ser Ala Pro Thr Gln Ala Lys Ser Pro Ser Pro Ala Thr Ser
65                  70                  75                  80

Val Glu Glu Ser Leu Pro Gly Ala Thr Ser Ala Arg Asp Ile Pro Arg
                85                  90                  95

Ser Thr Cys Gly Arg Arg Thr Arg Lys Gln Thr Lys Val Leu Trp Gly
            100                 105                 110
```

Ala Pro Thr Arg Trp Thr Ile Ser Ile Ser Thr Cys Trp Val Leu Met
115                 120                 125

Pro Ser Met Thr Leu Thr Trp Ile Cys Trp Glu Ala Thr His Trp Met
130                 135                 140

Thr Leu Ile Trp Thr Cys Ser Ala Pro Met Leu Trp Thr Ile Ser Ile
145                 150                 155                 160

Ser Ile Cys

<210> SEQ ID NO 72
<211> LENGTH: 576
<212> TYPE: DNA
<213> ORGANISM: Artificial Sequence
<220> FEATURE:
<223> OTHER INFORMATION: synthetic

<400> SEQUENCE: 72
atgcatccta tgaacaacct gctgaactac gtggtgccga agatgagacc ttacgcttgt    60
gatcgccgct tctccgtttc caccggctca acccatcaca tccgcatcca cacaggccag   120
aagcccttcc agtgccgcat ctgcatgcgc aacttcagcc tagcagaag actcacccag    180
cacatccgca cccacacagg cgaaaagccc ttcgcctgcg acatctgtgg aagaaagttt   240
gcccagagcg aggggcgcaa ggtccatacc aagatccact gcggcagaa ggacaagaaa    300
gcagacaaaa gtgttgtggg gcgcgccgac gcgctggacg atttcgatct cgacatgctg   360
ggttctgatg ccctcgatga ctttgacctg gatatgttgg aagcgacgc attggatgac    420
tttgatctgg acatgctcgg ctccgatgct ctggacgatt tcgatctcga tatgttaatt   480
aactacccgt acgacgttcc ggactacgct ggttatccct atgacgtccc ggattatgca   540
ggatcctatc catatgacgt tccagattac gcttga                             576

<210> SEQ ID NO 73
<211> LENGTH: 591
<212> TYPE: DNA
<213> ORGANISM: Artificial Sequence
<220> FEATURE:
<223> OTHER INFORMATION: synthetic

<400> SEQUENCE: 73
atgcatccta tgaacaacct gctgaactac gtggtgccga agatgagacc ttacgcttgc    60
ccagtggagt cctgtgatcg ccgcttctcc gggtccgtag tcctcaccaa acacatccgc   120
atccacacag gccagaagcc cttccagtgc cgcatctgca tgcgcaactt cagcataagc   180
actgttctca ccggtcacat ccgcacccac acaggcgaaa agcccttcgc ctgcgacatc   240
tgtggaagaa agtttgccaa cagcgagcca cgcaagaccc ataccaagat ccacttgcgg   300
cagaaggaca gaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a             591

<210> SEQ ID NO 74
<211> LENGTH: 591
<212> TYPE: DNA
<213> ORGANISM: Artificial Sequence
<220> FEATURE:
<223> OTHER INFORMATION: synthetic

<400> SEQUENCE: 74

```
atgcatccta tgaacaacct gctgaactac gtggtgccga agatgagacc ttacgcttgc    60
ccagtggagt cctgtgatcg ccgcttctcc cgatccaaaa atctcaccgc gcacatccgc   120
atccacacag gccagaagcc cttccagtgc cgcatctgca tgcgcaactt cagcggtagc   180
gttccactca ccatacacat ccgcacccac acaggcgaaa agcccttcgc ctgcgacatc   240
tgtggaagaa agtttgccat cagcgccatt cgcaagaaac ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a            591
```

<210> SEQ ID NO 75
<211> LENGTH: 591
<212> TYPE: DNA
<213> ORGANISM: Artificial Sequence
<220> FEATURE:
<223> OTHER INFORMATION: synthetic

<400> SEQUENCE: 75

```
atgcatccta tgaacaacct gctgaactac gtggtgccga agatgagacc ttacgcttgc    60
ccagtggagt cctgtgatcg ccgcttctcc cgttccatcc gtctcaccat acacatccgc   120
atccacacag gccagaagcc cttccagtgc cgcatctgca tgcgcaactt cagcggtagc   180
gttccactca ccatacacat ccgcacccac acaggcgaaa agcccttcgc ctgcgacatc   240
tgtggaagaa agtttgccat cagcgccatt cgcaagaaac ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a            591
```

<210> SEQ ID NO 76
<211> LENGTH: 582
<212> TYPE: DNA
<213> ORGANISM: Artificial Sequence
<220> FEATURE:
<223> OTHER INFORMATION: synthetic

<400> SEQUENCE: 76

```
atgcatccta tgaacaacct gctgaactac gtggtgccga agatgagacc ttacgattgc    60
ccagtggagt cctgtgatcg ccgcttctcc agatccatc ggccaccagc cacatccgca   120
tccacacagg ccagaagccc ttccagtgcc gcatctgcat gcgcaacttc agcgtcagcc   180
cgaccctcac ccgacacatc cgcacccaca caggcgaaaa gcccttcgcc tgcgacatct   240
gtggaagaaa gtttgccagg agcgaccagc gcaagagaca taccaagatc cacttgcggc   300
agaaggacaa gaaagcagac aaaagtgttg tggggcgcgc cgacgcgctg gacgatttcg   360
atctcgacat gctgggttct gatgccctcg atgactttga cctggatatg ttgggaagcg   420
acgcattgga tgactttgat ctggacatgc tcggctccga tgctctggac gatttcgatc   480
tcgatatgtt acccgtacga cgttccggac tacgctggtt atccctatga cgtcccggat   540
```

```
tatgcaggat cctatccata tgacgttcca gattacgctt ga                  582
```

<210> SEQ ID NO 77
<211> LENGTH: 576
<212> TYPE: DNA
<213> ORGANISM: Artificial Sequence
<220> FEATURE:
<223> OTHER INFORMATION: synthetic

<400> SEQUENCE: 77

```
atgcatccta tgaacaacct gctgaactac gtggtgccga agatgagacc ttacgcttgt   60
gatcgccgct tctccgtttc ccaccggctc acccatcaca tccgcatcca cacaggccag  120
aagcccttcc agtgccgcat ctgcatgcgc aacttcagcc tcagcctaac cctcaccaaa  180
cacatccgca cccacacagg cgaaaagccc ttcgcctgcg acatctgtgg aagaaagttt  240
gccaaaagca aaccacgcaa gacacatacc aagatccact gcggcagaaa ggacaagaaa  300
gcagacaaaa gtgttgtggg gcgcgccgac gcgctggacg atttcgatct cgacatgctg  360
ggttctgatg ccctcgatga cttttgacctg gatatgttgg gaagcgacgc attggatgac  420
tttgatctgg acatgctcgg ctccgatgct ctggacgatt tcgatctcga tatgttaatt  480
aactacccgt acgacgttcc ggactacgct ggttatccct atgacgtccc ggattatgca  540
ggatcctatc catatgacgt tccagattac gcttga                            576
```

<210> SEQ ID NO 78
<211> LENGTH: 591
<212> TYPE: DNA
<213> ORGANISM: Artificial Sequence
<220> FEATURE:
<223> OTHER INFORMATION: synthetic

<400> SEQUENCE: 78

```
atgcatccta tgaacaacct gctgaactac gtggtgccga agatgagacc ttacgcttgc   60
ccagtggagt cctgtgatcg ccgcttctcc cgttccatcc gtctcaccat acacatccgc  120
atccacacag gccagaagcc cttccagtgc cgcatctgca tgcgcaactt cagccccagc  180
ccgccactca cccctcacat ccgcacccac acaggcgaaa agcccttcgc ctgcgacatc  240
tgtggaagaa agtttgcccc aagccttctc cgcaagccac ataccaagat ccacttgcgg  300
cagaaggaca agaaagcaga caaaagtgtt gtggggcgcg ccgacgcgct ggacgatttc  360
gatctcgaca tgctgggttc tgatgccctc gatgactttg acctggatat gttgggaagc  420
gacgcattgg atgactttga tctggacatg ctcggctccg atgctctgga cgatttcgat  480
ctcgatatgt taattaacta cccgtacgac gttccggact acgctggtta tccctatgac  540
gtcccggatt atgcaggatc ctatccatat gacgttccag attacgcttg a            591
```

<210> SEQ ID NO 79
<211> LENGTH: 591
<212> TYPE: DNA
<213> ORGANISM: Artificial Sequence
<220> FEATURE:
<223> OTHER INFORMATION: synthetic

<400> SEQUENCE: 79

```
atgcatccta tgaacaacct gctgaactac gtggtgccga agatgagacc ttacgcttgc   60
ccagtggagt cctgtgatcg ccgcttctcc cgttccatcc gtctcaccat acacatacgc  120
atccacacag gccagaagcc cttccagtgc cgcatctgca tgcgcaacct cagccacagc  180
```

| | |
|---|---|
| gctcatctca ccacgcacat ccgcacccac acaggcgaaa agtccttcgc ctgcgacatc | 240 |
| tgtggaagaa agtttgccca cagcgaacct cgcaagacac ataccaagat ccacttgcgg | 300 |
| cagaaggaca agaaagcaga caaaagtgtt gtggggcgcg ccgacgcgct ggacgatttc | 360 |
| gatctcgaca tgctgggttc tgatgccctc gatgactttg acctggatat gttgggaagc | 420 |
| gacgcattgg atgactttga tctggacatg ctcggctccg atgctctgga cgatttcgat | 480 |
| ctcgatatgt taattaacta cccgtacgac gttccggact acgctggtta tccctatgac | 540 |
| gtcccggatt atgcaggatc ctatccatat gacgttccag attacgcttg a | 591 |

<210> SEQ ID NO 80
<211> LENGTH: 507
<212> TYPE: DNA
<213> ORGANISM: Artificial Sequence
<220> FEATURE:
<223> OTHER INFORMATION: synthetic

<400> SEQUENCE: 80

| | |
|---|---|
| atgcatccta tgaacaacct gctgaactac gtggtgccga agatgagacc ttacgcttgc | 60 |
| ccagtggagt cctgtgatcg ccgcttctcc ggctccaatc ggctcaccga gcacatccgc | 120 |
| atccacacag gcgaaaagcc cttcgcctgc gacatctgtg gaagaaagtt tgccaacagc | 180 |
| cccctacgca agggtcatac caagatccac ttgcggcaga aggacaagaa agcagacaaa | 240 |
| agtgttgtgg ggcgcgccga cgcgctggac gatttcgatc tcgacatgct gggttctgat | 300 |
| gccctcgatg actttgacct ggatatgttg ggaagcgacg cattggatga ctttgatctg | 360 |
| gacatgctcg gctccgatgc tctggacgat ttcgatctcg atatgttaat taactacccg | 420 |
| tacgacgttc cggactacgc tggttatccc tatgacgtcc cggattatgc aggatcctat | 480 |
| ccatatgacg ttccagatta cgcttga | 507 |

<210> SEQ ID NO 81
<211> LENGTH: 591
<212> TYPE: DNA
<213> ORGANISM: Artificial Sequence
<220> FEATURE:
<223> OTHER INFORMATION: synthetic

<400> SEQUENCE: 81

| | |
|---|---|
| atgcatccta tgaacaacct gctgaactac gtggtgccga agatgagacc ttacgcttgc | 60 |
| ccagtggagt cctgtgatcg ccgcttctcc gtatccgaca ctctcaccgt acacatccgc | 120 |
| atccacacag gccagaagcc cttccagtgc cgcatctgca tgcgcaactt cagcgacagc | 180 |
| gatgagctca ccgatcacat ccgcacccac acaggcgaaa agcccttcgc ctgcgacatc | 240 |
| tgtggaagaa agtttgccga aagccgtaaa cgcaaggaac ataccaagat ccacttgcgg | 300 |
| cagaaggaca agaaagcaga caaaagtgtt gtggggcgcg ccgacgcgct ggacgatttc | 360 |
| gatctcgaca tgctgggttc tgatgccctc gatgactttg acctggatat gttgggaagc | 420 |
| gacgcattgg atgactttga tctggacatg ctcggctccg atgctctgga cgatttcgat | 480 |
| ctcgatatgt taattaacta cccgtacgac gttccggact acgctggtta tccctatgac | 540 |
| gtcccggatt atgcaggatc ctatccatat gacgttccag attacgcttg a | 591 |

<210> SEQ ID NO 82
<211> LENGTH: 591
<212> TYPE: DNA
<213> ORGANISM: Artificial Sequence
<220> FEATURE:
<223> OTHER INFORMATION: synthetic

<400> SEQUENCE: 82

```
atgcatccta tgaacaacct gctgaactac gtggtgccga agatgagacc ttacgcttgc      60
ccagtggagt cctgtgatcg ccgcttctcc atatccggtg cgctcaccgg gcacatccgc     120
atccacacag gccagaagcc cttccagtgc cgcatctgca tgcgcaactt cagcagtagc     180
aatcaactca ccgcgcacat ccgcacccac acaggcgaaa agcccttcgc ctgcgacatc     240
tgtggaagaa agtttgccag aagcatacac cgcaagcgtc ataccaagat ccacttgcgg     300
cagaaggaca agaaagcaga caaaagtgtt gtggggcgcg ccgacgcgct ggacgatttc     360
gatctcgaca tgctgggttc tgatgccctc gatgactttg acctggatat gttgggaagc     420
gacgcattgg atgactttga tctggacatg ctcggctccg atgctctgga cgatttcgat     480
ctcgatatgt taattaacta cccgtacgac gttccggact acgctggtta tccctatgac     540
gtcccggatt atgcaggatc ctatccatat gacgttccag attacgcttg a              591
```

<210> SEQ ID NO 83
<211> LENGTH: 591
<212> TYPE: DNA
<213> ORGANISM: Artificial Sequence
<220> FEATURE:
<223> OTHER INFORMATION: synthetic

<400> SEQUENCE: 83

```
atgcatccta tgaacaacct gctgaactac gtggtgccga agatgagacc ttacgcttgc      60
ccagtggagt cctgtgatcg ccgcttctcc cgttccatcc gtctcaccat acacatccgc     120
atccacacag gccagaagcc cttccagtgc cgcatctgca tgcgcaactt cagccccagc     180
ccgccactca cccctcacat ccgcacccac acaggcgaaa agcccttcgc ctgcgacatc     240
tgtggaagaa agtttgccaa aagcgtaggt cgcaagagac ataccaagat ccacttgcgg     300
cataaggaca agaaagcaga caaaagtgtt gtggggcgcg ccgacgcgct ggacgatttc     360
gatctcgaca tgctgggttc tgatgccctc gatgactttg acctggatat gttgggaagc     420
gacgcattgg atgactttga tctggacatg ctcggctccg atgctctgga cgatttcgat     480
ctcgatatgt taattaacta cccgtacgac gttccggact acgctggtta tccctatgac     540
gtcccggatt atgcaggatc ctatccatat gacgttccag attacgcttg a              591
```

<210> SEQ ID NO 84
<211> LENGTH: 31
<212> TYPE: DNA
<213> ORGANISM: Artificial Sequence
<220> FEATURE:
<223> OTHER INFORMATION: synthetic

<400> SEQUENCE: 84

```
accatactct ataatactat cactaactta g                                     31
```

<210> SEQ ID NO 85
<211> LENGTH: 31
<212> TYPE: DNA
<213> ORGANISM: Artificial Sequence
<220> FEATURE:
<223> OTHER INFORMATION: synthetic

<400> SEQUENCE: 85

```
gattctaatc tcaattcatt ccataatcac t                                     31
```

<210> SEQ ID NO 86

```
<211> LENGTH: 31
<212> TYPE: DNA
<213> ORGANISM: Artificial Sequence
<220> FEATURE:
<223> OTHER INFORMATION: synthetic

<400> SEQUENCE: 86
taagattaga gttaagtaag gtattagtga c                                    31

<210> SEQ ID NO 87
<211> LENGTH: 31
<212> TYPE: DNA
<213> ORGANISM: Artificial Sequence
<220> FEATURE:
<223> OTHER INFORMATION: synthetic

<400> SEQUENCE: 87
ctggtatgag atattatgat agtgattgaa t                                    31

<210> SEQ ID NO 88
<211> LENGTH: 32
<212> TYPE: DNA
<213> ORGANISM: Artificial Sequence
<220> FEATURE:
<223> OTHER INFORMATION: synthetic

<400> SEQUENCE: 88
gaccatactc tataatacta tcactaactt ag                                   32

<210> SEQ ID NO 89
<211> LENGTH: 32
<212> TYPE: DNA
<213> ORGANISM: Artificial Sequence
<220> FEATURE:
<223> OTHER INFORMATION: synthetic

<400> SEQUENCE: 89
ctaagattag agttaagtaa ggtattagtg ac                                   32

<210> SEQ ID NO 90
<211> LENGTH: 32
<212> TYPE: DNA
<213> ORGANISM: Artificial Sequence
<220> FEATURE:
<223> OTHER INFORMATION: synthetic

<400> SEQUENCE: 90
ctggtatgag atattatgat agtgattgaa tc                                   32

<210> SEQ ID NO 91
<211> LENGTH: 32
<212> TYPE: DNA
<213> ORGANISM: Artificial Sequence
<220> FEATURE:
<223> OTHER INFORMATION: synthetic

<400> SEQUENCE: 91
gattctaatc tcaattcatt ccataatcac tg                                   32

<210> SEQ ID NO 92
<211> LENGTH: 576
<212> TYPE: DNA
<213> ORGANISM: Artificial Sequence
<220> FEATURE:
<223> OTHER INFORMATION: synthetic

<400> SEQUENCE: 92
```

```
atgcatccta tgaacaacct gctgaactac gtggtgccga agatgagacc ttacgcttgt    60
gatcgccgct tctccgtttc ccaccggctc acccatcaca tccgcatcca cacaggccag   120
aagcccttcc agtgccgcat ctgcatgcgc aacttcagcc ctagcagaag actcacccag   180
cacatccgca cccacacagg cgaaaagccc ttcgcctgcg acatctgtgg aagaaagttt   240
gccaggagcg accagcgcaa gagacatacc aagatccact tgcggcagaa ggacaagaaa   300
gcagacaaaa gtgttgtggg gcgcgccgac gcgctggacg atttcgatct cgacatgctg   360
ggttctgatg ccctcgatga ctttgacctg gatatgttgg gaagcgacgc attggatgac   420
tttgatctgg acatgctcgg ctccgatgct ctggacgatt tcgatctcga tatgttaatt   480
aactacccgt acgacgttcc ggactacgct ggttatccct atgacgtccc ggattatgca   540
ggatcctatc catatgacgt tccagattac gcttga                              576
```

<210> SEQ ID NO 93
<211> LENGTH: 591
<212> TYPE: DNA
<213> ORGANISM: Artificial Sequence
<220> FEATURE:
<223> OTHER INFORMATION: synthetic

<400> SEQUENCE: 93

```
atgcatccta tgaacaacct gctgaactac gtggtgccga agatgagacc ttacgcttgc    60
ccagtggagt cctgtgatcg ccgcttctcc cgttccatcc gtctcaccat acacatccgc   120
atccacacag gccagaagcc cttccagtgc cgcatctgca tgcgcaactt cagcggtagc   180
gttcaactca ccatacacat ccgcacccac acaggcgaaa agcccttcgc ctgcgacatc   240
tgtggaagaa agtttgccca cagcgaacct cgcaagacac ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a            591
```

<210> SEQ ID NO 94
<211> LENGTH: 591
<212> TYPE: DNA
<213> ORGANISM: Artificial Sequence
<220> FEATURE:
<223> OTHER INFORMATION: synthetic

<400> SEQUENCE: 94

```
atgcatccta tgaacaacct gctgaactac gtggtgccga agatgagacc ttacgcttgc    60
ccagtggagt cctgtgatcg ccgcttctcc gggtccagcg gctcaccat gcacatccgc   120 atccacacag gccagaagcc cttccagtgc cgcatctgca tgcgcaactt cagcctaagc   180
acaacactca ccaaccacat ccgcacccac acaggcgaaa agcccttcgc ctgcgacatc   240
tgtggaagaa agtttgccac aagccgtaca cgcaagcggc ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
```

```
gtcccggatt atgcaggatc ctatccatat gacgttccag attacgcttg a           591
```

<210> SEQ ID NO 95
<211> LENGTH: 591
<212> TYPE: DNA
<213> ORGANISM: Artificial Sequence
<220> FEATURE:
<223> OTHER INFORMATION: synthetic

<400> SEQUENCE: 95

```
atgcatccta tgaacaacct gctgaactac gtggtgccga agatgagacc ttacgcttgc    60
ccagtggagt cctgtgatcg ccgcttctcc cgttccatcc gtctcaccat acacatccgc   120
atccacacag gccagaagcc cttccagtgc cgcatctgca tgcgcaactt cagccacagc   180
ccgcaactca cccctcacat ccgcacccac acaggcgaaa agcccttcgc ctgcgacatc   240
tgtggaagaa agtttgccga agccgtaaa cgcaaggaac ataccaagat ccacttgcgg    300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a            591
```

<210> SEQ ID NO 96
<211> LENGTH: 591
<212> TYPE: DNA
<213> ORGANISM: Artificial Sequence
<220> FEATURE:
<223> OTHER INFORMATION: synthetic

<400> SEQUENCE: 96

```
atgcatccta tgaacaacct gctgaactac gtggtgccga agatgagacc ttacgcttgc    60
ccagtggagt cctgtgatcg ccgcttctcc cgttccatcc gtctcaccat acacatccgc   120
atccacacag gccagaagcc cttccagtgc cgcatctgca tgcgcaactt cagcggtagc   180
gttccactca ccatacacat ccgcacccac acaggcgaaa agcccttcgc ctgcgacatc   240
tgtggaagaa agtttgccag gagcgaccag cgcaagagac ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a            591
```

<210> SEQ ID NO 97
<211> LENGTH: 234
<212> TYPE: DNA
<213> ORGANISM: Artificial Sequence
<220> FEATURE:
<223> OTHER INFORMATION: synthetic

<400> SEQUENCE: 97

```
atgcatccta tgaacaacct gctgaactac gtggtgccga agatgagacc ttacgcttgc    60
ccagtggagc cctgtgatcg ccgcttctcc cgttccatcc gtctcaccat acacatccgc   120
atccacacag gccagaagcc cttccagtgc agcatctgca tgcgcaactt cagcggtagc   180
gatcaactca ccataaacaa ccgcaccaac acaggcgaaa agccatacgc atga          234
```

<210> SEQ ID NO 98
<211> LENGTH: 507
<212> TYPE: DNA
<213> ORGANISM: Artificial Sequence
<220> FEATURE:
<223> OTHER INFORMATION: synthetic

<400> SEQUENCE: 98

```
atgcatccta tgaacaacct gctgaactac gtggtgccga agatgagacc ttacgcttgc      60
ccagtggagt cctgtgatcg ccgcttctcc atatccggtg cgctcaccgg gcacatccgc     120
atccacacag gccagaagcc cttcgcctgc gacatctgtg gaagaaagtt tgccaggagc     180
gaccagcgca agagacatac caagatccac ttgcggcaga aggacaagaa agcagacaaa     240
agtgttgtgg ggcgcgccga cgcgctggac gatttcgatc tcgacatgct gggttctgat     300
gccctcgatg actttgacct ggatatgttg ggaagcgacg cattggatga ctttgatctg     360
gacatgctcg gctccgatgc tctggacgat ttcgatctcg atatgttaat taactacccg     420
tacgacgttc cggactacgc tggttatccc tatgacgtcc cggattatgc aggatcctat     480
ccatatgacg ttccagatta cgcttga                                         507
```

<210> SEQ ID NO 99
<211> LENGTH: 591
<212> TYPE: DNA
<213> ORGANISM: Artificial Sequence
<220> FEATURE:
<223> OTHER INFORMATION: synthetic

<400> SEQUENCE: 99

```
atgcatccta tgaacaacct gctgaactac gtggtgccga agatgagacc ttacgattgc      60
ccagtggagt cctgtgatcg ccgcttctcc cagtccgtga atctcaccgt gcacatccgc     120
atccacacag gccagaagcc cttccagtgc gcatctgca tgcgcaactt cagcgccagc     180
cccccgctca ccatacacat ccgcacccac acaggcgaaa agcccttcgc ctgcgacatc     240
tgtggaagaa agtttgccag gagcgaccag cgcaagagac ataccaagat ccacttgcgg     300
cagaaggaca agaaagcaga caaaagtgtt gtggggcgcg ccgacgcgct ggacgatttc     360
gatctcgaca tgctgggttc tgatgccctc gatgactttg acctggatat gttgggaagc     420
gacgcattgg atgactttga tctggacatg ctcggctccg atgctctgga cgatttcgat     480
ctcgatatgt taattaacta cccgtacgac gttccggact acgctggtta tccctatgac     540
gtcccggatt atgcaggatc ctatccatat gacgttccag attacgcttg a              591
```

<210> SEQ ID NO 100
<211> LENGTH: 591
<212> TYPE: DNA
<213> ORGANISM: Artificial Sequence
<220> FEATURE:
<223> OTHER INFORMATION: synthetic

<400> SEQUENCE: 100

```
atgcatccta tgaacaacct gctgaactac gtggtgccga agatgagacc ttacgattgc      60
ccagtggagt cctgtgatcg ccgcttctcc gtttcccacc ggctcaccca tcacatccgc     120
atccacacag gccagaagcc cttccagtgc gcatctgca tgcgcaactt cagcgtcagc     180
ccgaccctca cccgacacat ccgcacccac acaggcgaaa agcccttcgc ctgcgacatc     240
tgtggaagaa agtttgccag gagcgaccag cgcaagagac ataccaagat ccacttgcgg     300
```

| cagaaggaca agaaagcaga caaaagtgtt gtggggcgcg ccgacgcgct ggacgatttc | 360 |
| gatctcgaca tgctgggttc tgatgccctc gatgactttg acctggatat gttgggaagc | 420 |
| gacgcattgg atgactttga tctggacatg ctcggctccg atgctctgga cgatttcgat | 480 |
| ctcgatatgt taattaacta cccgtacgac gttccggact acgctggtta tccctatgac | 540 |
| gtcccggatt atgcaggatc ctatccatat gacgttccag attacgcttg a | 591 |

<210> SEQ ID NO 101
<211> LENGTH: 591
<212> TYPE: DNA
<213> ORGANISM: Artificial Sequence
<220> FEATURE:
<223> OTHER INFORMATION: synthetic

<400> SEQUENCE: 101

| atgcatccta tgaacaacct gctgaactac gtggtgccga agatgagacc ttacgcttgc | 60 |
| ccagtggagt cctgtgatcg ccgcttctcc cgttccatcc gtctcaccat acacatacgc | 120 |
| atccacacag gccagaagcc cttccagtgc cgcatctgca tgcgcaacct cagccacagc | 180 |
| gctcatctca cccgacacat ccgcacccac acaggcgaaa agcccttcgc ctgcgacatc | 240 |
| tgtggaagaa agtttgccag gagcgaccag cgcaagagag ataccaagat ccacttgcgg | 300 |
| cagaaggaca agaaagcaga caaaagtgtt gtggggcgcg ccgacgcgct ggacgatttc | 360 |
| gatctcgaca tgctgggttc tgatgccctc gatgactttg acctggatat gttgggaagc | 420 |
| gacgcattgg atgactttga tctggacatg ctcggctccg atgctctgga cgatttcgat | 480 |
| ctcgatatgt taattaacta cccgtacgac gttccggact acgctggtta tccctatgac | 540 |
| gtcccggatt atgcaggatc ctatccatat gacgttccag attacgcttg a | 591 |

<210> SEQ ID NO 102
<211> LENGTH: 591
<212> TYPE: DNA
<213> ORGANISM: Artificial Sequence
<220> FEATURE:
<223> OTHER INFORMATION: synthetic

<400> SEQUENCE: 102

| atgcatccta tgaacaacct gctgaactac gtggtgccga agatgagacc ttacgcttgc | 60 |
| ccagtggagt cctgtgatcg ccgcttctcc gtttcccacc ggctcaccca tcacatccgc | 120 |
| atccacacag gccagaagcc cttccagtgc cgcatctgca tgcgcaactt cagccctagc | 180 |
| agaagactca cccagcacat ccgcacccac acaggcgaaa agcccttcgc ctgcgacatc | 240 |
| tgtggaagaa agtttgccca gagcgagggg cgcaaggtcc ataccaagat ccacttgcgg | 300 |
| cagaaggaca agaaagcaga caaaagtgtt gtggggcgcg ccgacgcgct ggacgatttc | 360 |
| gatctcgaca tgctgggttc tgatgccctc gatgactttg acctggatat gttgggaagc | 420 |
| gacgcattgg atgactttga tctggacatg ctcggctccg atgctctgga cgatttcgat | 480 |
| ctcgatatgt taattaacta cccgtacgac gttccggact acgctggtta tccctatgac | 540 |
| gtcccggatt atgcaggatc ctatccatat gacgttccag attacgcttg a | 591 |

<210> SEQ ID NO 103
<211> LENGTH: 576
<212> TYPE: DNA
<213> ORGANISM: Artificial Sequence
<220> FEATURE:
<223> OTHER INFORMATION: synthetic

<400> SEQUENCE: 103

```
atgcatccta tgaacaacct gctgaactac gtggtgccga agatgagacc ttacgcttgt    60
gatcgccgct tctccgtttc ccaccggctc acccatcaca tccgcatcca cacaggccag   120
aagcccttcc agtgccgcat ctgcatgcgc aacttcagcg acagcgatga gctcaccgat   180
cacatccgca cccacacagg cgaaaagccc ttcgcctgcg acatctgtgg aagaaagttt   240
gccaggagcg accagcgcaa gagacatacc aagatccact tgcggcagaa ggacaagaaa   300
gcagacaaaa gtgttgtggg gcgcgccgac gcgctggacg atttcgatct cgacatgctg   360
ggttctgatg ccctcgatga ctttgacctg gatatgttgg gaagcgacgc attggatgac   420
tttgatctgg acatgctcgg ctccgatgct ctggacgatt tcgatctcga tatgttaatt   480
aactacccgt acgacgttcc ggactacgct ggttatccct atgacgtccc ggattatgca   540
ggatcctatc catatgacgt tccagattac gcttga                             576
```

<210> SEQ ID NO 104
<211> LENGTH: 591
<212> TYPE: DNA
<213> ORGANISM: Artificial Sequence
<220> FEATURE:
<223> OTHER INFORMATION: synthetic

<400> SEQUENCE: 104

```
atgcatccta tgaacaacct gctgaactac gtggtgccga agatgagacc ttacgcttgc    60
ccagtggagt cctgtgatcg ccgcttctcc gtttcccacc ggctcaccca tcacatccgc   120
atccacacag gccagaagcc cttccagtgc cgcatctgca tgcgcaactt cagcgacagc   180
gatgagctca ccgatcacat ccgcacccac acaggcgaaa agcccttcgc ctgcgacatc   240
tgtggaagaa agtttgccca gagcgagggg cgcaaggtcc ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a            591
```

<210> SEQ ID NO 105
<211> LENGTH: 576
<212> TYPE: DNA
<213> ORGANISM: Artificial Sequence
<220> FEATURE:
<223> OTHER INFORMATION: synthetic

<400> SEQUENCE: 105

```
atgcatccta tgaacaacct gctgaactac gtggtgccga agatgagacc ttacgcttgt    60
gatcgccgct tctccgtttc ccaccggctc acccatcaca tccgcatcca cacaggccag   120
aagcccttcc agtgccgcat ctgcatgcgc aacttcagcg tcagcccgac cctcacccga   180
cacatccgca cccacacagg cgaaaagccc ttcgcctgcg acatctgtgg aagaaagttt   240
gccaggagcg accagcgcaa gagacatacc aagatccact tgcggcagaa ggacaagaaa   300
gcagacaaaa gtgttgtggg gcgcgccgac gcgctggacg atttcgatct cgacatgctg   360
ggttctgatg ccctcgatga ctttgacctg gatatgttgg gaagcgacgc attggatgac   420
tttgatctgg acatgctcgg ctccgatgct ctggacgatt tcgatctcga tatgttaatt   480
aactacccgt acgacgttcc ggactacgct ggttatccct atgacgtccc ggattatgca   540
```

```
ggatccatc catatgacgt tccagattac gcttga                            576
```

<210> SEQ ID NO 106
<211> LENGTH: 591
<212> TYPE: DNA
<213> ORGANISM: Artificial Sequence
<220> FEATURE:
<223> OTHER INFORMATION: synthetic

<400> SEQUENCE: 106

```
atgcatccta tgaacaacct gctgaactac gtggtgccga agatgagacc ttacgcttgc    60
ccagtggagt cctgtgatcg ccgcttctcc gtatccgacg ctctcaccgt acacatccgc   120
atccacacag gccagaagcc cttccagtgc cgcatctgca tgcgcaactt cagcgtcagc   180
ccgaccctca cccgacacat ccgcacccac acaggcgaaa agcccttcgc ctgcgacatc   240
tgtggaagaa agtttgccag gagcgaccag cgcaagagac ataccaagat ccacttgcgg   300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a           591
```

<210> SEQ ID NO 107
<211> LENGTH: 591
<212> TYPE: DNA
<213> ORGANISM: Artificial Sequence
<220> FEATURE:
<223> OTHER INFORMATION: synthetic

<400> SEQUENCE: 107

```
atgcatccta tgaacaacct gctgaactac gtggtgccga agatgagacc ttacgattgc    60
ccagtggagt cctgtgatcg ccgcttctcc gtttcccacc ggctcaccca tcacatccgc   120
atccacacag gccagaagcc cttccagtgc cgcatctgca tgcgcaactt cagcctcagc   180
ctaaccctca ccaaacacat ccgcacccac acaggcgaaa agcccttcgc ctgcgacatc   240
tgtggaagaa agtttgccaa agcaaaccac gcaagacac ataccaagat ccacttgcgg    300
cagaaggaca agaaagcaga caaaagtgtt gtggggcgcg ccgacgcgct ggacgatttc   360
gatctcgaca tgctgggttc tgatgccctc gatgactttg acctggatat gttgggaagc   420
gacgcattgg atgactttga tctggacatg ctcggctccg atgctctgga cgatttcgat   480
ctcgatatgt taattaacta cccgtacgac gttccggact acgctggtta tccctatgac   540
gtcccggatt atgcaggatc ctatccatat gacgttccag attacgcttg a           591
```

<210> SEQ ID NO 108
<211> LENGTH: 591
<212> TYPE: DNA
<213> ORGANISM: Artificial Sequence
<220> FEATURE:
<223> OTHER INFORMATION: synthetic

<400> SEQUENCE: 108

```
atgcatccta tgaacaacct gctgaactac gtggtgccga agatgagacc ttacgcttgc    60
ccagtggagt cctgtgatcg ccgcttctcc gtatccgacg ctctcaccgt acacatccgc   120
atccacacag gccagaagcc cttccagtgc cgcatctgca tgcgcaactt cagcgtcagc   180
ccgaccctca cccgacacat ccgcacccac acaggcgaaa agcccttcgc ctgcgacatc   240
```

```
tgtggaagaa agtttgccga aagccgtaaa cgcaaggaac ataccaagat ccacttgcgg    300
cagaaggaca agaaagcaga caaaagtgtt gtggggcgcg ccgacgcgct ggacgatttc    360
gatctcgaca tgctgggttc tgatgccctc gatgactttg acctggatat gttgggaagc    420
gacgcattgg atgactttga tctggacatg ctcggctccg atgctctgga cgatttcgat    480
ctcgatatgt taattaacta cccgtacgac gttccggact acgctggtta tccctatgac    540
gtcccggatt atgcaggatc ctatccatat gacgttccag attacgcttg a            591
```

<210> SEQ ID NO 109
<211> LENGTH: 591
<212> TYPE: DNA
<213> ORGANISM: Artificial Sequence
<220> FEATURE:
<223> OTHER INFORMATION: synthetic

<400> SEQUENCE: 109

```
atgcatccta tgaacaacct gctgaactac gtggtgccga agatgagacc ttacgattgc     60
ccagtggagt cctgtgatcg ccgcttctcc gtatccgacg ctctcaccgt acacatccgc    120
atccacacag gccagaagcc cttccagtgc cgcatctgca tgcgcaactt cagcgacagc    180
gatgagctca ccgatcacat ccgcacccac acaggcgaaa agcccttcgc ctgcgacatc    240
tgtggaagaa agtttgccga aagccgtaaa cgcaaggaac ataccaagat ccacttgcgg    300
cagaaggaca agaaagcaga caaaagtgtt gtggggcgcg ccgacgcgct ggacgatttc    360
gatctcgaca tgctgggttc tgatgccctc gatgactttg acctggatat gttgggaagc    420
gacgcattgg atgactttga tctggacatg ctcggctccg atgctctgga cgatttcgat    480
ctcgatatgt taattaacta cccgtacgac gttccggact acgctggtta tccctatgac    540
gtcccggatt atgcaggatc ctatccatat gacgttccag attacgcttg a            591
```

<210> SEQ ID NO 110
<211> LENGTH: 492
<212> TYPE: DNA
<213> ORGANISM: Artificial Sequence
<220> FEATURE:
<223> OTHER INFORMATION: synthetic

<400> SEQUENCE: 110

```
atgcatccta tgaacaacct gctgaactac gtggtgccga agatgagacc ttacgattgt     60
gatcgccgct ctccgtttc ccaccggctc acccatcaca tccgcaccca cacaggcgaa    120
aagcccttcg cctgcgacat ctgtggaaga agtttgcca gaagcataca ccgcaagcgt    180
cataccaaga tccacttgcg gcagaaggac aagaaagcag acaaaagtgt tgtggggcgc    240
gccgacgcgc tggacgattt cgatctcgac atgctgggtt ctgatgccct cgatgacttt    300
gacctggata tgttgggaag cgacgcattg gatgactttg atctggacat gctcggctcc    360
gatgctctgg acgatttcga tctcgatatg ttaattaact acccgtacga cgttccggac    420
tacgctggtt atccctatga cgtcccggat tatgcaggat cctatccata tgacgttcca    480
gattacgctt ga                                                        492
```

<210> SEQ ID NO 111
<211> LENGTH: 21
<212> TYPE: DNA
<213> ORGANISM: Artificial Sequence
<220> FEATURE:
<223> OTHER INFORMATION: synthetic

<400> SEQUENCE: 111
tcaagcctca gacagtggtt c                                              21

<210> SEQ ID NO 112
<211> LENGTH: 70
<212> TYPE: DNA
<213> ORGANISM: Artificial Sequence
<220> FEATURE:
<223> OTHER INFORMATION: synthetic

<400> SEQUENCE: 112
tcactaatac cttacttaac tctaatctta gtcaagcgta atctggaacg tcatatggat     60
aggatcctgc                                                           70

<210> SEQ ID NO 113
<211> LENGTH: 28
<212> TYPE: DNA
<213> ORGANISM: Artificial Sequence
<220> FEATURE:
<223> OTHER INFORMATION: synthetic

<400> SEQUENCE: 113
tactatcact aacttagccg ccaccatg                                       28

<210> SEQ ID NO 114
<211> LENGTH: 55
<212> TYPE: DNA
<213> ORGANISM: Artificial Sequence
<220> FEATURE:
<223> OTHER INFORMATION: synthetic

<400> SEQUENCE: 114
gtgactggag ttcagacgtg tgctcttccg atctgtcctt ctgccgcaag tggat          55

<210> SEQ ID NO 115
<211> LENGTH: 80
<212> TYPE: DNA
<213> ORGANISM: Artificial Sequence
<220> FEATURE:
<223> OTHER INFORMATION: synthetic

<400> SEQUENCE: 115
aatgatacgg cgaccaccga gatctacact ctttccctac acgacgctct tccgatctgc     60
tgaactacgt ggtgccgaag                                                80

<210> SEQ ID NO 116
<211> LENGTH: 64
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 116
caagcagaag acggcatacg agatnnnnnn gtgactggag ttcagacgtg tgctcttccg     60
atct                                                                 64

<210> SEQ ID NO 117
<211> LENGTH: 18
<212> TYPE: DNA
<213> ORGANISM: Artificial Sequence

```
<220> FEATURE:
<223> OTHER INFORMATION: synthetic

<400> SEQUENCE: 117
tgtgatcgcc gcttctcc                                                 18

<210> SEQ ID NO 118
<211> LENGTH: 19
<212> TYPE: DNA
<213> ORGANISM: Artificial Sequence
<220> FEATURE:
<223> OTHER INFORMATION: synthetic

<400> SEQUENCE: 118
ctgtgtggat gcggatgtg                                                19

<210> SEQ ID NO 119
<211> LENGTH: 18
<212> TYPE: DNA
<213> ORGANISM: Artificial Sequence
<220> FEATURE:
<223> OTHER INFORMATION: synthetic

<400> SEQUENCE: 119
tgcatgcgca acttcagc                                                 18

<210> SEQ ID NO 120
<211> LENGTH: 24
<212> TYPE: DNA
<213> ORGANISM: Artificial Sequence
<220> FEATURE:
<223> OTHER INFORMATION: synthetic

<400> SEQUENCE: 120
ttcgcctgtg tgggtgcgga tgtg                                          24

<210> SEQ ID NO 121
<211> LENGTH: 18
<212> TYPE: DNA
<213> ORGANISM: Artificial Sequence
<220> FEATURE:
<223> OTHER INFORMATION: synthetic

<400> SEQUENCE: 121
tgtggaagaa agtttgcc                                                 18

<210> SEQ ID NO 122
<211> LENGTH: 20
<212> TYPE: DNA
<213> ORGANISM: Artificial Sequence
<220> FEATURE:
<223> OTHER INFORMATION: synthetic

<400> SEQUENCE: 122
cgcaagtgga tcttggtatg                                               20

<210> SEQ ID NO 123
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 123

Val Ser His Arg Leu Thr His
1               5
```

```
<210> SEQ ID NO 124
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 124

Pro Ser Arg Arg Leu Thr Gln
1               5

<210> SEQ ID NO 125
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 125

Gly Ser Val Val Leu Thr Lys
1               5

<210> SEQ ID NO 126
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 126

Ile Ser Thr Val Leu Thr Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 127

Pro Ser Met Thr Leu Thr Trp
1               5

<210> SEQ ID NO 128
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 128

Phe Ser Leu Ser Leu Thr Leu
1               5

<210> SEQ ID NO 129
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 129

Ile Ser Gly Ala Leu Thr Gly
1               5
```

```
<210> SEQ ID NO 130
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 130

Ser Ser Asn Gln Leu Thr Ala
1               5

<210> SEQ ID NO 131
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 131

Arg Ser Ile Arg Leu Thr Ile
1               5

<210> SEQ ID NO 132
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 132

Gly Ser Val Gln Leu Thr Ile
1               5

<210> SEQ ID NO 133
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 133

Gly Ser Ser Gly Leu Thr Met
1               5

<210> SEQ ID NO 134
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 134

Leu Ser Thr Thr Leu Thr Asn
1               5

<210> SEQ ID NO 135
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 135

His Ser Pro Gln Leu Thr Pro
1               5
```

```
<210> SEQ ID NO 136
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 136

Gly Ser Val Pro Leu Thr Ile
1               5

<210> SEQ ID NO 137
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 137

Gly Ser Asp Gln Leu Thr Ile
1               5

<210> SEQ ID NO 138
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 138

Val Ser Asp Thr Leu Thr Val
1               5

<210> SEQ ID NO 139
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 139

Asp Ser Asp Glu Leu Thr Asp
1               5

<210> SEQ ID NO 140
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 140

Gln Ser Val Asn Leu Thr Val
1               5

<210> SEQ ID NO 141
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 141

Ala Ser Pro Pro Leu Thr Ile
1               5

<210> SEQ ID NO 142
```

```
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 142

Val Ser Pro Thr Leu Thr Arg
1               5

<210> SEQ ID NO 143
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 143

His Ser Ala His Leu Thr Arg
1               5

<210> SEQ ID NO 144
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 144

Val Ser Asp Ala Leu Thr Val
1               5

<210> SEQ ID NO 145
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 145

Leu Ser Leu Thr Leu Thr Lys
1               5

<210> SEQ ID NO 146
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 146

Pro Ser Pro Pro Leu Thr Pro
1               5

<210> SEQ ID NO 147
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 147

Gly Ser Asn Arg Leu Thr Glu
1               5

<210> SEQ ID NO 148
<211> LENGTH: 7
```

```
<212> TYPE: PRT
<213> ORGANISM: Artificial Sequence
<220> FEATURE:
<223> OTHER INFORMATION: Artificial zinc finger variable domain

<400> SEQUENCE: 148

Ala Ser Pro Gly Leu Thr Ser
1               5

<210> SEQ ID NO 149
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 149

Arg Ser Thr Arg Leu Thr Gly
1               5

<210> SEQ ID NO 150
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 150

Lys Ser Arg Gly Leu Thr Thr
1               5

<210> SEQ ID NO 151
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 151

Gly Ser Gly Leu Leu Thr Arg
1               5

<210> SEQ ID NO 152
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 152

Leu Ser Arg Leu Leu Thr Gln
1               5

<210> SEQ ID NO 153
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 153

Val Ser Val Arg Leu Thr Arg
1               5

<210> SEQ ID NO 154
<211> LENGTH: 7
<212> TYPE: PRT
```

<213> ORGANISM: Artificial Sequence
<220> FEATURE:
<223> OTHER INFORMATION: Artificial zinc finger variable domain

<400> SEQUENCE: 154

Gly Ser Thr Val Leu Thr Val
1               5

<210> SEQ ID NO 155
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 155

Ile Ser Thr Met Leu Thr Gly
1               5

<210> SEQ ID NO 156
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 156

Met Ser Met Thr Leu Thr Gly
1               5

<210> SEQ ID NO 157
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 157

Gly Ser Ala Val Leu Thr Ala
1               5

<210> SEQ ID NO 158
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 158

Thr Ser Lys Val Leu Thr Glu
1               5

<210> SEQ ID NO 159
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 159

Met Ser Val Arg Leu Thr Thr
1               5

<210> SEQ ID NO 160
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 160

Asn Ser His Arg Leu Thr Ala
1               5

<210> SEQ ID NO 161
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 161

Val Ser Gly Glu Leu Thr Pro
1               5

<210> SEQ ID NO 162
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 162

Val Ser Glu Lys Leu Thr Lys
1               5

<210> SEQ ID NO 163
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 163

Gly Ser Gly Arg Leu Thr Pro
1               5

<210> SEQ ID NO 164
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 164

Gly Ser Leu Glu Leu Thr Ala
1               5

<210> SEQ ID NO 165
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 165

Asp Ser Ile Thr Leu Thr Ile
1               5

<210> SEQ ID NO 166
<211> LENGTH: 7
<212> TYPE: PRT
<213> ORGANISM: Artificial Sequence
<220> FEATURE:

```
<223> OTHER INFORMATION: Artificial zinc finger variable domain

<400> SEQUENCE: 166

Arg Ser Val Asp Leu Thr Thr
1               5

<210> SEQ ID NO 167
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 167

Pro Ser Lys Gly Leu Thr Arg
1               5

<210> SEQ ID NO 168
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 168

Arg Ser Ala Gly Leu Thr His
1               5

<210> SEQ ID NO 169
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 169

Lys Ser Gly His Leu Thr Val
1               5

<210> SEQ ID NO 170
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 170

Glu Ser Val Asn Leu Thr Gln
1               5

<210> SEQ ID NO 171
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 171

Glu Ser Pro Arg Leu Thr Thr
1               5

<210> SEQ ID NO 172
<211> LENGTH: 7
<212> TYPE: PRT
<213> ORGANISM: Artificial Sequence
<220> FEATURE:
<223> OTHER INFORMATION: Artificial zinc finger variable domain
```

<400> SEQUENCE: 172

Val Ser Ala Gly Leu Thr Ala
1               5

<210> SEQ ID NO 173
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 173

Ala Ser Ser Val Leu Thr Ile
1               5

<210> SEQ ID NO 174
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 174

Thr Ser Ala Val Leu Thr Glu
1               5

<210> SEQ ID NO 175
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 175

Thr Ser Ser Val Leu Thr Gly
1               5

<210> SEQ ID NO 176
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 176

His Ser Ile Val Leu Thr Val
1               5

<210> SEQ ID NO 177
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 177

Lys Ser Arg Pro Leu Thr Val
1               5

<210> SEQ ID NO 178
<211> LENGTH: 7
<212> TYPE: PRT
<213> ORGANISM: Artificial Sequence
<220> FEATURE:
<223> OTHER INFORMATION: Artificial zinc finger variable domain

```
<400> SEQUENCE: 178

Gly Ser Asn Pro Leu Thr Ile
1               5

<210> SEQ ID NO 179
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 179

Arg Ser Gly Gly Leu Thr Gly
1               5

<210> SEQ ID NO 180
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 180

Arg Ser Val Leu Leu Thr Thr
1               5

<210> SEQ ID NO 181
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 181

Ala Ser Leu Ile Leu Thr Thr
1               5

<210> SEQ ID NO 182
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 182

Lys Ser Leu Arg Leu Thr Val
1               5

<210> SEQ ID NO 183
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 183

Ile Ser Ala Asp Leu Thr Ala
1               5

<210> SEQ ID NO 184
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 184
```

Lys Ser Glu Ile Leu Thr Ala
1               5

<210> SEQ ID NO 185
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 185

Gly Ser Gly Pro Leu Thr Asn
1               5

<210> SEQ ID NO 186
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 186

Ser Ser Arg Gly Leu Thr Val
1               5

<210> SEQ ID NO 187
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 187

Leu Ser Arg Pro Leu Thr Arg
1               5

<210> SEQ ID NO 188
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 188

Asn Ser Gly Gly Leu Thr Pro
1               5

<210> SEQ ID NO 189
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 189

Pro Ser Arg Arg Leu Thr Lys
1               5

<210> SEQ ID NO 190
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 190

Lys Ser Glu His Leu Thr Gly
1               5

<210> SEQ ID NO 191
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 191

Leu Ser Gly Thr Leu Thr Leu
1               5

<210> SEQ ID NO 192
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 192

Pro Ser Lys Thr Leu Thr Gly
1               5

<210> SEQ ID NO 193
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 193

Val Ser Asp Glu Leu Thr Gly
1               5

<210> SEQ ID NO 194
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 194

Leu Ser Asp Arg Leu Thr Leu
1               5

<210> SEQ ID NO 195
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 195

Gly Ser Arg Asp Leu Thr Ile
1               5

<210> SEQ ID NO 196
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 196

Val Ser Gly Val Leu Thr Pro

```
1               5

<210> SEQ ID NO 197
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 197

Leu Ser Ser Leu Leu Thr Gly
1               5

<210> SEQ ID NO 198
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 198

Ile Ser Leu Ala Leu Thr Gly
1               5

<210> SEQ ID NO 199
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 199

Arg Ser Arg Ala Leu Thr Gly
1               5

<210> SEQ ID NO 200
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 200

Arg Ser Arg Leu Leu Thr Arg
1               5

<210> SEQ ID NO 201
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 201

Ala Ser Leu Pro Leu Thr Gly
1               5

<210> SEQ ID NO 202
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 202

Pro Ser Arg Glu Leu Thr Ile
1               5
```

```
<210> SEQ ID NO 203
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 203

Gly Ser Met Ser Leu Thr Gln
1               5

<210> SEQ ID NO 204
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 204

Ile Ser Arg Gly Leu Thr Val
1               5

<210> SEQ ID NO 205
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 205

Arg Ser Arg Gly Leu Thr Gly
1               5

<210> SEQ ID NO 206
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 206

Gln Ser Arg Glu Leu Thr Val
1               5

<210> SEQ ID NO 207
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 207

Lys Ser Ile Thr Leu Thr Ala
1               5

<210> SEQ ID NO 208
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 208

Arg Ser Gly Gly Leu Thr Glu
1               5
```

```
<210> SEQ ID NO 209
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 209

Gly Ser Gly Gln Leu Thr Arg
1               5

<210> SEQ ID NO 210
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 210

Arg Ser Ile Gln Leu Thr Arg
1               5

<210> SEQ ID NO 211
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 211

Ile Ser Thr Pro Leu Thr Leu
1               5

<210> SEQ ID NO 212
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 212

Val Ser Ser Thr Leu Thr Val
1               5

<210> SEQ ID NO 213
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 213

Lys Ser Leu Leu Leu Thr Arg
1               5

<210> SEQ ID NO 214
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 214

Ala Ser Leu Val Leu Thr Leu
1               5
```

```
<210> SEQ ID NO 215
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 215

Ser Ser Gln Glu Leu Thr Ala
1               5

<210> SEQ ID NO 216
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 216

Lys Ser Asp Gly Leu Thr Gly
1               5

<210> SEQ ID NO 217
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 217

Arg Ser Arg Lys Leu Thr Pro
1               5

<210> SEQ ID NO 218
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 218

Thr Ser Asp Arg Leu Thr Gln
1               5

<210> SEQ ID NO 219
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 219

Asp Ser Leu Val Leu Thr Glu
1               5

<210> SEQ ID NO 220
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 220

Ile Ser Gly Arg Leu Thr Arg
1               5

<210> SEQ ID NO 221
```

```
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 221

Lys Ser Met Thr Leu Thr Leu
1               5

<210> SEQ ID NO 222
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 222

Val Ser Glu Pro Leu Thr Pro
1               5

<210> SEQ ID NO 223
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 223

Gly Ser Leu Thr Leu Thr Glu
1               5

<210> SEQ ID NO 224
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 224

Val Ser Pro Glu Leu Thr Gly
1               5

<210> SEQ ID NO 225
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 225

Arg Ser Ile Pro Leu Thr Lys
1               5

<210> SEQ ID NO 226
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 226

Gly Ser Gly Arg Leu Thr Val
1               5

<210> SEQ ID NO 227
<211> LENGTH: 7
```

```
<212> TYPE: PRT
<213> ORGANISM: Artificial Sequence
<220> FEATURE:
<223> OTHER INFORMATION: Artificial zinc finger variable domain

<400> SEQUENCE: 227

Gly Ser Ala Ile Leu Thr Gly
1               5

<210> SEQ ID NO 228
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 228

Leu Ser Leu Ala Leu Thr Asn
1               5

<210> SEQ ID NO 229
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 229

Arg Ser Ser Met Leu Thr Ser
1               5

<210> SEQ ID NO 230
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 230

Asp Ser Val Arg Leu Thr Arg
1               5

<210> SEQ ID NO 231
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 231

Glu Ser Gly Gly Leu Thr Asn
1               5

<210> SEQ ID NO 232
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 232

Val Ser Gly Gly Leu Thr Asp
1               5

<210> SEQ ID NO 233
<211> LENGTH: 7
<212> TYPE: PRT
```

```
<213> ORGANISM: Artificial Sequence
<220> FEATURE:
<223> OTHER INFORMATION: Artificial zinc finger variable domain

<400> SEQUENCE: 233

Val Ser Arg Val Leu Thr Arg
1               5

<210> SEQ ID NO 234
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 234

Pro Ser Lys Arg Leu Thr Arg
1               5

<210> SEQ ID NO 235
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 235

Val Ser Met Met Leu Thr Gly
1               5

<210> SEQ ID NO 236
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 236

Leu Ser Thr Pro Leu Thr Val
1               5

<210> SEQ ID NO 237
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 237

Gly Ser Met Arg Leu Thr Ile
1               5

<210> SEQ ID NO 238
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 238

Pro Ser Gly Leu Leu Thr Lys
1               5

<210> SEQ ID NO 239
<211> LENGTH: 7
<212> TYPE: PRT
<213> ORGANISM: Artificial Sequence
```

```
<220> FEATURE:
<223> OTHER INFORMATION: Artificial zinc finger variable domain

<400> SEQUENCE: 239

Asn Ser Val Arg Leu Thr Val
1               5

<210> SEQ ID NO 240
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 240

Ile Ser Arg Leu Leu Thr Met
1               5

<210> SEQ ID NO 241
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 241

Arg Ser Gly Ala Leu Thr Ala
1               5

<210> SEQ ID NO 242
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 242

Val Ser Glu Ile Leu Thr Gly
1               5

<210> SEQ ID NO 243
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 243

Glu Ser Arg Ala Leu Thr Pro
1               5

<210> SEQ ID NO 244
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 244

Pro Ser Asp Ala Leu Thr Arg
1               5

<210> SEQ ID NO 245
<211> LENGTH: 7
<212> TYPE: PRT
<213> ORGANISM: Artificial Sequence
<220> FEATURE:
```

```
<223> OTHER INFORMATION: Artificial zinc finger variable domain

<400> SEQUENCE: 245

Gln Ser Leu Lys Leu Thr Val
1               5

<210> SEQ ID NO 246
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 246

Leu Ser Gln Ala Leu Thr Gln
1               5

<210> SEQ ID NO 247
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 247

Thr Ser Leu Pro Leu Thr Thr
1               5

<210> SEQ ID NO 248
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 248

Asp Ser Met Ala Leu Thr Pro
1               5

<210> SEQ ID NO 249
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 249

Leu Ser Lys Ile Leu Thr Leu
1               5

<210> SEQ ID NO 250
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 250

Thr Ser Pro Ile Leu Thr Gln
1               5

<210> SEQ ID NO 251
<211> LENGTH: 7
<212> TYPE: PRT
<213> ORGANISM: Artificial Sequence
<220> FEATURE:
<223> OTHER INFORMATION: Artificial zinc finger variable domain
```

```
<400> SEQUENCE: 251

Glu Ser Glu Gln Leu Thr Lys
1               5

<210> SEQ ID NO 252
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 252

Gly Ser Pro Thr Leu Thr Pro
1               5

<210> SEQ ID NO 253
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 253

Asp Ser Arg Pro Leu Thr Ser
1               5

<210> SEQ ID NO 254
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 254

Arg Ser Pro Ile Leu Thr Asp
1               5

<210> SEQ ID NO 255
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 255

Thr Ser Arg Val Leu Thr Val
1               5

<210> SEQ ID NO 256
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 256

Asp Ser Asn Asn Leu Thr Ala
1               5

<210> SEQ ID NO 257
<211> LENGTH: 7
<212> TYPE: PRT
<213> ORGANISM: Artificial Sequence
<220> FEATURE:
<223> OTHER INFORMATION: Artificial zinc finger variable domain
```

```
<400> SEQUENCE: 257

Gly Ser Ala Gly Leu Thr Asp
1               5

<210> SEQ ID NO 258
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 258

Leu Ser Pro Asn Leu Thr Ile
1               5

<210> SEQ ID NO 259
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 259

Arg Ser His Arg Leu Thr Arg
1               5

<210> SEQ ID NO 260
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 260

Thr Ser Val Gln Leu Thr Ile
1               5

<210> SEQ ID NO 261
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 261

Pro Ser Ser Ala Leu Thr Ser
1               5

<210> SEQ ID NO 262
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 262

Ile Ser Asn Asp Leu Thr Gly
1               5

<210> SEQ ID NO 263
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 263
```

```
Gly Ser Ala Leu Leu Thr Lys
1               5

<210> SEQ ID NO 264
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 264

Pro Ser Lys Asn Leu Thr Leu
1               5

<210> SEQ ID NO 265
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 265

Thr Ser Pro Ile Leu Thr Ile
1               5

<210> SEQ ID NO 266
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 266

Arg Ser His Pro Leu Thr His
1               5

<210> SEQ ID NO 267
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 267

Thr Ser Asn Thr Leu Thr Leu
1               5

<210> SEQ ID NO 268
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 268

Leu Ser Val Pro Leu Thr Thr
1               5

<210> SEQ ID NO 269
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 269
```

```
Ala Ser Thr Ile Leu Thr Gln
1               5

<210> SEQ ID NO 270
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 270

Thr Ser Pro Gly Leu Thr Pro
1               5

<210> SEQ ID NO 271
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 271

Ser Ser Ser Met Leu Thr Gly
1               5

<210> SEQ ID NO 272
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 272

Gln Ser Ala Thr Leu Thr Arg
1               5

<210> SEQ ID NO 273
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 273

Thr Ser Thr His Leu Thr Arg
1               5

<210> SEQ ID NO 274
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 274

Thr Ser Glu Glu Leu Thr Pro
1               5

<210> SEQ ID NO 275
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 275

Pro Ser Thr Gly Leu Thr Glu
```

```
1               5

<210> SEQ ID NO 276
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 276

Ala Ser His Leu Leu Thr Thr
1               5

<210> SEQ ID NO 277
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 277

Arg Ser Arg Ser Leu Thr Gly
1               5

<210> SEQ ID NO 278
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 278

Leu Ser Ile Leu Leu Thr Pro
1               5

<210> SEQ ID NO 279
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 279

Ile Ser Gly Ser Leu Thr His
1               5

<210> SEQ ID NO 280
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 280

Thr Ser Lys Ala Leu Thr Gln
1               5

<210> SEQ ID NO 281
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 281

Pro Ser Asn Ser Leu Thr Arg
1               5
```

```
<210> SEQ ID NO 282
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 282

His Ser Pro Met Leu Thr Ala
1               5

<210> SEQ ID NO 283
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 283

Ala Ser Arg Thr Leu Thr Lys
1               5

<210> SEQ ID NO 284
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 284

Lys Ser Gln Asn Leu Thr Asn
1               5

<210> SEQ ID NO 285
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 285

His Ser Pro Pro Leu Thr Pro
1               5

<210> SEQ ID NO 286
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 286

Asp Ser His Gly Leu Thr Arg
1               5

<210> SEQ ID NO 287
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 287

Arg Ser Asp Ala Leu Thr Leu
1               5
```

```
<210> SEQ ID NO 288
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 288

Leu Ser Pro Thr Leu Thr Gln
1               5

<210> SEQ ID NO 289
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 289

Ala Ser Gly His Leu Thr Glu
1               5

<210> SEQ ID NO 290
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 290

Thr Ser Arg Glu Leu Thr Arg
1               5

<210> SEQ ID NO 291
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 291

Asp Ser Pro Pro Leu Thr Ala
1               5

<210> SEQ ID NO 292
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 292

Asn Ser Ala Pro Leu Thr Pro
1               5

<210> SEQ ID NO 293
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 293

Leu Ser Thr Gln Leu Thr Ile
1               5
```

```
<210> SEQ ID NO 294
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 294

Asn Ser Thr Gln Leu Thr Ser
1               5

<210> SEQ ID NO 295
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 295

Met Ser Lys Pro Leu Thr Thr
1               5

<210> SEQ ID NO 296
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 296

Asp Ser Leu Lys Leu Thr Arg
1               5

<210> SEQ ID NO 297
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 297

Thr Ser Thr Leu Leu Thr Val
1               5

<210> SEQ ID NO 298
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 298

His Ser Gly Pro Leu Thr Leu
1               5

<210> SEQ ID NO 299
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 299

Ile Ser Lys Lys Leu Thr Pro
1               5

<210> SEQ ID NO 300
```

<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 300

Gln Ser Pro Asp Leu Thr Leu
1               5

<210> SEQ ID NO 301
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 301

Arg Ser Leu Leu Leu Thr Arg
1               5

<210> SEQ ID NO 302
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 302

Ile Ser Thr Pro Leu Thr Glu
1               5

<210> SEQ ID NO 303
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 303

Asn Ser Lys Thr Leu Thr Thr
1               5

<210> SEQ ID NO 304
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 304

His Ser Arg Ile Leu Thr Asn
1               5

<210> SEQ ID NO 305
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 305

Leu Ser Pro Leu Leu Thr Ile
1               5

<210> SEQ ID NO 306
<211> LENGTH: 7

```
<212> TYPE: PRT
<213> ORGANISM: Artificial Sequence
<220> FEATURE:
<223> OTHER INFORMATION: Artificial zinc finger variable domain

<400> SEQUENCE: 306

Leu Ser His Pro Leu Thr Met
1               5

<210> SEQ ID NO 307
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 307

Pro Ser Pro Ile Leu Thr Thr
1               5

<210> SEQ ID NO 308
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 308

Thr Ser Pro Pro Leu Thr Leu
1               5

<210> SEQ ID NO 309
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 309

Pro Ser Ala Thr Leu Thr Asn
1               5

<210> SEQ ID NO 310
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 310

Val Ser Thr Met Leu Thr Leu
1               5

<210> SEQ ID NO 311
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 311

His Ser Ser His Leu Thr His
1               5

<210> SEQ ID NO 312
<211> LENGTH: 7
<212> TYPE: PRT
```

```
<213> ORGANISM: Artificial Sequence
<220> FEATURE:
<223> OTHER INFORMATION: Artificial zinc finger variable domain

<400> SEQUENCE: 312

Asp Ser Arg Ile Leu Thr Ser
1               5

<210> SEQ ID NO 313
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 313

Thr Ser Ile Ala Leu Thr Gly
1               5

<210> SEQ ID NO 314
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 314

Pro Ser Thr Lys Leu Thr Arg
1               5

<210> SEQ ID NO 315
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 315

Pro Ser Val Ala Leu Thr Lys
1               5

<210> SEQ ID NO 316
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 316

Thr Ser Pro Thr Leu Thr Gln
1               5

<210> SEQ ID NO 317
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 317

Thr Ser Leu Pro Leu Thr Ala
1               5

<210> SEQ ID NO 318
<211> LENGTH: 7
<212> TYPE: PRT
<213> ORGANISM: Artificial Sequence
```

```
<220> FEATURE:
<223> OTHER INFORMATION: Artificial zinc finger variable domain

<400> SEQUENCE: 318

Ala Ser Asn Leu Leu Thr Ser
1               5

<210> SEQ ID NO 319
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 319

Ile Ser Val Gly Leu Thr Gln
1               5

<210> SEQ ID NO 320
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 320

Gln Ser Val Ala Leu Thr Glu
1               5

<210> SEQ ID NO 321
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 321

Ala Ser Lys Asn Leu Thr Gln
1               5

<210> SEQ ID NO 322
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 322

Arg Ser Pro Leu Leu Thr Leu
1               5

<210> SEQ ID NO 323
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 323

Ile Ser Pro Arg Leu Thr Asn
1               5

<210> SEQ ID NO 324
<211> LENGTH: 7
<212> TYPE: PRT
<213> ORGANISM: Artificial Sequence
<220> FEATURE:
```

<223> OTHER INFORMATION: Artificial zinc finger variable domain

<400> SEQUENCE: 324

Ser Ser Pro Ile Leu Thr Asp
1               5

<210> SEQ ID NO 325
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 325

Pro Ser Arg Arg Leu Thr Leu
1               5

<210> SEQ ID NO 326
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 326

Ile Ser Ile Pro Leu Thr Asp
1               5

<210> SEQ ID NO 327
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 327

Glu Ser Ala Pro Leu Thr Gly
1               5

<210> SEQ ID NO 328
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 328

Leu Ser Arg Lys Leu Thr Asn
1               5

<210> SEQ ID NO 329
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 329

Pro Ser Arg Leu Leu Thr Val
1               5

<210> SEQ ID NO 330
<211> LENGTH: 7
<212> TYPE: PRT
<213> ORGANISM: Artificial Sequence
<220> FEATURE:
<223> OTHER INFORMATION: Artificial zinc finger variable domain

```
<400> SEQUENCE: 330

Gln Ser Pro Arg Leu Thr Gly
1               5

<210> SEQ ID NO 331
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 331

Lys Ser Gly Gly Leu Thr Val
1               5

<210> SEQ ID NO 332
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 332

Ile Ser Leu His Leu Thr Gln
1               5

<210> SEQ ID NO 333
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 333

His Ser Pro Ala Leu Thr Ser
1               5

<210> SEQ ID NO 334
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 334

Ile Ser Val Ala Leu Thr Val
1               5

<210> SEQ ID NO 335
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 335

Asp Ser Ser Leu Leu Thr Thr
1               5

<210> SEQ ID NO 336
<211> LENGTH: 7
<212> TYPE: PRT
<213> ORGANISM: Artificial Sequence
<220> FEATURE:
<223> OTHER INFORMATION: Artificial zinc finger variable domain
```

```
<400> SEQUENCE: 336

Arg Ser Arg Pro Leu Thr Lys
1               5

<210> SEQ ID NO 337
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 337

Pro Ser Ala Pro Leu Thr Ala
1               5

<210> SEQ ID NO 338
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 338

Pro Ser Ala Lys Leu Thr Pro
1               5

<210> SEQ ID NO 339
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 339

Gln Ser Ile Gln Leu Thr Pro
1               5

<210> SEQ ID NO 340
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 340

Asn Ser Pro Ala Leu Thr Pro
1               5

<210> SEQ ID NO 341
<211> LENGTH: 7
<212> TYPE: PRT
<213> ORGANISM: Artificial Sequence
<220> FEATURE:
<223> OTHER INFORMATION: Artificial zinc finger variable domain

<400> SEQUENCE: 341

Thr Ser Gly Thr Leu Thr Asn
1               5
```